United States Patent [19]

Baldwin et al.

[11] Patent Number: 5,206,240

[45] Date of Patent: Apr. 27, 1993

[54] NITROGEN-CONTAINING SPIROCYCLES

[75] Inventors: John J. Baldwin, Gwynedd Valley; Jason M. Elliott, Blue Bell; David A. Claremon, Audubon; Gerald S. Ponticello, Lansdale; David C. Remy, North Wales; Harold G. Selnick, Ambler, all of Pa.

[73] Assignee: Merck & Co., Inc., Rahway, N.J.

[21] Appl. No.: 709,686

[22] Filed: Jun. 3, 1991

Related U.S. Application Data

[63] Continuation-in-part of Ser. No. 612,091, Nov. 16, 1990, abandoned, which is a continuation-in-part of Ser. No. 447,950, Dec. 8, 1989, abandoned.

[51] Int. Cl.$^5$ .................. A61K 31/445; C07D 211/94
[52] U.S. Cl. .................. 514/231.5; 514/253; 514/278; 544/70; 544/71; 544/230; 544/231; 546/17
[58] Field of Search ............... 546/17; 514/278, 231.5, 514/253; 544/70, 71, 230, 331

[56] References Cited

U.S. PATENT DOCUMENTS

| | | | |
|---|---|---|---|
| 3,686,186 | 8/1972 | Houlihan et al. | 260/293.58 |
| 4,420,485 | 12/1983 | Davis et al. | 546/17 X |
| 4,788,196 | 11/1988 | Cross et al. | 514/252 |
| 4,806,536 | 2/1989 | Cross et al. | 514/252 |
| 4,810,792 | 3/1989 | Kosley, Jr. | 546/207 |

FOREIGN PATENT DOCUMENTS

| | | |
|---|---|---|
| 229391 | 7/1987 | European Pat. Off. . |
| 235752 | 9/1987 | European Pat. Off. . |
| 284384 | 9/1988 | European Pat. Off. . |
| 296560 | 12/1988 | European Pat. Off. . |
| 63-63533 | 12/1988 | Japan . |

OTHER PUBLICATIONS

Yamato et al, *Chem. Pharm. Bull.*, 29, 3494, (1981).
Bauer et al, *J. Med. Chem.*, 19, 1315 (1976).
Parham et al, *J. Org. Chem.*, 41, 2629, (1976).
Lorio et al, *Il Farmaco-Ed Sci.*, 32, 212-219, (1977).

*Primary Examiner*—Joseph P. Brust
*Assistant Examiner*—Jacqueline Haley
*Attorney, Agent, or Firm*—Mark R. Daniel; Joseph F. DiPrima

[57] ABSTRACT

Spirocycles of general structural formula:

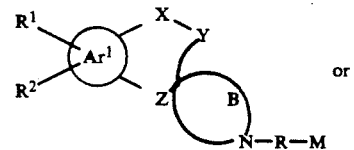

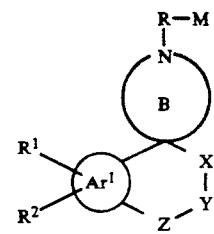

are Class III antiarrhythmic agents.

4 Claims, No Drawings

NITROGEN-CONTAINING SPIROCYCLES

This application is a continuation-in-part of copending application Ser. No. 612,091, filed Nov. 16, 1990, now abandoned, which is in turn a continuation-in-part of copending application Ser. No. 447,950, filed Dec. 8, 1989, now abandoned.

SUMMARY OF THE INVENTION

This invention is concerned with novel spirocycles of general structural formula:

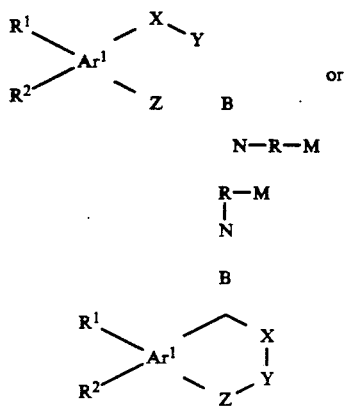

which are Class III antiarrhythmic agents, and positive inotropic or cardiotonic agents, wherein $Ar^1$ is a carbocyclic or heterocyclic group, M is a carbocyclic or heterocyclic group, or a functional group, R is a bridging group and X, Y and Z are independently a carbon or a heteroatom.

The invention is also concerned with pharmaceutical formulations comprising one or more of the novel compounds as active ingredient, either alone or in combination with one or more of a Class I, Class II or Class IV antiarrhythmic agent.

The invention is also concerned with a method of treatment of arrhythmia and impaired cardiac pump functions with the above-described novel compounds and formulations thereof.

The invention is further concerned with processes for preparing the novel compounds.

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, those, having both satisfactory effects and high safety, have not been obtained. For example, antiarrythmic agents of Class I according to the classification of Vaughan-Williams which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severly limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

A number of antiarrhythmic agents have been reported in the literature, such as those disclosed in:

(1) EP 397,121-A,
(2) EP 300,908-A,
(3) EP 307,121,
(4) U.S. Pat. No. 4,629,739,
(5) U.S. Pat. No. 4,544,654,
(6) U.S. Pat. No. 4,788,196,
(7) EP application 88302597.5,
(8) EP application 88302598.3,
(9) EP application 88302270.9,
(10) EP application 88302600.7,
(11) EP application 88302599.1,
(12) EP application 88300962.3,
(13) EP application 235,752,
(14) DE 3633977-A1,
(15) U.S. Pat. No. 4,804,662,
(16) U.S. Pat. No. 4,797,401,
(17) U.S. Pat. No. 4,806,555,
(18) U.S. Pat. No. 4,806,536.

Compounds of similar structure are found in Japanese patent publication 88-63533-B of Daiichi Pharmaceutical Co.; *J. Med. Chem.*, 19, 1315 (1976) by Bauer et al; Iorio et al in *Il Farmaco-Ed Sci.*, 32, 212–219 (1977): Houlihan et al, U.S. Pat. No. 3,686,186; Davis et al, U.S. Pat. No. 4,420,485; Kealey, U.S. Pat. No. 4,810,792; Parham et al, *J. Org. Chem.*, 41, 2629 (1976). None of the compounds disclosed in the foregoing references are alleged to have antiarrhythmic activity.

Now with the present invention, there is provided a new use as antiarrhythmic agent for many of these known compounds and a group of new compounds of similar structure with an increased degree of activity.

DETAILED DESCRIPTION OF THE INVENTION

The novel compound of this invention has structural formula:

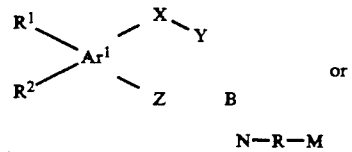

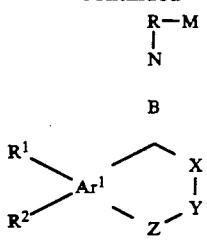

or a pharmaceutically acceptable salt thereof, wherein Ar¹ is an aromatic ring selected from
1) benzo,
2) thieno,
3) furo, and
4) pyrido;

the ring system comprising X, Y and Z is a 5-, 6- or 7-membered ring system wherein X, Y and Z are independently —O—, C=O, CHOR⁶, —NR⁶—, CHNR⁷R⁸, —S(O)$_n$—, C=NOR⁹, —(CR⁴R⁵)$_n$—, =CH—, =N—, or a bond, wherein:

R⁴ and R⁵ are independently
  a) hydrogen, or
  b) C$_{1-6}$alkyl;
R⁶ is
  a) hydrogen,
  b) C$_{1-6}$alkyl,
  c) (CH$_2$)$_n$—C$_6$H$_4$—R¹⁰, wherein R¹⁰ is
    i) —NO$_2$,
    ii) C$_{1-3}$alkyl,
    iii) —O—C$_{1-3}$alkyl,
    iv) halo,
    v) —CF$_3$, or
    vi) hydrogen,
  d) —CO—C$_{1-6}$alkyl, or
  e) —CO—C$_6$H$_4$—R¹⁰;
  f) —COO—C$_{1-6}$alkyl, or
  g) —CONR⁴R⁵;
R⁷ and R⁸ are independently
  a) hydrogen,
  b) C$_{1-6}$alkyl, unsubstituted or substituted with —(CR⁴R⁵)$_n$—(CR⁴R⁵)$_g$—R¹¹, wherein g is 1-5, and R¹¹ is
    i) hydrogen,
    ii) —OH, or
    iii) —OC$_{1-6}$alkyl,
  c) —CO—C$_{1-6}$alkyl, unsubstituted or substituted with
    i) —OH,
    ii) —N(R⁴R⁵),
    iii) —OC$_{1-6}$alkyl, or
    iv) —CO$_2$R⁵,
  d) —CO—C$_6$H$_4$—R¹⁰, or
  e) R⁷ and R⁸ taken together with the nitrogen atom to which they are attached represent a 5 or 6 membered saturated heterocyclic ring, unsubstituted or substituted with oxygen or hydroxy, which may contain an additional heteroatom selected from N, S(O)$_n$ or O, such as pyrrolidine, morpholine, piperidine, pyrrolidinone, piperidinone, piperazine or N-methylpiperazine;
R⁹ is
  a) hydrogen, or
  b) C$_{1-6}$alkyl, unsubstituted or substituted with —COOR⁵;
n is 0, 1 or 2;

with the proviso that in Structure I, if X or Y is a heteroatom, the other of the two is a carbon atom; and that in Structure II, if Y is a heteroatom, both X and Z are carbon atoms; if X is a heteroatom Y is not; and if Z is a heteroatom Y is not, i.e. X, Y and Z must be selected so that there are not two adjacent heteroatoms;

M is
1) —H,
2) —OH,
3) —O(C$_{1-6}$alkyl),
4) —CN,
5) —NHSO$_2$C$_{1-6}$alkyl,
6) —COOH,
7) —COOC$_{1-6}$alkyl,
8) —CONR¹²R¹³, wherein R¹² and R¹³ are independently
  a) hydrogen,
  b) C$_{1-6}$alkyl, or
  c) R¹² and R¹³ taken together with the nitrogen atom to which they are attached represent a 5 or 6 membered saturated heterocyclic ring which may contain an additional heteroatom selected from N, S(O)$_n$ or O, such as pyrrolidine, morpholine, piperidine, piperazine or N-methylpiperazine,
9) —NR¹²R¹³,
10) halo,
12) C$_{5-8}$cycloalkane,
13) C$_{5-8}$cycloalkene, or
14)

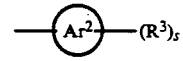

wherein s is 1-3 and the R³ groups may be the same or different;

R is —(CR⁴R⁵)$_m$—Q—(CR⁴R⁵)$_q$—, wherein R⁴ and R⁵ are as defined above, m and q are independently 0-5, Q is a bond, —O—, C=O, CHOH, N—R⁵ or —S(O)$_n$—, with the proviso that if Q is —O—, N—R⁵ or —S(O)$_n$—, m is other than 0 or 1, and the further proviso that if Q is —O—, N—R⁵ or —S(O)$_n$—, and M is any functional group connected through a heteroatom, q is other than 0 or 1, and with the proviso that when n and q are both 0 and Q is a bond (making R a bond), M is other than —H;

R¹, R², and R³ are independently selected from:
1) hydrogen,
2) C$_{1-6}$ alkyl, either unsubstituted or substituted with
  a) —NR⁴R⁵, wherein R⁴ and R⁵ are as defined above,
  b) —N(R⁵)COC$_{1-6}$alkyl,
  c) —NHSO$_2$(C$_{1-6}$alkyl),
  d) —CONR¹²R¹³, wherein R¹² and R¹³ are as defined above,
  e) —CO(C$_{1-6}$alkyl),
  f) —OH,
  g) —O(C$_{1-6}$alkyl),
  h) —O(C$_{1-6}$alkyl)—O—(C$_{1-3}$alkyl),
  i) —S(O)$_n$(C$_{1-6}$alkyl),
  j) imidazole,
  k) 2-imidazolidinone,
  l) 2-pyrrolidinone,
  m) —NH—C(NHR⁵)=N—CN, or
  n) —NH—C(SR⁵)=N—CN,
3) —OH, 4) $C_{1-3}$ alkoxy, either unsubstituted or substituted with $C_{1-3}$ alkoxy,
5) —N($R^5$)SO$_2$($C_{1-6}$alkyl),
6) —N($R^5$)SO$_2$(CH$_2$)$_g$CO$_2$H,
7) —N($R^5$)SO$_2$(CH$_2$)$_g$CO$_2$C$_{1-6}$alkyl,
8) —NO$_2$,
9) —N($R^5$)COC$_{1-6}$alkyl,
10) —N($R^5$)SO$_2$—C$_6$H$_4$—$R^4$,
11) —N($R^5$)CO—C$_6$H$_4$—$R^4$,
12) —NR$^4$R$^5$,
13) halo,
14) —CO—$C_{1-6}$alkyl,
15) —CONR$^{12}$R$^{13}$,
16) —CN,
17) —CO$_2$R$^5$,
18) —C($R^5$)=N—OR$^9$,
19) benzoyl, either unsubstituted or substituted with $C_{1-6}$alkyl, $C_{1-6}$alkoxy, halo, or hydroxy,
20) —N($R^5$)COO($C_{1-6}$alkyl),
21) —N($R^5$)COO-phenyl either unsubstituted or substituted with $C_{1-6}$alkyl, $C_{1-6}$alkoxy, hydroxy or halo,
22) —N($R^5$)CONR$^4$R$^5$,
23) —S(O)$_n$C$_{1-6}$alkyl,
24) —S(O)$_n$—C$_6$H$_4$—R$^4$,
25) —CF$_3$,
26) phenyl, either unsubstituted or substituted with $C_{1-6}$alkyl, $C_{1-6}$alkoxy, halo or hydroxy,
27) imidazolyl,
28) —SO$_2$NR$^{12}$R$^{13}$,
29) —N[S(O)$_2$C$_{1-6}$alkyl][(CH$_2$)$_p$CN], wherein p is 2-5,
30) —N($R^5$)—C(NR$^4$R$^5$)=N—CN,
31) —N($R^5$)—C(SR$^5$)=N—CN, or $R^1$ and $R^2$ on adjacent carbon atoms taken together with the Ar$^1$ to which they are attached represent:

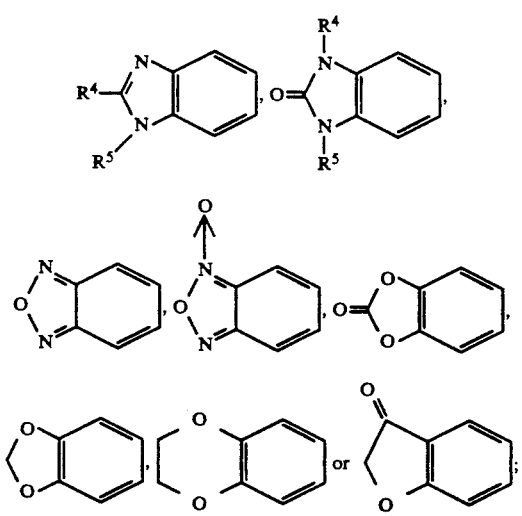

B is a ring of 5 to 8 members; and
Ar$^2$ is a single or fused ring carbocyclic or heterocyclic ring system containing up to 4 heteroatoms such as a mono- or bicyclic system selected from:
1) benzene,
2) pyridine,
3) benzofuran,
4) quinoline,
5) benzofurazan,
6) benzofurazan-N-oxide,
7) benzimidazole,
8) indole,
9) indoline,
10) benzothiafurazan,
11) benzothiafurazan-N-oxide,
12) 1,3-dihydro-2,1,3-benzothiadiazole,
13) 1,3-dihydro-2,1,3-benzothiadiazole-2,2-dioxide,
14) 1,3-dihydro-2H-benzimidazole-2-one,
15) 2,1-benzisoxazole,
16) quinoxaline,
17) 1,2-benzisoxazole,
18) indane,
19) tetralin,
20) benzocycloheptane,
21) benzodioxane,
22) 1,3-benzodioxole,
23) imidazole,
24) naphthalene,
25) benzocyclobutane,
26) thiophene,
27) thiazole,
28) phthalimide,
29) pyrimidine,
30) imidazolidin-2-one,
31) furan,
32) pyridine-N-oxide,
33) pyridone,
34) indolin-2-one,
35) tetrazolopyridine,
36) 2,3-dihydrobenzofuran,
37) benzomorpholine,
38) isoquinoline,
39) pyrimidindione,
40) N,N-di($C_{1-6}$alkyl)pyrimidindione,
40) benzothiophene,
41) pyrazine, and
42) pyridazine;

with the proviso that if Ar$^1$ is benzo, and $R^1$ and $R^2$ are hydrogen, hydroxyalkyl or alkoxy, then M is other than unsubstituted phenyl or hydrogen.

In a preferred embodiment of the novel compound Ar$^1$ is benzo or thieno, especially benzo substituted with an electron withdrawing group such as nitro or methanesulfonamido.

In a particular it is preferred that $R^1$ and $R^2$ are independently selected from:
a) —NO$_2$,
b) —NHSO$_2$($C_{1-6}$alkyl),
c) —SO$_2$($C_{1-6}$alkyl),
d) —NHSO$_2$—C$_6$H$_4$—R4,
e) —SO$_2$—C$_6$H$_4$—R4,
f) hydrogen, or $R^1$ and $R^2$ taken together with the Ar$^1$ group to which they are attached represent:

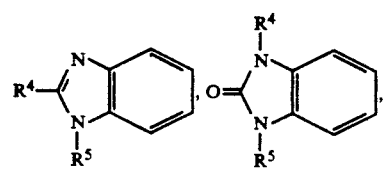

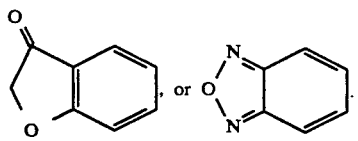

It is also preferred that the spirocycle B is spiropiperidine, especially wherein the nitrogen atom is in the 3'- or 4'-position, and more especially in the 4'-position.

It is also preferred that R is a bond, or $C_{1-8}$ alkyl, unsubstituted or substituted with hydroxyl; and M is:
a) —OH,
b) —CN, or
c) —(Ar$^2$)—(R$^3$)$_s$, wherein Ar$^2$ is:
  i) benzene,
  ii) pyridine,
  iii) benzofurazan,
  iv) tetralin,
  v) thiophene,
  vi) furan, or
  vii) 2,3-dihydrobenzofuran,
and wherein s is 1 or 2, and R$^3$ is:
  i) hydrogen,
  ii) $C_{1-6}$ alkyl, either unsubstituted or substituted with
    A) —OH, or
    B) —NR$^4$R$^5$, wherein R$^4$ and R$^5$ are hydrogen or $C_{1-6}$ alkyl,
  iii) —OH,
  iv) $C_{1-3}$ alkoxy, either unsubstituted or substituted with $C_{1-3}$ alkoxy,
  v) —N(R$^5$)SO$_2$(C$_{1-6}$alkyl),
  vi) —NO$_2$,
  vii) —N(R$^5$)COC$_{1-6}$alkyl,
  viii) —N(R$^5$)COO(C$_{1-6}$alkyl),
  ix) halo,
  x) —CO—C$_{1-6}$alkyl,
  xi) —CONR$^4$R$^5$,
  xii) —CH=N—OR$^4$,
  xiii) —CN, or
  xiv) —S(O)$_n$C$_{1-6}$alkyl, wherein n is 0–2.

It is more preferred that —R—M be n—hexyl; unsubstituted or substituted with hydroxy or cyano, or that M be Ar$^2$R$^3$, wherein Ar$^2$R$^3$ is phenyl, 4-fluorophenyl, 4-cyanophenyl, benzofurazanyl, 2- or 4-pyridyl, 4-methoxyphenyl, 4-chlorophenyl, 3,4-methylenedioxyphenyl, 4-sulfamoylphenyl 4-methanesulfonamidophenyl, cyanotetralin or 2-methyl-6-pyridyl, especially benzofurazanyl, phenyl, 4-fluorophenyl, tetralin-2-yl, 6-cyano-tetralin-2-yl or 4-cyanophenyl.

In the cyclic moiety comprising X, Y and Z preferred structures are as follows:

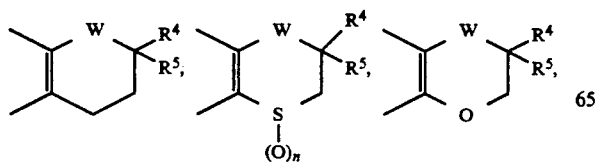

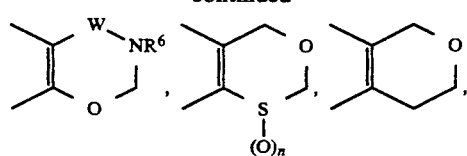

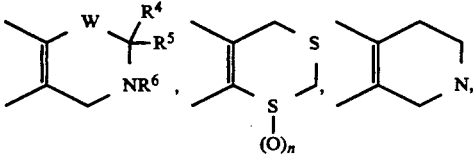

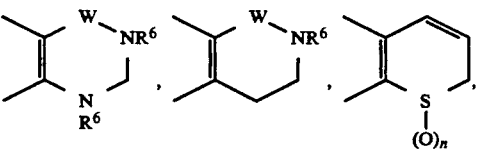

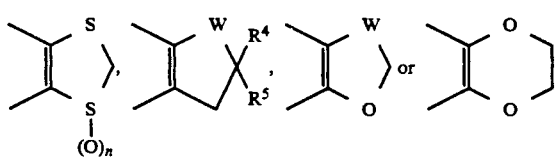

where W is C=O, CH$_2$, CHOR$^6$, C=NOR$^9$, or CHNR$^7$R$^8$, and R$^4$, R$^5$, R$^6$, R$^7$, R$^8$, R$^9$ and n are as defined above.

It is even more preferred that the cyclic moiety comprising X, Y and Z is:

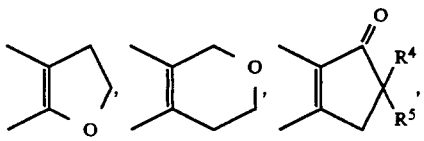

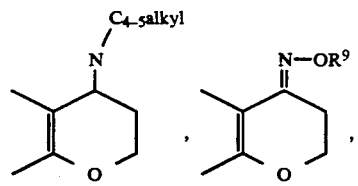

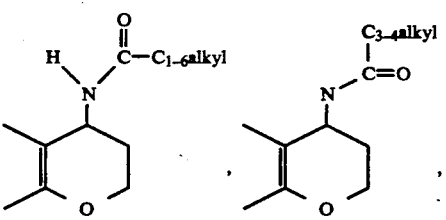

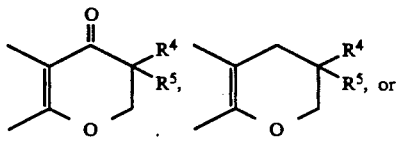

It is further preferred that the cyclic moiety comprising X, Y, and Z is:

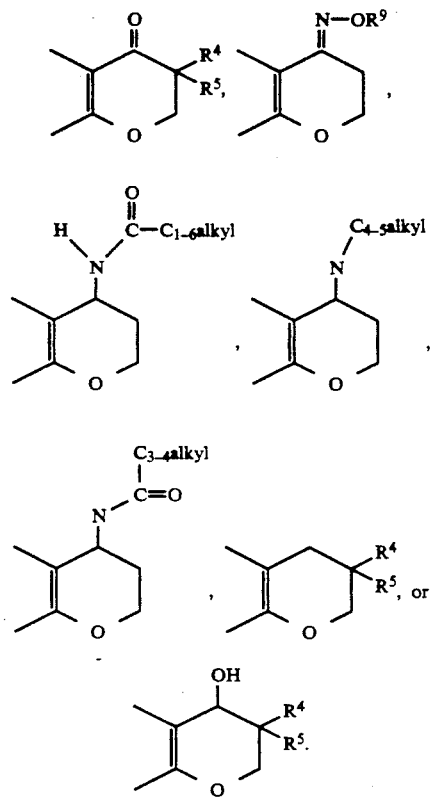

It is most preferred that the cyclic moiety comprising X, Y and Z is:

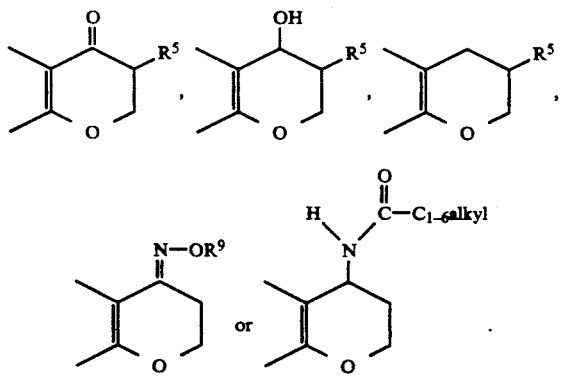

Preferred compounds include:
3,4-dihydro-1'-[(6-cyano-1,2,3,4-tetrahydronaphthalene)-2-yl]-6-methanesulfonyl-spiro[(2H)-1-benzopyran-2,4'-piperidine]-4-one;
3,4-dihydro-1'-[(6-cyano-1,2,3,4-tetrahydronaphthalene)-2-yl]-6-methanesulfonamido-spiro[(2H)-1-benzopyran-2,4'-piperidine]-4-ol;
3,4-dihydro-1'-[(6-cyano-1,2,3,4-tetrahydronaphthalene)-2-yl]-6-methanesulfonamido-spiro[(2H)-1-benzopyran-2,4'-piperidine];
1-[(5,6,7,8-tetrahydro-2-naphthalenecarbonitrile)-6-yl]-7',8'-dihydro-8'-oxo-spiro[piperidine-4,6'(1'H)pyrano[2,3-f]benzimidazole];
1-[(5,6,7,8-tetrahydro-2-naphthalenecarbonitrile)-6-yl]-2',3',7',8'-tetrahydro-2',8'-dioxo-spiro[piperidine-4,6'(1'H)-pyrano[2,3-f]benzimidazole];
3,4-dihydro-1'-[2-(benzofurazan-5-yl)ethyl]-6-methanesulfonamido-spiro[(2H)-1-benzopyran-2,4'-piperidine]-4-ol;
3,4-dihydro-3-methyl-6-methanesulfonamido-1'-[2-(benzofurazan-5-yl)ethyl]spiro[(2H)-1-benzopyran-2,4'-piperidine]-4-ol;
3,4-dihydro-1'-[2-(4-cyanophenyl)ethyl]-6-methanesulfonamido-3-methyl-spiro[(2H)-1-benzopyran-2,4'-piperidine]-4-one;
6-methanesulfonamido-1'-hexyl-4-hydroxy-3,4-dihydrospiro[(2H)-1-benzopyran-2,4'-piperidine];
3,4-dihydro-3-methyl-6-methanesulfonamido-1'-[2-(benzofurazan-5-yl)ethyl]spiro[(2H)-1-benzopyran-2,4'-piperidine]-4-one;
methanesulfonamide, N-[1'-(6-cyano-1,2,3,4-tetrahydro-2-naphthalenyl)-3,4-dihydro-4-oxospiro[2H-1-benzopyran-2,4'-piperidin]-6-yl]-;
cis or trans-3,4-dihydro-1'-[(6-cyano-1,2,3,4-tetrahydro-1-hydroxy-naphthalene)-2-yl]-6-methanesulfonamido-spiro[(2H)-1-benzopyran-2,4'-piperidine]-4-one;
4-acetamido-3,4-dihydro-1'-[(6-cyano-1,2,3,4-tetrahydronaphthalene)-2-yl]-6-methanesulfonamido-spiro[(2H)-1-benzopyran-2,4'-piperidine];
4-amino-3,4-dihydro-1'-[(6-cyano-1,2,3,4-tetrahydronaphthalene)-2-yl]-6-methanesulfonamido-spiro-[(2H)-1-benzopyran-2,4'-piperidine];
3,4-dihydro-1'-[(6-cyano-1,2,3,4-tetrahydronaphthalene)-2-yl]-6-methanesulfonyl-spiro[(2H)-1-benzopyran-2,4'-piperidine]-4-ol;
3,4-dihydro-1'-[(6-cyano-1,2,3,4tetrahydronaphthalene)-2-yl]-6-methanesulfonyl-spiro[(2H)-1-benzopyran-2,4'-piperidine];
1-[2-(4-cyanophenyl)ethyl]-7',8'-dihydro-8'-oxospiro[piperidine-4,6'(1'H)-pyrano[2,3-f]benzimidazole];
1-[2-(4-cyanophenyl)ethyl]-2',3',7',8'-tetrahydro-2',8'-dioxo-spiro[piperidine-4,6'(1'H)-pyrano[2,3-f]benzimidazole;
3,4-dihydro-1'-[2-(4-cyanophenyl)ethyl]-6-methanesulfonyl-spiro[(2H)-1-benzopyran-2,4'-piperidine]-4-one;
3,4-dihydro-1'-hexyl-6-methanesulfonamido-spiro[(2H)-1-benzopyran-2,4'-piperidine];
3,4-dihydro-1'-hexyl-6-methanesulfonamido-spiro[(2H)-1-benzopyran-2,4'-piperidine]-4-one;
1-hexyl-2',3',7',8'-tetrahydro-2',8'-dioxospiro[piperidine-4,6'(1H)-pyrano[2,3-f]benzimidazole];
3,4-dihydro-1'-[2-(benzofurazan-5-yl)ethyl]-6-methanesulfonamido-spiro[2H)-1-benzopyran-2,4'-piperidine]-4-one;
3,4-dihydro-1'-[2-(benzofurazan-5-yl)ethyl]-6-methanesulfonamido-spiro[(2H)-1-benzopyran-2,4'-piperidine];
7',8'-dihydro-1-hexyl-8'-oxospiro[piperidine-4,6'-(1H)-pyrano[2,3-f]benzimidazole];
3,4-dihydro-1'-(7-hydroxyheptyl)-6-methanesulfonamidospiro[(2H)-1-benzopyran-2,4'-piperidine]-4-one;

3,4-dihydro-1'-(6-hydroxyhexyl)-6-methanesul-
fonamidospiro[(2H)-1-benzopyran-2,4'-piperidine]-
4-one; or 3,4-dihydro-1'-heptyl-6-methanesulfonamido-
spiro[(2H)-1-benzopyran-2,4'-piperidine]-4-one;

3,4-dihydro-1'-[2-(4-acetylphenyl)ethyl]-6-methanesul-
fonamido-spiro[(2H)-1-benzopyran-2,4'-piperidine]-
4-one;

3,4-dihydro-1'-hexyl-6-methanesulfonyl-spiro[(2H)-1-
benzopyran-2,4'-piperidine]-4-one;

1-[(5,6,7,8-tetrahydro-2-naphthalenecarbonitrile)-6-yl]-
7',8'-dihydro-8'-hydroxy-spiro[piperidine-4,6'(1'H)-
pyrano[2,3-f]benzimidazole];

1-[(5,6,7,8-tetrahydro-2-naphthalenecarbonitrile)-6-yl]-
2',3',7',8'-tetrahydro-8'-hydroxy-2'-oxo-spiro[piperi-
dine-4,6'(1'H)-pyrano[2,3-f]benzimidazole];

1-[(5,6,7,8-tetrahydro-2-naphthalenecarbonitrile)-6-yl]-
7',8'-dihydro-spiro[piperidine-4,6'(1'H)pyrano[2,3-
f]benzimidazole];

3,4-dihydro-1'-(6-hydroxyhexyl)-6-methylsulfonyl-
spiro[(2H)-1-benzopyran-2,4'-piperidine];

1-[(5,6,7,8-tetrahydro-2-naphthalenecarbonitrile)-6-yl]-
2',3',7',8'-tetrahydro-2'-oxo-spiro[piperidine-
4,6'(1'H)-pyrano[2,3-f]benzimidazole];

4-acetamido-3,4-dihydro-1'-[(6-cyano-1,2,3,4-tetrahy-
dronaphthalene)-2-yl]-6-methanesulfonyl-spiro[(2H)-
1-benzopyran-2,4'-piperidine];

cis or trans-3,4-dihydro-1'-[(6-cyano-1,2,3,4-tetrahydro-
1-hydroxy-naphthalene)-2-yl]-6-methanesulfonyl-
spiro[(2H)-1-benzopyran-2,4'-piperidine];

3,4-dihydro-1'-[(6-cyano-1,2,3,4-tetrahydronaph-
thalene)-2-yl]-6-methanesulfonamido-3-methyl-
spiro[(2H)-1-benzopyran-2,4'-piperidine]-4-one;

3,4-dihydro-1'-[(6-cyano-1,2,3,4-tetrahydronaph-
thalene)-2-yl]-6-methanesulfonyl-3-methyl-
spiro[(2H)-1-benzopyran-2,4'-piperidine]-4-one;

cis or trans-3,4-dihydro-1'-[(6-cyano-1,2,3,4-tetrahydro-
1-hydroxy-naphthalene)-2-yl]-6-methanesul-
fonamido-spiro[(2H)-1-benzopyran-2,4'-piperidine];

and pharmaceutically acceptable salts thereof.

The term "alkyl", if the number of carbons is unspeci-
fied, means $C_{1-6}$alkyl and "alkyl" of three or more car-
bon atoms includes straight chain, branched chain and
cycloalkyl.

Also included within the scope of the present inven-
tion are the non-toxic pharmaceutically acceptable salts
of the novel compounds. Acid addition salts are formed
by mixing a solution of the compound with a solution of
a pharmaceutically acceptable non-toxic acid such as
hydrochloric acid, fumaric acid, maleic acid, succinic
acid, acetic acid, citric acid, tartaric acid, phosphoric
acid, or the like. Also included within the scope of this
invention are N-oxides. Furthermore, included within
the scope of this invention are $C_{1-6}$alkyl, $C_{1-6}$alkyl-phe-
nyl, and $C_{3-6}$alkenyl-phenyl quaternary ammonium
salts.

Also included within the scope of this invention are
diastereomers and enantiomers of the novel compounds
and mixtures thereof. In particular if the two bridging
groups joining the spiro carbon with the nitrogen of B
are not identical, such as in a spiro-3-piperidine, chiral-
ity is introduced and the racemate and both enantiomers
thereof are embraced within the scope of this invention.

Nomenclature utilized herein is intended to unambig-
uously identify specific chemical entities. However,
there may be more than one way to refer to a particular
compound. For example, the compound:

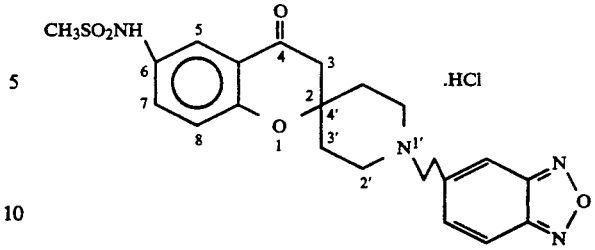

may be named as:
3,4-dihydro-1'-[2-(benzofurazan-5-yl)-ethyl]-6-
methanesulfonamido-spiro[(2H)-1-benzopyran-2,4'-
piperidine]-4-one hydrochloride and also named as:
N-[1'-[2-(5-benzofuranzanyl)ethyl]-3,4-dihydro-4-oxo-
spiro[2H-1-benzopyran-2,4'-piperidin]-6-yl]me-
thanesulfonamide, monohydrochloride.

Both methods of nomenclature have been utilized
herein.

The novel processes of this invention can be exempli-
fied by the following Reaction Schemes:

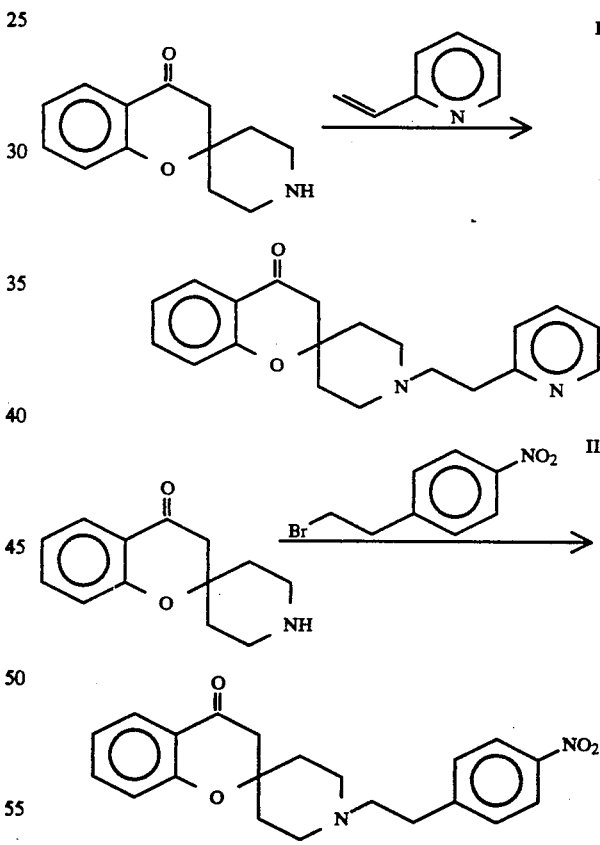

The process of Scheme I comprises addition of the
piperidine across the vinyl group by heating a mixture
of 1 part of the piperidine compound with about 1-2
parts of the vinyl compound in an aqueous lower alka-
nol such as methanol or ethanol in the presence of 1-2
parts of sodium or potassium acetate for about 2-20
hours at about reflux temperature.

Reaction Scheme II comprises N-alkylation of the
piperidine with a slight excess of the phenalkyl alkylat-
ing agent. Although the leaving group exemplified is
bromo, equivalent leaving groups are chloro, mesyl, tosyl, or the like. The two reagents are stirred at about 15° C. to about reflux temperature in a suitable solvent, preferably one in which the reagents are soluble such as a lower alkanol, such as acetonitrile, methanol, ethanol or propanol in the presence of an acid scavenger such as sodium or potassium bicarbonate or carbonate, an organic amine or an appropriate ion exchange resin for about 10 to 40 hours.

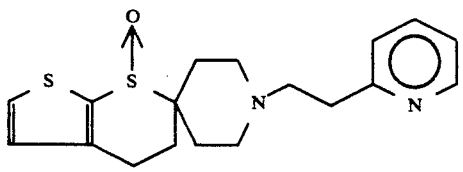

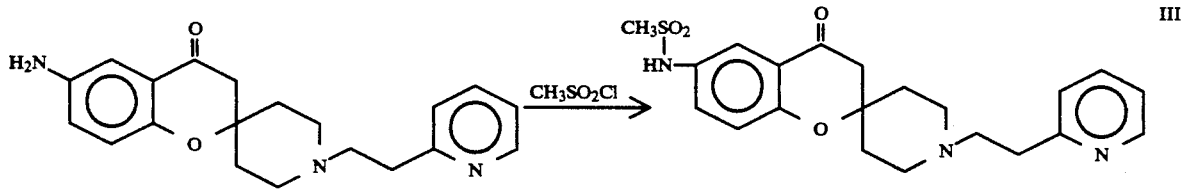

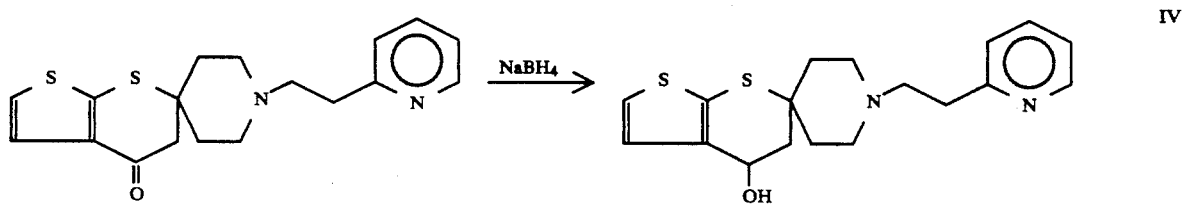

Reaction Scheme III depicts alterations of substituents such as sulfonylation with an alkanesulfonyl chloride by standard procedures.

Reaction Scheme IV is reduction of a dihydrothiopyranone carbonyl with a complex metal hydride such as sodium borohydride in methanol, lithium aluminum hydride in THF or di-isobutylaluminum hydride in THF at about room temperature.

Reaction Scheme V demonstrates dehydration to provide compounds unsaturated in the 3,4-position and proceeds at about room temperature in an ethereal solvent such as THF over a period of about 10 to 20 hours under the influence of dilute strong acid.

Reaction Scheme VI shows preparation of sulfoxides which proceeds readily with sodium metaperiodate in aqueous solution at about room temperature over a period of about 2 to 10 hours.

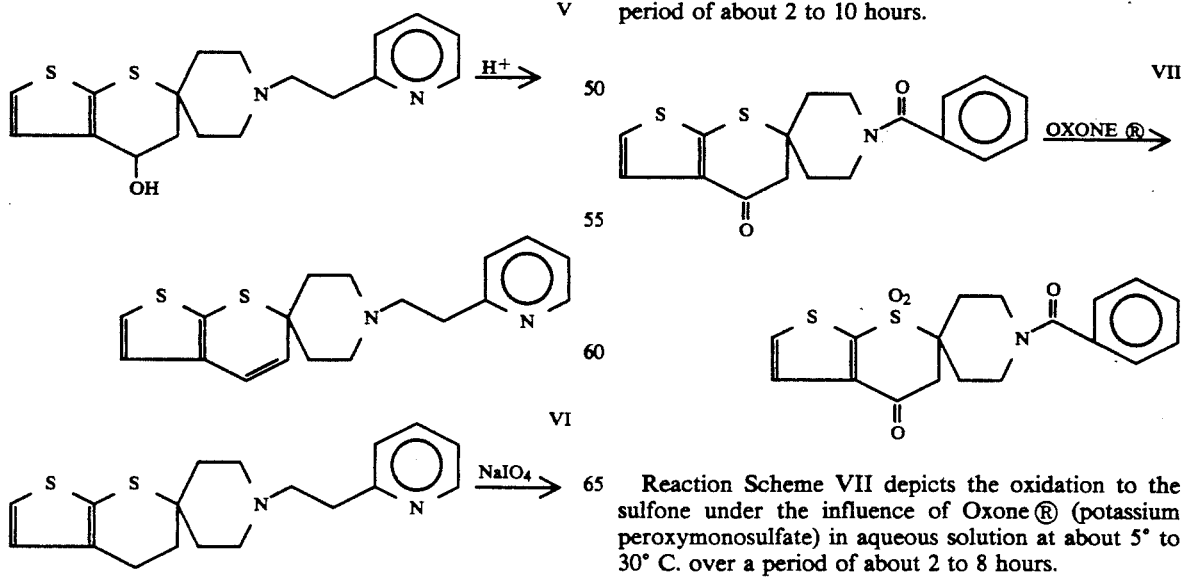

Reaction Scheme VII depicts the oxidation to the sulfone under the influence of Oxone ® (potassium peroxymonosulfate) in aqueous solution at about 5° to 30° C. over a period of about 2 to 8 hours.

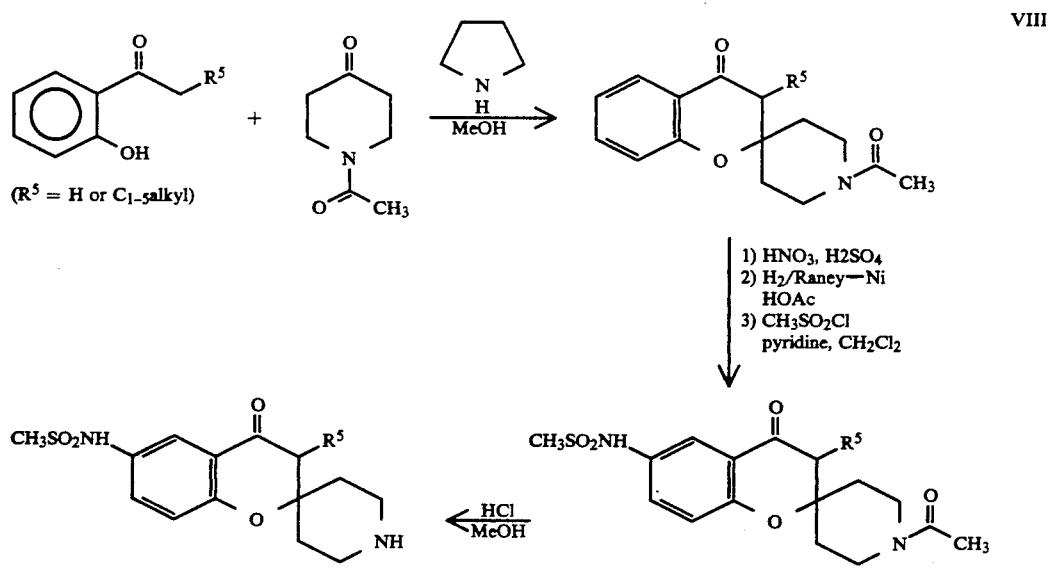

Reaction Scheme VIII illustrates the preparation of compounds bearing a substituent on the benopyranone by condensation of an ortho-hydroxyacetophenone with 1-acetyl-4-piperidone in the presence of pyrrolidine in methanol at or near solvent reflux temperature for a period of about 1 to 14 days. Reaction Scheme VIII further illustrates the incorporation of substituents on the aromatic rings. Nitration with nitric acid, catalytic reduction of the nitro group with hydrogen and Raney-Nickel catalyst in acetic acid (or by standard procedures) gives the amine which may be sulfonylated with an alkansulfonyl chloride by standard procedures. The acetamide may be cleaved by treatment with hydrochloric acid in methanol at or near solvent reflux temperature for about 2 to 10 hours. The 4-piperidinyl compound so obtained may be utilized for the process of Reaction Scheme I or II.

As shown in Reaction Scheme IX 2-oxoindolines may be sequentially alkylated with (2-bromoethyl)-N-carbethoxyethanamine as a solution in N,N-dimethyl formamide in the presence of sodium hydride. The resultant 1-ethoxycarbonyl-piperidinyl compound is reacted under the procedures of Reaction Scheme VIII followed by the procedures of Reaction Scheme I or II.

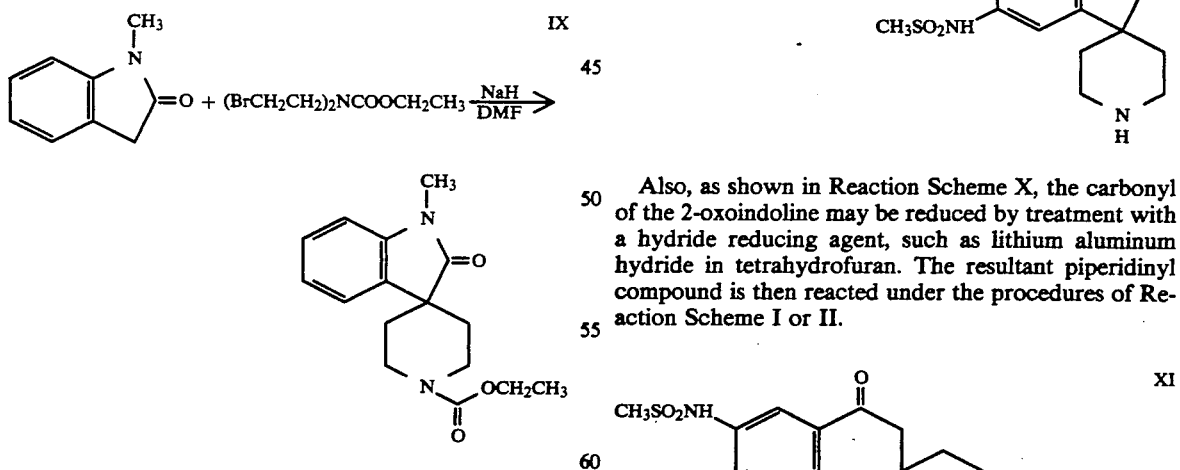

Also, as shown in Reaction Scheme X, the carbonyl of the 2-oxoindoline may be reduced by treatment with a hydride reducing agent, such as lithium aluminum hydride in tetrahydrofuran. The resultant piperidinyl compound is then reacted under the procedures of Reaction Scheme I or II.

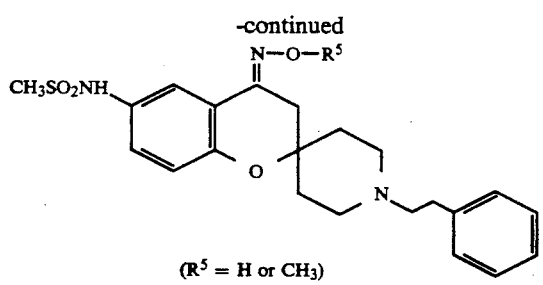

(R⁵ = H or CH₃)

Reaction Scheme XI illustrates the preparation of oximes of the ketone on the benzopyranone ring. Treatment of the ketone with hydroxylamine hydrochloride or methylamine hydrochloride in N,N-dimethylformamide in the presence of pyridine gives the corresponding hydroxylimine, or methoxylimine, respectively.

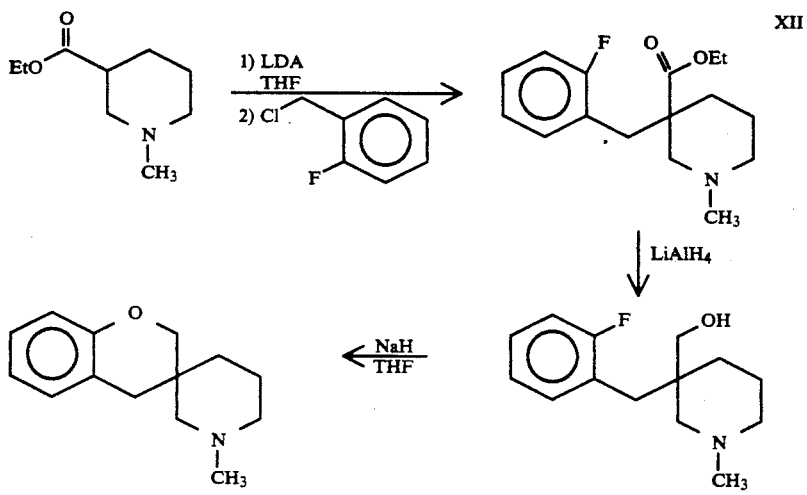

Reaction Scheme XII depicts the preparation of N-substituted dihydrospirobenzopyran-3,3'-piperidine starting from an appropriately N-substituted ethyl nipecotate. Formation of the enolate by treatment with a strong non-nucleophilic base, such as lithium diisopropylamide or lithium bis(trimethylsilyl)amide is followed by alkylation with a 2-fluorobenzyl halide. The ester is reduced with a hydride reducing agent, such as lithium aluminum hydride and the resultant alcohol is cyclized by treatment with sodium hydride to give the dihydrospirobenzopyran-3,3'-piperidine.

The novel compounds of the present invention, have the pharmacological properties required for the antiarrhythmic agents of Class III, namely the prolongation of the myocardial action potential in vitro, without a significant depression of the Vmax, and the prolongation of QTc-interval in anesthetized dogs.

In addition those compounds wherein $R^3$ represents hydrogen, when M is $Ar^2$ and $Ar^2$ is phenyl, $Ar^1$ is benzo and $R^1$ and $R^2$ are independently hydrogen, hydroxyalkyl or alkoxy also have the pharmacological properties required for the antiarrhythmic agents of Class III. Moreover, the members of both groups of compounds in general are much more potent than the reference drug, sotalol.

These compounds are effective in treating and preventing all types of arrhythmias including ventricular and atrail (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The following examples are given for the purpose of illustrating the present invention and shall not be construed as being limitations on the scope or spirit of the instant invention.

EXAMPLE 1

2'-Nitro-1-(2-(2-pyridyl)ethyl)-spiro(piperidine-4,6'-(6'H)thieno[2,3-b]thiopyran)-4'(5'H)-one Step A: Preparation of N-Benzoyl-4-carboxymethyl-4-(2-thienothio)piperidine A solution of 21.2 g (182 mmol) of 2-mercaptothiophene and 40 g (163 mmoles) of N-benzoyl-4-(carboxymethylidene)piperidine in THF (400 ml) was treated with 8.4 g (11.6 mL, 83 mmole) of triethylamine and heated to reflux for 5 hours. The reaction mixture was concentrated to dryness and partitioned between ethyl acetate and 0.5N HCl. The aqueous phase was then extracted with the ethyl acetate and the combined organics were dried over MgSO₄, filtered and concentrated in vacuo. The residue was crystallized from ethyl acetate to give 55 g (93%) of the product, mp=185°–187° C.

'H NMR (CDCl₃) δ7.4 (d, 1H), 7.38 (s, 5H), 7.25 (m, 1H), 7.05 (m, 1H), 4.45 (m, 1H), 3.6 (m, 3H), 2.6 (s, 2H), 1.8 (m, 4H).

| Elemental analysis for $C_{18}H_{19}NO_3S_2$: | | | |
|---|---|---|---|
| | N | C | H |
| Calculated: | 3.87 | 59.80 | 5.29 |
| Found: | 3.84 | 60.07 | 5.17 |

Step B: Preparation of 1-(Benzoyl)-spiro(piperidine-4,6'(6H)thieno[2,3-b]thiopyran)-4'(5'H)-one A stirring suspension of 42 g (110 mmoles) of N-benzoyl-4-(acetic acid)-4-(2-mercaptothiophene) in 800 mL CH₂Cl₂ at 10° C. was treated with 2 mL dimethylformamide and then 16.6 g (127 mmole) of oxalyl chloride. The resulting solution was then treated with 52.2 g (348 mmol) of trifluormethanesulfonic acid and warmed slowly to room temperature. The reaction became heterogeneous and was diluted with 700 ml CH₂Cl₂ to facilitate stirring. The reaction was stirred for 3 hours at room temperature and then poured into 2 l H₂O. The layers were separated and the aqueous phase was extracted with ethyl acetate. The combined organics were dried over MgSO₄, filtered and concentrated in vacuo. The residue was crystallized from ethyl acetate to obtain 38.4 g product. mp=145°-147° C.

'H NMR (CDCl₃) δ7.45 (d, 1H), 7.40 (s, 5H), 7.05 (d, 1H), 4.6-4.4 (m, 1H), 3.7-3.65 (m, 1H), 3.5-3.25 (m, 2H), 2.9-2.8 (m, 2H), 2.3-1.6 (m, 4H).

Step C: Preparation of 2'-Nitro-1-benzoyl)spiro(-piperidine-4,6'-(6H)thieno[2,3-b]thiopyran)-4'(5'H)-one A solution of 1 g (3 mmol) of 1-benzoylspiro(piperidine-4,6'(6H)thieno[2,3-b]thiopyran)-4'(5'H)-one in 10 ml of methylene chloride at 0° C. was treated with 612 mg of acetic anhydride and then 380 mg of nitric acid (spg=1.5). The reaction was stirred at room temperature for 9 hours and then poured into 150 ml H₂O. The phases were separated and the aqueous phase was extracted with ethyl acetate. The combined organics were dried over MgSO₄, filtered and concentrated in vacuo. The residue was chromatographed on silica gel (ethyl acetate/hexane) to give 760 mg of the product.

'H NMR (CDCl₃) δ8.18 (s, 1H), 7.5-7.38 (m, 5H), 4.3-4.15 (m, 1H), 3.60-3.45 (m, 1H), 3.38-3.15 (m, 3H), 3.09 (s, 2H), 2.2-1.8 (m, 4H).

Step D: Preparation of 2'-Nitrospiro(piperidine-4,6'-(6H)thieno[2,3-b]thiopyran)-4'(5'H)-one hydrochloride A suspension of 1.1 g (2.9 mmol) of 2'-nitro-1-(benzoyl)spiro(piperidine-4,6'-(6H)thieno[2,3-b]thiopyran)-4'(5'H)-one in 25 mL methanol was treated with 25 ml of 6N HCl and heated to reflux for 3 days. The reaction was cooled to ambient temperature and the solid collected and dried in vacuo, to give 680 mg (73%) of the product, mp=262° C.

'H NMR (CDCl₃) δ9.29-9.0 (m, 2H), 8.05 (s, 1H), 3.20-3.00 (m, 2H), 3.00-2.85 (m, 4H), 2.12-1.91 (m, 4H).

| Elemental analysis for $C_{11}H_{12}N_2O_3S_2 \cdot HCl \cdot 0.5H_2O$ | | | |
|---|---|---|---|
| | N | C | H |
| Calculated: | 8.49 | 40.05 | 4.27 |
| Found: | 8.40 | 39.80 | 3.92 |

Step E: Preparation of 2'-Nitro-1-(2-(2-pyridyl)ethyl)-spiro(piperdine-4,6'-(6H)thieno[2,3-b]thiopyran)-4'(5'H)-one A solution containing 660 mg (2.05 mmol) of 2'-Nitro-spiro(piperidine-4,6'-(6H)thieno[2,3-b]thiopyran)-4'(5'H)-one dihydropyran, 430 mg (4.1 mmol) of 2-vinylpyridine and 557 mg (4.1 mmol) of sodium acetate trihydrate in 10 ml of 1:1 methanol/water was heated at reflux for 4 hours. The reaction was cooled to room temperature and a solid separated. The solid was collected and dissolved in methanol and treated with excess ethanolic HCl. The dihydro chloride separated and was collected and dried over night in vacuo to give 482 mg of the product.

mp=189°-192° C.

'H NMR (DMSO) δ11.6 (br s, 1H), 8.78 (d, 1H), 8.36 (t, 1H), 8.10 (s, 1H), 7.83 (d, 1H), 7.75 (appt, 1H), 3.7-3.4 (m, 6H), 3.4-3.2 (m, 2H), 3.19 (brs, 2H), 2.4-2.3 (m, 4H).

| Elemental analysis for $C_{18}H_{19}N_3O_3S_2 \cdot 2HCl \cdot 1\frac{1}{4}H_2O$ | | | |
|---|---|---|---|
| | N | C | H |
| Calculated: | 8.66 | 44.58 | 4.88 |
| Found: | 8.68 | 44.63 | 4.65 |

EXAMPLE 2

1-(2-(2-pyridyl)ethyl)spiro(piperidine-4,6'(6H)-thieno[2,3-b]thiopyran)-4'(5'H)-one dihydrochloride Step A: Preparation of Spiro(piperidine-4,6'-(6H)-thieno[2,3-b]thiopyran)-4'(5'H)-one hydrochloride A solution of 14 g (40.99 mmol) of 1-benzoylspiro(-piperidine-4,6'-(6H)thieno[2,3-b]thiopyran)-4'-(5'H)-one in 150 ml of ethanol was treated with 50 ml of 6 N HCl and heated at reflux for 2 days. The reaction was cooled to room temperature and the solid collected by filtration. The solid was dried overnight in vacuo to give 9.03 g of the product. mp=280° C.

'H NMR (DMSO) δ9.4-9.0 (m, 2H), 7.47 (d, J=5 Hz, 1H), 7.38 (d, J=5 Hz, 1H), 3.27-3.17 (m, 2H), 3.10-2.95 (m, 2H), 2.96 (s, 2H), 2.17-2.00 (m, 4H).

| Elementary analysis for $C_{11}H_{13}NOS_2 \cdot HCl \cdot H_2O$ | | | |
|---|---|---|---|
| | N | C | H |
| Calculated: | 4.76 | 44.96 | 5.48 |
| Found: | 4.77 | 45.17 | 5.45 |

Step B: Preparation of 1-(2-(2-pyridyl)ethyl)-spiropiperidine-4,6'(6H)thieno[2,3-b]thiopyran)-4'(5'H)-one dihydrochloride Employing the procedures substantially as described in Example 1, Step E but starting with the product of Example 2, Step A, there was obtained the title compound with m.p. 213°-215° C.

'H NMR (DMSO) δ11.5 (br s, 1H), 8.77 (d, J=5 Hz, 1H), 8.30 (appt, J=8 Hz, 1H), 7.83 (d, J=8 Hz, 1H), 7.75 (appt, J=6 Hz, 1H), 7.50 (d, J=3 Hz, 1H), 7.40 (d, J=3 Hz, 1H), 3.6-3.4 (m, 6H), 3.4-3.2 (m, 2H), 3.0 (brs, 2H), 2.4-2.2 (m, 4H).

| Elemental analysis for $C_{18}H_{20}N_2OS_2 \cdot 2HCl \cdot 1\frac{1}{4}H_2O$ | | | |
|---|---|---|---|
| | N | C | H |
| Calculated: | 6.64 | 51.23 | 5.37 |
| Found: | 6.61 | 51.37 | 5.22 |

EXAMPLE 3

1-(2-(2-Pyridyl)ethyl)spiro(piperidine-4,6'(6H)-thieno[2,3-b]thiopyran)-4'(5'H)-one-7',7'-dioxide Step A: Preparation of 1-Benzoyl-spiro(piperidine-4,6'-(6H)thieno[2,3-b]thiopyran)-4'(5H)-one-7'7'-dioxide A solution of 4 g (11.7 mmole) of 1-benzoylspiro(-piperidine-4,6'-(6H)-thieno[2,3-b]thiopyran)-4'-(5H)-one in 50 ml THF at 10° C. was treated with a solution of OXONE ® in $H_2O$ (10.82 g, 17.6 mmole in 50 mL $H_2O$) and warmed slowly to room temperature. After 4 hours at room temperature the reaction mixture was poured into 200 ml of saturated $NaHCO_3$ and extracted with ethyl acetate. The combined organics were dried over anhydrous $MgSO_4$, filtered and concentrated in vacuo. Chromatography of the residue on silica gel (1:1 ethyl acetate/hexane) gave 2.2 g of product, mp=170°-172° C.

'H NMR ($CDCl_3$) δ7.60 (d, J=5 Hz, 1H), 7.50 (d, J=5 Hz, 1H), 7.41 (m, 5H), 4.45–4.2 (m, 1H), 4.10–3.80 (m, 1H), 3.6–3.35 (m, 2H), 3.34 (s, 2H), 2.50–2.20 (m, 2H), 2.01–1.65 (m, 2H).

Step B: Preparation of Spiro(piperidine-4,6'-(6H)-thieno[2,3-b]thiopyran)4-(5'H)-one-7,7-dioxide Employing the procedure substantially as described in Example 1, Step D but starting with the product of Step A of this Example there was produced the title compound, m.p. 110° C.

'H NMR (DMSO) δ9.4 (m, 1H), 9.0 (m, 1H), 8.18 (d, J=5 Hz, 1H), 7.55 (d, J=5 Hz, 1H), 3.70–3.6 (m, 2H), 3.55 (s, 2H), 3.4–3.0 (m, 4H), 2.4–2.25 (m, 2H), 2.09–1.95 (m, 2H).

Step C: Preparation of 1-(2-(2-pyridyl)ethyl)spiro(-piperidine-4,6'(6H)thieno[2,3-b]thiopyran)-4'(5')-one-7',7'dioxide Employing the procedures substantially as described in Example 1, Step E but starting with the product of Step B of this Example there is produced the title compound, m.p. 148°–150° C.

'H NMR ($CDCl_3$) δ8.55 (m, 1H), 7.6 (m, 1H), 7.58 (d, J=5 Hz, 1H), 7.48 (d, J=5 Hz, 1H), 7.1 (m, 2H), 3.35 (s, 2H), 3.05–2.80 (m, 6H), 2.50–2.30 (m, 4H), 1.90–1.78 (m, 2H).

| Elemental analysis for $C_{18}H_{20}N_2O_3S_2$ | | | |
|---|---|---|---|
| | N | C | H |
| Calculated: | 7.44 | 57.42 | 5.35 |
| Found: | 7.46 | 57.70 | 5.44 |

EXAMPLE 4

2'-Nitro-1-(2-(6-Methyl-2-pyridyl)ethyl)-spiropiperidine-4,6'-(6H)thieno[2,3-b]thiopyran)-4'(5'H)-one- Dihydrochloride Employing the procedure substantially as described in Example 1, Step E but starting with 2-methyl-6-vinylpyridine instead of 2-vinylpyridine, there was produced the title compound, with m.p. 115°–117° C.

'H NMR (DMSO) δ11.9 (brs, 1H), 8.30 (m, 1H), 8.20 (s, 1H), 7.70 (m, 1H), 3.7–3.4 (m, 6H), 3.4–3.2 (m, 2H), 3.18 (s, 2H), 2.4–2.3 (m, 4H).

| Elementary analysis for $C_{19}H_{21}N_3O_3S.2HCl.\frac{1}{2}H_2O$ | | | |
|---|---|---|---|
| | N | C | H |
| Calculated: | 8.57 | 46.57 | 5.03 |
| Found: | 8.22 | 46.57 | 5.05 |

EXAMPLE 5

1-(2-(6-Methyl-2-pyridyl)ethyl)spiro-piperidine-4,6'-(6H)thieno[2,3-b]thiopyran-4'(5'H)-one Dihydrochloride Employing the procedure substantially as described in Example 2, Step B but employing 2-methyl-6-vinylpyridine instead of 2-vinylpyridine, there was produced the title compound, with
m.p. 219°–222° C.

'H NMR (DMSO) δ11.6 (br s, 1H), 8.3 (m, 1H), 7.7 (m, 2H), 7.5 (d, J=3 Hz, 1H), 7.38 (d, J=3 Hz, 1H), 3.6–3.4 (m, 6H), 3.4–3.2 (m, 2H), 3.0 (br s, 2H) 2.70 (s, 3H), 2.38–2.2 (m, 4H).

| Elemental analysis for $C_{19}H_{22}N_2OS_2.2HCl$ | | | |
|---|---|---|---|
| | N | C | H |
| Calculated: | 6.49 | 52.89 | 5.60 |
| Found: | 6.43 | 52.84 | 5.51 |

EXAMPLE 6

2'-Methanesulfonamido-1-(2-(6-Methyl-2-pyridyl)ethyl)spiro-piperidine-4,6'(6H)thieno[2,3-b]thiopyran-4'(5'H)-one A suspension of 1.02 g (2.14 mmol) of 2'-nitro-1-(2-(6-Methyl-2-pyridyl)ethyl)spiropiperidine-4,6'(6H)thieno[2,3-b]thiopyran-4'-one in 20 ml of concentrated HCl was treated with 760 mg (6.4 mmole) of tin powder and heated on a steam bath for 15 minutes. The reaction mixture was diluted with $H_2O$ and the pH adjusted to approximately pH 9 with 2N NaOH and saturated sodium bicarbonate solution. The aqueous phase was then extracted with ethyl acetate. The organics were dried over $MgSO_4$, filtered and concentrated in vacuo. The crude material was dissolved in $CH_2Cl_2$, and excess triethylamine and methanesulfonyl chloride were added. After about 1 hour, the reaction was poured into saturated bicarbonate and extracted with ethyl acetate. The combined ethyl acetate layers were dried over $MgSO_4$, filtered and concentrated in vacuo to give 380 mg of bis sulfonamide after chromatography (5% $CH_3OH/CHCl_3$). This material was dissolved in methanol and treated with 1 ml of 1 N NaOH, concentrated in vacuo and partitioned between saturated sodium bicarbonate and methylene chloride. The layers were separated and the aqueous phase was extracted repeatedly with methylene chloride. The combined organics were dried over $MgSO_4$, filtered and concentrated in vacuo. Chromatography of the residue on silica gel (5% $CH_3OH/CHCl_3$) gave 220 mg of the product which was crystallized from HCl/ethanol/methanol to obtain 165 mg of the dihydrochloride.
m.p. 204°–206° C.

'H NMR (DMSO) δ11.4 (br s, 1H), 10.58 (br s, 1H), 8.25 (m, 1H), 7.65 (m, 2H), 6.95 (s, 1H), 3.85–3.60 (m, 6H), 3.6–3.4 (m, 2H), 3.03 (s, 3H) 3.02–2.9 (m, 2H), 2.7 (s, 3H), 2.35–2.19 (m, 4H).

| Elemental analysis for $C_{20}H_{25}N_3O_3S_3 \cdot 2HCl \cdot \frac{1}{2}H_2O$ | | | |
|---|---|---|---|
| | N | C | H |
| Calculated: | 7.87 | 45.02 | 5.28 |
| Found: | 7.85 | 45.08 | 5.11 |

EXAMPLE 7

4'-Hydroxy-1-(2-(2-pyridyl)ethyl)spiro(-piperidine4,6'(6H)-thieno[2,3-b]thiopyran)

A solution of 1.6 g (4.6 mmole) of 1-(2-(2-pyridyl)ethyl)spiro(piperidine-4,6'-(6H)thieno[2,3-b]thiopyran-4'(5'H)-one) in 25 mL ethanol was treated with excess sodium borohydride at room temperature. After stirring for 1 hour the reaction mixture was poured into 100 ml of saturated sodium bicarbonate solution and extracted with ethyl acetate. The combined organics were dried over MgSO$_4$, filtered and concentrated in vacuo. The material was crystallized from ethyl acetate to give 745 mg, of product, m.p. 154°–155° C.

$^1$H NMR (CDCl$_3$) δ8.5 (m, 1H), 7.6 (m, 1H), 7.25–7.00 (m, 4H), 4.9 (m, 1H), 3.04–2.95 (m, 2H), 2.85–2.70 (m, 4H), 2.6–1.75 (m, 8H).

| Elemental analysis for $C_{18}H_{22}N_2OS_2$ | | | |
|---|---|---|---|
| | N | C | H |
| Calculated: | 8.08 | 62.38 | 6.46 |
| Found: | 8.01 | 62.16 | 6.39 |

EXAMPLE 8

4'-Hydroxy-1-(2-(2-pyridyl)ethyl)spiro(piperidine-4,6'(6H)thieno[2,3-b]thiopyran-(5'H)-7',7'-dioxidehydrochloride Using the procedure substantially as described in Example 7 but starting with the 4'-oxo-7',7'-dioxide from Example 3, Step C there was produced the title compound, with m.p. 275° C.

$^1$H NMR (DMSO) δ11.4–11.2 (m, 1H), 8.78 (m, 1H), 8.35 (m, 1H), 8.0 (d, J=5 Hz, 1H), 7.85 (d, 1H), 7.25 (d, J=5 Hz, 1H), 7.79 (m, 1H), 4.88 (m, 1H), 3.70–3.2 (m, 8H), 2.85–2.7 (m, 1H), 2.60–2.35 (m, 3H), 2.25–2.00 (m, 2H).

| Elemental analysis for $C_{18}H_{22}N_2O_3S_2 \cdot HCl$ | | | |
|---|---|---|---|
| | N | C | H |
| Calculated: | 6.20 | 47.88 | 5.35 |
| Found: | 6.12 | 47.52 | 5.41 |

EXAMPLE 9

1-(2-(2-pyridyl)ethyl)spiro(piperidine-4,6'-thieno[2,3-b]thiopyran)

A solution of 600 mg (1.73 mmole) of 4'(5'H)-hydroxy-1-(2-(2-pyridyl)ethyl)spiro(piperidine 4,6'(6H)thieno[2,3-b]thiopyran in 5 mL THF was treated with 1 ml of 2N HCl and stirred at room temperature for 15 hours and then heated gently overnight. The reaction was cooled to room temperature poured into saturated sodium bicarbonate and extracted with ethylacetate. The organic phases were dried over MgSO$_4$, filtered and concentrated in vacuo. Chromatography on silica gel eluting with 3% CH$_3$OH/CHCl$_3$ gave 88 mg of the product as a free base.

$^1$H NMR (CDCl$_3$) δ8.5 (appd, J=5 Hz, 1H), 7.60 (m, 1H), 7.19 (d, J=8 Hz, 1H), 7.15 (m, 1H), 7.0 (d, J=5 Hz, 1H), 6.88 (d, J=5 Hz, 1H), 6.47 (d, J=10 Hz, 1H), 5.56 (d, J=10 Hz, 1H), 3.0 (m, 2H), 2.8 (m, 2H), 2.7–2.55 (m, 4H), 2.10–1.80 (m, 4H).

The material was crystallized from ethanol as the di HCl salt, m.p. 198°–200° C.

| Elemental analysis for $C_{18}H_{20}N_2S_2 \cdot 2HCl$ | | | |
|---|---|---|---|
| | N | C | H |
| Calculated: | 6.98 | 53.85 | 5.52 |
| Found: | 7.02 | 54.07 | 5.59 |

EXAMPLE 10

1-(2-(2-Pyridyl)ethyl)spiro(piperidine-4,6'-(5'H,6'H)thieno[2,3-b]thiopyran) dihydrochloride A solution of 800 mg (3.27 mmoles) of 1-(2-(2-pyridyl)ethyl)spiro(piperidine-4,6'(6H,)thieno[2,3-b]thiopyran)-4'(5'H)-one in 10 ml THF at room temperature was treated with 1 ml of 10M BH$_3$.DMS (10 mmole) and heated to reflux for 12 hours. The reaction was cooled to room temperature and treated carefully with 2 ml of 6N HCl and reheated to reflux for 2 hours. The reaction was then cooled to room temperature and poured into 100 ml H$_2$O. The pH was then adjusted to 9 with 1N NaOH and saturated sodium bicarbonate. This was extracted with ethylacetate. The combined organics were dried over anhydrous MgSO$_4$, filtered and concentrated in vacuo. The hydrochloride was generated in ethanol and recrystallized from ethanol/ether to give 241 mg of product m.p. 200°–202° C.

$^1$H NMR (d$_6$ DMSO) δ11.6–11.45 (m, 1H), 8.79 (m, 1H), 8.35 (m, 1H), 7.9 (appd, J=9 Hz, 1H), 7.80 (m, 1H), 7.35 (d, J=5 Hz, 1H), 6.90 (d, J=5 Hz, 1H), 3.7–3.4 (m, 8H), 3.4–3.1 (m, 2H), 2.8 (m, 2H), 2.4–2.0 (m, 4H).

| Elemental analysis for $C_{18}H_{22}N_2S_2 \cdot 2HCl$ | | | |
|---|---|---|---|
| | N | C | H |
| Calculated: | 6.94 | 53.58 | 5.99 |
| Found: | 6.94 | 53.41 | 6.02 |

EXAMPLE 11

1-(2-(2-Pyridyl)ethyl)spiro(piperidine-4,6'(5'H)(6'H)thieno[2,3-b]thiopyran-7'-oxide A solution of 700 mg (2.11 mmoles) of 1-(2-(2-pyridyl)ethyl)spiro(piperidine-4,6'(5'H)(6'H)-thieno[2,3-b]thiopyran in methanol (35 mL) was treated with 700 mg (3.27 mmole) of sodium metaperiodate in 35 ml H$_2$O. The reaction was stirred for 5 hours and then poured into water and extracted with ethyl acetate and methylene chloride. The organic layers were combined, dried over anhydrous magnesium sulfate (MgSO$_4$), filtered and concentrated in vacuo. The residue was chromatographed on silica gel eluting with 3% CH$_3$OH/CHCl$_3$ to give 495 mg of the product as a free base. The dihydrochloride was generated in ethanol and recrystallized from isopropanol/ethyl acetate to give 175 mg of product m.p. 150° C. (dec).

$^1$H NMR (d$_6$ DMSO) δ11.4 (m, 1H), 8.78 (appd, J=6 Hz, 1H), 8.35 (m, 1H), 7.98 (d, J=5 Hz, 1H), 7.85 (appd, J=9 Hz, 1H), 7.75 (m, 1H), 7.15 (d, J=5 Hz, 1H), 3.8-3.2 (m, 10 Hz), 3.05-2.70 (m, 2H), 2.50-2.20 (m, 2H), 2.20-1.80 (m, 2H).

Elemental analysis for $C_{18}H_{22}N_2OS_2 \cdot 2HCl \cdot 1\frac{1}{4}H_2O$

|  | N | C | H |
|---|---|---|---|
| Calculated: | 6.34 | 48.91 | 6.04 |
| Found: | 6.28 | 48.96 | 6.10 |

EXAMPLE 12

1-(p-Nitrobenzyl)spiro(piperidine-4,6'(6H)thieno-[2,3-b]thiopyran)-4'(5'H)-one hydrochloride A suspension of 1 g (3.62 mmoles) of spiro (piperidine-4,6'-6H-thieno[2,3-b]thiopyran-4'(5'H)-one, 780 mg (3.62 mmoles) of p-nitrobenzyl bromide and 0.5 g of sodium bicarbonate in methanol (20 ml) was stirred at room temperature for 24 hours. The reaction mixture was poured into 100 ml $H_2O$ and extracted with methylene chloride. The organic layers were dried over $MgSO_4$, filtered and concentrated in vacuo. The hydrochloride salt was generated in ethanol and crystallized from $C_2H_5OH/CH_3OH$ to give product with m.p. 238° C.

Elemental analysis for $C_{18}H_{18}N_2O_3S_2 \cdot HCl$

|  | N | C | H |
|---|---|---|---|
| Calculated: | 6.81 | 52.60 | 4.66 |
| Found: | 6.83 | 52.49 | 4.59 |

Employing the procedure substantially as described in Example 12, but substituting for the p-nitrobenzyl bromide used therein the appropriate alkyl or aryl bromide there were produced the N-substituted spiropiperidines described in Table I.

TABLE I

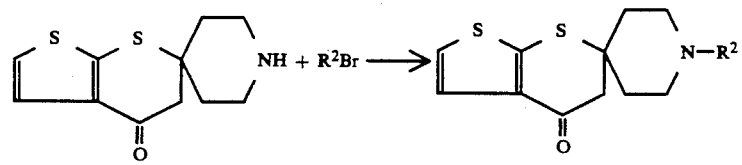

| Example | R² | mp (°C.) | Analysis (Calc'd / Found) C | H | N |
|---|---|---|---|---|---|
| 13 | —CH₂CH₂-C₆H₄-NO₂ (HCl·0.5H₂O) | 248 | 52.58 / 52.51 | 5.11 / 5.38 | 6.45 / 6.16 |
| 14 | —CH₂-C₆H₄-NO₂ (meta) | 139-140 | 57.73 / 58.00 | 4.84 / 4.81 | 7.48 / 7.48 |
| 15 | —CH₂CH₂C(O)-C₆H₄-NHSO₂CH₃ ·HCl | 269-271 | 49.31 / 49.49 | 4.75 / 4.66 | 5.75 / 5.54 |
| 16 | —CH₂-pyridyl ·HCl | 243-245 | 54.45 / 54.21 | 4.85 / 4.85 | 7.93 / 7.68 |
| 17 | —CH₂-pyridyl ·2HCl | 250-255 | 50.61 / 50.88 | 4.99 / 5.13 | 6.94 / 6.88 |
| 18 | —CH₂CH₂-pyridyl ·2HCl | 278-280 | 50.61 / 50.46 | 4.99 / 4.80 | 6.94 / 6.97 |
| 19 | —CH₂CH₂-pyridyl ·2HCl·½H₂O·½IPA | 235-238 | 50.44 / 50.36 | 5.36 / 5.29 | 6.62 / 6.38 |

TABLE I-continued

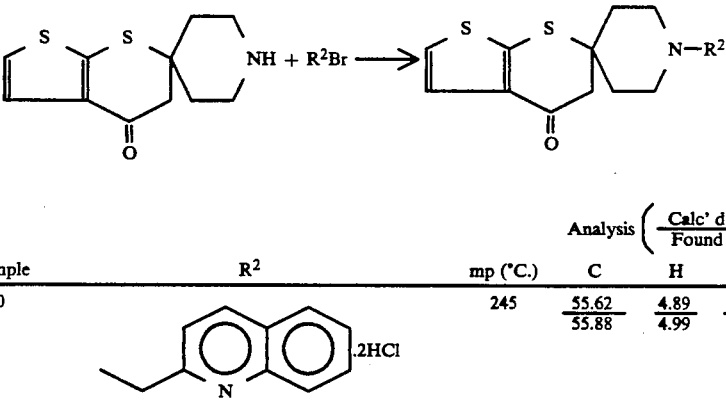

| Example | R² | mp (°C.) | Analysis (Calc'd / Found) C | H | N |
|---|---|---|---|---|---|
| 20 | ethyl-quinoline .2HCl | 245 | 55.62 / 55.88 | 4.89 / 4.99 | 6.17 / 6.21 |
| 21 | -C₆H₄-NO₂ | 208–210 | 56.64 / 56.77 | 4.47 / 4.49 | 7.77 / 7.77 |
| 22 | propylphenyl .HCl | >275 | 60.05 / 60.09 | 5.83 / 5.88 | 3.68 / 3.65 |
| 23 | butylphenyl N.2HCl.0.5H₂O | 180–184 | 52.85 / 52.80 | 5.99 / 6.05 | 6.16 / 6.12 |
| 24 | butylphenyl .HCl | 210 | 60.96 / 60.69 | 6.13 / 6.05 | 3.55 / 3.49 |

EXAMPLE 25

1-(2-(4-Aminophenyl)ethyl)spiro(piperidine-4,6'-(6H)-thieno[2,3-b]thiopyran)-4'(5'H)-one dihydrochloride hemihydrate A solution of 1.1 g (2.8 mmoles) of 1-(2-(p-nitrophenyl)ethyl)spiro(piperidine-4,6'-(6H)-thieno-[2,3-b]thiopyran)-4'(5'H)-one in 15 mL acetic acid and 20 mL H₂O was treated with 15 mL of a solution of 15% TiCl₃ in 20% HCl. The dark purple reaction mixture was stirred at room temperature for 45 minutes and poured into 200 mL water. The pH was adjusted to 9 with 2N NaOH and saturated sodium bicarbonate. The aqueous mixture was extracted several times with ethyl acetate. The combined organics were dried over anhydrous MgSO₄, filtered and concentrated in vacuo to give 955 mg. A small amount was treated with excess ethanolic HCl and the hydrochloride was crystallized from ethanol to give 55 mg of product, m.p. 240° C.

| Elemental analysis for C₁₉H₂₂N₂OS₂.2HCl.½H₂O | | | |
|---|---|---|---|
| | N | C | H |
| Calculated: | 6.36 | 51.81 | 5.72 |
| Found: | 6.35 | 51.95 | 5.43 |

Employing the procedure of Example 25 and the appropriate starting materials there are prepared the compounds of Examples 26 and 27

EXAMPLE 26

1-(m-Aminobenzyl)spiro(piperidine-4,6'-(6H)-thieno[2,3-b]thiopyran-4'(5'H)-one m.p. 128°–129° C.

| Elemental analysis for C₁₈H₂₀N₂OS₂.0.1H₂O | | | |
|---|---|---|---|
| | N | C | H |
| Calculated: | 8.09 | 62.42 | 5.85 |
| Found: | 8.04 | 62.41 | 5.83 |

EXAMPLE 27

1-(4-Aminophenyl)spiro(piperidine-4,6'-thieno[2,3-b]thiopyran)-4'(5'H)-one m.p. 163°–164° C.

| Elemental analysis for C₁₇H₁₈N₂OS₂ | | | |
|---|---|---|---|
| | N | C | H |
| Calculated: | 8.47 | 61.78 | 5.49 |
| Found: | 8.39 | 61.60 | 5.49 |

EXAMPLE 28

1-(2-(4-Methanesulfonamidophenyl)ethyl)spiro(piperidine-4,6'(6H)-thieno[2,3-b]thiopyran)-4(5'H)-one A solution of 850 mg (2.37 mmoles) of 1-(2-(4-aminophenyl)ethyl)spiro(piperidine-4,6'-thieno[2,3-b]thiopyran)-4,40 5(H)-one in 10 ml methylene chloride was treated with 500 μl pyridine and 220 ml 2.85 mmole) of methanesulfonyl chloride at room temperature. The reaction was stirred at room temperature for ½ hour and then poured into 200 ml saturated sodium bicarbonate solution. The aqueous mixture was extracted several times with ethyl acetate. The organics were dried over MgSO$_4$, filtered and concentrated in vacuo. The residue was chromatographed on silica gel eluting with 3% CH$_3$OH/CHCl$_3$ to give 690 mg. The free base was crystallized from CH$_3$OH to give 605 mg of product, m.p. 173°–174° C.

| Elemental analysis for C$_{20}$H$_{24}$N$_2$O$_3$S$_3$.CH$_3$OH | | | |
|---|---|---|---|
| | N | C | H |
| Calculated: | 5.97 | 53.81 | 6.02 |
| Found: | 5.95 | 54.03 | 6.08 |

Following the procedure described in Example 28 and using the appropriate starting materials there were produced the products of Examples 29 and 30.

EXAMPLE 29

1-(4-Methanesulfonamidophenyl)methyl)spiro(piperidine-4,6'-(6H)-thieno[2,3-b]thiopyran)-4'(5'H)-one hydrochloride m.p. 270° C.

| Elemental analysis for C$_{19}$H$_{22}$N$_2$O$_3$S$_3$.HCl | | | |
|---|---|---|---|
| | N | C | H |
| Calculated: | 6.10 | 49.71 | 5.05 |
| Found: | 6.18 | 49.95 | 5.04 |

EXAMPLE 30

1-(4-Methanesulfonamidophenyl)spiro(piperidine-4,6'-thieno[2,3-b]thiopyran)-4'(5'H)-one m.p. 158°–159° C.

| Elemental analysis for C$_{18}$H$_{20}$N$_2$O$_3$S$_3$.½H$_2$O | | | |
|---|---|---|---|
| | N | C | H |
| Calculated: | 6.78 | 52.33 | 5.00 |
| Found: | 6.92 | 52.52 | 4.90 |

EXAMPLE 31

1,3-Dihydro-1-oxo-1'-[2-(2-pyridyl)-1-ethyl]spiro[2H-indene-2,4'-piperidine]

Step A: Preparation of ethyl-1-benzoyl-4-(phenylmethyl)-4-piperidinecarboxylate

To a solution of 7.84 g (30.0 mmoles) ethyl 1-benzoyl-4-piperidinecarboxylate (G. R. Clemo and E. Hoggarth, *J. Chem. Soc.*, 41, (1941) in 60 ml dry tetrahydrofuran at −78° C. under argon was added dropwise over 10 minutes 33.0 ml (33.0 mmoles) lithium bis(trimethylsilyl)amide in tetrahydrofuran and the resulting solution was stirred 30 minutes. To this solution was added dropwise over 2 minutes 5.64 g (33.0 mmoles) benzyl bromide in 10 ml dry tetrahydrofuran and the resulting solution was stirred overnight while warming from −78° C. to room temperature. The reaction was quenched with 20 ml saturated ammonium chloride solution and extracted with 2×100 ml ethyl acetate. The combined extracts were washed with 20 ml water and brine, dried, and the solvent removed in vacuo to give an oil. The oil was stirred under 25 ml hexane at −15° C., the hexane was decanted and the oil was dried in vacuo to give 12.5 g crude product as a viscous oil;

'H NMR (deuteriochloroform): δ1.20 (t, 3H), 1.40 (m, 1H), 1.60 (m, 1H), 2.07 (m, 1H), 2.22 (m, 1H), 2.85 (d, 2H), 3.08 (m, 1H), 3.65 (m, 1H), 4.12 (q, 2H), 4.65 (m, 1H), 7.04 (m, 2H), 7.24 (m, 3H), 7.38 (m, 5H).

Step B: Preparation of 1-Benzoyl-4-(phenylmethyl)-4-piperidinecarboxylic acid

To 10.7 g (26 mmoles) crude ethyl 1-benzoyl-4-(phenylmethyl)-4-piperidinecarboxylate was added a solution of 14.6 g (130 mmoles) potassium tert-butoxide in 130 ml dimethyl sulfoxide. The resulting purple solution was stirred 2 hours to give a dark orange solution. The solution was poured into 500 ml rapidly stirred ice-water and acidified with 12 ml concentrated hydrochloric acid. The resulting white precipitate was filtered off, washed with 3×20 ml cold water, then dissolved in 200 ml ether. The ether solution was washed with 3×20 ml water, and brine, dried, and the solvent was removed in vacuo to give a pale yellow foam. The product was recrystallized from ether to give 6.63 g (75%) product, m.p. 183°–189° C.

'H NMR (deuteriochloroform): δ1.40 (m, 1H), 1.60 (m, 1H), 2.03 (m, 1H), 2.22 (m, 1H), 2.89 (d, 2H), 2.90 (m, 1H), 3.15 (m, 1H), 4.67 (m, 1H), 4.57 (m, 1H), 7.09 (m, 2H), 7.24 (m, 3H), 7.38 (m, 5H).

Step C: 1'-Benzoyl-1,3-dihydro-1-oxospiro-[2H-indene-2,4'-piperidine]

A solution of 6.14 g (19.0 mmoles) 1-benzoyl-4-(phenylmethyl)-4-piperidinecarboxylic acid in 61 ml concentrated sulfuric acid was stirred 18 hours at room temperature to give a deep red solution. The solution was carefully diluted with ice-bath cooling with 300 ml H$_2$O and extracted with 3×300 ml ethyl acetate. The extract was washed with 25 ml water and brine, dried, and the solvent was removed in vacuo to give a white foam. The foam was stirred under ether and filtered off to give 3.61 g (62%) product, m.p. 149°–154° C.

'H NMR (deuteriochloroform): δ1.50 (m, 2H), 2.00 (m, 2H), 3.12 (m, 2H), 3.25 (d of d of d, 2H), 3.90 (d, 1H), 4.62 (m, 1H), 7.43 (m, 7H), 7.63 (d of d, 1H), 7.79 (d, 1H).

Step D: Preparation of 1,3-Dihydro-1-oxospiro[2H-indene-2,4'-piperidine]

A solution of 3.66 g (12.0 mmoles) 1'-benzoyl-1,3-dihydro-1-oxospiro-[2H-indene-2,4'-piperidine] in 90 ml ethanol and 30 ml 6N hydrochloric acid was heated at reflux for 42 hours. An additional 10 ml 6N hydrochloric acid was added and the solution was heated at reflux for 6 hours. The cooled solution was concentrated in vacuo to remove ethanol and the resulting aqueous solution was washed with 2×20 ml ethyl acetate. The aqueous layer was made basic with 10N sodium hydroxide and extracted with 3×75 ml ethyl acetate. The extract was washed with 20 ml water and brine, dried, and the solvent was removed in vacuo to give 1.87 g (77%) product as an oil.

'H NMR (deuteriochloroform): δ1.35 (d of d, 2H), 1.62 (broad s, 1H), 1.88 (d of d of d, 2H), 2.81 (d of d of d, 2H), 3.10 (s, 2H), 3.17 (m, 2H), 7.38 (t, 1H), 7.46 (d, 1H), 7.60 (t, 1H), 7.77 (d, 1H).

Step E: Preparation of 1,3-Dihydro-1-oxo-1-[2-(2-pyridyl)-1-ethyl]spiro[2H-indene-2,4'-piperidine]

A solution of 1.01 g (5 mmoles) 1,3-dihydro-1-oxospiro[2H-indene-2,4'-piperidine] and 1.58 g (15 mmoles) 2-vinylpyridine in 10 ml methanol was heated at reflux for 18 hours. The solvent was removed in vacuo and the residue was purified by flash chromatography on silica gel eluting with 5:95 methanol/chloroform. The material obtained was crystallized from 5:1 ether/hexane to give 0.80 g (52%) product, m.p. 71°–72.5° C.

Anal. Calc'd. for $C_{20}H_{22}N_2O$: C, 78.40; H, 7.24; N, 9.14. Found: C, 78.58; H, 7.37; N, 9.14.

EXAMPLE 32

1,3-Dihydro-1-hydroxy-1'-[2-(2-pyridyl)-1-ethyl]-spiro[2H-indene-2,4'piperidine]

To a solution of 0.306 g (1.0 mmole) 1,3-dihydro-1-oxo-1'-[2-(2-pyridyl)-1-ethyl]-spiro[2H-indene-2,4'-piperidine] in 2 ml ethanol was added 0.035 g (1.0 mmole) sodium borohydride. The mixture was stirred under argon for 30 minutes, another 0.035 g (1.0 mmole) sodium borohydride was added, and the mixture was stirred 1 hour. The reaction was quenched with 10 ml saturated ammonium chloride solution, diluted with 3 ml water, and extracted with 3×20 ml methylene chloride. The combined extracts were washed with 5 ml water and brine, dried, and the solvent was removed in vacuo to give 0.32 g crude product as a gum. This was purified by flash chromatography on silica gel eluting with 5:95 methanol:chloroform. The material obtained was crystallized from ether to give 0.215 g (69%) product, m.p. 108°–113° C.

Anal. Calc'd. for $C_{20}H_{24}N_2O.0.35\ H_2O$: C, 76.32; H, 7.91; N, 8.90. Found: C, 76.42; H, 7.94; N, 8.81.

EXAMPLE 33

1,3-dihydro-1-oxo-1'-[2-(4-nitrophenyl)-1-ethyl]-spiro[2H-indene-2,4'-piperidine]

A mixture of 0.60 g (3.0 mmoles) 1,3-dihydro-1-oxospiro[2H-indene-2,4'-piperidine], 0.71 g (3.1 mmoles) 4-nitrophenethyl bromide, and 0.28 g (3.3 mmoles) sodium bicarbonate in 3 ml ethanol was heated at reflux for 6 hours. The solvent was removed in vacuo and the residue was partitioned between 20 ml ethyl acetate and 5 ml dilute bicarbonate solution. The layers were separated and the aqueous layer was extracted with 20 ml ethyl acetate. The combined extract was washed wth 5 ml water and brine, dried, and the solvent was removed in vacuo to give 1.08 g crude product as a gum. This was purified by flash chromatography on silica gel eluting with methanol:chloroform (2:98). The material obtained was crystallized from 1:10 methylene chloride: ether to give 0.61 g (58%) product, m.p. 187°–188° C.

Anal. Calc'd. for $C_{21}H_{22}N_2O_3.0.30\ H_2O$: C, 70.89; H, 6.40; N, 7.87. Found: C, 70.90; H, 6.25; N, 7.82.

EXAMPLE 34

1,3-Dihydro-1-hydroxy-1'-[2-(4-nitrophenyl)-1-ethyl]-spiro[2H-indene-2,4'-piperidine]

To a suspension of 0.21 g (0.60 mmole) 1,3-dihydro-1-oxo-1'-[2-(4-nitrophenyl)-1-ethyl]-spiro[2H-indene-2,4'-piperidine] in 4 ml ethanol under argon added in 4 equal portions at 30 minute intervals 0.080 g (2.4 mmoles) sodium borohydride. After the final addition 3 ml dimethyl formamide was added and the mixture was stirred 30 minutes. The reaction was quenched with 5 ml saturated ammonium chloride solution, diluted with 3 ml water. Ethanol was removed in vacuo and the aqueous mixture was extracted with 2×15 ml methylene chloride. The combined extracts were washed with brine, dried, and the solvent was removed in vacuo to give the crude product. This was purified by flash chromatography on silica gel eluting with methanol:chloroform (10:90). The material obtained was crystallized from methylene chloride:ether (1:10) to give 0.053 g (25%) product, m.p. 134°–137° C.

Anal. Calc'd. for $C_{21}H_{24}N_2O_3.0.10(C_2H_5)_2O.0.10\ CH_2Cl_2$: C, 70.10; H, 6.90; N, 7.61. Found: C, 70.16; H, 6.72; N, 7.76.

EXAMPLE 35

1,3-Dihydro-1'-{2-[4-(methanesulfonamido)phenyl]-1-ethyl}-1-oxospiro[2H-indene-2,4'-piperidine]

A mixture of 0.60 g (3.0 mmoles)1,3-dihydro-1-oxospiro[2H-indene-2,4'-piperidine], 0.28 g (3.3 mmoles) sodium bicarbonate, and 0.91 g (3.1 mmoles) 2-[4-methanesulfonamido)phenyl]ethylmethanesulfonate in 4 ml ethanol was heated at reflux for 2.5 hours. The solvent was removed in vacuo and the residue was partitioned between 25 ml ethyl acetate and 10 ml dilute sodium bicarbonate solution. The layers were separated and the aqueous layer was extracted with 2×25 ml chloroform. The combined extract was washed with 5 ml $H_2O$ and brine, dried, and the solvent was removed in vacuo to give 1.00 g (83%) crude product as a gum. This was purified by flash chromatography on silica gel eluting with methanol:chloroform (5:95) to give 0.39 g (28%) product as a gum.

To a solution of 0.17 g (0.42 mmoles) product in 1 ml ethanol was added 0.07 ml (0.42 mmoles) of 6N HCl in ethanol. The resulting white precipitate was filtered off to give 0.12 g (66%) hydrochloride salt, m.p. 246°–249° C.

Anal. Calc'd. for $C_{22}H_{26}N_2O_3S.HCl$: C, 60.75; H, 6.26; N, 6.44. Found: C, 60.42; H, 6.45; N, 6.37.

EXAMPLE 36

1,3-Dihyro-6-nitro-1-oxo-1'-[2-(2-pyridyl)-1-ethyl]-spiro[2H-indene-2,4'-piperidine]

Step A: Preparation of 1'-acetyl-1,3-dihydro-6-nitro-1-oxospiro[2H-indene-2,4'-piperidine]

Step 1

To a solution of 1.13 g (5.6 mmoles) 1,3-dihydro-1-oxospiro[2H-indene-2,4'-piperidine] in 15 ml methylene chloride cooled to 0° C. was added 1.23 g (12.0 mmoles) acetic anhydride. The solution was stirred at 0° for 1 hour and the solvent was removed in vacuo to give crude 1'-acetylspiro[2H-indene-2,4'-piperidine]-1(3H)-one.

Step 2

To a solution of the crude acetyl derivative in 17 ml concentrated sulfuric acid cooled to 0° was added 0.60 g of 90% nitric acid. The solution was stirred at 0° C. for 1 hour, at room temperature for 2 hours, then poured into 100 ml ice water. The mixture was extracted with 3×75 ml methylene chloride. The combined extract was washed with 20 ml $H_2O$ and brine, dried, and the solvent was removed in vacuo to give 1.54 g (96%) crude product as a foam. This was recrystallized from ethyl acetate to give 1.14 g (71%) product, m.p. 176°–179° C.

'H NMR (deuteriochloroform): δ2.47 (m, 1H), 2.92 (m, 3H), 2.14 (s, 3H), 3.10 (m, 3H), 3.30 (m, 1H), 3.92 (m, 1H), 4.50 (m, 1H), 7.41 (t, 1H), 7.47 (d, 1H), 7.63 (t, 1H), 7.78 (d, 1H).

Step B: Preparation of 1,3-Dihydro-6-nitro-1-oxo-spiro[2H-indene-2,4'-piperidine]hydrochloride A solution of 0.216 g (0.75 mmol) 1'-acetyl-1,3-dihydro-1-oxo-6-nitrospiro[2H-indene-2,4'-piperidine] and 2 ml (6 mmol) 3N hydrochloric acid in 6 ml ethanol was heated at reflux for 18 hours. Another 0.2 ml (0.6 mmol) 3N hydrochloric acid was added and the solution was heated at reflux for 4 hours, then cooled to room temperature to give a white precipitate. The precipitate was filtered off, washed with ethanol, and dried to give 0.158 g (74%) product.

'H NMR (DMSO-$d_6$): δ1.60 (d, 2H), 1.96 (m, 2H), 3.06 (m, 2H), 3.3 (m, 4H), 7.88 (d, 1H), 8.35 (d, 1H), 8.55 (d of d, 1H), 8.9 (broad s, 2H).

Step C: Preparation of 1,3-Dihydro-6-nitro-1-oxo-1'-[2-(2-pyridyl)-1-ethyl]spiro[2H-indene-2,4'-piperidine]

A solution of 0.150 g (0.53 mmole) 1,3-dihydro-6-nitro-1-oxospiro[2H-indene-2,4'-piperidine] hydrochloride, 0.116 g (1.1 mmoles) 2-vinylpyridine, and 0.090 g (1.1 mmoles) sodium acetate in 1.5 ml of 1:1 methanol: water was heated at reflux for 8 hours. Ethanol was removed in vacuo. The aqueous residue was diluted with 3 ml saturated sodium bicarbonate solution and extracted with 2×10 ml ethyl acetate. The combined extracts were washed with 3 ml water brine, dried, and the solvent was removed in vacuo to give 0.195 g crude product. This was recrystallized from ethyl acetate to give 0.123 g (66%) product, m.p. 142°-144° C.

Anal. Calc'd. for $C_{20}H_{21}N_3O_3$.0.25$H_2O$: C, 67.49; H, 6.09; N, 11.81. Found: C, 67.59; H, 6.13; N, 11.97.

EXAMPLE 37

1,3-Dihydro-6-methanesulfonamido-1-oxo-1'-[2-(2-pyridyl)-1-ethyl]spiro[2H-indene-2,4'-piperidine]

Step A: Preparation of 1'-acetyl-1,3-dihydro-6-methanesulfonamido-1-oxospiro[2H-indene-2,4'-piperidine]

Step 1

To a solution of 0.29 g (1.0 mmole) 1'-acetyl-1,3-dihydro-6-nitro-1-oxospiro[2H-indene-2,4'-piperidine] in 4 ml acetic acid was added 3.75 ml (4.3 mmoles) of 15% titanium (III) chloride solution in 20-30% aqueous hydrochloric acid dropwise and portionwise over 2 hours. The reaction mixture was made basic (pH 10) with saturated sodium bicarbonate solution and 10N sodium hydroxide solution, diluted with 50 ml water, and extracted with 3×50 ml ethyl acetate. The combined extracts were washed with 20 ml water and brine, dried, and the solvent was removed in vacuo to give 0.29 g crude 1'-acetyl-6-amino-1,3-dihydro-1-oxospiro[2H-indene-2,4'-piperidine].

Step 2

To a solution of 0.29 g crude 1'-acetyl-6-amino-1,3-dihydro-1-oxospiro[2H-indene-2,4'-piperidine] in 4 ml methylene chloride were added 0.16 g (2.0 mmoles) pyridine and 0.15 g (1.3 mmoles) methanesulfonyl chloride. The solution was stirred 1 hour, diluted with 10 ml methylene chloride and quenched with 5 ml saturated sodium bicarbonate solution. The layers were separated and the aqueous layer was extracted with 10 ml methylene chloride. The combined extracts were washed with 3 ml water and brine, dried and the solvent was removed in vacuo to give 0.35 g crude product. This was crystallized from 1:20 methylene chloride: ether to give 0.30 g (89%) product as a gummy solid.

'H NMR (deuteriochloroform): δ1.50 (m, 2H), 1.80 (m, 2H), 2.15 (s, 3H), 3.04 (s, 3H), 3.06 (m, 3H), 3.31 (m, 1H), 3.92 (m, 1H), 4.50 (m, 1H), 7.46 (d, 1H), 7.66 (m, 2H), 8.10 (s, 1H, —NH).

Step B: Preparation of 1,3-Dihydro-6-methanesulfonamido-1-oxospiro[2H-indene-2,4'-piperidine]

A solution of 1.29 g (3.3 mmoles) crude 1'-acetyl-1,3-dihydro-6-methanesulfonamido-1-oxospiro-[2H-indene-2,4'-piperidine]-1(3H)-one in 27 ml ethanol and 30 ml 3N hydrochloric acid was heated at reflux for 18 hours. An additional 1.5 ml 3N hydrochloric acid was added and the solution was heated at reflux for 4 hours. The cooled solution was concentrated in vacuo to remove ethanol and the resulting aqueous solution was washed with 2×10 ml ethyl acetate. The aqueous layer was made basic with 10N and 1N sodium hydroxide, then evaporated to dryness in vacuo. The solid residue was extracted with 3×50 ml of 1:99 methanol: methylene chloride. The extract was filtered and the solvent was removed in vacuo to give 0.50 g crude product as a foam. This was stirred under methylene chloride to give a solid which was filtered off to give 0.47 g (48.%) product, m.p. 236°-238° C.

'H NMR (DMSO-$d_6$): δ1.25 (d, 2H), 1.65 (m, 2H), 2.66 (d of d, 2H), 2.95 (m, 4H), 3.02 (s, 3H), 4.4-5.4 (broad s, 2H), 7.42 (s, 1H), 7.50 (m, 2H).

Step C: Preparation of 1,3-Dihydro-6-Methanesulfonamido-1-oxo-1'-[2-(2-pyridyl)-1-ethyl]-spiro[2H-indene-2,4'-piperidine]

A solution of 0.38 g (1.3 mmoles) 1,3-dihydro-6-methanesulfonamido-1-oxospiro[2H-indene-2,4'-piperidine], 0.41 g (3.9 mmoles) 2-vinylpyridine and 0.074 ml (0.078 g, 1,3 mmoles) acetic acid in 2.6 ml methanol was heated at reflux for 18 hours. The solvent was removed in vacuo and the residue was purified by flash chromatography on silica gel eluting with methanol:chloroform (5:95). The material obtained was crystallized from 1:20 methylene chloride: ether to give 0.37 g (71%) product, m.p. 209°-212° C.

Anal. Calc'd. for $C_{21}H_{27}N_3O_3S$.0.10$(C_5H_5)_2O$.0.75 $H_2O$: C, 61.19; H, 6.71; N, 9.82. Found: C, 61.25; H, 6.55; N, 9.87.

EXAMPLE 38

1,3-Dihydro-1-hydroxy-6-methanesulfonamido-1'-[2-(2-pyridyl)-1-ethyl)spiro[2H-indene-2,4'-piperidine]

To a solution of 0.120 g (0.30 mmol) 1,3-dihydro-6-methanesulfonamido-1-oxo-1'-[2-(2-pyridyl)-1-ethyl]-spiro[2H-indene-2,4'-piperidine] in 1 ml ethanol under argon was added 0.010 g (0.30 mmmol) sodium borohydride. Added at 30 minutes intervals were 0.010 g (0.30 mmol), 0.005 g (0.15 mmole), and 0.005 g (0.15 mol) portions of sodium borohydride. The reaction mixture was stirred 30 minutes, quenched with 3 ml saturated ammonium chloride solution, diluted with 1 ml water and extracted with 3×10 ml methylene chloride. The combined extracts were washed with 3 ml water and brine, dried, and the solvent was removed in vacuo to give 0.115 g (96%) crude product as an oil. This was crystallized from 1:20 methylene chloride: ether to give 0.096 g (80%) product, m.p. 178°-182° C.

Anal. Calc'd. for $C_{21}H_{27}N_3O_3S$.0.10$(C_2H_5)_2O$.0.50 $H_2O$: C, 61.49; H, 6.99; N, 10.05. Found: C, 61.66; H, 6.90; N, 10.11.

EXAMPLE 39

1,3-Dihydro-6-methanesulfonamido-1'-{2-[4-(methanesulfonamido)phenyl]-1-ethyl}-1-oxospiro[2H-indene-2,4'-piperidine Step 1

Reaction of a mixture of 0.206 g (0.70 mmole) 1,3-dihydro-6-methanesulfonamido-1-oxospiro-[2H-indene-2,4'-piperidine] 0.071 g (0.85 mmole) sodium bicarbonate and 0.173 g (0.75 mmole) 4-nitrophenethyl bromide in 1.5 ml ethanol was carried out by the procedure of Example 33 to give 0.145 g (47%) 1,3-dihydro-6-methanesulfonamido-1-[2-(4-nitrophenyl)-1-ethyl]-1-oxospiro[2H-indene-2,4'-piperidine] as a solid foam, m.p. 73°-77° C.

Step 2

Reduction of 0.142 g (0.32 mmole) of the above nitrocompound in 1.2 ml acetic acid with 1.29 ml (1.5 mmoles) of 15% titanium (III) chloride solution in 20-30% aqueous hydrochloric acid according to the procedure of Example 37, Step A, followed by evaporation of the aqueous layer, and extraction of the solid residue with 2:98 methanol: chloroform gave 0.27 g crude 1-[2-(4-aminophenyl)-1-ethyl]-1,3-dihydro-6-methanesulfonamido-1-oxospiro[2H-indene-2,4'-piperidine].

Step 3

Reaction of 0.27 g (approx. 0.32 mmole) of the above crude amino compound with 0.046 (0.40 mmole) methanesulfonyl chloride and 0.048 ml (0.047 g, 0.60 mmole) pyridine in 2 ml methylene chloride was carried out by the procedure of Example 37, Step A step 2 to give 0.043 g (27%) product as a gum. To a solution 0.043 g (0.087 mmole) product in 0.5 ml ethanol was added 0.015 ml (0.089 mmole) of 5.9N hydrogen chloride in ethanol. The mixture was stirred 30 minutes and the solvent was removed in vacuo. The residue was crystallized from 4:1 isopropanol: ether to give 0.027 g (59%) hydrochloride salt, m.p. 174°-180° C.

EXAMPLE 40

3,4-Dihydro-1-oxo-1'-[2-(2-pyridyl)-1-ethyl]spiro[naphthalene-2(1H), 4'-piperidine]

Step A: Preparation of Ethyl-3,4-dihydro-1-oxospiro-[naphthalene-2(1H), 4'-piperidine]-1'-carboxylate To a solution of 2.92 g (20.0 mmoles) 1-tetralone and 9.0 g (30.0 mmoles) ethyl bis(2-bromoethyl)carbamate (S. Huybuchts and G. J. Hoornaert, Synth. Commum., 11, 17 (1981) in 20 ml dry dimethylformamide heated to 50° C. under argon was added in portions 2.00 g (50.0 mmol) of 60% sodium hydride dispersion is mineral oil. The mixture was stirred 14 hours at 50° C. and the solvent was removed in vacuo. The residue was taken up in 50 ml ether, quenched with 5 ml saturated ammonium chloride solution, diluted with 10 ml water, and the layers were separated. The aqueous layer was extracted with 2×50 ml ether. The combined extracts were washed with 2×15 ml water and brine, dried, and the solvent was removed in vacuo to give 7.77 g crude product as an oil. This was purified by flash chromatography on silica gel eluting with ethyl acetate: hexane (30:70) to give 1.47 g (26%) product as an oil; ¹H NMR (deuteriochloroform): δ1.26 (t, 3H), 1.52 (m, 2H), 1.97 (m, 2H), 2.06 (t,2H), 3.01 (t, 3H), 3.59 (m, 4H), 4.14 (q, 2H), 7.24 (t, 1H), 7.31 (t, 1H), 7.97 (m, 1H), 8.01 (d, 1H).

Step B: Preparation of 3,4-Dihydro-1-oxospiro[naphthalene-2(1H),4'-piperidine]

A solution of 1.84 g (6.4 mmoles) ethyl 3,4-dihydro-1-oxospiro[naphthalene-2(1H), 4'piperidine] in 32 ml ethanol and 16 ml of 50% potassium hydroxide solution was heated at reflux for 18 hours. The solution was concentrated in vacuo to remove ethanol and the aqueous residue was extracted with 3×40 ml ether. The combined organic extracts were extracted with 2×40 ml 3N hydrochloric acid. The combined aqueous extracts were made basic with 10N sodium hydroxide and extracted with 3×75 ml ether. The combined organic extracts were washed with 20 ml water and brine, dried, and the solvent was removed in vacuo to give 1.07 g (78%) product as an oil;

¹H NMR (deuteriochloroform): δ1.52 (m, 2H), 1.81 (broad s, 1H), 1.96 (m, 2H), 2.10 (t, 2H), 2.90 (m, 2H), 3.00 (m, 4H), 7.22 (d, 1H), 7.30 (t, 1H), 7.46 (m, 1H), 8.01 (d, 1H).

Step C: Preparation of 3,4-Dihydro-1-oxo-1'-[2-(2-pyridyl)-1-ethyl]spiro[naphthalene-2(1H), 4'-piperidine]

A solution of 0.32 g (1.5 mmoles) 3,4-dihydro-1-oxospiro[naphthalene-2(1H), 4'-piperdine] 0.47 g (4.5 mmoles) 2-vinylpyridine, and 0.086 ml (0.090 g, 1.5 mmoles) acetic acid in 3 ml methanol was heated at reflux for 18 hours. The solvent was removed in vacuo and the residue was purified by flash chromatography. The material obtained was dissolved in 40 ml ethyl acetate. The solution was washed with 5 ml saturated sodium bicarbonate solution, water, and brine, dried, and the solvent was removed in vacuo to give 0.35 g (73%) product as an oil.

To a solution of 0.35 g (1.1 mmoles) product in 2 ml ethanol was added 0.37 ml (2.2 mmoles) of 6N hydrogen chloride in ethanol. The solution was diluted with 1 ml ether to give a precipitate which was filtered off to give 0.34 g (79%) dihydrochloride salt, m.p. 182°-184° C.

Anal. Calc'd. for $C_{21}H_{24}N_2O \cdot 2HCl \cdot 0.35\ H_2O$: C, 63.11; H, 6.73; N, 7.01. Found: C, 63.13; H, 6.66; N, 7.05.

EXAMPLE 41

3,4-Dihydro-1-hydroxy-1'-[2-(2-pyridyl)-1-ethyl]-spiro[naphthalene-2(1H),4'-piperidine]

To a solution of 0.098 (0.25 mmole) 3,4-dihydro-1-oxo-1'-[2-(2-pyridyl)-1-ethyl]spiro[naphthalene-2-(1H), 4'-piperidine] dihydrochloride salt in 1 ml ethanol was added 0.026 g (0.75 mmole) sodium ml ethanol was added 0.026 g (0.75 mmole) sodium borohydride. Added at 30 minutes intervals were 0.009 g (0.25 mmole) and 0.009 g (0.25 mmole) portions of sodium borohydride. The reaction mixture was stirred 30 minutes, quenched with 3 ml saturated ammonium chloride solution, diluted with 1 ml water, and extracted with 3×10 ml methylene chloride. The combined extracts were washed with 3 ml water and brine, dried, and the solvent was removed in vacuo to give 0.075 g (93%) crude product as an oil. This was purified by flash chromatography on silica gel eluting with 10:90 methanol:-chloroform to give 0.055 g (68%.) product as an oil.

To a solution of 0.051 g (0.16 mmole) product in 0.5 ml ethanol was added 0.054 ml (0.32 mmole) of 5.9N hydrogen chloride in ethanol. The solution was diluted with 1 ml ether to give a precipitate which was filtered off to give 0.056 g (89%.) dihydrochloride salt, m.p. 198°-199° C.

Anal. Calcd for $C_{21}H_{26}N_2O \cdot 2HCl \cdot 0.35H_2O$: C, 62.79; H, 7.20; N, 6.97. Found: C, 62.85; H, 7.16; N, 6.94.

EXAMPLE 42

3,4-Dihydro-7-methanesulfonamido-1-oxo-1'-[2-(2-pyridyl-1-ethyl]spiro[naphthalene-2(1H),4'-piperidine]

Step A: Preparation of 1'-acetyl-3,4-dihydro-7-nitro-1-oxospiro[napthalene-2(1H),4'-piperidine]

The title compound was prepared by the procedure of Example 36, Step A from 0.82 g (3.8 mmoles) 3,4-dihydro-1-oxospiro[naphthalene-2(1H),4'-piperidine] and 0.76 ml (0.82 g, 8.0 mmoles) acetic anhydride in 10 ml methylene chloride to give crude 1'-acetyl-3,4-dihydro-1-oxospiro[naphthalene-2-(1H),4'-piperidine]. This was nitrated with 0.35 g (4.1 mmoles) 90% nitric acid in 11.5 ml sulfuric acid to give 0.54 g (47%) product after ethyl acetate crystallization, mp 162°-166° C.

'H NMR (deuteriochloroform): δ1.55 (m, 2H), 1.95 (m, 1H), 2.12 (s, 3H), 2.13 (m, 1H), 3.13 (m, 2H), 3.45 (m, 2H), 3.60 (m, 1H), 3.71 (m, 2H), 3.92 (m, 1H), 7.44 (d, 1H), 8.31 (d of d, 1H), 8.85 (d, 1H).

Step B: Preparation of 1'-Acetyl-3,4-Dihydro-7-methanesulfonamido-1-oxospiro[naphthalene-2(1H),4'-piperidine]

Employing the procedure of Example 37, Step A part 1, 0.57 g (1.9 mmoles) 1'-acetyl-3,4-dihydro-7-nitro-1-oxospiro[naphthelene-2(1H),4'-piperidine] in 8 ml acetic acid was treated portionwise with 8.3 ml (9.6 mmoles) of 15% titanium (III) chloride solution in 20-30% aqueous hydrochloric acid to give 0.48 g (92%) crude 1'-acetyl-7-amino-3,4-dihydro-1-oxospiro[naphthalene-2(1H),4'-piperidine]. In part 2, 0.48 g (1.8 mmole) of the crude amino compound, 0.28 ml (0.28 g, 3.5 mmoles) pyridine, and 0.25 g (2.2 mmoles) methanesulfonyl chloride in 7 ml methylene chloride gave 0.55 g (90%) product as a gum.

'H NMR (dewteriochloroform): δ1.52 (m, 2H), 1.95 (m, 1H), 2.06 (m, 4H), 2.12 (s, 3H), 3.01 (m, 2H), 3.03 (S, 3H), 3.50 (m, 2H), 3.68 (m, 1H), 3.83 (m, 1H), 7.25 (d, 1H), 7.35 (broad S, 1H,-NH), 7.53 (d of d, 1H), 7.78 (d, 1H).

Step C: Preparation of 3,4-Dihydro-7-methanesulfonamido-1-oxospiro[napthalene-2(1H),4'-piperidine]-hydrochloride A solution of 0.53 g (1.5 mmoles) 1'-acetyl-3,4-dihydro-7-methanesulfonamido-1-oxospiro[naphthalene-2(1H),4'-piperidine] in 15 ml ethanol and 5 ml 3N hydrochloric acid was heated at reflux for 18 hours. An additional 10 ml 3N hydrochloric acid was added and the solution was heated at reflux for 5 hours, then cooled to room temperature. The solvents were removed in vacuo and the residue was stirred with 3 ml ethanol to give a solid which was filtered off and dried to give 0.35 g (67%) product, m.p. 277°-279° C.

'H NMR (DMSO-d$_6$): δ1.70 (m, 2H), 2.00 (m, 2H), 2.06 (t, 2H), 2.94 (t, 2H), 2.98 (s, 3H), 3.13 (m, 4H), 7.37 (d, 1H), 7.41 (d of d, 1H), 7.73 (d, 1H), 8.75-8.95 (m, 2H), 9.91 (s, 1H, CH$_3$SO$_2$NH—).

Step D: Preparation of 3,4-Dihydro-7-methanesulfonamido-1-oxo-1'-[2-(2-pyridyl-1-ethyl]spiro(naphthalene-2(1H),4'-piperidine]

The title compound was prepared by the procedure of Example 36 Step C from 0.207 g (0.60 mmole) 3,4-dihydro-7-methanesulfonamido-1-oxospiro[naphthalene-2(1H),4'-piperidine], hydrochloride salt, 0.126 g (1.2 mmoles) 2-vinylpyridine, and 0.098 g (1.2 mmoles) sodium acetate in 2 ml of 1:1 methanol:water to give 0.253 g crude product. This was purified by flash chromatography on silica gel eluting with 5:95 methanol:- chloroform (activated with ammonia) to give 0.206 g (83%) product as an oil.

To a solution of 0.206 g (0.50 mmole) product in 0.5 ml ethanol was added 0.180 ml (1.05 mmoles) 5.9N hydrogen chloride in ethanol to give a precipitate. The mixture was diluted with 2 ml ether, the precipitate was filtered off and dried to give 0.169 (70%) hydrochloride salt, m.p. 196°-197° C.

Anal. Calcd for C$_{22}$H$_{27}$N$_3$O$_3$S.2HCl.H$_2$O: C, 52.37; H, 6.19; N, 8.33. Found: C, 52.35; H, 6.11; N, 8.36.

EXAMPLE 43

3,4-Dihydro-7-methanesulfonamido-1'-{2-[4-(methanesulfonamido)phenyl]-1-ethyl}-1-oxospiro[naphthalene2(1H),4'-piperidine]

A mixture of 0.138 g (0.40 mmol) 3,4-dihydro7-methanesulfonamido-1-oxospiro[naphthalene-2(1H),4'-piperidine], hydrochloride salt, 0.168 g (2.00 mmol) sodium bicarbonate, 0.027 g (0.20 mmol) lithium iodide, and 0.129 g (0.44 mmole) 2-[4'-(methanesulfonamido)-phenyl]ethyl methanesulfonate in 10 ml acetonitrile was heated at reflux for 6 hours. The mixture was cooled and the solvent was removed in vacuo. The residue was partitioned between 3 ml dilute sodium bicarbonate solution and 10 ml methylene chloride. The layers were separated and the aqueous layer was extracted with 10 ml methylene chloride. The combined extracts were washed with 1 ml water and brine, dried, and the solvent was removed in vacuo to give 0.24 g crude product. This was purified by flash chromatography on silica gel eluting with methanol:chloroform (5:95) (saturated with ammonia) to give 0.175 g (87%) product as a foam.

To a solution of 0.175 g (0.346 mmole) product in 1 ml ethanol was added 0.064 ml (0.38 mmol) 5.9N hydrogen chloride in ethanol. The resulting precipitate was filtered off to give 0.129 g (69%) hydrochloride salt, mp. 258°-260° C.

Anal. Calcd. for C$_{24}$H$_{31}$N$_3$O$_5$S$_2$.HCl.0.25H$_2$O: C, 52.74; H, 5.99; N, 7.69. Found: C, 52.69; H, 5.70; N, 7.65.

EXAMPLE 44

1'-(2-(2-Pyridyl)ethyl)-2,3-Dihydrospiro(benzofuran-2,4'-piperidine)

A solution of 0.5 g (2.2 mmol) of 2,3-Dihydrospiro(-benzofuran-2,4'-piperidine) and 465 mg (4.4 mmol) of 2-vinylpyridine in 20 mL of 1:1 methanol/water was treated with 598 mg (4.4 mmole) of sodium acetate and heated to reflux for 11 hours. The reaction was then cooled to room temperature and poured into a saturated solution of sodium bicarbonate and extracted with ethyl acetate. The ethyl acetate solution was dried over anhydrous magnesium sulfate, filtered and concentrated in vacuo. The hydrochloride salt was prepared in ethanol and recrystallized from ethanol/ether to give 460 mg., 200°-202° C.

Elemental analysis for C$_{14}$H$_{23}$N$_2$O.2HCl.½H$_2$O Calcd: N, 7.50; C, 61.12; H, 6.66. Found: N, 7.42; C, 61.04; H, 6.54.

EXAMPLE 45

1'-(2-(4-Methanesulfonamidophenyl)ethyl)-2,3-dihydrospiro(benzofuran-2,4'-piperidine A solution of 500 mg (2.21 mmoles) of 2,3-dihydrospiro(benzofuran-2,4'-piperidine) in 10 mL ethanol was treated with 185 mg sodium bicarbonate and 650 mg (2.21 mmoles) of 4-methanesulfonamidophenethyl mesylate and heated to reflux for 2 hours. The reaction was cooled to room temperature and stored overnight. The reaction mixture was then poured into saturated sodium bicarbonate solution and extracted with ethyl acetate. The ethyl acetate solution was dried over magnesium sulfate, filtered and concentrated in vacuo. The hydrochloride salt was generated in ethanol with excess ethanolic HCl. The solid was collected and recrystallized from ethanol to give 420 mg, mp=269°-271° C.

Elemental analysis for $C_{21}H_{26}N_2O_3S \cdot HCl \cdot \frac{1}{4}H_2O$ Calcd: N, 6.49; C, 58.99; H, 6.36. Found: N, 6.55; C, 59.00; H, 6.48.

EXAMPLE 46

1'-(2-(2-Pyridyl)ethyl-2,3-dihydro-5-methanesulfonamidospiro(benzofuran-2,4'-piperidine)

Step A: 1'-Acetyl-2,3-dihydro-5-methanesulfonamidospiro[benzofuran-2,4'-piperidine]

A solution of 2.3 g (8.3 mmoles) of 1'-Acetyl-2,3-dihydro-5-nitrospiro(benzofuran-2,4'-piperidine) in 20 mL acetic acid and 20 mL water was treated with 35 mL 15% TiCl$_3$ in 20–30% HCl at room temperature. The reaction was stirred at ambient temperature for 1.5 hours. The reaction mixture was poured into 500 mL water and the pH was adjusted to about 9 with 2N NaOH and saturated NaHCO$_3$ and the mixture extracted with ethyl acetate. The combined organics were dried over magnesium sulfate, filtered and concentrated to give 1.52 g residue. This material was dissolved in 15 mL methylene chloride and treated with 1 mL pyridine and 0.570 mL (7.4 mmole) methanesulfonyl chloride. After 10 minutes the reaction was poured into 150 mL saturated sodium bicarbonate solution and extracted with ethyl acetate. The organics were dried over magnesium sulfate, filtered and concentrated. The residue was chromatographed on silica gel eluting with 2.5% methanol/chloroform to give 1.2 g of product.

$^1$H NMR (CDCl$_3$) δ7.14 (brs, 1H). 7.00 (dd, J=2, 8Hz, 1H) 6.84 (brs, 1H). 6.72 (d, J=8Hz, 1H) 4.2 (m, 1H), 3.6 (m, 2H), 3.3 (m, 1H), 3.0 (s, 2H), 2.94 (s, 3H), 2.13 (s, 3H), 2.05–1.9 (m, 2H), 1.8–1.6 (m, 2H).

Step B: Preparation of 2,3-Dihydro-5-(methanesulfonamido)spiro(benzofuran-2,4'-piperidine)

A solution of 1.2 g (3.6 mmole) of 1'-acetyl-2,3-dihydro-5-methanesulfonamidospiro(benzofuran-2,4'-piperidine) in 15 mL ethanol was treated with 15 mL of 6N HCl and heated to reflux per 6 hours. The reaction was poured into water (50 mL) and neutralized with 1N NaOH and saturated sodium bicarbonate. The aqueous mixture was extracted with ethyl acetate, dried over magnesium sulfate, filtered and concentrated in vacuo to give 598 mg of the intermediate 2,3-dihydro-5-(methanesulfonamido)spiro(benzofuran-2,4'-piperidine), 295 mg of which (1.04 mmole) was dissolved in 20 mL of 1:1 methanol/water and treated with 0.5 mL of 2-vinylpyridine. The reaction was heated to reflux for 6 hours, poured into 100 mL saturated sodium bicarbonate solution, and extracted with ethyl acetate. The ethyl acetate solution was dried over magnesium sulfate, filtered and concentrated in vacuo. The crude material was crystallized from ethyl acetate to give 122 mg, mp=171°-174° C.

Elemental analysis for $C_{20}H_{25}N_3O_3S \cdot \frac{1}{4}C_4H_8O_2$ Calcd: N, 10.26; C, 61.58; H, 6.64. Found: N, 10.27; C, 61.28; H, 6.71.

EXAMPLE 47

1'-(2-(2-Pyridyl)ethyl)-2,3-dihydrospiro(benzofuran-2,3'-piperidine)

Step A: Preparation of 1'-Benzyl-2,3-dihydrospiro(benzofuran-2,3'-piperidine)

The Grignard reagent derived from 19.17 g (132 mmoles) o-fluorobenzylchloride and 3.32 g (13 mmole) Mg turnings in 200 mL ether was treated with 25 g (132 mmoles) of N-benzyl-3-piperidone in 200 mL THF at room temperature. The reaction was stirred at room temperature for 1 hour, poured into 1L H$_2$O, and extracted with ether and ethyl acetate. The combined organics were dried over magnesium sulfate, filtered and concentrated in vacuo. The crude material was dissolved in 200 mL dimethylformamide and treated with 10 g of 60% sodium hydride and heated to 110° C. for 1 hour. The reaction was cooled to room temperature poured into 1L water and extracted with ethyl acetate. The combined organics were then washed with several portions of 1N HCl which was then basified to pH 9 and extracted with ethyl acetate. The ethyl acetate solution was dried over magnesium sulfate, filtered and concentrated at reduced pressure to give 13.5 g product. The hydrochloride of a small sample was generated in ethanol and recrystallized from ethyl acetate/methylene chloride to give product with mp=207°-209° C.

Elemental analysis for $C_{19}H_{21}NO \cdot HCl$; Calcd: N, 4.44; C, 72.25; H, 6.97. Found: N, 4.38; C, 72.07; H, 7.04.

Step B: Preparation of 2,3-Dihydrospiro(benzofuran-2,3'-piperidine)

A solution of 13 g (46 mmole) of 1'-benzyl-2,3-dihydrospiro(benzofuran-2,3'-piperidine) in 100 mL dichloroethane was treated with 7.13 g (5.2 mL, 51 mmoles) of 1-chloroethylchloroformate at room temperature for $\frac{1}{2}$ hour. The reaction mixture was concentrated and the residue dissolved in CH$_3$OH and heated to reflux for $\frac{1}{2}$ hour. The methanol was evaporated at reduced pressure, and the residue partitioned between ethyl acetate and 1N HCl. The ethyl acetate layer was discarded and the aqueous phase was basified to pH 9 and reextracted with ethyl acetate. The ethyl acetate solution was dried over magnesium sulfate, filtered and concentrated in vacuo to give 8.2 g product.

$^1$H NMR (CDCl$_3$) δ:7.2–7.05 (m, 2H) 6.8 (t, J=6 Hz, 1H), 6.78 (d, J=8 Hz, 1H), 305–295 (m, 4H), 2.82–2.7 (m, 2H), 2.08–1.5 (m, 4H).

Step C: 1'-(2-(2-Pyridyl)ethyl)-2,3-dihydrospiro(benzofuran-2,3'-piperidine) dihydrochloride A solution of 500 mg (2.64 mmoles) of 2,3-dihydrospiro(benzofuran-2,3'-piperidine) and 2-vinylpyridine (1 g) in 20 mL methanol was treated with 3 drops of acetic acid and heated to reflux for 16 hours. The reaction was then cooled, poured into 50 mL saturated sodium bicarbonate and extracted with ethyl acetate. The organics were dried over magnesium sulfate, filtered and concentrated in vacuo. Chromatography on silica gel eluting with 3% methanol/chloroform gave 420 mg. The hydrochloride salt was prepared with excess ethanolic HCl in ethanol and crystallized from isopropanol to give 200 mg of product with m.p.=187°-189° C.

Elemental analysis for $C_{19}H_{22}N_2O \cdot 2HCl \cdot \frac{1}{4}H_2O$: Calcd: N, 7.53; C, 61.37; H, 6.69. Found: N, 7.49; C, 61.26; H, 6.73.

EXAMPLE 48

1'-(2-(2-Pyridyl)ethyl)-2,3-dihydro-5-(methanesulfonamido)spiro(benzofuran-2,3'-piperidine)dihydrochloride Step A: Preparation of 1'-acetyl-2,3-dihydro-5-nitrospiro(benzofuran-2,3'-piperidine)

A solution of 7.2 g (38 mmoles) of 2,3-dihydrospiro(benzofuran-2,3'-piperidine) in 100 mL methylene chloride at room temperature was treated with 4.27 g (3.95 mL, 41.8 mmoles) of acetic anhydride and 3.84 g (5.29 mL, 38 mmoles) of triethylamine. The reaction was stirred at room temperature for 1 hour, poured into 400 mL saturated sodium bicarbonate, and extracted with ethyl acetate. The ethyl acetate solution was dried over magnesium sulfate, filtered and concentrated in vacuo to give 8.3 g crude acetamide. This material was dissolved in 100 mL acetic acid and treated with 5 mL (d=1.49) nitric acid. The reaction was heated gently to 50° C. over ¼ hour and then 80° C. for 5 minutes. The reaction was cooled to room temperature and poured into 1L of water and the pH adjusted to 9 with 1N NaOH and saturated sodium bicarbonate. The aqueous mixture was extracted several times with ethyl acetate. The ethyl acetate layers were combined, dried over magnesium sulfate, filtered and concentrated in vacuo. The residue was chromatographed on silica gel using 20% hexane/ethyl acetate as eluant to give 5.7 g of product, mp=165°-167° C.

Step B: Preparation of 1'-acetyl-2,3-dihydro-5-methanesulfonamidospiro(benzofuran-2,3'-piperidine)

Prepared in an analogous manner to that described in Example 46, Step A to give product with mp=201°-203° C.

Step C: Preparation of 2,3-dihydro-5-(methanesulfonamido)spiro(benzofuran-2,3'-piperidine)hydrochloride A solution of 3.6 g (11.09 mmole) of 1'-Acetyl-2,3-dihydro-5-methanesulfonamidospiro(benzofuran-2,3'-piperidine) in 100 mL ethanol was treated with 50 mL 6N hydrochloric acid and heated to reflux for 18 hours. The reaction was concentrated to dryness and the residue crystallized from ethanol to give 2.77 g of products mp=243°-244° C. $^1$H NMR (DMSO) δ9.6 (brs, 1H), 9.4 (s, 1H), 7.11 (d, J=1.6 Hz, 1H), 7.0 (dd, J=1.6, 8.5 Hz), 6.70 (d, J=8.5 Hz, 1H), 3.5-2.8 (m, 6H), 2.88 (s, 3H), 2.0-1.30 (m, 4H).

Step D: Preparation of 1'-(2-(pyridyl)ethyl)-2,3-dihydro-5-(methanesulfonamido)spiro(benzofuran-2,3'-piperidine) dihydrochloride A solution of 400 mg (1.25 mmoles) of 2,3-dihydro-5-methanesulfonamidospiro(benzofuran-2,3'-piperidine)-hydrochloride in 20 mL ethanol was treated with about 1 g of 2-vinyl pyridine and heated to reflux for 2 hours. The reaction was cooled to room temperature, poured into 100 mL saturated sodium bicarbonate solution, and extracted with ethyl acetate. The ethyl acetate extracts were combined, dried over magnesium sulfate, filtered and concentrated in vacuo. Chromatography on silica gel eluting with 3% $CH_3OH$/Chloroform gave 410 mg product as a free base. The material was dissolved in ethanol and treated with excess ethanolic HCl to generate the hydrochloride salt, which was crystallized from ethanol to give 360 mg of product; 230°-234° C.

Elemental analysis for $C_{20}H_{25}N_3O_3S.2HCl$ Cacld: N, 9.12; C, 52.17; H, 5.91. Found: N, 9.05; C, 52.51; H, 6.10.

EXAMPLE 49

1'-(2-(4-Nitrophenyl)ethyl)-2,3-dihydro-5-(methanesulfonamido)spiro(benzofuran-2,3'-piperidine) oxalate A solution of 1 g (3.1 mmole) of 2,3-dihydro-5-methanesulfonamido-spiro(benzofuran-2,3'-piperidine), 790 mg (3.45 mmole) of p-nitrophenethylbromide, and 588 mg (7 mmole) sodium bicarbonate was heated to reflux overnight. The reaction was cooled to ambient temperature, poured into 100 mL saturated sodium bicarbonate and extracted with ethyl acetate. The extracts were dried over magnesium sulfate, filtered and concentrated in vacuo to give 440 mg product as a free base. A small sample was treated with oxalic acid and crystallized from ethanol to give 89 mg of product mp=147°-151° C.

Elemental analysis for $C_{21}H_{24}N_3O_5S.C_2H_2O_4.\frac{1}{2}H_2O.\frac{1}{4}(C_2H_6O)$ Calcd: N, 7.68; C, 51.63; H, 5.34. Found: N, 7.75; C, 51.51; H, 5.13.

EXAMPLE 50

1'-(2-(4-Methanesulfonamidophenyl)ethyl)-2,3-dihydro-5-(methanesulfonamido)spiro(benzofuran-2,3'-piperidine)oxalate A solution of 0.92 g of 1'-(2-(4-nitrophenyl)ethyl)-2,3-dihydro-5-methanesulfonamidospiro(benzofuran-2,3'-piperidine in 10 mL acetic acid was converted into the product by a procedure analogous to that described in Example 48, step B. The product was isolated as the oxalate salt to give 198 mg of product; mp=141°-150° C.

Elemental analysis for $C_{22}H_{29}N_3O_5S_2.C_2H_2O_4$: Calcd: N, 7.37; C, 50.60; H, 5.48. Found: N, 7.34; C, 50.48; H, 5.29.

EXAMPLE 51

1'-(2-(4-Nitrophenoxy)ethyl)-2,3-Dihydro-5-(methanesulfonamido)spiro(benzofuran-2,3'-piperidine)oxalate This product was prepared in a manner analogous to that described for Example 49 except that p-Nitrophenoxyethylbromide is used instead of p-Nitrophenethylbromide to give product with mp=129°-135° C.

Elemental analysis for $C_{21}H_{25}N_3O_6S.C_2H_2O_4.\frac{1}{4}C_3H_6O$: Calcd: N, 7.54; C, 51.75; H, 5.15. Found: N, 7.39; C, 51.48; H, 5.31.

EXAMPLE 52

1'-(2-(2-Pyridyl)ethyl)-3,4-dihydrospiro-[(2H)-1-benzopyran-2,3'-piperidine]-4-one hydrochloride Step A: Preparation of 3,4-Dihydrospiro-1'-benzyl-2H-1-benzopyran-2,3'-piperidine-4-one A solution of 5 g (36 mmole) of ortho hydroxyacetophenone and 8.2 g (36 mmole) of N-benzyl-3-piperidone in 200 mL methanol was treated with 5.24 g (72 mmole) of pyrrolidine and heated to reflux for 4 hours. The reaction was cooled to room temperature concentrated in vacuo and partitioned between ethyl acetate and saturated sodium bicarbonate. The ethyl acetate solution was washed with 1N HCl which was then basified to pH 9 and reextracted with ethyl acetate. The ethyl acetate layer was dried over magnesium sulfate, filtered and concentrated in vacuo. The residue was chromatographed on silca gel eluting with 20% ethyl acetate/hexanes to give 8.1 g product. A small portion was treated with excess ethanolic HCl and crystallized from CH₃OH/C₂H₅OH to give product with mp=255°-258° C.

Elemental analysis for $C_{20}H_{21}NO_2 \cdot HCl$: Calcd: N, 4.07; C, 69.85; H, 6.45. Found: N, 4.05; C, 69.73; H, 6.54.

In a manner analogous to the above Step A except substituting 5-Acetamido-2-hydroxyacetophenone for ortho hydroxyacetophenone there was produced 6-Acetamido-3,4-dihydrospiro-1'-benzyl-2H-1-benzopyran-2,3'-piperidine-4-one, mp=262°-265° C.

Step B: Preparation of 3,4-Dihydrospiro-[(2H)-1-benzopyran-2,3'-piperidine]-4-one A solution of 20.3 g (66 mmole) of 3,4-Dihydrospiro-1'-benzyl-2H-1-benzopyran-2,3'-piperidine in 200 mL dichloroethane at room temperature and was treated with 7.4 mL (10.38 g, 72 mmole) of α-chloroethyl chloroformate. The reaction was heated to reflux for ½ hour, cooled to room temperature concentrated in vacuo. The residue was dissolved in 200 mL of methanol and heated to reflux for ½ hour. The reaction was then cooled to room temperature and concentrated to ¼ volume. The solid was collected to give 14.1 g of product, mp=273°-274° C.

Step C: Preparation of 1'-(2-(2-pyridyl)ethyl)-3,4-dihydrospiro-[(2H)-1-benzopyran-2,3'-piperidine]4-one hydrochloride A solution of 520 mg (2.05 mmole) of 3,4-Dihydro-2H-1-benzopyran-2,3'-piperidine-4-one hydrochloride in 15 mL methanol was treated with 237 mg (2.25 mmole) of 2-vinylpyridine and heated to reflux for 48 hours. The reaction was cooled to room temperature, poured into 50 mL of saturated sodium bicarbonate and extracted with ethyl acetate. The ethyl acetate solution was dried over magnesium sulfate, filtered and concentrated in vacuo. The hydrochloride salt was prepared in ethanol with excess ethanolic HCL. The solid was collected to give 188 mg of product; mp 195°-198° C.

Elemental analysis for $C_{20}H_{22}N_2O_2 \cdot 2HCL \cdot \frac{1}{4}H_2O$: Calcd: N, 6.93; C, 59.40; H, 6.23. Found: N, 6.40; C, 59.53; H, 6.20.

EXAMPLE 53

1'-(2-(4-Methanesulfonamidophenyl)ethyl)-3,4-dihydrospiro-[(2H)-1-benzopyran-2,3'-piperidine]-4-one oxalate A solution of 560 mg (258 mmole) of 3,4-dihydrospiro-[(2H)-1-benzopyran-2,3'-piperidine]4-one in 20 mL ethanol was treated with 880 mg (3 mmoles) of 2-(4-methanesulfonamidophenyl)ethyl mesylate and 0.5 g sodium bicarbonate and heated to reflux for 48 hours. The reaction was cooled to room temperature, poured into saturated sodium bicarbonate and extracted with ethyl acetate. The ethyl acetate solution was dried over magnesium sulfate, filtered and concentrated in vacuo. The crude material was treated with 1 eq. oxalic acid and the salt was recrystallized from acetone to give product with mp=204°-210° C.

Elemental analysis for $C_{22}H_{26}N_2O_4S \cdot C_2H_2O_4 \cdot \frac{1}{2}H_2O$: Calcd: N, 5.45; C, 56.12; H, 5.69. Found: N, 5.52; C, 56.35: H, 5.54.

EXAMPLE 54

1'-(2-(4-Methanesulfonamidophenoxy)ethyl)-3,4-dihydrospiro-[(2H)-1-benzopyran-2,3'-piperidine]-4-one oxalate hemihydrate Prepared in a manner analogous to the previous Example 53 except that 2-(4-Methanesulfonamidophenoxy)ethyl bromide was used instead of 2-(4-methanesulfonamidophenyl)ethyl mesylate. The product had mp=175° C.

Elemental analysis for $C_{22}H_{26}N_2O_5S \cdot C_2H_2O_4 \cdot \frac{1}{2}H_2O$: Calcd: N, 5.32; C, 54.43; H, 5.51. Found: N, 5.20; C, 54.22; H, 5.44.

EXAMPLE 55

6-Methanesulfonamido-1'-(2-(2-pyridinyl)ethyl)-3,4-dihydrospiro-[(2H)-1-benzopyran-2,3'-piperidine]-4-one hydrochloride Step A: Preparation of 6-Methanesulfonamido-1'-benzyl-3,4-dihydrospiro-[(2H)-1-benzopyran-2,3'-piperidine]-4-one A solution of 12.2 g (33.47 mmole) of 6-acetamido-3,4-dihydrospiro-1'-benzyl-2-H-1-benzopyran-2,3'-piperidine-4-one in 200 mL ethanol was treated with 80 mL of 6N HCl and heated to reflux for 5 hours and then stirred at room temperature overnight. The reaction was concentrated to ¼ volume and then poured into 300 mL water. The pH was adjusted to 9 with 2N NaOH and saturated sodium bicarbonate, and extracted with ethyl acetate. The ethyl acetate solution was dried over magnesium sulfate filtered and concentrated in vacuo. The 10.2 g of crude material was dissolved in 100 mL pyridine and treated with 2.7 mL (3.99 g, 34 mmole) methanesulfonyl chloride. The reaction was stirred at room temperature for 3 hours, evaporated to ~¼ volume and poured into a mixture of ethyl acetate and saturated sodium bicarbonate. The layers were separated and the aqueous phase extracted several times with ethyl acetate.

The combined organics were dried over magnesium sulfate, filtered and concentrated in vacuo. The residue was chromatographed on silica gel eluting with 3% methanol/chloroform, to give 12.2 g product which was crystallized from ethyl acetate to yield 9.2 g, mp=150° C.

Elemental analysis for $C_{21}H_{24}N_2O_4S \cdot \frac{1}{4}C_4H_8O_2$: Calcd: N, 6.63; C, 62.53; H, 6.15. Found: N, 6.64; C, 62.52; H, 6.17.

Step B: Preparation of 6-Methanesulfonamido-3,4-dihydrospiro-[(2H)-1-benzopyran-2,3'-piperidine]-4-one hydrochloride A solution of 7 g (17.47 mmols) of 6-methanesulfonamido-1'-benzyl-3,4-dihydrospiro-[(2H)-1-benzopyran-2,3'-piperidine]-4-one in 250 mL dichloroethane was treated with 5.6 g (43.7 mmole) of diisopropylethylamine, and 6.24 g (43.7 mmoles) of 1-chloroethyl chloroformate. The reaction was stirred at room temperature for 24 hours and then poured into 500 mL saturated sodium bicarbonate, and extracted with ethyl acetate. The ethyl acetate layers were washed with dilute acid to remove excess diisopropylethylamine. The ethyl acetate solution was then dried over MgSO₄, filtered and concentrated in vacuo. The crude material was dissolved in 250 mL CH₃OH and heated to reflux for 24 hours. The reaction mixture was cooled to room temperature and the solid collected by filtration to give 4.1 g of product, mp=290° C.

Step C: Preparation of 6-Methanesulfonamido-1'-(2-(2-pyridyl)ethyl)-3,4-dihydrospiro-[(2H)-1-benzopyran-2,3'-piperidine]-4-one hydrochloride hydrate Prepared according to the procedure as described previously in Example 52 Step C starting with 6-methanesulfonamido-3,4-dihydrospiro-2H-1-benzopyran-2,3'-piperidine-4-one. mp=205°-210° C.

Elemental analysis for $C_{21}H_{25}N_3O_4S \cdot 2HCl \cdot H_2O$: Calcd: N, 8.29; C, 49.80; H, 5.77. Found: N, 8.28; C, 49.95; H, 5.62.

EXAMPLE 56

6-Acetamido-3,4-dihydrospiro-1'-(2-(6-methyl)pyridyl-)ethyl)[(2H)-1-benzopyran-2,4'-piperidine]-4-one dihydrochloride A solution of 1.3 g (4.7 mmoles) of 6-acetamido-3,4-dihydrospiro(2H-1-benzopyran-2,4'-piperidine)-4-one in 20 mL $CH_3OH$ was treated with 560 mg (4.7 mmole) of 2-vinyl-6-methylpyridine and 5 drops of acetic acid and heated to reflux for 36 hours. The reaction was cooled to room temperature, poured into 100 mL sat'd $NaHCO_3$, and extracted with ethyl acetate. The ethyl acetate solution was dried over magnesium sulfate, filtered and concentrated at reduced pressure. The free base was dissolved in ethanol and treated with ethanolic HCl. The dihydrochloride separated and was collected by filtration to give 610 mg of product. mp=214°–217° C.

Elemental analysis for $C_{23}H_{27}N_3O_3 \cdot 2HCl \cdot \frac{3}{4}H_2O$: Calcd: N, 8.75; C, 57.56; H, 6.40. Found: N, 8.74; C, 57.76; H, 6.08.

EXAMPLE 57

1'-[2-(2-Benzofurazan-5-yl)ethyl]spiro[1-methyl-5-methanesulfonamidoindoline-3,4'-piperidine dihydrochloride (L-692,184)

A mixture of 0.2 g (0.000716 mol) of spiro [1-methyl-5-methanesulfonamidoindoline-3,4'-piperidine], 0.325 g (0.00143 mol) of 5-(2-bromoethyl) benzfurazan, 0.119 g (0.000716 mol) of potassium iodide, 0.241 g (0.00286 mol) of sodium bicarbonate, and 15 ml of absolute ethanol was stirred and refluxed for 24 hours. The mixture was filtered and the filtrate was evaporated to dryness. The residue was purified by chromatography on silica gel using 5% methanol in chloroform as an eluant. The purified product was converted to its hydrochloride salt. Recrystallization of this salt from methanol-isopropyl alcohol gave the title compound, mp 241°–250° C. (dec).

Anal. Calcd. for $C_{22}H_{27}N_5O_3S \cdot 2HCl$: C, 51.36; H, 5.68; N, 13.61. Found: C, 51.01; H, 5.53; N, 13.42.

EXAMPLE 58

6-Methanesulfonamido-3,4-dihydro-1'-(2-(2-(6-methyl)-pyridyl)ethyl)spiro[(2H-)1-benzopyran-2,4'-piperidine]-4-one A solution of 1.3 g of 6-acetamido-3,4-dihydro-1'-(2-(2-(6-methyl)pyridyl)ethyl)(2H-1-benzopyran-2,4'-piperidine)-4-one in 20 mL methanol was treated with 10 mL 6N HCl heated to reflux for 4 hours. The reaction was cooled to room temperature, concentrated to dryness, and partitioned between ethyl acetate and saturated sodium bicarbonate. The ethyl acetate layers were dried over magnesium sulfate, filtered and concentrated. The crude material was dissolved in 10 mL pyridine and treated with 460 mg (4 mmoles) of methanesulfonyl chloride. The reaction was stirred at room temperature for 5 hours, concentrated to ½ volume and poured into saturated sodium bicarbonate solution. The mixture was extracted with several portions of ethyl acetate. The ethyl acetate layers were dried over magnesium sulfate, filtered and concentrated in vacuo. The free base crystallized from ethyl acetate to give 206 mg of product mp=176°–178° C.

Elemental analysis for $C_{22}H_{27}N_3O_4S$: Calcd: N, 9.78; C, 61.51; H, 6.33. Found: N, 9.65; C, 61.32; H, 6.34.

EXAMPLE 59

6-Methanesulfonamido-3,4-dihydro-1'-(2-(4-methanesulfonamidophenyl)ethyl)spiro[(2H)-1-benzopyran 2,4'-piperidine]-4-one This compound was prepared in a manner analogous to that of Example 58 and isolated as the hydrochloride salt to give 240 mg of product. mp=285°–288° C.

Elemental analysis for $C_{23}H_{29}N_3O_6S \cdot HCl$: Calcd: N, 7.72; C, 50.77; H, 5.55. Found: N, 7.70; C, 50.84; H, 5.62.

EXAMPLE 60

1,4-Dihydro-1'-[2-(4-methanesulfonamidophenyl)ethyl]-7-methanesulfonamido-spiro[(3H)-2-benzopyran-3',4'-piperidine]hydrochloride Step A: Preparation of 1,4-Dihydro-1'-methyl-7-nitrospiro[(3H)-2-benzopyran-3,4'-piperidine-1-one]

1,4-Dihydro-1'-(methyl)-spiro[2-benzopyran-3,4'-piperidine-1-one hydrochloride (4.05 g, 15.1 mm) was stirred while suspended in 30 mL of concentrated $H_2SO_4$ cooled to 0° C. Nitric Acid (0.95 mL of d=1.49) was added dropwise over 5 minutes and the mixture stirred at 0° C., for 3 hours. The reaction mixture was then poured onto ice (200 grams) and the pH adjusted with 40% aq. NaOH to pH 10 while the temperature was kept below 20° C. with external cooling. Extraction with $CH_2Cl_2$, drying the organic portion ($Na_2SO_4$), and concentration to dryness gave 3.70 grams of product as a pale pink solid (88% yield).

$^1$H NMR ($CDCl_3$) δ: 1.82 (m, 2H); 1.98 (m, 2H); 2.34 (s, 3H); 2.52 (dt, 2H); 2.62 (dt, 2H); 3.13 (s, 2H); 7.47 (d, 1H); 8.40 (dd, 1H); 8.94 (d, 1H).

Step B: Preparation of 1,4-Dihydro-1'-methyl-7-methanesulfonamido-spiro[(3H)-2-benzopyran-3,4'-piperidin-1-one]

9.00 grams (32.6 mm) of 1,4-dihydro-1'-methyl-7-nitro-spiro[(3H)-2-benzopyran-3,4'-piperidine-1one] was dissolved in THF (175 mL) and stirred while 36 grams (160 mm) of $SnCl_2 \cdot 2(H_2O)$ was added in one portion. The mixture was heated to 65° C. for 3 hours and then poured into 400 mL of saturated aqueous $NaHCO_3$. This was extracted with $CHCl_3$ (5×400 mL), the organic layer dried ($Na_2SO_4$) and concentrated to a solid to give quantitative recovery of crude anilino lactone. This material was redissolved in pyridine (100 mL) cooled to 0° C., and treated with 4.2 mL of methanesulfonyl chloride. After stirring for 15 hours at 25° C., the mixture was diluted with 1.0 liter of $CHCl_3$ and washed with 50 mL of saturated aqueous $NaHCO_3$. The organic portion was dried ($Na_2SO_4$) and concentrated to an oily residue which was redissolved in 100 mL of $CH_2Cl_2$. The product crystallized on standing at 25° C. to give after isolation and drying in vacuo 9.0 grams (85%) of a white solid which contained ¼ mole of $CH_2Cl_2$ by $^1$H NMR.

$^1$H NMR ($CDCl_3$): δ: 1.79 (m, 2H); 1.98 (m, 2H); 2.33 (s, 3H); 2.45–2.75 (m, 4H); 3.00 (s, 2H); 3.06 (s, 3H); 7.27 (d, 1H); 7.56 (dd, 1H); 7.82 (d, 1H).

Step C: Preparation of 1,4-Dihydro-1'-(methyl)-7-methanesulfonamido-spiro[(3H)-2-benzopyran-3,4'-piperidine]

To a solution of 1,4-dihydro-1'-(methyl)-7-methanesulfonamido-spiro[(3H)-2-benzopyran-3,4'- piperidine-1-one] (1.5 g) in THF (15 ml) at 0° C. under nitrogen was added a 1.0M lithium aluminum hydride in THF (5.55 ml). The reaction was stirred at 0° C. until complete and then quenched by addition of saturated brine. Methanol (50 ml) was added and the reaction filtered through a cake of Na$_2$SO$_4$. The Na$_2$SO$_4$ cake was washed with methanol (300 ml) and the filtrates concentrated to a solid. The solid was dissolved in 85% H$_3$PO$_4$ and heated to 100° C. for 30 minutes. The reaction was quenched into ice/water (100 ml) and chloroform (200 ml) added. The pH was adjusted to 8.7 with 40% NaOH and the chloroform layer was separated. The aqueous layer was washed with chloroform (250 ml), the organics were combined, dried over Na$_2$SO$_4$ and concentrated to a solid (1.3 g). Crystallization from ethyl acetate/hexanes yielded 0.9 g of product.

'H NMR (300 MHz, CDCl$_3$) δ: 7.08 (d, 1H), 7.0 (d, 1H), 6.92 (s, 1H), 4.7 (s, 2H), 3.0 (s, 3H), 2.65 (s, 2H), 2.55 (m, 2H), 2.4 (m, 2H), 2.30 (s, 3H) 1.8 (m, 2H) 1.6 (m, 2H).

Step D: Preparation of 1,4-Dihydro-7-methanesulfonamido-spiro[(3H)-2-benzopyran-3,4'-piperidine]hydrochloride To a solution of 1,4-dihydro-1'-methyl-7-methanesulfonamido-spiro[(3H)-2-benzopyran-3,4'-piperidine] (0.575 g) and N,N,N',N'-tetramethyl-1,8-napthalenediamine (proton sponge) (0.6 g) in dichloroethane under nitrogen at 0° C. was added 1-chloroethyl chloroformate (0.613 ml). The mixture was stirred at reflux for 2 hours, cooled filtered through silca gel (20 g) and the product eluted with ethyl acetate. The eluate was concentrated and the residue dissolved in methanol (20 ml) and refluxed for 18 hours. The reaction was concentrated to a foam and crystallized from ethanol/hexanes yielding 0.548 g of product.

'H NMR (300 MHz, DMSO): δ8.7 (Broad S, 1H) 8.6 (Broad S, 1H) 7.15 (d, 1H) 7.05 (d, 1H), 6.9 (s, 1H), 4.7 (s, 2H), 3.1 (m, 4H), 3.0 (s, 3H), 2.65 (s, 2H), 1.85 (m, 2H), 1.7 (m, 2H).

Step E: Preparation of 1,4-Dihydro-1'-[2-(4-methanesulfonamidophenyl)ethyl]-7-methanesulfonamido-spiro[(3H)-2-benzopyran-3,4'-piperidine]hydrochloride A mixture of 1,4-dihydro-7-methanesulfonamido-spiro[(3H)-2-benzopyran-3,4'-piperidine]hydrochloride (0.080 g) and the 2-[4-(methanesulfonamido)-phenyl]ethyl methanesulfonate (0.106 g), KI (0.020 g), and sodium bicarbonate (0.061 g) in CH$_3$CN was refluxed for 24 hours. The reaction was concentrated and chromotographed on silica using methylene chloride/methanol (95:5) to give upon concentration 0.130 g of a white foam. The foam was dissolved in ethanol and an ethanol/HCl solution was added. The resulting slurry was diluted with hexanes, filtered and yielded 0.130 g of product, mp 160°–163° C.

Employing the procedure substantially as described in Example 60, Step E but substituting for the 2-[4-(methanesulfonamido)phenyl]ethyl methanesulfonate used therein, the appropriate electrophiles there were produced the spiropiperidines described in Table II.

TABLE II

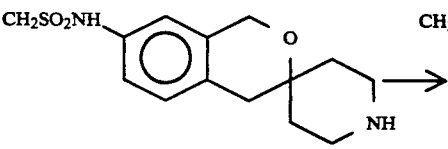

| Example | —R—M | salt | mp. (°C.) |
|---|---|---|---|
| 61 | 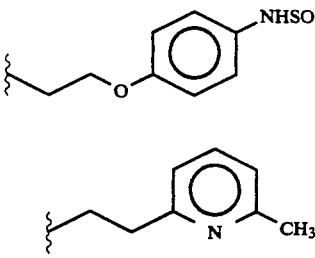 | .HCl .0.75 H$_2$O | 148–150 |
| 62 | 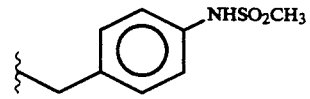 | .2HCl .2.5 H$_2$O .0.2 EtOAc | 160–170 (dec.) |
| 63 | 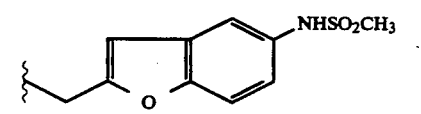 | .HCl | 249–252 |
| 64 | 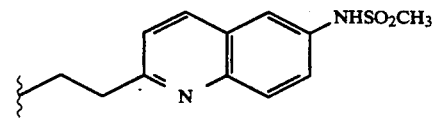 | .HCl | 192–195 |
| 65 |  | .2HCl | 184 (dec.) |

TABLE II-continued
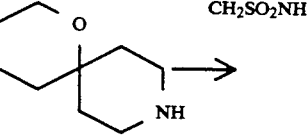
| Example | —R—M | salt | mp. (°C.) |
|---|---|---|---|
| 66a | 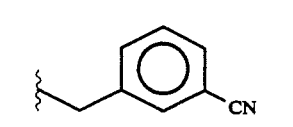 | .HCl | >250 |
| 66b | 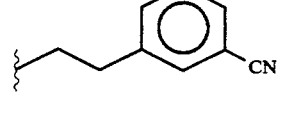 | .HCl | 238–245 |
| 66c | 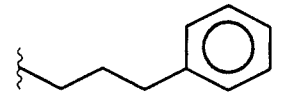 | .HCl | 140–142 |
| 66d | 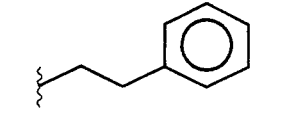 | .HCl | 234–235 |
| 66e | 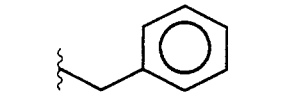 | .HCl .0.35 H₂O | 246–248 |
| 66f | 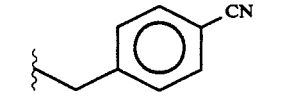 | .HCl .0.3 H₂O | 251–253 |
| 66g | 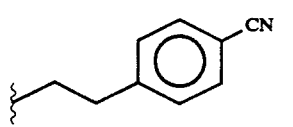 | .HCl | 254–255 |
| 66h | 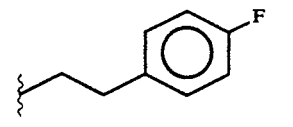 | .HCl | 230–232 (dec.) |
| 66i | 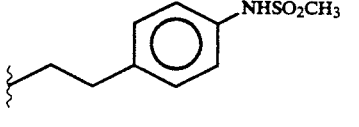 | .HCl .0.2 H₂O | 211–213 |
| 66j |  | .HCl .0.75 H₂O .0.2 EtOH | 160–163 |

TABLE II-continued

[Structure: benzopyran-piperidine with CH₂SO₂NH-phenyl substituent, NH group → N-R-M]

| Example | —R—M | salt | mp. (°C.) |
|---|---|---|---|
| 66k | [-(CH₂)₂-(3-pyridyl)] | .2HCl .0.5 H₂O | 202–203.5 |

The compounds of Table IIa were prepared from 1,4-dihydro-spiro[(3H)-2-benzopyran-3,4′-piperidine]-hydrochloride by the method described in Example 92, Step B using the appropriate mesylate or bromide.

TABLE IIa

[Structure: benzopyran-spiro-piperidine with N-RM]

| Example | RM | salt | mp(°C.) |
|---|---|---|---|
| 66l | —(CH₂)₂—C₆H₄—NHSO₂CH₃ | .HCl | 248–250 |
| 66m | —(CH₂)₂—C₆H₄—NO₂ | — | 116–118 |
| 66n | —(CH₂)₂—(pyridyl) | .2HCl .0.5H₂O | 174–176 |

EXAMPLE 67

3,4-Dihydro-1′-[2-(2-pyridyl)ethyl]spiro[(2H)-1-benzopyran-2-4′-piperidine]-4-one hydrochloride Step A: Preparation of 3,4-Dihydro-spiro[(2H)-1-benzopyran-2,4′-piperidine]-4-one hydrochloride Method 1

A solution of 2-acetylphenol (5 g, 0.037 mmol), 1-benzoyl-4-piperidone (7.5 g, 0.037 mmol), pyrrolidine (2.6 g, 0.037 mol) and CH₃OH (50 ml) was heated at reflux for 8 hours. After cooling to room temperature overnight, the solid was filtered to yield 8.2 g of 1′-benzoyl-3,4-dihydro-spiro[(2H)-1-benzopyran-2,4′-piperidin]-4-one. The mother liquor was concentrated to dryness and the residue triturated with ether to yield an additional 1.7 g (83% total yield).

A solution of the benzoyl compound (3.2g, 0.01 mol), in ethanol (50 ml) and 6N HCl (50 ml) was heated at reflux. After 18 hours, the reaction was concentrated to dryness and the residue was flushed with ethanol (3×).

The residue was crystallized from ethanol to yield 2.4 g of title compound (92%); mp 238°–240° C. (ethanol).

Analysis for C₁₃H₁₅NO₂.HCl: Calcd: N, 5.52; C, 61.54; H, 6.36. Found: N, 5.38; C, 61.62; H, 6.42.

Method 2

Utilizing the chemistry described in Method 1 but substituting 1-methyl-4-piperidone in place of 1-benzoyl-4-piperidone provided an 82% yield of the corresponding 1′-methyl compound; mp>300° C. (ethanol).

Analysis for C₁₄H₁₇NO₂.HCl: Calcd: N, 5.23; C, 62.80; H, 6.78. Found: N, 5.02; C, 62.51; H, 6.90.

A solution of the 1′-methyl compound (1.45 g, 0063 mol) in benzene (30 ml) was added dropwise to a solution of 5M CNBr in CH₃CN (1.5 ml) in benzene (30 ml). The solution was stirred overnight at room temperature and then concentrated to dryness. The residue was treated with acetic acid (66 ml), 12N HCl (8 ml) and H₂O (35 ml). The solution was heated at reflux for 4 hours. After stirring at room temperature, the reaction was concentrated to dryness and the residue crystallized from ethanol to yield 1.6 g (75%) of title compound.

Step B: Preparation of 3,4-Dihydro-1′-[2-(2-pyridyl)ethyl]spiro[(2H)-1-benzopyran-2,4′-piperidin]-4-one hydrochloride A solution of the product from Step A (0.4 g, 0.0018 mol) in ethanol (10 ml) and 2-vinylpyridine (0.39 g, 0.0037 mmol) was heated at reflux. After 18 hours, the reaction was concentrated to dryness and the residue was chromatographed on silica gel (Still column, 50 mm). The product was eluted with 20% CH₃OH—CHCl₃ with 2% aqueous NH₃. The product was crystallized as the hydrochloride salt from CH₃CN to yield 0.37 g (51%) of title compound; mp 229°–230° C.

Analysis for C₂₀H₂₂N₂O₂.2HCl: Calcd: N, 7.09; C, 60.76; H, 6.12. Found: N, 7.06; C, 60.70; H, 6.17.

EXAMPLE 68

3,4-Dihydro-1′-[2-p-nitrophenyl)ethyl]spiro[(2H)-1-benzopyran-2,4′-piperidine]-4-one hydrochloride hemihydrate Under N₂, a mixture of the product of Example 67, Step A (0.91 g, 0.0042 mol), 4-nitrophenethylbromide (1.2 g, 0.005 mol), NaHCO₃ (1.3 g, 0.015 mol) in ethanol (25 ml) was heated at reflux. After 1 day, 4-nitrophenylethylbromide (1.2 g) and NaHCO₃ (1.3 g) was added and the mixture heated at reflux an additional 24 hr. The reaction was then concentrated to dryness and the residue was chromatographed on silica gel (Still column, 50 mm). The product was eluted with 10% CH₃OH—CHCl₃ and the product crystallized as the hydrochloride salt to yield 0.45 g (25%) of the title compound; mp 250°–251° C. (CH$_3$CN).

Analysis for C$_{21}$H$_{22}$N$_2$O$_4$.HCl.$\frac{1}{2}$H$_2$O: Calcd: N, 6.70; C, 60.98; H, 5.51. Found: N, 6.80; C, 61.23; H, 5.87.

EXAMPLE 69

3,4-Dihydro-1'-(4-pyridyl)spiro[(2H)-1-benzopyran-2-4'-piperidine]-4-one.hydrochloride A mixture of product from Example 67, Step A (1.0 g, 0.0046 mol), 4-bromopyridine (1.99, 0.0092 mol), NaHCO$_3$ (2.3 g, 0.027 mol) in ethanol (40 ml) was heated at reflux. After 24 h, K$_2$CO$_3$ (3.7 g, 0.0027 mol) was added and the reaction was heated at reflux. After 24 hour, DMF (25 ml) was added, the ethanol boiled off and additional 4-bromopyridine (0.5 g) was added. After 24 hours at reflux, the reaction was poured into H$_2$O and the aqueous phase extracted with ethyl acetate (3×). The organic layers were dried, filtered and concentrated to dryness. The residue was chromatographed on Silica gel (Still column (50 mn) and the product was eluted with 10% CH$_3$OH-CHCl$_3$. The product was crystallized as the hydrochloride salt from ethanol to yield 0.4 g (27%) of product mp 251°–253° C.

| Analysis for C$_{18}$H$_{18}$N$_2$O$_2$.HCl | |
|---|---|
| Calc'd | Obs. |
| N 8.47 | 8.30 |
| C 65.35 | 65.06 |
| H 5.79 | 5.72 |

EXAMPLE 70

3,4-Dihydro-1'-[2-(2-pyridyl)ethyl-6-methanesulfonamido-spiro[2H-1-benzopyran-2-4'-piperidin]-4-one dihydrochloride mono-hydrate

METHOD 1

Step A: Preparation of 6-acetamido-3,4-dihydro-spiro[2H-1-benzopyran-2-4'-piperidine]-4-one A solution of 4-acetamido-2-acetylphenol (13 g, 0.067 mol), CH$_3$OH (90 ml), piperidine-4-one .HCl.H$_2$O (11 g, 0.072 mol) and pyrrolidine (10.2 g, 0.14 mol) was heated at reflux. After 20 hr, piperidine-4-one.HCL.H$_2$O (1.5 g, 0.01 mol) and pyrrolidine (1.7 g, 0.024 mol) were added and the reaction was heated at reflux. After 18 hr, the reaction was concentrated to dryness and the residue was dry packed with silica gel. The dry pack was added to a Still column (100 mm) and the residue eluted with 10% CH$_3$OH-CHCl$_3$ with 1% aq. NH$_3$ to yield 3.5 g of phenolic starting material and then 11.8 g (64%) of title compound.

Step B: 6-Acetamido-3,4-Dihydro-1'-[2-(2-pyridyl)-ethyl]spiro[(2H)-1-benzopyran-2,4'-piperidin]-4-one-hydrochloride A solution of product from Step A (7.0 g, 0.026 mol), CH$_3$OH (150 ml), 2-vinylpyridine (8.4 ml, 8.2 g, 0.078 mol) and acetic acid (10 drops) was heated at reflux. After 24 hr, the reaction mixture was poured into saturated NaHCO$_3$ and the mixture extracted with ethyl acetate (4×). The organic extracts were dried, filtered and concentrated to dryness (quantitative yield). An analytical sample was prepared by crystallization of the HCl salt from ethanol, m.p. 228°–230°(dec)

| Analysis for C$_{22}$H$_{25}$N$_3$O$_3$.2HCl.$\frac{1}{2}$H$_2$O | |
|---|---|
| Calc'd | Found |
| N 9.02 | 9.08 |
| C 56.71 | 56.74 |
| H 5.78 | 6.08 |

Step C: Preparation of 3,4-Dihydro-1'-[2-(2-pyridyl)ethyl]-6-methanesulfonamido-spiro[(2H)-1-benzopyran-2-4'-piperidin]-4-one. dihydrochloride monohydrate A solution of product from Step B (9.7 g, 0.025 mol) in ethanol (150 ml) and 6 N HCL (150 ml) was heated at reflux for 19 h. The reaction was then concentrated to dryness and the residue was flushed (2×) with ethanol toluene to yield 8.0 g (71%) of deacetylated product. The residue was treated with CH$_2$Cl$_2$. (250 ml), pyridine (40 ml) and methanesulfonyl chloride (2 ml, 2.96 g, 0.026 mol). After stirring overnight at room temperature, the reaction mixture was washed with 2.5N NaOH (3×), the basic layer was adjusted to pH 8.5 and extracted with ethyl acetate (5×). The organic extracts were dried, filtered and concentrated to dryness to yield a 6.1 g residue which was crystallized as the dihydrochloride salt to yield the title compound.

METHOD 2

Step A: Preparation of 1'-benzoyl-3,4-dihydro-8 nitro-spiro[(2H)-1-benzopyran-2-4'piperidine]-4-one and 1'-benzoyl-3,4-dihydro-6-nitro-spiro [(2H)-1-benzopyran-2-4'-piperidene]-4-one Under N$_2$, HNO$_3$ (15 ml, 1.49 density, 22.3 g, 0.35 mol) was added dropwise to a cooled solution of the 1'-benzoyl product from Example 67, Step A of Method 1 (12.6 g, 0.039 mol) in acetic anhydride (120 ml). After the addition, the solution was stirred at room temperature. After 3 hours, the reaction was poured into sat'd Na$_2$CO$_3$ and ice and the mixture was extracted with ethyl acetate (3×). The organic extract was dried, filtered and concentrated to dryness. The residue was chromatographed on silica gel (Still column, 100 mm) to yield 1.2 g (8.2%) of the 8-nitro product and then with 50% ethyl acetate-hexane to yield 6.4 g (44%) of the 6-nitro product.

Step B: Preparation of 6-amino-1'-benzoyl-3,4-dihydro-spiro[(2H)-1-benzopyran-2-4'-piperidine]-4-one A suspension of the 6-nitro compound from Step A (3.2 g, 0.0087 mol) in ethanol (200 ml) and acetic acid (50 ml) with one teaspoonful of Raney nickel was hydrogenated at 5 psi. After the theoretical amount of H$_2$ was absorbed, the mixture was filtered under N$_2$ through a super cel pad and the solution was concentrated to dryness. The residue was partitioned between saturated NaHCO$_3$ and CHCl$_3$ (3×) and the organic extracts were dried, filtered and concentrated to dryness to yield 2.8 g (95%) of title compound.

Step C: Preparation of 1'-benzoyl-3,4-dihydro-6-methanesulfonamido-spiro[(2H)-1-benzopyran-2-4'-piperidine]-4-one Under N$_2$, methanesulfonyl chloride (0.7 ml, 1 g, 0.009 mol) was added dropwise at room temperature to a solution of product from Step B (2.6 g, 0.0077 mol) and pyridine (2 ml) in CH$_2$Cl$_2$ (80 ml ). After 18 hours, the reaction was poured into diluted acid and the mixture was extracted with ethyl acetate (5×). The organic extracts were dried, filtered and concentrated to dryness. The mixture was crystallized from CH$_3$OH—C$_2$H$_5$OH to yield 2.2 g (69%) of product.

Step D: Preparation of 3,4-dihydro-6-methanesulfonamido-spiro[(2H)-1-benzopyran-2-4'-piperidin]-4-one A solution of product from Step C (2.6 g, 0.0063 mol) in ethanol and 6N HCl (40 ml) was heated at reflux. After 18 hours, the solution was concentrated to dryness. The residue was crystallized from $CH_3OH$—$C_2H_5OH$ to yield 1.8 g (82%) of product mp 285°–287° C.

| Analysis for $C_{14}H_{18}N_2O_4S.HCl$ | |
| --- | --- |
| Calc'd | Found |
| N 8.08 | 7.97 |
| C 48.48 | 48.42 |
| H 5.52 | 5.49 |

Step E: Preparation of 3,4-dihydro-1'-[2-(2-pyridyl)ethyl]-6-methanesulfonamido-spiro[(2H)-1-benzopyran-2-4'-piperidin]-4-one dihydrochloride .monohydrate.

Under $N_2$, product from Step D (0.5 g, 0.0014 mol), 2-vinylpyridine (0.36 g, 0.0034 mol), sodium acetate trihydrate (0.45 g, 0.0033 mol), and 1:1 $CH_3OH:H_2O$ (5.4 ml) was heated at reflux for 10 hours. The reaction was then partitioned between 10% NaOH and ethyl acetate and the organic layer was discarded. The aqueous layer was then adjusted to pH 8.5 and extracted with ethyl acetate (3×). The organic extract was dried, filtered and concentrated to dryness. The residue was crystallized as the hydrochloride salt from $CH_3OH$ to yield 0.4 g (55%) of product mp 214°–215° C.

| Analysis for $C_{21}H_{25}N_3O_4S.2HCl.H_2O$ | |
| --- | --- |
| Calc'd | Found |
| N 8.30 | 8.41 |
| C 49.70 | 50.00 |
| H 5.33 | 5.51 |

METHOD 3

Step A: Preparation of 3,4-Dihydro-1'-methyl-6-nitro-spiro-[(2H)-1-benzopyran-2,4'-piperidin]-4-one Sulfuric acid (55 ml) was cooled to 0° C. and was stirred as 3,4-dihydro-1'-methyl-spiro[2H-1-benzopyran-2,4'-piperidin]-4-one (11.56 g, 0.05 mol) was added over 20 minutes. Some gum separated. A solution of 90% nitric acid (2.5 ml, 0.0525 mol) in sulfuric acid (5 ml) was added over 20 minutes. The mixture was stirred for 2 hours at 0° C. and then for 1 hour at room temperature. A solution resulted but nitration was not complete. 90% Nitric acid (0.3 ml, 0.007 mol) was added and stirring was continued for 1½ hours at room temperature. The reaction solution was poured into a mixture of ice, ethyl acetate, and sodium bicarbonate (210 g). The basic mixture was filtered, the ethyl acetate layer was separated and the aqueous layer was extracted with ethyl acetate (150 ml). The combined ethyl acetate extracts were washed with saturated NaCl, dried, filtered and concentrated in vacuo to yield 10.6 g (77%) of product Step B: Preparation of 3,4-dihydro-6-amino-1'-methyl-spiro[(2H)-1-benzopyran-2,4'-piperidin]-4-one The 3,4-dihydro-1'-methyl-6-nitro-spiro[2H -1-benzopyran-2,4'-piperdin]-4-one (11.2 g, 0.04 mol) was dissolved in acetic acid (200 ml) and was hydrogenated using two "lab spoon" spatulas of Raney nickel catalyst in a Parr shaker. The theoretical amount of hydrogen was absorbed in 4 hours. The reaction mixture was filtered under nitrogen and the acetic acid was removed in vacuo. The residual oil was taken up in 3N HCl (150 ml), washed with ethyl acetate and neutralized with solid sodium bicarbonate. The product was extracted into ethyl acetate (3×100 ml), washed with sat'd. NaCl, dried, filtered and concentrated in vacuo to yield 7.4 g (75%) of product.

Step C: Preparation of 3,4-dihydro-6-methanesulfonamido-1'-methyl-spiro[(2H)-1-benzopyran-2,4'-piperidin]-4-one 3,4-Dihydro-6-amino-1'-methyl-spiro[2H-1-benzopyran-2,4'-piperidin]-4-one (5.6 g, 0.0027 mol) was stirred in methylene chloride (50 ml) and pyridine (16 ml) at room temperature under a nitrogen atmosphere as methanesulfonyl chloride (2.7 ml, 0.035 mol) was added dropwise over several minutes. Some gum separated so additional pyridine (25 ml) was added. The mixture was stirred at ambient temperature for 16 hours. The methylene chloride and pyridine were removed in vacuo and the residue was taken up in saturated $NaHCO_3$ (150 ml) and methylene chloride (150 ml). The methylene chloride layer was separated and the aqueous phase was again extracted with methylene chloride. The combined extracts were washed with sodium bicarbonate, dried filtered and concentrated in vacuo. The residual mixture was chromatographed on silica gel (500 g) using 15% methanol/chloroform to yield 3.67 g (50%) of product.

Step D: Preparation of 3,4-dihydro-6-methanesulfonamido-1'-spiro[2H-1-benzopyran-2,4'-piperidine]-4-one hydrochloride 3,4-Dihydro-6-methanesulfonamido-1'-methyl-spiro[2H-1-benzopyran-2,4'-piperidin]-4-one (324 mg, 0.001 mol) was dissolved in dry tetrahydrofuran (10 ml) and 1-chlorethyl chloroformate (0.3 ml, 0.003 mol) was added at room temperature followed by triethylamine (0.37 ml, 0.003 mol). The mixture was stirred in an oil bath at 70° C. for 1 hour. Additional triethylamine (0.13 ml, 0.001 mol) was added and stirring at 70° C. was continued for 1 hour. The reaction mixture was concentrated to dryness in vacuo. The residue was taken up in chloroform (25 ml) and was washed with cold 3N HCL and with water, dried, filtered and concentrated in vacuo to an amber oil. This oil was refluxed in methanol (15 ml) over night. The methanol was removed in vacuo. The residual oil was triturated in ethanol (5 ml) the solid that separated, was diluted with ether (10 ml) and then filtered to obtain 246 mg (71%) of product.

Step E: Preparation of 3,4-dihydro-1'-[2-(2-pyridyl)ethyl]6-methanesulfonamido-spiro[2H-1-benzopyran-2,4'-piperidine]-4-one dihydrochloride monohydrate Prepared as described in Method 2, Step E of this Example

EXAMPLE 71

3,4-Dihydro-1'-[2-(2-pyridyl)ethyl]spiro[2H-1-benzothiopyran-2-4'-piperidine]-4-one hydrochloride hemihydrate Step A: Preparation of methyl 1-benzoyl-4-piperidinylidene acetate:

Under $N_2$, a mixture of 1-benzoyl-4-piperidone (10.2 g, 0.05 mol), methyl (triphenylphosphoranylidene) acetate (25 g. 0.074 mol) in toluene (100 ml) was heated at reflux for 7 hours. After stirring at room temperature overnight, the solid was filtered off to yield 13.9 g (100%) of triphenylphosphine oxide. The mother liquor was concentrated to dryness and the residue was treated with acetic acid (42 ml), H₂O, (6 ml) and 12N HCl (6 ml). The mixture was heated at 80°-85° C. with stirring for 15 hours. The reaction was then concentrated to dryness and the residue was partitioned between saturated Na₂CO₃ and ethyl acetate. The aqueous layer was further extracted with ethyl acetate (1×), neutralized to pH 3 with 6N HCl and extracted with ethylacetate (4×). The organic layer was dried, filtered and concentrated to dryness to yield 7.2 g (59%) of title compound.

Step B: Preparation of 3-phenylthio-1'-benzoyl-spiro[3,4'-piperidin]propionic acid Under N₂, a solution of product from Step A (10 g, 0.041 mol), thiophenol (9.0 g, 0.082 mol), and (C₂H₅)₃N (4.1 g, 0.041 mol) in THF (100 mL) was heated at reflux. After 18 hours, tetrabutylammonium fluoride (1.0 Molar in THF, 3 ml) was added. After an additional 24 hours at reflux, the reaction was concentrated to dryness. The residue was treated with 5% NaOH and the aqueous extracted with (C₂H₅)₂O (2×), acidified and extracted with ethyl acetate (3×). The organic extracts were dried, filtered and concentrated to dryness. The residue was triturated with ether and filtered to yield 13.7 g (96%) of product.

Step C: Preparation of 1'-benzoyl-3,4-dihydro-spiro[2H-1-benzothiopyran-2,4'-piperidin]-4-one Under N₂, a mixture of product from Step B (4.0 g, 0.011 mol) and concentrated H₂SO₄ (40 ml) was stirred at room temperature. After 18 hours, the reaction was poured onto ice and the aqueous was extracted with ethyl acetate (3×). The organic extracts were dried, filtered and concentrated to dryness. The residue was covered with ether and the solid was filtered off to yield 2.6 g (84%) of product.

Step D: Preparation of 3,4-dihydro-spiro[2H-1-benzothiopyran-2,4'-piperidin]-4-one.hydrochloride A solution of product from Step C (3.2 g, 0.0095 mol) in ethanol (50 ml) and 6N HCl (50 ml) was heated at reflux. After 18 hours, the reaction was concentrated to dryness and the residue crystallized from ethanol to yield 2.9 g (92%) of product.

Step E: Preparation of 3,4-dihydro-1'-[2-(2-pyridyl)ethyl]spiro[2H-1-benzothiopyran-2,4'-piperidin]-4-one.-hydrochloride.hemihydrate Under N₂, a mixture of product from Step D (0.54 g, 0.002 mol), 2-vinylpyridine (0.62 g, 0.0059 mol), NaHCO₃ (0.6 g, 0.0071 mol) in absolute ethanol (20 ml) was heated at reflux. After 24 hours, acetic acid (4 drops) was added and refluxing was continued. After 24 hours, H₂O (20 ml), and 2-vinylpyridine (2 ml) were added. After another 72 hours at reflux, the reaction was concentrated to dryness. The residue was chromatographed on silica gel (Still column, 50 mm) and the product eluted with 5% CH₃OH—CHCl₃. The compound was crystallized as the hydrochloride salt from ethanol to yield 0.62 g (80%) of product.

| Analysis for $C_{20}H_{22}N_2OS.HCl.\frac{1}{2}H_2O$ | |
|---|---|
| Calc'd | Found |
| N 7.27 | 7.30 |
| C 62.23 | 62.56 |
| H 6.11 | 6.30 |

EXAMPLE 72

1'-[2-2-Pyridylethyl]spiro[1,3-benzodithiole-2,4'-piperidine]dihydrochloride.

500 mgs (3.52 mmol) of 1,2-dimercaptobenzene and 725 mgs of 1-(2-2'-pyridylethyl)-4-piperidone in 15 mL of CH₂Cl₂ were stirred at 25° C. while anhydrous HCl gas was introduced. Na₂SO₄ (20 g) was added and stirring continued for 24 hours. The whole was diluted with H₂O and made basic with NaOH (20% aq) and extracted with CH₂Cl₂. The organic portion was dried (Na₂SO₄) filtered, concentrated and flash chromatographed over silica gel (5% methanol in CH₂Cl₂) to give 420 mgs of free base. This was converted to the dihydrochloride salt.

¹H NMR (CDCl₃) δ:2.32 (t, 4H); 2.63 (m, 4H) 2.80 (m, 2H); 2.90 (m, 2H); 7.00 (m, 2H); 7.12 (m, 1H); 7.19 (m, 2H); 7.60 (dt, 1H); 8.53 (dd, 1H).

EXAMPLE 73

5-Nitro-1'-[2-2-pyridylethyl]-spiro[1,3-benzodithiole-2,4'-piperidine dihyrochloride Step A: Preparation of 1'-benzoyl-spiro[1,3-benzodithiole-2,4'-piperidine]

500 mgs (3.52 mmol) of 1,2-dimercaptobenzene and 610 mgs (3.00 mmol) of N-benzoyl-4-piperidone were stirred in CH₂Cl₂ while anhydrous HCl gas was introduced Na₂SO₄ (2 grams) was added and the mixture stirred 15 hours. The mixture was diluted with CH₂Cl₂ filtered and washed with H₂O, and 10% NaOH. The organics were dried (Na₂SO₄) and concentrated to a solid (yield 740 mgs).

¹H NMR (CDCl₃) δ:2.30 (bm, 4H); 3.5–4.0 (bd, 4H); 7.04 (m, 2H); 7.20 (m, 2H); 7.40 (m, 5H).

Step B: Preparation of 5-Nitro-1'-benzoyl-spiro[1,3-benzodithiole-2,4'-piperidine]

7.00 grams (21.4 mmol) of the spiro dithiol ketal from Example 73 Step A in 50 mL of acetic acid cooled to 10° C. was treated dropwise with 1.35 mL of HNO₃ (d=1.49) dissolved in 10 mL of acetic acid. The reaction was allowed to warm to 25° C., and stirred for 15 hours and then poured into ice water. The aqueous phase was extracted with CH₂Cl₂ and the extract was washed with H₂O, 5% NaHCO₃ and brine, dried (Na₂SO₄), concentrated and flash chromatographed (silica-/ethyl acetate). The faster eluting component was identified as the nitration product.

¹H NMR (CDCl₃) δ:2.33 (bm, 4H); 3.50–4.00 (bm, 4H); 7.31 (d, 1H); 7.42 (m, 5H); 7.91 (dd, 1H); 8.05 (d, 1H). A slower eluting product was identified as the mono sulfoxide 1-oxa-1'benzoyl-spiro [1,3-benzodithiole-2,4'-piperidine].

¹H NMR (CDCl₃) δ=2.10 (bm, 3H); 2.45 (bm, 1H); 3.55 (bm, 3H); 4.30 (bm, 1H); 7.31 (dt, 1H); 7.43 (m, 6H); 7.48 (m, 1H); 7.85 (d, 1H).

Step C: Preparation of 5-Nitro-spiro[1,3-benzodithiole-2,4'-piperidine]

1.20 grams of the nitro dithioacetal from Step B in 46 mL of ethanol was treated with 18 mL of 40% aqueous NaOH and heated to 70° C. for 8 hours. The solution was diluted with water and extracted with CH₂Cl₂. The organics were combined, washed with water, saturated aqueous sodium carbonate, brine, dried (Na₂SO₄) and concentrated to an oil. The oil was filtered through silica gel eluting with 10% CH₃OH in CH₂Cl₂ to give the product as a yellow solid.

'H NMR (CDCl₃) δ: 2.38 (t, 4H); 2.98 (t, 4H) 7.28 (d, 1H); 7.89 (dd, 1H); 8.03 (d, 1H).

Step D: Preparation of 5-Nitro-1'-[2-2-pyridylethyl]-spiro[1,3-benzodithiole-2,4'-piperidine]dihydrochloride 50 mgs of the nitrophenyl dithioacetal from Step C and 0.75 mL of 2-vinylpyridine were stirred at 70° C. in 1.5 mL of methanol and 0.5 mL of H₂O containing 108 mgs of sodium acetate for 18 hours. The reaction mixture was concentrated to an oily residue and flash chromatographed (Silica gel 5% MeOH in CH₂Cl₂) to give 20 mgs of the product as its free base. This was converted to the dihydrochloride salt with 2M HCl in isopropanol. After trituration with ethyl acetate the salt was obtained by filtration as the hemihydrate 'H NMR of freebase (CDCl₃) δ: 2.35 (m, 4H) 2.65 (m, 4H); 2.80 (m, 2H); 3.00 (m, 2H); 7.15 (dd, 1H); 7.18 (d, 1H); 7.27 (d, 1H); 7.61 (dt, 1H); 7.89 (dd, 1H), 8.03 (d, 1H); 8.52 (d, 1H).

EXAMPLE 74

1-Oxa-1'-(2-(4-nitrophenyl)ethyl)-spiro(1,3-benzodithiole-2,4'-piperdine)hydrochloride Step A: Preparation of 1-oxa-spiro[1,3-benzodithiole-2,4'-piperdine]

The sulfoxide from Example 72, Step B was treated with ethanolic sodium hydroxide in a manner similar to that described for the nitrophenyldithioacetal in Example 73, Step C to furnish the unsubsituted piperidine product.

'HNMR (CDCl₃) δ: 1.85 (m, 1H); 2.00 (m, 1H)2.20 (m, 1H); 2.40 (m, 1H); 2.90-3.30 (m, 4H) 7.27 (m, 1H); 7.43 (m, 2H); 7.84 (d, 1H).

Step B: Preparation of 1-Oxa-1'-(2-(4-nitrophenyl)ethyl)-spiro(1,3-benzodithiole-2,4'-piperdine)hydrochloride 220 mgs of the dithioacetal monosulfoxide from Example 74, Step A and 490 mgs of 2-(4-nitrophenyl)ethyl bromide in 3 mL of ethanol containing 580 mgs of NaHCO₃ was stirred and heated to 75° C. for 20 hours. The reaction was diluted with CH₂Cl₂ and H₂O, extracted with CH₂Cl₂ and the combined organics extracted with 1N HCl (aq). The aqueous acid extract was washed twice with ether and then basified to pH 10 with 10% NaOH. The aqueous layer was extracted with ethyl acetate, dried (Na₂SO₄), concentrated to a yellow oil and dissolved in Ethyl acetate. The hydrochloride salt was formed with 2N HCl in isopropanol. After concentration and recrystalization from ethanol the product was obtained as a solid.

'H NMR of freebase (CDCl₃) δ: 1.90 (m, 1H); 2.10 (m, 1H); 2.30 (m, 1H); 2.50-2.80 (m, 5H); 2.80-3.00 (m, 2H); 2.95 (t, 2H) 7.28 (ddd, 1H); 7.37 (d, 2H); 7.42 (M, 2H); 7.82 (dd, 2H); 8.16 (d, 2H).

EXAMPLE 75

5-nitro-1'-(2-(4-nitrophenyl)ethyl-spiro(1,3-Benzodithiole-2,4'-piperidine]

267 mgs (1.0 mmol) of dithioacetal from Example 73, Step C in 1 mL of DMF was treated with 345 mgs (1.5 mmol) of 2-(4-nitrophenyl)ethyl bromide and 0.52 mL of diisopropylethylamine and was heated to 60° C. for 8 hours. The mixture was cooled to 25° C. and dissolved in ether and 1N aq. HCl. The aqueous layer was washed with ether and then basified to pH 10.0 with 20% NaOH. Extraction with ethyl acetate, drying (Na₂SO₄) of the organic extracts, and concentration gave 370 mgs of a crude yellow solid. An analytical sample was obtained by crystalization from ether mp 150°-152° C.

EXAMPLE 76

5-Methanesulfonamido-1'-(2-(4-methanesulfonamidophenyl)ethyl-spiro[1,3-benzodithiole-2,4'-piperidine] hydrochloride Step A: Preparation of 5-amino-1'-(2-(4-aminophenyl) ethyl-spiro(1,3-benzodithiole-2,4'-piperidine The compound from Example 75 was dissolved in 4.5 mL of acetic acid at 25° C. and treated dropwise over 2 hours with 15% TiCl₃ in aqueous HCl (15 mL). The mixture was diluted with CH₂Cl₂ and H₂O, the pH adjusted to a 10 with 20% aq. NaOH and extracted with CH₂Cl₂ (3×). The combined organic layers were washed with saturated aq Na₂CO₃ dried (Na₂SO₄) and concentrated to an oil which crystallized from ether to give 300 mg of a pale yellow solid.

'H NMR (CDCl₃) δ: 2.35 (m, 4H); 2.70 (m, 8H); 3.58 (bs, 4H); 6.38 (dd, 1H); 6.58 (d, 1H); 6.63 (d, 2H) 6.95 (d, 1H); 6.99 (d, 2H)

Step B: Preparation of 5-Methanesulfonamido-1'-(2-(4-methanesulfonamidophenyl)ethyl-spiro [1,3-benzodithiole-2,4'-piperidine] hydrochloride 100 mgs (0.28 mm) of the bis-aniline from Step A was dissolved in 1 mL of CH₂Cl₂, cooled to −10° C., and treated with diisopropylethylamine (0.29 mL) followed by 0.11 mL of methanesulfonyl chloride. The reaction was stirred for 2 hours and allowed to warm to 0° C. The mixture was diluted with CH₂Cl₂ and washed with saturated aq. Na₂CO₃ and brine, dried (Na₂SO₄), and concentrated to a foam. The foam was redissolved in methanol and THF (10 mL;) and stirred at 25° C. while 5% aqueous NaOH was added (0.5 mL). The mixture was diluted with CH₂Cl₂ and washed with saturated aqueous NaHCO₃, dried (Na₂SO₄) and concentrated to a foam. The foam was dissolved in ethyl acetate/methanol and 2M HCl in isopropanol was added to give an off-white precipitate of the hydrochloride salt. Yield 66 mg.

'H NMR (DMSO, d₆) δ: 2.58 (m, 2H); 2.95 (s, 3H); 3.00 (s, 3H); 3.15 (m, 4H); 3.40 (m, 4H); 3.60 (m, 2H) 6.98 (m, 1H); 7.23 (m, 6H); 9.70 (s, 1H); 9.80 (d, 1H); 10.70 (m, 1H).

EXAMPLE 77

5-Methanesulfonamido-1'-(2-(2-pyridyl)ethyl-spiro[1,3-benzodithiole-2,4'-piperidine] dihydrochloride Nitrophenyldithioacetal (163 mg) from Example 73, Step D was dissolved in 8 mL of ethanol and treated with 1.60 grams of SnCl₂.2 H₂O at 25° C. The mixture was heated to 70° C. for 2 hrs., poured into saturated aqueous Na₂CO₃, and extracted with CH₂Cl₂. The organic portion was washed with H₂O, dried (Na₂SO₄), and concentrated to a foam to give 120 mgs of crude aniline compound. The crude aniline was dissolved in 2 mL of pyridine and treated with 0.05 mL of methanesulfonyl chloride at 25° C. After stirring for 12 hrs the mixture was diluted with CH₂Cl₂ and washed with aqueous NaHCO₃, dried (Na₂SO₄) and concentrated to a foam. The foam was converted to a dihydrochloride salt from ethanol using 2M HCl in isopropanol. Yield, 90 mgs 'H NMR (DMSO, d₆) δ2.60 (m, 4H); 3.02 (s, 3H) 3.40 (m, 6H); 3.60 (m, 2H); 6.98 (dd, 1H); 7.18 (d, 1H) 7.34 (d, 1H); 7.55 (bt, 1H); 7.61 (bd, 1H); 8.08 (bt, 1H); 8.77 (d, 1H); 9.80 (s, 1H).

EXAMPLE 78

1'-(2-(2-Pyridyl)ethyl)-spiro(4H-1,3-benzodithiin-2,4'-piperidine) dihydrochloride 2-Mercaptobenzylmercaptan (110 mg, 0.70 mmol) in 2.0 mL of $CH_2Cl_2$ was stirred with N-[2-(2'-pyridyl)ethyl]-4-piperidone hydrochloride (163 mg, 0.63 mmol) while anhydrous hydrochloride acid was introduced via a gas inlet tube. Anhydrous $MgSO_4$ (0.50 grams) was added after saturation with HCl, and stirring was continued for 15 hrs. The crude mixture was diluted with water and basified to pH 10 with aqueous 10% NaOH. The mixture was extracted with $CH_2Cl_2$, and the extract was dried ($Na_2SO_4$) and concentrated to give a crude oil which was dissolved in ethyl acetate. Anhydrous HCl in isopropanol (2N) was added to give the dihydrochloride salt which was collected by filtration and recrystallized from $CH_3OH$/ethyl acetate.

'H NMR (DMSO, $d_6$) δ: 2.34 (m, 4H); 3.20–3.70 (m, 8H) 3.97 (s, 2H); 7.15–7.70 (m, 4H); 7.70 (m, 2H); 8.18 (m, 1H); 8.70 (d, 1H); 11.35 (bs, 1H).

EXAMPLE 79

1-(2-(4-Nitrophenyl)ethyl)spiro-(4H-1,3-benzodithiin-2,4'-piperidine)

Step A: Preparation of spiro-(4H-1,3-benzodithiin-2,4'-piperidine)

To 2.86 grams (0.018 mol) of 2-mercaptobenzyl mercaptan in 100 mL of $CH_2Cl_2$ was added 3.72 grams of 4-N-benzoylpiperidone. Anhydrous HCl gas was introduced and the reaction was stirred for 15 hrs at 25° C. $MgSO_4$ (anhydrous, 3.00 grams) was introduced and the reaction stirred 8 hrs then diluted with $CH_2Cl_2$, filtered and washed with $H_2O$, 5% NaOH (aq) and $H_2O$. The organic phase was dried ($Na_2SO_4$) and concentrated to an oil (1.85 grams). The crude oil was dissolved in 20 mL of ethanol and 7.2 mL of 40% aqueous NaOH, heated to 70° C. for 15 hrs and then concentrated to remove ethanol. The product was obtained by extraction with $CH_2Cl_2$ of the remaining aqueous phase. Yield 1.08 grams of product as an oil.

'H NMR ($CDCl_3$) δ:1.98 (m, 4H); 2.90 (m, 2H) 3.04 (m, 2H); 3.82 (s, 2H); 7.18–7.28 (m, 3H); 7.36 (m, 1H)

Step B: Preparation of 1-(2-(4-nitrophenyl)ethyl) spiro-(4H-1,3-benzodithiin-2,4'-piperidine)

To 111 mgs (0.47 mmol) of dithioketal from Step A in 1 mL of methanol was added 157 mgs of sodium bicarbonate and 118 mg (0.54 mmol) of 2-(4-nitrophenyl)ethyl bromide. The reaction was refluxed for 6 hrs and then concentrated at reduced pressure. The residue was chromotographed (silica gel, 2.5% $CH_3OH/CH_2Cl_2$) to give after concentration and crystallization from ethyl acetate/Hexanes, 120 mgs of product as the free base.

'H NMR ($CDCl_3$) δ:2.06 (m, 4H); 2.55 (m, 2H) 2.70 (m, 4H); 2.89 (dd, 2H); 3.82 (s, 2H); 7.25 (m, 3H); 7.35 (m, 3H); 8.14 (m, 2H).

EXAMPLE 80

1-(2-(4-(Methanesulfonamidophenyl)ethyl-spiro(4H-1,3-benzodithiin-2,4'-piperidine) hydrochloride The nitrophenyl piperidine (75 mg) from Example 79 Step B was dissolved in 50% aqueous acetic acid and treated dropwise with 15% $TiCl_3$ in 20–30% aqueous HCl until the reaction was complete by TLC.

The mixture was diluted with water and extracted with $CH_2Cl_2$, the aqueous phase was basified to pH 10 with 40% aqueous NaOH and extracted with $CH_2Cl_2$. The organic extracts from the base were dried ($Na_2SO_4$) and concentrated to yield 40 mgs of crude aniline. The product was dissolved in 1 mL of $CH_2Cl_2$, cooled to −10° C., and treated with 0.070 mL of triethylamine. Methanesulfonyl chloride was added (0.03 mL) and the mixture held below 0° C. for 1 hr. Water (1 mL), 40% aqueous NaOH (10 drops) and methanol (10 mL) were added and the reaction was allowed to reach 25° C. and then concentrated to remove methanol and $CH_2Cl_2$. The pH was adjusted to ~6.0 and extracted with $CH_2Cl_2$. The organic portion was concentrated to an oil, dissolved in ethanol/ethyl acetate (1/1) and treated with anhydrous 2M HCl in isopropanol. Concentration of the solvents and trituration with ethyl acetate gave 50 mgs of a solid hydrochloride salt.

'H NMR (DMSO $d_6$) δ:2.30 (m, 4H); 3.00 (s, 3H) 3.10 (m, 2H); 3.35 (m, 6H); 3.95 (s, 1H); 4.05 (s, 1H); 7.15–7.50 (m, 8H); 9.72 (s, 1H).

EXAMPLE 81

6-Nitro-1'-(2-(2-pyridyl)ethyl)-spiro[4H-3,1-Benzoxathiin-2,4'-piperidine]

2-Mercapto-5-nitrobenzyl alcohol (150 mg, 0.81 mmol) and 208 mg (0.80 mm) of N-[2-(2'-pyridylethyl]-4-piperidone was dissolved in 5 mL of $CHCl_3$. HCl Gas was bubbled in to saturate the solution, the mixture stirred at 25° C. for 2 days, then diluted with water and the pH adjusted to 10.0 with 40% aqueous NaOH. Extraction with $CHCl_3$ and drying the organic phase ($Na_2SO_4$) gave after concentration and recrystallization from ethyl acetate 75 mg of an orange solid.

'H NMR ($CDCl_3$) δ:2.15 (m, 4H); 2.70 (m, 4H); 2.83 (dd, 2H); 3.01 (dd, 2H); 4.95 (s, 2H); 7.15 (dd, 1H); 7.20 (m, 2H); 7.62 (dt, 1H); 7.95 (d, 1H); 8.03 (dd, 1H); 8.54 (d, 1H).

EXAMPLE 82

1'-(2-(4-Nitrophenyl)ethyl)-spiro[3H-4-oxo-1,3-Benzoxazine-2,4'-piperidine]

Salicylamide (250 mg, 1.82 mmol) and 1-(2-[4-nitrophenyl]ethyl-4-piperidone (238 mg, 0.96 mmol) in 13 mL of $CHCl_3$ was stirred while 400 mgs of p-toluenesulfonic acid monohydrate was added. The mixture was refluxed for 12 hours through a Soxhlet apparatus containing anhydrous $MgSO_4$ to remove $H_2O$ formed. The mixture was concentrated to dryness and dissolved with 10% aqueous NaOH and ethyl acetate. The aqueous phase was separated and extracted with ethyl acetate. The combined organic portions were washed with brine, dried ($Na_2SO_4$) and concentrated to a yellow solid to give 280 mg and converted to the hydrochloride salt with 2N HCl in isopropanol. The solid was triturated with ethyl acetate/ether and dried in vacuo.

'H NMR (DMSO $d_6$) δ:2.25 (m, 4H); 3.10–3.60 (m, 8H); 7.10 (d, 1H); 7.18 (t, 1H); 7.60 (m, 3H); 7.79 (d, 1H); 8.22 (d, 2H); 9.04 (s, 1H); 10.52 (bs, 1H).

EXAMPLE 83

6-Methanesulfonamido-1'-[(2-(benzofurazan-5-yl)ethyl] 3,4-dihydrospiro[(2H)-1-benzopyran-2,3'-piperidine]-4-one A solution of 500 mg (1.44 mmole) of 6-methanesulfonamido-3,4-dihydrospiro-2H-benzopyran-2,3'-piperidine-4-one hydrochloride in 10 mL acetonitrile was treated with 400 mg (1.7 mmoles) of 5-(2-bromoethyl)-benzofurazan, 190 mg (1.44 mmole) of lithium iodide and 250 mg (3 mmoles) of sodium bicarbonate. The mixture was heated to reflux for 48 hrs, cooled to room temperature and poured into 50 mL H$_2$O. The mixture was acidified to pH 1 and extracted with 2×50 mL portions of ethyl acetate which were discarded. The aqueous phase was basified to pH 8-9 and extracted with ethyl acetate. The organic layers were dried over magnesium sulfate, filtered and concentrated in vacuo. The crude material was chromatographed on silica gel eluting with 5% methanol/chloroform to give 188 mg product. This material was dissolved in ethanol and treated with excess ethanolic HCl. The solid was collected and dried in vacuo to give 108 mg of the product with m.p. 255°-257° C.

| Elemental analysis for C$_{22}$H$_{24}$N$_4$O$_5$S.HCl.$\frac{1}{4}$H$_2$O | | | |
|---|---|---|---|
| | N | C | H |
| Calc'd | 11.26 | 53.11 | 5.16 |
| Found | 11.12 | 53.20 | 5.13 |

EXAMPLE 84

6-Methanesulfonamido-1'-(2-(4-methanesulfonamidophenyl)ethyl-3,4-dihydrospiro-[(2H)-1-benzopyran-2,3'-piperidine]-4-one oxalate The title compound was prepared following the procedure substantially as described in Example 83 but using 4-methanesulfonamidophenylethyl mesylate. The product has mp. 195°-199° C.

| Elemental analysis for C$_{23}$H$_{29}$N$_3$O$_6$S$_2$.$\frac{1}{2}$C$_2$H$_2$O$_4$.H$_2$O | | | |
|---|---|---|---|
| | N | C | H |
| Calc'd | 7.49 | 51.42 | 5.57 |
| Found | 7.52 | 51.32 | 5.23 |

EXAMPLE 85

1'-(2-(4-Methanesulfonamidophenyloxy)ethyl)-2,3-dihydro-5-methanesulfonamido spiro (benzofuran-2,3'-piperidine oxalate A solution of 300 mg (0.94 mmoles) 2,3-dihydro-5-methanesulfonamido-spiro(benzofuran-2,3'-piperidine hydrochloride in 20 mL acetonitrile was treated with 304 mg (1.035 mmole) of 2-(4-methanesulfonamidophenoxy)ethyl bromide, 170 mg (2 mmole) of sodium bicarbonate and 134 mg (1 mmole) of lithium iodide. The mixture was heated to reflux for 24 hr. The reaction was cooled to room temperature, and poured into 50 mL of 1N HCl. The aqueous phase was extracted once with ethyl acetate which was basified to pH 9 and extracted repeatedly with ethyl acetate. The organics were combined, dried over magnesium sulfate; filtered and concentrated in vacuo to give 220 mg. The crude material was dissolved in acetone and treated with 50 mg oxalic acid. The solid was collected to give 168 mg of product with mp 125°-130° C.

| Elemental analysis for C$_{22}$H$_{29}$N$_3$O$_6$S$_2$.C$_2$H$_2$O$_4$.H$_2$O.C$_3$H$_6$O | | | |
|---|---|---|---|
| | N | C | H |
| Calc'd | 6.64 | 48.40 | 5.73 |
| Found | 6.52 | 48.63 | 5.50 |

EXAMPLE 86

1-(Benzofurazan-5-methyl)spiro[piperidine-4,6'-(6H)thieno[2,3-b]thiopyran-4'(5'H)-one]

Step A: Preparation of 5-Methanesulfonyloxymethyl)benzofurazan

5-Benzofurazanmethanol (0.6 g, 4 mmol) and triethylamine (0.84 mmol, 0.61 g, 6 mmol) were dissolved in dichloromethane (20 ml) and cooled to −20° C. Methanesulfonyl chloride (0.37 ml, 0.55 g, 4.8 mmol) was added dropwise and the mixture was stirred at −20° C. for 20 min., diluted with dichloromethane (30 ml) washed with water (30 ml), dried (Na$_2$SO$_4$), and evaporated under reduced pressure to give the benzofurazan as a white solid (0.91 g, 99%). $^1$H NMR (CDCl$_3$) δ7.95 (1H, d, j 9.2 Hz), 7.93 (1H, s), 7.46(1H, d, J 9.2 Hz), 5.35 (2H, s), 3.14 (3H, s).

Step B: Preparation of 1-(Benzofurazan-5-methyl)-spiro[piperidine-4,6'-(6H)thieno[2,3-b]thiopyran-4'(5'H)-one]

5-(Methanesulfonyloxymethyl)benzofurazan (137 mg, 0.6 mmol) and diisopropylethylamine (0.52 ml, 0.39 g, 3 mmol) were dissolved in DMF (2 ml) and spiro(-piperidine-4,6'-(6H)thieno[2,3-b]thiopyran)-4'-(5'H)-one hydrochloride(248 mg, 0.9 mmol) was added. The mixture was stirred at room temperature for 2 h and then the solvent was evaporated under reduced pressure. Aqueous sodium bicarbonate (saturated, 10 ml) was added and the mixture was extracted with dichloromethane (3×10 ml). The combined organic fractions were dried (Na$_2$SO$_4$) and evaporated under reduced pressure to give a yellow oil. The oil was purified by flash column chromatography on silica gel, eluting with ethyl acetate/40% hexane to give an off white solid (192 mg, 86%). The compound was crystallized from ethyl acetate/hexane to give the thiopyranone, m.p. 142°-143° C.

$^1$H NMR (CDCl$_3$) δ7.81 (1H, d, J=9.3 Hz), 7.71 (1H, s), 7.50 (1H, d, J 9.3 Hz), 7.46 (1H, d, J 5.4 Hz), 7.06 (1H, d, J 5.4 Hz), 3.64 (2H, s), 2.88 (2H, s), 2.70, 2.54, 2.10, 1.90 (Each 2H, m).

Elemental analysis for C$_{18}$H$_{17}$N$_3$O$_2$S$_2$: Calculated; C 58.20; H 4.61; N 11.31. Found; C 58.42; H 4.53; N 11.35.

EXAMPLE 87

1-(Benzofurazan-5-methyl)spiro(4H-1,3-benzodithiin-2,4'piperidine)

5-(Methanesulfonyloxymethyl)benzofurazan (91 mg, 0.4 mmol) in DMF (0.5 ml) was added dropwise to a stirred solution of spiro (4H-1,3-benzodithiin-2,4'-piperidine) (142 mg, 0.6 mmol) prepared as in Example 79, Step A and diisopropylethylamine (0.35 ml, 0.26 g, 2 mmol) in DMF (1 ml). The mixture was stirred at room temperature for 1 h. then the solvent was evaporated under reduced pressure. The residue was purified by flash column chromatography on silica gel, eluting with hexane/40% EtOAc and the product was crystallized from ethyl acetate/Hexane to give the benzodithiin as microcrystals (64 mg, 43%), m.p. 82°-83° C.

$^1$H NMR (CDCl$_3$) δ7.77 (1H, d,J=9.3 Hz), 7.69 (1H, s), 7.48 (1H, d, J=9.3 Hz), 7.38-7.21 (4H m), 3.83 (2H, s), 3.59 (2H, s), 2.73-2.66 (2H, m), 2.57-2.50 (2H, m), and 2.10-2.04 (4H, m).

Elemental analysis for C$_{19}$H$_{19}$N$_3$OS$_2$: Calculated; C 61.76; H 5.18; N 11.37. Found; C 61.64; H 5.14; N 11.36.

EXAMPLE 88

3,4-Dihydro-1'-(benzofurazan-5-methyl)spiro[2H-1-benzopyran-2,4'-piperidine]-4-one In the same way, 5-(methanesulfonyloxymethyl) benzofurazan (91 mg, 0.4 mmol), 3,4-dihydrospiro[2H-1-benzopyran-2,4'-piperidine]-4-one (130 mg, 0.6 mmol) and diisopropylethlamine (0.35 ml, 0.26 g, 2 mmol) in DMF (1.5 ml) gave, after purification by flash column chromatography on silica gel eluting with EtOAc/40% hexane and crystallization from EtOAc/hexane, the benzopyranone as rods (70 mg, 50%), m.p. 126°–127° C.

'H NMR (CDCl$_3$) δ7.86 (1H, dd, J=8.0, 1.7 Hz), 7.78 (1H, d, J 9.3 Hz), 7.70 (1H, s), 7.5 (2H m), 7.0 (2H, m), 3.62 (2H, s), 2.74 (2H, s), 2.6 (4H, m), 2.1 (2H, m) 1.8 (2H, m).

Elemental analysis for $C_{20}H_{19}N_3O_3.0.33H_2O$: Calculated; C 67.59; H 5.58; N 11.82. Found; C 67.45; H 5.40; N 11.82.

EXAMPLE 89

3,4-Dihydro-1'-(benzofurazan-5-yl)ethyl]spiro[2H-1-benzopyran-2,4'-piperidine]-4-one Step A: Preparation of 5-(2-Hydroxyethyl)benzofuroxan 4-(2-Acetoxyethyl)-2-nitroacetanilide (4.16 g, 15.6 mmol) was dissolved in methanol (25 ml) and methanolic potassium hydroxide (20% 25 ml) was added dropwise. The mixture was stirred at room temperature for 40 min., then cooled in ice. Aqueous sodium hypochlorite (Ca. 5%, 50 ml) was added dropwise over 30 min., with vigorous stirring. Water (50 ml) was added and the mixture was extracted with dichloromethane (3×100 ml). The combined organic fractions were dried (Na$_2$SO$_4$) and evaporated under reduced pressure to give the benzofuroxan as a yellow oil (2.76 g, 98%).

'H NMR (CDCl$_3$) δ7.6–6.1 (3H, br m), 3.95 (2H, t, J=6.2 Hz), 2.91 (2H, t J=6.2 Hz), 2.1 (1H br s).

Step B: Preparation of 5-(2-Hydroxyethyl)benzofurazan 5-(2-Hydroxyethyl)benzofuroxan (2.23 g, 12. 4 mmol) was dissolved in methanol (25 ml) and trimethylphosphite (4.38 ml, 4.60g, 37.1 mmol) was added. The mixture was heated under reflux for 3h., cooled and the solvent was evaporated under reduced pressure. The residue was purified by flash column chromatography on silica gel eluting with Et$_2$O to give the benzofurazan as a yellow oil (1.52 g, 75%).

$^1$H NMR (CDCl$_3$) δ7.78 (1H, d, J=9.2 Hz), 7.65 (1H, s) 7.34 (1H, d, J 9.2 Hz), 3.98 (2H, t J=6.3 Hz), 2.98 (2H, t J=6.3 Hz), 1.9 (1H, br s).

Step C: Preparation of 5-[2-(Methanesulfonyloxy)ethyl]benzofurazan 5-(2-Hydroxyethyl)benzofurazan (1.48 g, 9 mmol) was dissolved in dichloromethane (45 ml) and triethylamine (1.88 ml, 1.37 g, 13.5 mmol) was added. The mixture was cooled to −30° C. and methanesulfonyl chloride (0.84 ml, 1.24 g, 10.8 mmol) was added dropwise over 5 min. The mixture was stirred at −30° C. for 15 min. and dichloromethane (100 ml) was added. The mixture was washed with water (100 ml), dried (Na$_2$SO$_4$) and evaporated under reduced pressure to give the benzofurazan as a yellow solid (2.10 g, 96%).

$^1$H NMR (CDCl$_3$) δ7.83 (1H, d, J=9.5 Hz), 7.70 (1H, s), 7.32 (1H, d, J=9.5 Hz), 4.53 (2H, t, J=6.4 Hz) 3.19 (2H, t, J=6.4 Hz), 2.99 (3H, s).

Step D: Preparation of 3,4-Dihydro-1'-[2-benzofurazan-5-yl)ethyl]spiro[2H-1-benzopyran-2,4'-piperidine]-4-one:

5-[2-(Methanesulfonyloxy)ethyl]benzofurazan (169 mg, 0.7 mmol) in DMF (1 ml) was added to a stirred mixture of 3,4-dihydrospiro[2H)-1-benzopyran-2,4'-piperidine]-4-one (266 mg, 1.05 mmol) and diisopropylethylamine (0.61 ml, 0.45 g, 3.5 mmol) in DMF (1 ml). The mixture was stirred at room temperature for 28 h, then at 50° C. for 1 hr. The solvent was evaporated under reduced pressure and the residue was purified by flash column chromatography on silica gel, eluting with CH$_2$Cl$_2$/MeOH/NH$_3$(Aq.) (96:4:0.4). The appropriate fractions were combined and concentrated to dryness and the residue was recrystallized from ethyl acelate/hexane to give the benzopyranone as pale yellow microcrystals (20 mg, 8%), m.p. 117°–119° C.

$^1$H NMR (CDCl$_3$) δ7.86 (1H, dd, J 8.2, 2.7 Hz) 7.76 (1H, d, J 9.3 Hz), 7.61 (1H, br s), 7.50 (1H, dt, Jt 7.8, Jd 1.7 Hz), 7.30 (1H, dd, J 9.3, 1.2 Hz), 7.0 (2H, m), 2.92 (2H, t, J 7.5 Hz), 2.73 (6H m), 2.54 (2H, m) 2.09 (2H, m), 1.79 (2H, m).

Elementary analysis for $C_{21}H_{21}N_3O_3.0.1H_2O$: Calculated; C 69.06; H 5.85; N 11.50. Found; C 68.97; H 5.90; N 11.16.

EXAMPLE 90

1-[2-(Benzofurazan-5-yl)ethyl]spiro[(5'H)piperidine-4,-6'-(6H)thieno[2,3-b]thiopyran-4'(5'H)-one] hydrochloride Spiro(piperidine-4,6'-(6H)thieno[2,3-b]thiopyran)-4'(5'H)-one](230 mg, 0.82 mmol), 5-[2-(methanesulfonyloxy)ethyl]benzofurazan (100 mg, 0.41 mmol) and sodium bicarbonate (72 mg, 0.86 mmol) in DMF (8 ml) were stirred together at 80° C. overnight. The solvent was evaporated under reduced pressure and the residue was dissolved in dichloromethane, washed with water, dried (Na$_2$SO$_4$) and evaporated under reduced pressure. The residue was purified by flash column chromatography on silica gel eluting with EtOAc/75% hexane, treated with ethanolic HCl and recrystallized from EtOH/EtOAc to give the hydrochloride as an off-white solid (17 mg, 10%), m.p. 255°–257 ° C.

Elementary analysis for $C_{19}H_{21}N_3O_2S_2$.HCl: Calculated; C 54.07; H 4.79; N 9.96. Found C 53.96; H 4.66; N 9.87.

EXAMPLE 91

1'-[2-(benzofurazan-5-yl)ethyl]-2,3-dihydrospiro-(benzofuran-2,4'-piperidine) hydrochloride 2,3-Dihydrospiro(benzofuran-2,4'-piperidine) (hydrochloride, 50 mg, 0.21 mmol), 5-[2-methanesulfonyloxy)ethyl]benzofurazan (50 mg, 0.22 mmol) and sodium bicarbonate (40 mg, 0.48 mmol) in ethanol (4 ml) were stirred together under reflux overnight. The solvent was evaporated under reduced pressure and the residue was dissolved in dichloromethane, washed with water, dried (Na$_2$SO$_4$) and evaporated under reduced pressure. The residue was purified by flash column chromatography on silica gel eluting with EtOAc/40% hexane, treated with ethanolic HCl and triturated with EtOAc to give the hydrochloride as an off-white solid (14 mg, 17%), m.p. 225°–257° C.

Elementary analysis for $C_{20}H_{21}N_3O_2$.HCl; Calculated; C 63.82; H 6.04; N 11.17. Found C 64.06; H 6.10; N 11.23.

EXAMPLE 92

3,4-Dihydro-1'-[2-(benzofurazan-5-oxy)ethyl]-6-methanesulfonamido-spiro[(2H)-1-benzopyran-2,4'-piperidine]-4-one hydrochloride Step A: Preparation of 5-(2-Bromoethoxy)benzofurazan:

Sodium hydroxide (40 mg, 1 mmol) was added to a solution of 5-hydroxybenzofurazan (136 mg, 1 mmol) in ethanol (2 ml) and the mixture was stirred at room temperature for 30 min. 1,2-dibromoethane (0.26 ml, 0.56 g, 3 mmol) was added and the mixture was heated under reflux for 20 hr., cooled and the solvent was evaporated under reduced pressure. Aqueous sodium bicarbonate (saturated, 10 ml) was added and the mixture was extracted with dichloromethane (3×10 ml). The combined organic fractions were dried ($Na_2SO_4$) and evaporated under reduced pressure. The residue was purified by flash column chromatography on silica gel, eluting with hexane/10% EtOAc to give the benzofurazan as a pale yellow oil (99 mg, 41%).

$^1H(CDl_3)$ δ7.74 (1H, d J 9.6 Hz), 7.16 (1H, dd, J 9.6, 2.0 Hz), 6.85 (1H, d, J 2.0 Hz) 4.39 (2H, t J 6.0 Hz), 3.72 (2H, t, J 6.0 Hz).

Step B: Preparation of 3,4-Dihydro-1'-[2-(benzofurazan-5-oxy)ethyl]-6-methanesulfonamidospiro[(2H)-1-benzopyran-2,4'-piperidine]-4-one hydrochloride:

5-(2-Bromoethoxy)benzofurazan (87 mg, 0.36 mmol), 3,4-Dihydro-6-methanesulfonamidospiro[(2H)-1-benzopyran-2,4'-piperidine]-4-one hydrochloride (125 mg, 0.36 mmol), sodium bicarbonate (91 mg, 1.08 mmol) and potassium iodide (30 mg, 0.18 mmol) in acetonitrile (4 ml) were heated under reflux for 24 hr, cooled and aqueous sodium bicarbonate (saturated, 10 ml) was added. The mixture was extracted with dichloromethane (3×10 ml) and the combined organic fractions were dried ($Na_2SO_4$) and evaporated under reduced pressure. The residue was purified by flash column chromatography on silica gel, eluting with $CH_2Cl_2$/MeOH/$NH_3$ (97:3:0.3), to give a yellow foam which was dissolved in EtOAc (2 ml). Ethanolic HCl (Ca. 1M, 2 ml) was added, the mixture was stirred for 2 h. and the solid was collected and dried in vacuo to give the hydrochloride as a white solid (114 mg, 62%), m.p.>250° C.

$^1H$ NMR (DMSO) δ11.2–10.8 (1H, br m), 9.68 (1H br s), 8.0–7.1 (6H, m), 4.6 (2H, br s), 3.6–3.2 (6H, m) 2.92 (3H, s), 2.84 (2H s), 2.1 (4H, m).

Elementary analysis for $C_{22}H_{24}N_4O_6S.HCl.0.25H_2O$; Calculated: C 51.46; H 5.01; N 10.91. Found C 51.45; H 5.05; N 10.61.

EXAMPLE 93

1-[2-(4-Nitrophenyl)ethyl]spiro[piperidine-4,2'-(1',2',3',4'-tetrahydroquinazolin)]-4'-one hydrochloride 2-Aminobenzamide (272 mg, 2 mmol) and 1-[2-(4-nitrophenyl)ethyl]-4-piperidone (0.51 g, 2.05 mmol) in trifluoroacetic acid (10 ml) were heated under reflux for 8 hr, cooled and the solvent was evaporated under reduced pressure. Dichloromethane (30 ml) and sodium hydroxide (2M, 30 ml) were added and the layers were separated. The aqueous layer was extracted with dichloromethane (2×30 ml) and the combined organic fractions were dried ($Na_2SO_4$) and evaporated under reduced pressure. The residue was purified by flash column chromatography on silica gel, eluting with $CH_2Cl_2$/MeOH/$NH_3$ (Aq) (95:5:0.5), to give a pale yellow solid which was dissolved in THF (50 ml) and treated with ethanolic HCl (Ca. 1M, 10 ml). The solvent was evaporated under reduced pressure and the solid was triturated with ethanol to give the hydrochloride as a pale yellow solid (0.43 g, 53%), m.p. 285°–290° C.

$^1H$ NMR (CDCl₃) δ10.95 10.35 (Each 0.5H, br s), 8.36 (1H br s), 8.23 (2H, d, J 8.6 Hz), 7.62 (1H, m), 7.60 (2H, d, J 8.6 Hz) 7.28 (1.5H, m), 7.08 (0.5H, br s) 6.96, 6.78 (Each 0.5H, d, J 8.1 Hz), 6.70 (1H, m), 3.6–3.2 (8H, m), 2.1 (4H, m).

Elementary analysis for $C_{20}H_{22}N_4O_3.HCl$; Calculated: C 59.62; H 5.75; N 13.91. Found C 59.23; H 5.51 ; N 13.79.

EXAMPLE 94

3,4-Dihydro-1'-[2-(benzofurazan-5-yl)ethyl]-6-methanesulfonamido spiro[(2H)-1-1-benzopyran-2,4'-piperidine]-4-one hydrochloride Step A: Preparation of 5-(2-Bromoethyl) benzofurazan A solution of 5-(2-hydroxyethyl)benzofurazan (1.0 g, 6.1 nmol) and carbon tetrabromide (2.6 g, 7.9 nmol) in methylene chloride (10 ml) was cooled to 0° C. A solution of triphenyl phosphine (1.9 g, 7.3 nmol) in methylene chloride (10 ml) was added dropwise and the reaction was stirred for 5 min. Solvent evaporation and flash chromatography (silica gel, ethyl acetatehexane, 5/95) gave 5-(2 bromoethyl)benzofurazan (1.2 g, 86%).

$^1H$ NMR (CDCl₃) δ3.32 (t, 2H), 3.69 (t, 2H), 7.32 (d, 1H), 7.69 (s, 1H), 7.84 (d, 1H).

Step B: Preparation of 3,4-Dihydro-1'-[2-(benzofurazan-5-yl)ethyl]-6-methanesulfonamidospiro[(2H)-1-benzopyran-2,4'-piperidine]-4-one hydrochloride A suspension of 5-(2-bromoethyl)benzofurazan (0.39 g, 1.72 mmol), 3,4-dihydro-6-methanesulfonamido spiro[(2H)-1-benzopyran-2,4'-piperidine]4-one hydrochloride (0.24 g, 0.69 mmol) and sodium bicarbonate (0.21 g, 2.55 mmol) in ethanol (13.2 ml) was heated at reflux temperature for 24 hr. Solvent evaporation and chromatography (silica gel, chloroform-methanol-ammonium hydroxide, 97/3/0.3) gave an oil; conversion to the hydrochloride gave the hydrochloride (0.14 g, 41%); mp>250° C. Anal. Calcd for $C_{22}H_{24}N_4O_3.HCl$: C, 53.59; H, 5.12; N, 11.37. Found: C, 53.55; H, 5.15; N, 11.12.

Employing the procedure substantially as described in Example 94, Step B but substituting for the 3,4-dihydro-6-methanesulfonamidospiro[(2H)-1-benzopyran-2,4'-piperidine]-4-one used therein, the starting materials shown in Table III, there are produced the N-substituted spiro-piperidines also described in Table III.

TABLE III

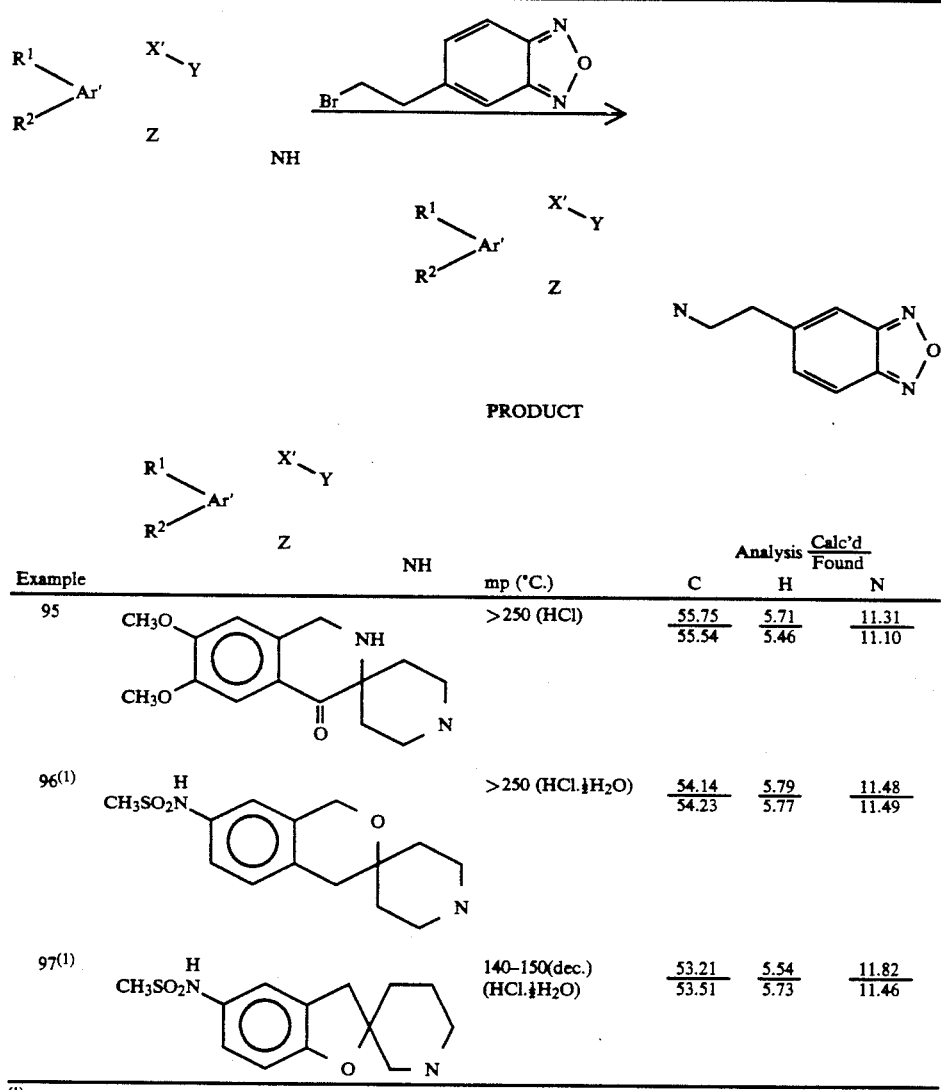

| Example | | mp (°C.) | Analysis Calc'd/Found C | H | N |
|---|---|---|---|---|---|
| 95 | CH₃O-/CH₃O-Ar-CH₂-NH-C(=O)-piperidine | >250 (HCl) | 55.75/55.54 | 5.71/5.46 | 11.31/11.10 |
| 96⁽¹⁾ | CH₃SO₂NH-Ar-CH₂-O-piperidine | >250 (HCl·½H₂O) | 54.14/54.23 | 5.79/5.77 | 11.48/11.49 |
| 97⁽¹⁾ | CH₃SO₂NH-Ar-(fused)-O-piperidine | 140-150(dec.) (HCl·½H₂O) | 53.21/53.51 | 5.54/5.73 | 11.82/11.46 |

⁽¹⁾Catalytic amount of LiI added to reaction mixture

EXAMPLE 98

3,4-Dihydro-6-acetamido-1'-(4-nitrobenzyl)-spiro[(2H)1-benzopyran-2,4'-piperidine]-4-one hydrochloride A solution of 4-nitrobenzyl bromide (0.73 g, 3.4 mmol), 3,4-dihydro-6-acetamido spiro[(2H)-benzopyran-2,4'-piperidine]-4-one (0.94 g, 3.4 mmol) and diisopropylethylamine (0.61 ml, 3.5 mmol) in dimethylformamide (15 ml) was stirred at room temperature for 3 hr. The reaction mixture was then concentrated under reduced pressure. The residue was diluted with methylene chloride and washed with saturated sodium bicarbonate solution, water and brine. Drying and solvent evaporation gave an oil; flash chromatography (silica gel, methanol-chloroform 2/98) gave 3,4-dihydro-6-acetamido-1'-(4-nitrobenzyl)spiro[(2H)-1-benzopyran-2,4'-piperidine]-4-one (0.83 g, 59%); 75 mg converted to hydrochloride; mp>250° C.

Anal. Calcd for $C_{22}H_{23}N_3O_5 \cdot HCl \cdot \frac{1}{4} H_2O$: C, 58.08, H, 5.55; N, 9.24. Found: C, 57.88; H, 5.33; N, 9.18.

EXAMPLE 99

3,4-Dihydro-6-methanesulfonamido-1'-(4-methanesulfonamidobenzyl)spiro[(2H)-1-benzopyran-2,4'-piperidine]4-one Step A: Preparation of 3,4-Dihydro-6-acetamido-1'-(4-aminobenzyl)spiro[(2H)-1-benzopyran-2,4'-piperidine]

To a solution of 3,4-dihydro-6-acetamido-1'-(4-nitrobenzyl)spiro[(2H)-1-benzopyran-2,4'-piperidine]-4-one (0.58 g, 1.4 mmol) in acetic acid (6.4 ml) was added titanium (III) chloride (15% wt. in 20-30% wt. hydrochloric acid, 7 ml) dropwise. The reaction mixture was stirred at room temperature for 1 hr, cooled to 0° C. and basified with saturated sodium bicarbonate and 20% sodium hydroxide solutions. Extraction with ethyl acetate, drying and solvent evaporation gave an oil (0.42 g). Chromatography (silica gel, chloroform-methanolammonium hydroxide, 95/2/0.5) gave 3,4-dihydro-6-acetamido-1'-(4-aminobenzyl)spiro[(2H)-1-benzopyran-2, 4'-piperidine]-4-one (136 mg, 26%);

¹H NMR (CDCl₃) d 1.71 (m, 2H), 2.04 (m, 2H), 2.18 (s, 3H), 2.42 (t, 2H), 2.62 (m, 2H), 2.69 (s, 2H), 3.45 (s,

2H), 6.66 (d, 2H, J=8.3 Hz), 6.98 (d, 1H, J=8.8 Hz), 7.10 (d, 2H, J=8.3 Hz),7.63 ((d, 1H, J=2.7 Hz), 7.93 (dt, 1H, J=8.8 Hz, J=2.8 Hz).

Step B: Preparation of 3,4-Dihydro-6-amino-1'-(4-aminobenzyl)spiro[(2H)-1-benzopyran-2,4'-piperidine]-4-one A solution of 3,4-dihydro-6-acetamido-1'-(4-aminobenzyl)spiro[(2H)-1-benzopyran-2,4'-piperidine](136 mg, 0.36 mmol) and hydrochloric acid (6N solution, 13. 6 ml) in methanol (13.6 ml) was heated at reflux temperature for 1 hr. The reaction mixture was cooled to 0° C. and basified with 20% sodium hydroxide solution. Extraction with methylene chloride, drying and solvent evaporation gave 3,4-dihydro-6-amino-1'-(4-aminobenzyl)spiro[(2H)-1-benzopyran-2,4'-piperidine]-4-one (107 mg, 88%);

'H NMR (CDCl$_3$) d 1.73 (m, 2H), 2.01 (m, 2H), 2.40 (m, 2H), 2.60 (m, 2H), 2.66 (s, 2H), 3.42 (s, 2H), 3.52 (bs, 2H), 3.63 (bs, 2H,) 6.65 (d, 2H, J=8.4 Hz), 6.86 (m, 2H,), 7.09 (d, 2H, J=8.3 Hz), 7.13 (d, 1H, J=2.7 Hz).

Step C: Preparation of 3,4-Dihydro-6-methanesulfonamido-1'-(4-methanesulfonamidobenzyl)spiro [(2H)-1-benzopyran-2,4'-piperidine]-4-one A solution of 3,4-dihydro-6-amino-1'(4-aminobenzyl) spiro [(2H)-1-benzopyran-2,4'-piperidine]-4-one (107 mg, 0.32 mmol) and methanesulfonyl chloride (78 ml, 1.0 mmol) in pyridine (3 ml) was stirred at room temperature for 3 h. Solvent evaporation gave a foam; flash chromatography (silica gel, chloroform-methanol-ammonium hydroxide, 96/4/0.4) and trituration with ethanol gave 3,4-dihydro-6-methanesulfonamido-1'-(4-methanesulfonamidobenzyl) spiro [(2H)-1-benzopyran-2,4'-piperidine-4-one (32 mg, 20%); mp 209°-210° C.

'H NMR (DMSO) δ1.70 (m, 2H), 1.88 (m, 2H), 2.34 (t, 2H), 2.55 (m, 2H), 2.81 (s, 2H), 2.94 (s, 2H), 2.98 (s, 3h), 3.46 (s, 2H,) 7.06 (d, 1H, J=8.8 Hz), 7.16 (d, 2H, J=8.3 Hz), 7.27 (d, 2H, J=8.5 Hz), 7.43 (dd, 1H, J=8.8 Hz, J=2.7 Hz), 7.57 (d, 1H, J=2.7 Hz), 9.63 (s, 1H), 9.69 (s, 1H).

Anal. Calcd. for $C_{22}H_{27}N_3O_6S_2$: C, 53.52; H, 5.52, N, 8.51. Found: C, 53.25, H, 5.50, N, 8.41.

EXAMPLE 100

3,4-Dihydro-6-methanesulfonamido-1'-(5-methanesulfonamidobenzofuryl)-2-methyl-4-oxospiro[(2H)-1-benzopyran-2,4'-piperidine]

Step A: Preparation of 6-Acetamido-3,4-dihydro-1'-(5-nitrobenzofuryl-2-methyl)-4-oxospiro[(2H)-1-benzopyran-2,4'-piperidine]

A mixture of 1.12 g (3.6 mmoles)-6-acetamido-3,4-dihydro-4-oxospiro[(2H)-1-benzopyran-2,4'-piperidine], 0.83 g (6.0 mmoles) potassium carbonate, 0.61 g (4.1 mmoles) sodium iodide, and 1.05 g (4.1 mmoles) 2-bromoethyl-5-nitro-benzofuran (European Patent Application no. 88300962.3, May 2, 1988) in 75 ml acetonitrile was heated at reflux for 7 hours. The solvent was removed in vacuo and the residue was partitoned between 75 ml methylene chloride and 15 ml dilute sodium bicarbonate solution. The layers were separated and the aqueous layer was extracted with 75 ml methylene chloride. The combined extracts were washed with 15 ml water and brine, dried, and the CH$_2$Cl$_2$ was removed in vacuo to give 2.08 g crude product. The compound was purified by flash chromatography on silica gel eluting with 2.5: 97.5 methanol: chloroform to give 1.12 g (69%) of product as a solid foam, m.p. 99°-104° C.

$^1$H NMR (CDCl$_3$): δ1.81 (m, 2H), 2.08 (d, 2H), 2.17 (s, 3H), 2.56 (m, 2H), 2.70 (s, 2H), 2.72 (m, 2H), 3.76 (s, 2H), 6.75 (s, 1H), 6.97 (d, 1HO, 7.21 (s, 1H—NH), 7.55 (d, 1H), 7.63 (d, 1H), 7.92 (d of d, 1H), 8.20 (d of d 1H), 8.47 (d, 1H).

Step B: Preparation of 6-acetamido-1'-(5-aminobenzofuryl-2-methyl)-dihydro-4-oxospiro[(2H)-1-benzopyran-2,4'-piperidine]

To a solution of 1.08 g (2.4 mmoles) of the compound from Step A in 10 ml acetic acid was added 7.7 ml (8.8 mmoles) of 15% titanium (III) chloride solution in 20–30%. aqueous hydrochloride acid dropwise in portions over 1 hour. The reaction mixture was made basic (pH 10) with saturated sodium bicarbonate solution and 10N sodium hydroxide solution diluted in 300 ml water, and extracted with 3×300 ml ethyl acetate. The combined extracts were washed with 60 ml water and brine, dried and the solvent was removed in vacuo to give 0.99 g (98%) product.

'H NMR (deuteriochloroform): δ1.65 (broad s, 2H, NH$_2$), 1.80 (m, 2H), 2.04 (d, 2H), 2.16 (s, 3H), 2.51 (m, 2H) 2.68 (s, 2H), 2.70 (m, 2H), 3.66 (s, 2H), 6.44 (s, 1H), 6.64 (d of d 1H), 6.80 (d, 1H), 6.97 (d, 1H), 7.26 (d, 1H), 7.62 (d, 1H), 7.92 (d of d, 1H).

Step C: Preparation of 6-Amino-1'-(5-aminobenzofuryl-2-methyl)-3,4-dihydro-4-oxospiro[(2H)-1-benzopyran-2,4'-piperidine]trihydrochloride A solution of 1.01 g (2.4 mmoles) of the compound from Step B in 30 ml ethanol and 10 ml (30 mmoles) of 3N hydrochloric acid was heated at reflux for 6 hours. The solution was cooled and the solvent was removed in vacuo. The residue was stirred under 20 ml ethanol to give a solid which was filtered off and dried to give 0.90 g (77%) product, mp 277°-279° C.

'H NMR (DMSO-d$_6$): δ2.18 (m, 4H), 2.92 (m, 2H), 3.35 (m, 6H), 3.68 (m, 2H), 4.69 (s, 2H), 7.18 (d, 2H), 7.34 (s, 1H), 7.40 (d of d, 1H), 7.58 (d of d, 1H), 7.67 (d, 1H), 7.75 (d, 1H), 7.77 (s, 1H), 10.4 (broad s, 3H).

Step D: Preparation of 3,4-Dihydro-6-methanesulfonamido-1'-(5-methanesulfonamidobenzofuryl-2-methyl-4-oxospiro[(2H)-1-benzopyran-2,4'-piperidine]

To a solution of 0.24 g (0.50 mmole) of the compound from Step C and 0.21 ml (1.5 mmoles) triethylamine in 2 ml pyridine was added 0.081 ml (1.05 mmoles) methanesulfonyl chloride. The resulting red mixture was stirred 5 hours. The solvent was removed in vacuo and the residue was partitioned between 5 ml saturated sodium bicarbonate solution and 15 ml ethyl acetate. The layers were separated and the aqueous layer was extracted with 2×15 ml ethyl acetate. The combined extracts were washed with 3 ml water and brine, dried, and the solvent was removed in vacuo to give 0.28 g (97%) crude product which was purified by flash chromatography on silica gel eluting with 5:95 methanol: chloroform (saturated with ammonia) to give 0.167 g (63%) of product as a foam.

To a solution of 0.167 g (0.313 mmole) of product in 3 ml ethanol was added 0.058 ml (0.34 mmole) 5.9N hydrogen chloride in ethanol. The mixture was stirred 1 hour and the resulting yellow precipitate was filtered off to give 0.114 g (64%) hydrochloride salt, mp 199°-202° C.

Anal Calcd for $C_{24}H_{27}N_3O_7S_2$·HCl·0.30 $C_2H_5OH$·0.65 $H_2O$: C, 49.60; H, 5.26; N, 7.06. Found C, 49.63; H, 5.25; N, 7.04.

EXAMPLE 101

1,4-Dihydro-1'-[(6-methanesulfonamidoquinolin-2-yl)methyl]-7-methanesulfonamido-spiro-[(3H)-2-benzopyran-3,4'-piperidine] dihydrochloride To a solution of 100 mg (0.3 mmole) 1,4-dihydro-7-methanesulfonamido-spiro-[(3H)-2-benzopyran-3,4;-piperidine]hydrochloride and 122 mg (0.45 mmole) 2-chloromethyl-6-methanesulfonamidoquinoline in 10 ml acetonitrile was added 76 mg (0.90 mmole) sodium bicarbonate. The mixture was heated at reflux under nitrogen for 19 hours. The reaction mixture was concentrated in vacuo to dryness. The residue was treated with a small amount of water and the crude product was filtered off. The crude product was chromatographed (silica gel), 5% methanolchloroform). The free base was converted to the dihydrochloride salt by the addition of ethanolic hydrogen chloride solution and recrystallization from ethanol-methanol-ether to give the title compound (80 mg, 44.2%), m.p. 207° C.

Analysis Calculated for $C_{25}H_{30}N_4O_5S_2 \cdot 2HCl$: C, 49.75; H, 5.34; N, 9.28. Found: C, 49.44; H, 5.29; N, 9.22.

Employing the procedure substantially as described in Example 101, but substituting for the 2-benzopyran-spiropiperidine used therein, there were produced the spiropiperidines described in Table IV, and the quinolinylmethylspiropiperidines, also described in Table IV.

methanesulfonamidospiro[(2H)-1-benzopyran-2,4'-piperidine]-4-one (see Example 70, Method 2, Step D) for the 3,4,-dihydro-6-methanesulfonamidospiro[(2H)-1-benzopyran-2,3'-piperidine]-4-one used therein, and substituting an appropriate electrophile (wherein the leaving-group is methanesulfonyl, bromo or chloro) for the 5-(2-bromoethyl)benzofurazan, the following compounds of Tables V, VI, VII, VIII, IX, X and Xa were prepared:

TABLE V

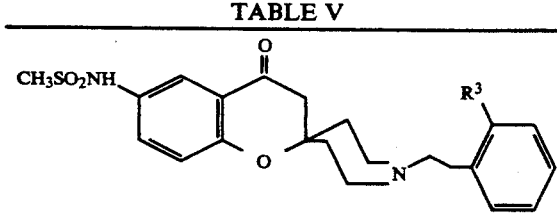

| Example | $R^3$ | Salt | mp (°C.) | Note |
|---|---|---|---|---|
| 104 | H— | HCl | 262 (dec) | |
| 105 | $CH_3SO_2$— | — | 192–193 | a |
| 106 | $NO_2$— | $HCl \cdot \frac{1}{4}H_2O$ | 258–261 | |
| 107 | $NH_2$— | 2HCl | 204–209 | b |
| 108 | $CH_3CONH$— | $HCl \cdot \frac{1}{4}H_2O$ | 165–167 | c |
| 109 | $C_2H_5OCONH$— | HCl | 232–234 | d |
| 110 | $CH_3SO_2NH$— | — | 128–129 | e |
| 111 | $CH_3$— | $HCl \cdot 0.75H_2O$ | 277–278 | |
| 112 | F— | HCl | 276–277 | |
| 113 | $CH_3O$— | $HCl \cdot CH_3OH$ | 267–269 | |

TABLE IV

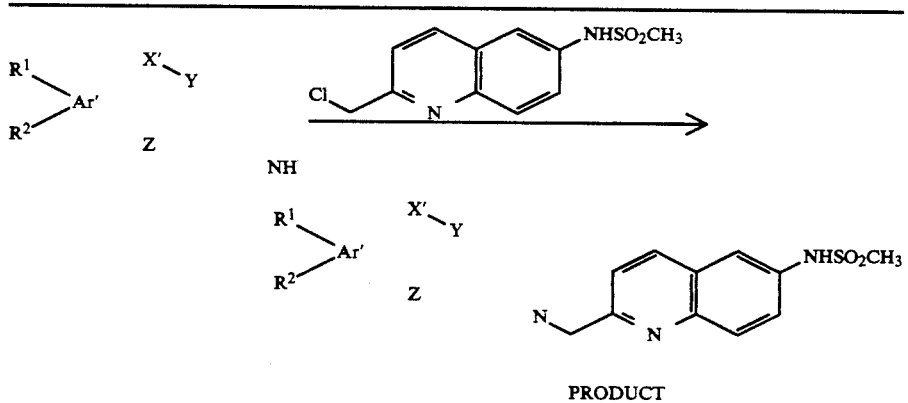

PRODUCT

| Example | | mp (°C.) (salt) | Analysis Calc'd/Found | | |
|---|---|---|---|---|---|
| | | | C | H | N |
| 102 | $CH_3SO_2NH$—[spiropiperidine benzopyranone], H | 179–183 (2 HCl) | 48.62/48.31 | 4.90/4.89 | 9.07/8.87 |
| 103 | $CH_3SO_2NH$—[spiropiperidine benzopyranone], H | 198–202 $(HCl \cdot \frac{1}{2}H_2O)$ | 49.37/49.36 | 5.30/5.44 | 9.21/9.03 |
| 114 | Cl— | 272–274 $HCl \cdot 0.25H_2O$ | | | |

Employing the procedure substantially as described in Example 83 but substituting 3,4-dihydro-6-

TABLE V-continued

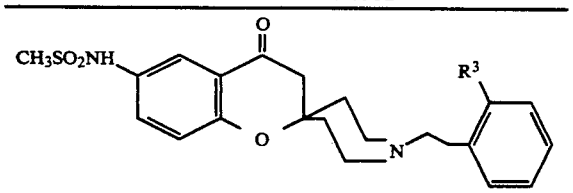

| Example | R³ | Salt | mp (°C.) | Note |
|---|---|---|---|---|
| 115 | CF₃— | HCl | 288–289 | |
| 116 | CN— | HCl | 264–266 | |
| 117 | H₂N—C(O)— | HCl.½H₂O | 274–276 | f |

Notes:
a The p-methylsulfonylphenethyl alcohol was prepared by the method of G. M. Bennett and M. M. Hafez, J. Chem. Soc. 1941, 652; and the mesylate of this alcohol was prepared by the method described in Example 89, Step C.
b Prepared from the corresponding nitro compound by the method described in Example 70, Method 2, Step B.
c Prepared from the corresponding amino compound by treatment with acetyl chloride
d Prepared from the corresponding amino compound essentially by treatment with ethyl chloroformate.
e Prepared from the corresponding amino compound essentially by the method, described in Example 70, Method 3, Step C.
f Prepared from the corresponding cyano compound essentially by the method described in Example 369.

TABLE VI

| Example | R³ | Salt | mp (°C.) |
|---|---|---|---|
| 118 | CH— | HCl.½H₂O | 265–296 (dec) |
| 119 | CH₃O— | HCl | 298–300 (dec) |
| 120 | CN— | HCl | 292–293 (dec) |
| 121 | NO₂— | HCl.½H₂O | 275–277 |
| 122 | Cl— | HCl.½H₂O | 285–287 (dec) |
| 123 | CH₃SO₂NH— | HCl | 266–268 (dec) |

TABLE VII

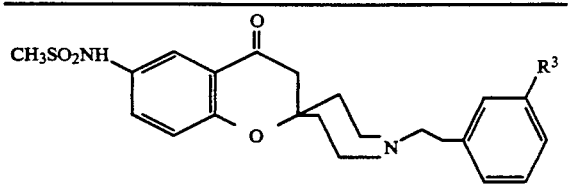

| Example | R³ | Salt | mp (°C.) | Note |
|---|---|---|---|---|
| 124 | CH₃SO₂— | HCl | 291–292 (dec) | a |
| 125 | CH₃S— | HCl | 278–279 (dec) | a |
| 126 | CH₃CO— | HCl | 264 (dec) | |
| 127 | Br— | HCl | 277–278 | |
| 128 | HOCH₂— | HCl.CH₃OH | 270 | |
| 129 | CF₃— | HCl.0.3H₂O | 276 | |
| 130 | Cl— | HCl | 269–270 | |
| 131 | H₂NSO₂— | HCl.½H₂O | >300 (dec) | |
| 132 | CH₃OOC— | HCl | 267–268 (dec) | |
| 133 | CH₃O—N=CH— | — | 132–132 | b |
| 134 | CH₃— | HCl.½H₂O | 258–260 | |
| 135 | CH₃O— | HCl.½H₂O | 264–266 (dec) | |
| 136 | C₆H₅— | HCl | 281–282 (dec) | |
| 137 | CH₃SCH₂— | HCl | 260–263 | |
| 138 | NO₂— | HCl.½CHOH | 262 (dec) | |
| 139 | F— | HCl | 270–272 (dec) | |
| 140 | CN— | HCl | 284–285 (dec) | |
| 141 | H— | HCl | 262 (dec) | | a p-Methylthio- and p-methylsulfonylphenethyl alcohols were prepared by the method of G. M. Bennett and M. M. Hafez, J. Chem. Soc., 1941, 652; and the mesylates of these alcohols were prepared by the method described in Example 89, Step C.
b Prepared from p-cyanophenethyl alcohol by reduction of the nitrile to the aldehyde using 2.0 equivalents of diisobutyl aluminum hydride, followed by reaction with methoxylamine hydrochloride to give the O-methyloximino ether, followed by conversion to the mesylate as described in Example 89, Step C.

TABLE VIII

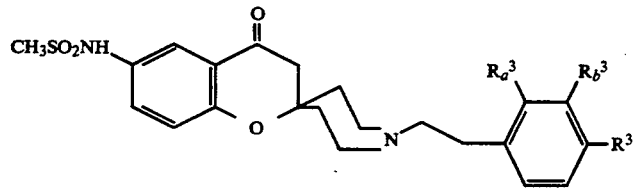

| Example | Rₐ³ | R_b³ | R_c³ | Salt | mp (°C.) |
|---|---|---|---|---|---|
| 142 | H | OCH₃ | OCH₃ | HCl | 243 |
| 143 | H | F | F | HCl | 295–297 (dec) |
| 144 | F | H | F | HCl.0.3H₂O | 265 |
| 145 | H | Cl | Cl | HCl | 269–270 (dec) |
| 146 | H | —O—CH₂—O— | | HCl | >250 |

TABLE IX

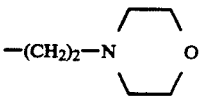

| Example | RM | salt | M.P. (°C.) |
|---|---|---|---|
| 147 | —(CH$_2$)$_4$CO$_2$CH$_2$CH$_3$ | .HCl | 253 |
| 148 | —(CH$_2$)$_3$CO$_2$CH$_2$CH$_3$ | .¼H$_2$O.HCl | 190–192 |
| 149 | —(CH$_2$)$_2$CO$_2$CH$_2$CH$_3$ | .HCl | 211–213 |
| 150 | —(CH$_2$)$_2$O—CH$_2$CH$_3$ | .HCl.¼H$_2$O.¼C$_2$H$_5$OH | 134–137 |
| 151 | —(CH$_2$)$_2$O(CH$_2$)$_2$OH | .HCl.0.5C$_2$H$_5$OH | 94–98 |
| 152 | —(CH$_2$)$_4$OH | .HCl.0.5C$_2$H$_5$OH | 141.5–144.5 |
| 153 | —(CH$_2$)$_5$OH | .HCl.0.5C$_2$H$_5$OH | 172–177 |
| 154 | —(CH$_2$)$_6$OH | .HCl | 175–181 |
| 155 | —(CH$_2$)$_7$OH | .HCl.0.2C$_2$H$_5$OH | 240–242 |
| 156 | 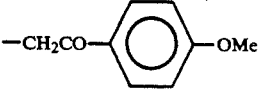 | .2HCl.H$_2$O | 242–244 |
| 157 | —(CH$_2$)$_8$OH | .HCl | 232–233 |
| 158 | —CH$_2$CHOHC$_6$H$_5$ | .0.25H$_2$O | 197–198 |
| 159 | —CH$_2$COC$_6$H$_5$ | .HCl.0.25H$_2$O | 265 (dec) |
| 160 | —(CH$_2$)$_2$O(CH$_2$)$_2$OCH$_3$ | .HCl | 129–134 |
| 161 | 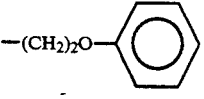 | .¼C$_2$H$_5$OH | 201–202 |
| 162 | 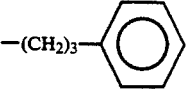 | — | 160–161 |
| 163 | —(CH$_2$)$_3$C$_6$H$_5$ | .HCl | 223–225 |
| 164 | 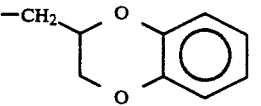 | .HCl.0.5H$_2$O | 148–151 |
| 165 | trans —CH$_2$CH=CH—C$_6$H$_5$ 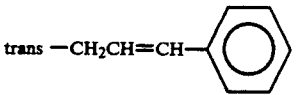 | .HCl | 257–259 (dec) |
| 167 | —CH$_2$—C$_6$H$_4$(CH$_2$)$_2$OH | .HCl | 255–260 |
| 168 | —(CH$_2$)$_3$CN | .HCl | 228–229 |
| 169 | —(CH$_2$)$_3$CN | .HCl | 268–269 (dec) |
| 170 | —(CH$_2$)$_4$CN | .HCl | 264–265 (dec) |
| 171 | —(CH$_2$)$_5$CN | .HCl | 267 (dec) |
| 172 | —(CH$_2$)$_6$CN | .HCl.0.35H$_2$O.0.15C$_2$H$_5$OH | 220–223 |
| 173 | —(CH$_2$)$_2$NHSO$_2$CH$_3$ | .HCl | 260–261 dec |
| 174 | —(CH$_2$)$_4$NHSO$_2$CH$_3$ | .HCl | 205–215 |
| 175 | —(CH$_2$)$_5$NHSO$_2$CH$_3$ | .HCl 0.5C$_2$H$_5$OH 0.25H$_2$O | 133–135 |
| 176 | —(CH$_2$)$_6$NHSO$_2$CH$_3$ | .HCl | 186–191 |
| 177 | 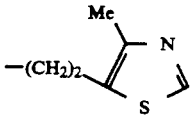 | .HCl.0.25H$_2$O | >270 |
| 178 | —(CH$_2$)$_3$CH$_3$ | .HCl | 270 (dec) |
| 179 | —(CH$_2$)$_4$CH$_3$ | .HCl.0.2C$_2$H$_5$OH | 215–217 |
| 180 | —(CH$_2$)$_5$CH$_3$ | .HCl.0.25C$_2$H$_5$OH | 240–241 |

TABLE IX-continued
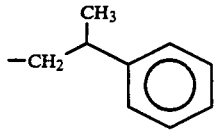
| Example | RM | salt | M.P. (°C.) |
|---|---|---|---|
| 181 | —(CH₂)₆CH₃ | .HCl | 244–246 |
| 182 | —(CH₂)₇CH₃ | .HCl | 235–237 |
| 183 | —(CH₂)₈CH₃ | .HCl | 252–254 |
| 184 | —(CH₂)₂CHC(CH₃)₂ | .HCl | 221–222 |
| 185 | —CH(CH₃)(CH₂)₂CH₃ | .HCl<br>0.35 C₂H₅OH | 260 (dec) |
| 186 | —(CH₂)₃CH(CH₃)₂ | .HCl<br>0.5 C₂H₅OH | 258–260 (dec) |
| 187 | —CH₂CH(CH₂CH₃)₂ | .HCl | 220–262 (dec) |
| 188 | 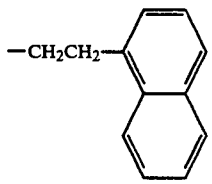 | .HCl | 258–260 (d) |
| 189 | 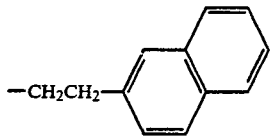 | .HCl<br>0.30 H₂O | 279–280 (d) |
| 190 | 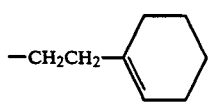 | .HCl | 276–278 (d) |
| 191 | 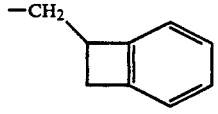 | .maleate<br>.0.3 H₂O | 105 (d) |
| 192 | 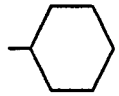 | .HCl | 239–241 |
| 193 | 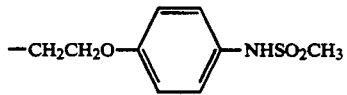 | .HCl | 273–274 (d) |
| 194 | —CH₂CH₂O—⟨⟩—NHSO₂CH₃ | .HCl<br>.0.1 IPA | 185–187 |
| 195 | 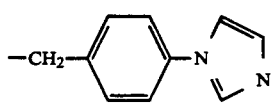 | .2HCl<br>.2.5 H₂O<br>0.35 IPA | 200 (d) |

TABLE IX-continued
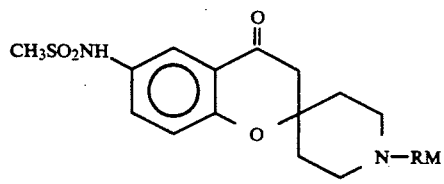
| Example | RM | salt | M.P. (°C.) |
|---|---|---|---|
| 196 | —(CH₂)₂-(3-indolyl) | .HCl | >285 |
| 197 | —(CH₂)₂-(benzo[1,3]dioxol-5-yl) | .HCl | >250 |
| 198 | —(CH₂)₂-cyclohexyl | HCl 0.5 EtOH | >285 |
| 199 | —(CH₂)₂-(2-thienyl) | .HCl .0.5 H₂O | 270–272 (dec) |
| 200 | —(CH₂)₂-(3-thienyl) | .HCl .0.5 H₂O | 263–265 (dec) |
| 201 | —(CH₂)₂-phthalimido | .HCl | 278–280 (dec) |
| 202 | —(CH₂)₂-(2-oxoimidazolidin-1-yl) | .HCl | 251–253 (dec) |
| 203 | —(CH₂)₂-(3-furyl) | HCl .0.33 H₂O | 265–267 (dec) |
| 204 | —(CH₂)₂-(2-furyl) | .HCl | 238–241 |
| 205 | —(CH₂)₂-(2,3-dihydrobenzofuran-5-yl) | .HCl | >285 |

TABLE IX-continued

[Structure: CH₃SO₂NH-phenyl-C(=O)-CH₂-spiro[chroman-piperidine]-N-RM]

| Example | RM | salt | M.P. (°C.) |
|---|---|---|---|
| 206 | —(CH₂)₂-(5-indolinyl with N-Ac) | .HCl | >285 |
| 207 | —(CH₂)₅C(CH₃)₂OH | .HCl | 230–232 |
| 208 | —(CH₂)₅C(CH₃)₂OH | .HCl | 201–203 |
| 209 | —CH₂CH(CH₂CH₃)(CH₂)₃CH₃ | .HCl | 260–262 |
| 210 | cycloheptyl | — | 195–196 |
| 211 | cyclooctyl | HCl 0.25H₂O | 279–281 |
| 212 | —CH[(CH₂)₂CH₃]₂ | .HCl .0.1 H₂O | 231–233 |
| 213 | —(CH₂)₂CH(CH₃)₂ | .HCl .0.75H₂O | 246–248 |
| 214 | —CH(C₂H₅)(CH₂)₄CH₃ | .HCl .0.25H₂O | 220–221 (dec) |
| 215 | —(CH₂)₄OHC₃ | .HCl .0.35H₂O | 192–194 |
| 216 | —(CH₂)₃OCH₂CH₃ | .HCl | 195–196 |
| 217 | —CH₂-cyclohexyl | .HCl 0.05H₂O | 255 (dec) |
| 218 | —CH₂-(tetrahydropyran-2-yl) | HCl .0.5H₂O .0.5EtOH | 183–184 (dec) |
| 218a | —(CH₂)₃CH(CH₃)CH₂CH₃ | .HCl | 272–273 |
| 218b | —(CH₂)₄CH(CH₃)₂ | .HCl | 255–260 |
| 218c | —(CH₂)₃S(CH₂)₂CH₃ | .HCl | 230–232 |
| 218d[a] | —(CH₂)₃SO(CH₂)₂CH₃ | .HCl | 203.5–204.5 |
| 218e | —(CH₂)₅CONH₂ | .HCl .0.5H₂O | 158–160 |
| 218f | —(CH₂)₅CONH(CH₂)₂CH₃ | .HCl | 234–236 |
| 218g | —(CH₂)₂CONH(CH₂)₂CH₃ | .HCl | 22–224 |
| 218h | —(CH₂)₆NHCOCH₃ | .HCl | 195–197 |
| 218i | —(CH₂)₆NH₂ | .HCl .0.35C₂H₅OH .0.9 H₂O | 160 |
| 218j | —(CH₂)₃CON(CH₃)₂ | .HCl .0.25C₂H₅OH | 243–245 |
| 218k | —(CH₂)₆SCH₃ | .HCl | 247–250 |
| 218l[a] | —(CH₂)₆SOCH₃ | .HCl | 176–177 |
| 218m[b] | —(CH₂)₆SO₂CH₃ | .HCl | 224–226 |

TABLE IX-continued

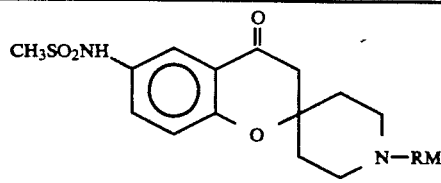

| Example | RM | salt | M.P. (°C.) |
|---|---|---|---|
| 218n | —(CH₂)₄—[cyclohexyl-NH] | 2HCl | >250 |

$^{(a)}$This compound was produced by oxidation of the corresponding sulfide using sodium meta periodate (1.1 moles per mole of sulfide) in a aqueous methanol mixture at room temperature.
$^{(b)}$This compound was prepared by reaction of the corresponding sulfides with two equivalents of OXONE ® in aqueous methanol (1:1) for 1 to 5 hours at room temperature.

TABLE X

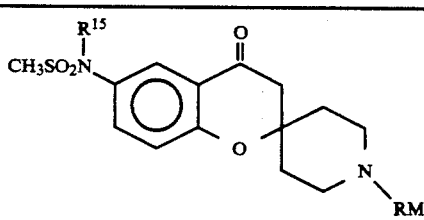

| Example | RM | R¹⁵ | salt | mp (°C.) |
|---|---|---|---|---|
| 219 | —(CH₃)₂CN | —(CH₃)₂CN | .HCl | 216–218 (dec) |

TABLE Xa

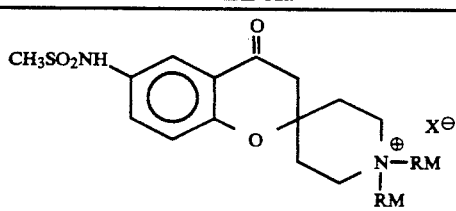

| Example | RM | X⁻ | MP (°C.) |
|---|---|---|---|
| 219a | ⸺CH=CH—CH₂Ph | .Cl⁻ .0.75H₂O | 235–237 |
| 219b | —(CH₂)₅CH₃ | .Cl⁻ .0.3H₂O | 197–199 |

EXAMPLE 220

Preparation of
6-Methanesulfonamido-3,4-dihydro-spiro[(2H)-1-benzopyran-2,4'-piperidin]-4-one-3-methyl hydrochloride Step A:
A solution of 2-hydroxypropiophenone (15 g, 0.1 mol), 1-acetyl-4-piperidone (14.2 g, 0.1 mol), and pyrrolidine (7.1 g, 0.1 mol) in CH₃OH (150 ml) was heated at reflux for 6 days. After cooling to room temperature, the reaction was concentrated to dryness. The residue was chromatographed on silica gel using a Still column (90 mm) and the mixture eluted with 30% EtOAc-hexanes to yield 9.5 g of starting material and then 60% EtOAc-hexanes to yield 10 g (37%) of 1'-acetamido-3,4-dihydro-3methyl-spiro[(2H)-1-benzopyran-2-4'-piperidin]-4-one.

Step B:
To a solution of concentrated H₂SO₄ (18 mol) was added the product of Step A (5 g, 0.018 mol) at room temperature with stirring. After 0.5 hours, the mixture was cooled to −10° C. and nitric acid (0.9 ml, 1.2 g, 0.019 mol) in (1.8 ml concentrated H₂SO₄) was added via syringe. After stirring for 0.5 hours at 0°-4° C., the mixture was carefully added to NaHCO₃ (76 g) in and EtOAc. After separation, the aqueous layer was further extracted with EtOAc (2X). The combined organic layers were dried, filtered, and concentrated to dryness to yield 5.8 g (88%) of 1'-acetamido-3,4-dihydro-3-methyl-6-nitro-spiro[(2H)-1-benzopyran-2-4'-piperidin]-4-one.

Step C:
Under N₂, Ra-Ni (2 scoops in H₂O) was added to the product of Step B (5.1 g, 0.016 mol) in AcOH (50 ml) and hydrogenated on a Parr shaker under 12 psi. After 8 hours, the theoretical amount of H₂ was absorbed and the reaction was then filtered through super cel under a blanket of N₂ and the filtrate was concentrated to dryness. The residue was dissolved in CH₂Cl₂ (275 ml) and piperidine (13.6 ml, 13.2 g, 0.17 mol) and then methanesulfonyl chloride (2.2 g, 0.017 mol) was added at room temperature. After 15 hours, the reaction was washed with H₂O, cold 1.5 N HCl, saturated NaHCO₃, dried, filtered and concentrated to dryness to yield 5.2 g (89%) of 1'-acetamido-3,4-dihydro-6-methanesulfonamido-3-methyl-spiro[(2H)-1-benzopyran-2-4'-piperidin]-4-one.

Step D:
The product of Step C (5.2 g, 0.014 mol) in CH₃OH (80 ml) and 6N HCl (80 ml) was heated at reflux. After 7 hours, the reaction was concentrated to dryness and the residue flushed with EtOH (4X) and then toluene to yield 5.0 g (98%) of the title compound.

Employing the procedure substantially as described in Example 83 but substituting 6-methanesulfonamido-3,4-dihydro-spiro[(2H)-1-benzopyran-2,4'-piperidin]-4-one-3-methyl hydrochloride for the 3,4-dihydro-6-methanesulfonamido-spiro[(2H)-1-benzopyran-2,3'-piperidine]-4-one hydrochloride used therein, and substituting an appropriate electrophile for the 5-(2-bromoethyl)benzofurazan, the following compounds of Table XI were prepared:

TABLE XI

Structure: CH₃SO₂NH-benzopyran-piperidine with C=O, CH₃, and N-CH₂CH₂-phenyl-R³ substituent

| Example | R³ | Salt | mp (°C.) |
|---|---|---|---|
| 221 | 2-CN | HCl.¼H₂O | 191–193 |
| 222 | 2-CH₃ | HCl.¼CH₃OH | 267–269 |
| 223 | 4-Cl | HCl | 238–240 (dec) |
| 224 | 4-CN | HCl.¼H₂O | 300 (dec) |

EXAMPLE 225

3,4-Dihydro-6-methanesulfonamido-3-methyl-1'-[2-(2-pyridyl)ethyl]-spiro[(2H)-1-benzopyran-2,4'-piperidine]-4-one The title compound was prepared from 3,4-dihydro-6-methanesulfonamido-3-methyl-spiro[(2H)-benzopyran-2,4'-piperidine]-4-one hydrochloride in a manner analogous to that described in Example 52, Step C, mp 210°–211° C.

Anal. Calc'd for $C_{22}H_{27}N_3O_4S.2HCl.\frac{1}{4}H_2O$ C, 51.72; H, 5.79; N, 8.22. Found: C, 51.66; H, 5.91; N, 8.22.

EXAMPLE 225A 3,4-Dihydro-6-methanesulfonamido-3-methyl-1'-hexyl-spiro[(2H)-1-benzopyran-2,4'-piperidine-4-one The title compound was prepared from 3,4-dihydro-6-methanesulfonamido-3-methyl-spiro [(2H)-benzopyran-2,4'-piperidine]-4-one hydrochloride and hexyl bromide in a manner similar to that described in Example 83; mp=261°–264° C.

EXAMPLE 226

3,4-Dihydro-3-methyl-6-methanesulfonamido-1'-[2-(benzofurazan-5-yl)ethyl]spiro[(2H)-1-benzopyran-2,4'-piperidine]-4-one hydrochloride The title compound was prepared from 3,4-dihydro-3-methyl-6-methanesulfonamido-spiro[(2H)-1-benzopyran-2,4'-piperidine-4-one hydrochloride (Example 220) and 5-(2-bromoethyl)benzofurazan in a manner analogous to that described in Example 83; mp 240°–243° C.

Anal. Calc'd for $C_{23}H_{26}N_4O_5S.HCl$: C, 54.48; H, 5.37; N, 11.05. Found: C, 54.14; H, 5.36; N, 11.01.

EXAMPLE 227

3,4-Dihydro-3-methyl-6-methanesulfonamido-1'-[2-(benzofurazan-5-yl)ethyl]spiro[(2H)-1-benzopyran-2,4'-piperidine-4-ol hemihydrate 3,4-Dihydro-3-methyl-6-methanesulfonamido-1'-[2-(benzofurazan-5-yl)ethyl]spiro[(2H)-1-benzopyran-2,4'-piperidine-4-one was reduced with sodium borohydride in a manner analogous to that described in Example 429 to give the title compound as a mixture of diastereomers.

Anal. Calc'd for $C_{23}H_{28}N_4O_5S.\frac{1}{2}H_2O$: C, 57.36; H, 6.07; N, 11.64. Found: C, 57.17; H, 5.75; N, 11.42.

EXAMPLE 228

1-(Hydroxymethyl)-4-(1H-imidazol-1-yl)benzene

To a mixture of 4-(1H-imidazol-1-yl)benzoic acid methyl ester (prepared as described in U.S. Pat. No. 4,804,662) (1.5 g) in THF (25 ml) at −15° C. was added a solution of 1M LAH/THF (10.4) ml). The mixture was stirred for ¼ hour and allowed to warm to room temperature. The reaction was quenched by addition of water (0.5 ml), and then diluted with methanol (50 ml) and filtered. Concentration of the filtrate yielded 1.2 g (98%) of 1-(hydroxymethyl)-4-(1H-imidazol-1-yl)-benzene.

¹H NMR (300 MHz, CDCl₃): δ4.75 (s, 3H), 7.15 (s, 1H), 7.25 (s, 1H), 7.32 (d, 2H, J=12 Hz), 7.48 (d, 2H, J=12 Hz), 7.75 (s, 1H).

EXAMPLE 229

6-Methanesulfonamido-3,4-dihydro-1'-(2-methylsulfinylethyl)spiro[(2H)-1-benzopyran-2,4'-piperidine]-4-one A solution of 6-methanesulfonamido-3,4-dihydro-1'-(2-methylthioethyl)spiro[(2H)-1-benzopyran-2,4'-piperidine]-4-one (0.30 g, 0.78 mmol) in 15 mL of methanol was treated dropwise with a solution of sodium periodate (0.17 g, 0.78 mmol) in 15 mL of water. The solution was stirred at 25° C. for 3 hours, and was then poured into 25 ml of water and extracted with a total of 100 mL of ethyl acetate. The organic phase was dried (MgSO₄), filtered and concentrated in vacuo to give the product as a pale yellow foam. The foam was dissolved in 30 mL of absolute ethanol and was treated with excess 4.8N ethanolic HCl. The resulting solid was collected and dried for 4 hours at 100° C. under vacuum to give 0.083 g (24%) of product, mp 181°–183° C.

Anal. Calc'd. for $C_{17}H_{25}ClN_2O_5S_2$: C, 46.72; H, 5.77; N, 6.41. Found: C, 46.60; H, 5.69; N, 6.42.

EXAMPLE 230

6-Methanesulfonamido-3,4-dihydro-1'-(2-methanesulfonylethyl)spiro[(2H)-1-benzopyran-2,4'-piperidine]-4-one A solution of 6-methanesulfonamido-3,4-dihydro-1'-(2-methylthioethyl)spiro[(2H)-1-benzopyran-2,4'-piperidine]-4-one (0.335 g, 0.871 mmol) in 15 mL of methanol was treated dropwise with a solution of Oxone® (0.803 g, 1.31 mmol) in 15 mL of water. The resulting mixture was stirred at 25° C. for 2 hours. The reaction mixture was then poured into 50 mL of saturated aqueous NaHCO₃ and extracted with a total of 100 mL of ethyl acetate. The organic phase was dried (MgSO₄), filtered, and concentrated in vacuo to a pale yellow oil which was shown to be a mixture by thin layer analysis. The mixture was chromatographed on silica gel using 5% methanol in methylene chloride eluant. The pure oil was dissolved in 20 mL of absolute ethanol and was treated with excess 4.8N ethanolic HCl. The solid was collected, washed with diethyl ether, and dried for 4 hours at 100° C. under vacuum to give 0.176 g (44.6%) of product, mp 250°–251° C.

Anal. Calc'd. for $C_{17}H_{26}ClN_2O_5S_2$: C, 45.07; H, 5.56; N, 6.19. Found: C, 45.26; H, 5.65; N, 6.21.

EXAMPLE 231

3,4-Dihydro-6-methoxy-spiro[(2H)-1-benzopyran-2,4'-piperidine]-4-one hydrochloride The title compound was prepared according to the procedure described in Example 67, Step A but substituting 5-methoxy-2-hydroxyacetophenone for 2-acetylphenol; mp 235°–237° C.

Anal. Calc'd. for $C_{14}H_{18}NO_2 \cdot HCl$: C, 59.25; H, 6.39; N, 4.93. Found: C, 59.00; H, 6.20; N, 4.84.

EXAMPLE 232

6-Methoxy-3,4-dihydro-1'-(2-(4-methanesulfonamidophenyl)ethyl)spiro[(2H)-2-benzopyran-2,4'-piperidine-4-one A mixture of 3,4-dihydro-5-methoxy-spiro [(2H)-benzopyran-2,4'-piperidine]-4-one hydrochloride (1 g, 3.52 mmol) and 2-[4-(methanesulfonamido)phenyl]ethylmethanesulfonate (1.5 g, 5.1 mmol) and sodium bicarbonate (excess) and LiI (680 mg, 5.1 mmole) in 30 mL acetonitrile was heated to reflux for 8 hours. The reaction was cooled to room temperature and poured into 200 mL saturated sodium bicarbonate and extracted with ethyl acetate. The ethyl acetate layers were dried over $MgSO_4$, filtered and concentrated in vacuo. The residue was chromatographed on silica gel using 2% to 5% $MeOH/CHCl_3$ as eluant to give 1.2 g. The solid was dissolved in ethanol and treated with excess ethanolic HCl. The solid was collected and dried under vacuum to give 0.900 g product, mp 225° C.

Anal. Calc'd. for $C_{23}H_{28}N_2O_5 \cdot HCl$: C, 56.95; H, 6.02; N, 5.77. Found: C, 56.81; H, 5.91; N, 5.76.

Employing the procedure substantially as described in Example 232, but substituting for the 2-[4-(methanesulfonamido)phenyl]ethylmethanesulfonate used therein, the appropriate electrophiles there were produced the compounds of Table XII.

TABLE XII

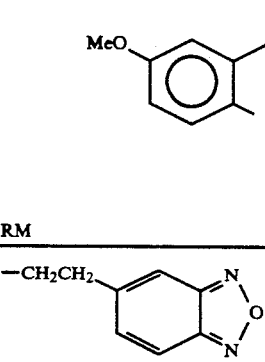

| Example | RM | salt | mp (°C.) | notes |
|---|---|---|---|---|
| 233 | 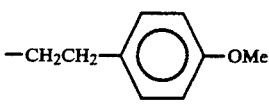 | .0.25 $H_2O$ | 146–148 | |
| 234 | —CH₂CH₂—⟨⟩—OMe | .HCl | 281–283 | |
| 235 | —CH₂CH₂—⟨⟩—COCH₃ | .HCl | 261–263 | |
| 236 | 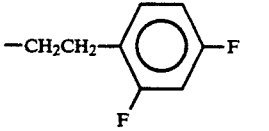 | .HCl | 264–266 | |
| 237 | —CH₂CH₂—⟨⟩—CN | — | 155–156 | |
| 238 | 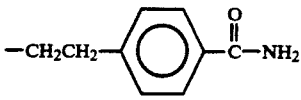 | — | 184–185 | |
| 239 | 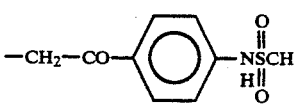 | .HCl .$C_2H_5OH$ | 200 | |

TABLE XII-continued
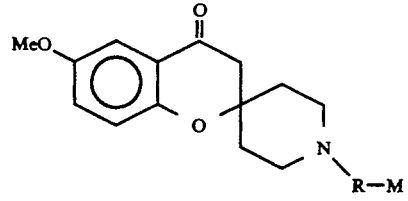
| Example | RM | salt | mp (°C.) | notes |
|---|---|---|---|---|
| 240 | —CH₂—CO—C₆H₅ | .HCl | 245 (dec) | |
| 241 | —CH₂CH₂-(5-(4-methylthiazolyl)) | .2HCl .0.75 H₂O | 213 | |
| 242 | —CH₂CH₂—C₆H₄(2-CN) | .HCl | 229–231 | |
| 243 | —CH₂CH₂—C₆H₄(3-CN) | .HCl .¼H₂O | 191–193.5 | |
| 244 | —CH₂CH₂—C₆H₄(3-CONH₂) | .HCl .¼H₂O | 248–250.5 | a |
| 245 | —CH₂CH₂—C₆H₄(4-SCH₃) | — | 101–105 | b |
| 246 | —CH₂CH₂—C₆H₄(2-Cl) | .HCl | 254–256 | |
| 247 | —CH₂CH₂—C₆H₄(2-CH₃) | .HCl | 256–258 (dec) | |
| 248 | —CH₂CH₂—C₆H₄(4-SO₂CH₃) | — | 136–138 | b |
| 249 | —CH₂CH₂—C₆H₄(4-F) | HCl .2/10H₂O | 247–249 (dec) | |

TABLE XII-continued

| Example | RM | salt | mp (°C.) | notes |
|---------|----|------|----------|-------|
| 250 | —CH₂CH₂—C₆H₄—NHSO₂CH₃ | .HCl | 275 | |
| 251 | —CH₂CH₂—C₆H₄—C(O)NH₂ (ortho) | .HCl | 197–199 (dec) | a |
| 252 | —CH₂CH₂—C₆H₄—CH₂OH | — | 162–163 | |
| 253 | —CH(CH₂C₆H₅)₂ | .HCl .0.35H₂O | 132–134 | |

Notes:
a Prepared from the corresponding cyano compounds essentially by the methods described in Example 369.
b The p-methylthio and p-methylsulonylphenethyl alcohols were prepared by the method of G. M. Bennett and M. M. Hafez, J. Chem. Soc., 1941, 652; and the mesylates of the these alcohols were prepared by the method described in Example 89, Step C.

EXAMPLE 254

6-Methoxy-3,4-dihydro-spiro(2H)-1-benzopyran-2,3'-piperidine-4-one hydrochloride Employing a procedure analogous to that described for Example 52, Steps A and B, but substituting 5-methoxy-2hydroxyacetophenone for the orthohydroxyacetophenone used therein there was obtained 6-methoxy-3,4-dihydro-spiro(2H)-1-benzopyran-2,3'-piperidine-4-one hydrochloride, mp 276°–278° C. (dec).

Employing the procedure substantially as described in Example 53, but substituting 6-methoxy-3,4-dihydro-spiro(2H)-1-benzopyran-2,3'-piperidine-4-one for the 3,4-dihydro-spiro(2H)-1-benzopyran-2,3'-piperidine]-4-one used therein, and substituting the appropriate electrophiles for the 2-(4-methanesul-fonamidophenyl)ethyl mesylate used therein, there were obtained the spiropiperidines described in the following table.

TABLE XIII

| Example | RM | salt | mp (°C.) |
|---------|----|------|----------|
| 254a | 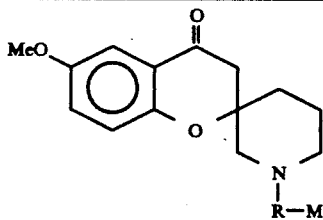 —CH₂CH₂—C₆H₄—NHSO₂CH₃ | .HCl .0.25C₂H₅ .0.15 H₂O | 207–209 |

TABLE XIII-continued

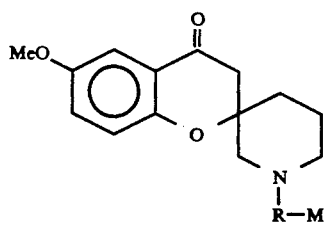

| Example | RM | salt | mp (°C.) |
|---|---|---|---|
| 255 | —CH₂CH₂—C₆H₄—CN | .HCl .0.75C₂H₅ 0.35H₂O | 251–253 |
| 256 | —CH₂CH₂—(benzofurazan) | HCl .0.1ETOH .0.1 H₂O | 275 |

Employing the procedure substantially as described in Example 52, Step C, but starting with 6-methanesulfonamido-3,4-dihydrospiro-2H-1-benzopyran-2,3′-piperidine-4-one and the appropriate vinyl pyridines there were obtained the following compounds.

TABLE XIV

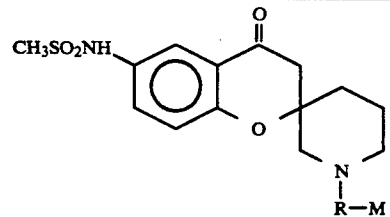

| Example | RM | salt | mp (°C.) |
|---|---|---|---|
| 257 | —CH₂CH₂—(2-methylpyridin-3-yl) | .2HCl | 285 (dec) |
| 258 | —CH₂CH₂—(pyridin-4-yl) | .2HCl .0.5H₂O | 192 |

Employing the procedure substantially as described in Example 83, but substituting for the 5-(2-bromethyl)-benzofurazan used therein, an appropriate electrophile, there were produced the following compounds.

TABLE XV

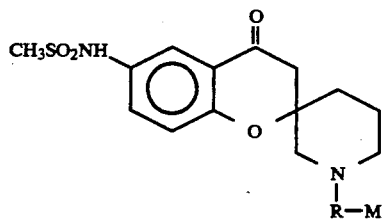

| Example | RM | salt | mp (°C.) |
|---|---|---|---|
| 259 | —CH₂CH₂—C₆H₄—NHSO₂CH₃ | .HCl .0.5H₂O .0.25C₂H₅OH | 173 |

TABLE XV-continued

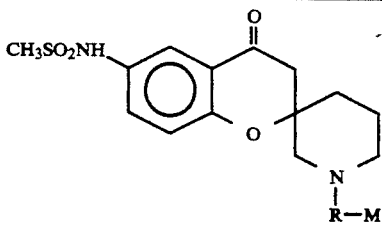

| Example | RM | salt | mp (°C.) |
|---|---|---|---|
| 260 | —CH₂CH₂—(2-Cl,3-Cl-phenyl) | .HCl .0.25H₂O | 240–242 |
| 261 | —CH₂CH₂—(4-CN-phenyl) | .HCl .0.5H₂O | 235–236 |
| 262 | —(CH₂)₅CN | .HCl .0.5H₂O | 173–175 |
| 263 | —(CH₂)₆CH₃ | .HCl | 164–166 |

EXAMPLE 264

6-Methanesulfonamido-3,4-dihydro-1'-(2-(4-amino-phenyl)ethyl)-spiro[(2H)-1-benzopyran-2,4'-piperidine]-4-one The title compound was prepared from 6-methanesulfonamido-3,4-dihydro-1'-(2-(4-nitro-phenyl)ethyl)-spiro[(2H)-1-benzopyran-2,4'-piperi-dine]-4-one by a procedure analogous to that described in Example 25, mp 271° C. (dec).

Employing a procedure substantially as described in Example 28 but substituting 6-methansulfonamido-3,4-dihydro-1'-(2-(4-amino-phenyl)ethyl)-spiro[(2H)-1benzopyran-2,4'-piper-indine]-4-one for the 1-(2-(4-amino-phenyl)ethyl) spiro(piperidine-4,6'-thieno[2,3-b]thiopyran)-4'5(H)-one used therein and the appropriate alkyl or aryl sulfonyl chlorides, there were produced the following compounds.

TABLE XVI

CH₃SO₂NH—[chroman-4-one]—spiro—[piperidine]—N—CH₂CH₂—[phenyl]—NHSO₂—R¹⁶

| Example | R¹⁶ | Salt | MP (°C.) |
|---|---|---|---|
| 265 | —CH₂CH₃ | .HCl | 250 (dec) |
| 266 | —CH₂CH₂CH₃ | .HCl | 257 (dec) |
| 267 | —CH(CH₃)₂ | .HCl | 272 (dec) |
| 268 | —CH₂CH₂CH₂CH₃ | .HCl | 205–207 |
| 269 | —C₆H₄CH₃ | .HCl .H₂O | 204–205 |

EXAMPLE 270

6-Methanesulfonamido-3,4-dihydro-1'-(2-(4-acetamido-phenyl)ethyl)-spiro[(2H)-1-benzopyran-2,4'phenyl)ethyl)-spiro[(2H)-1-benzopyran-2,4'-piperi--piperi-dine]-4one A suspension of 6-methanesulfonamido-3,4-dihydro-1'-(2-(4-aminophenyl)ethyl)-spiro[(2H)-1-benzopyran-2,4'-piperidine]-4-one (0.50 g, 1.2 mmol), and pyridine (0.09 mL, 1.2 mmol) in 25 mL of methylene chloride was cooled in an ice bath and treated dropwise with acetyl chloride (0.09 mL, 1.2 mmol). The mixture was stirred at 0° C. for 2 hours, and then filtered. The tan solid was washed with methylene chloride and dried in the air. The solid was found to be a mixture by thin layer analysis, and was chromatographed on silica gel using 10% methanol in methylene chloride eluant. The pure oil was dissolved in 20 mL of absolute ethanol and was treated with excess 4.8N ethanolic HCl. The solution was then concentrated to 10 mL. The resulting ivory colored solid was collected, washed with diethyl ether, and dried 3 hours at 100° C. under vacuum to give 0.10 g (18%) of product, mp 294° C.(dec).

Anal. Calc'd. for C₂₄H₃₀ClN₃O₅S: C, 56.74; H, 5.95; N, 8.27. Found: C, 56,70; H, 5.90; N, 8,08.

EXAMPLE 271

6-Methanesulfonamido-3,4-dihydro-1'-(2-(4-(methylsulfonylmethyl)phenyl)ethyl)-spiro[(2H)-1-benzopyran-2,4'-piperidine]-4-one (A) and
6-Methanesulfonamido-3,4-dihydro-1'-(2-(4-(methylsulfinylmethyl)phenyl)ethyl)-spiro[(2H)-1-benzopyran-2,4'-piperidine]-4-one (B)

A solution of 6-methanesulfonamido-3,4-dihydro-1'-(2-(4-(methylthiomethyl)phenyl)ethyl)-spiro [(2H)-1-benzopyran-2,4'-piperidine]-4-one (450 mg, 0.88 mmol) in 10 mL methanol was treated with a solution of Oxone ® (450 mg, 0.71 mmol) in 10 mL water. The reaction was stirred at room temperature for 1 hour and then poured into 100 mL saturated sodium bicarbonate and extracted with ethyl acetate. The ethyl acetate layers were dried over anhydrous magnesium sulfate, filtered and concentrated in vacuo. The residue was chromatographed on silica gel eluting with 2% MeOH/CHCl₃ to give in order of elution 218.8 mg of (A) free base and 170 mg of (B) free base. Each was dissolved in ethanol and treated with excess ethanolic HCl. The solids were collected and dried in vacuo to give 180 mg (A).HCl.0.3H₂O, mp 285° C.

Anal. Calc'd. for $C_{24}H_{30}N_2O_6S_2$.HCl.0.3 H₂O: C, 52.55; H, 5.81; N, 5.11. Found: C, 52.54; H, 5.75; N, 4.96.

The sample of (B) was treated in a similar manner to give 140 mg (B) .HCl.0.35H₂O, mp 274° C.

Anal. Calc'd. for $C_{24}H_{30}N_2O_5S_2$.HCl.0.35 H₂O: C, 54.04; H, 5.99; N, 5.25. Found: C, 54.08; H, 5.78; N, 5.23.

EXAMPLE 272

6-Methanesulfonamido-3,4-dihydro-1'-(2-(4-pyridyl)ethyl)spiro[(2H)-1-benzopyran-2,4'-piperidine]-4-one A solution of 6-methanesulfonamido-3,4-dihydrospiro[(2H)-1-benzopyran-2,4'-piperidine]-4-one (920 mg, 2.65 mmol3) and 4-vinyl-pyridine (1 g) in 15 mL methanol and 15 mL water was treated with NaOAc (200 mg) and heated to reflux for 16 hours. The reaction was cooled to room temperature and poured into ~100 mL of 1N NaOH. The mixture was extracted with ethyl acetate. The ethyl acetate extracts were discarded and the pH of the aqueous phase was adjusted to pH ~8–9 and extracted with ethyl acetate. The organic layer was dried over magnesium sulfate, filtered and concentrated in vacuo. The product was crystallized from ethyl acetate to give 470 mg of material that melted at 202°–204° C.

Anal. Calc'd. for $C_{21}H_{25}N_3O_4S$: C, 60.70; H, 6.06; N, 9.67. Found: C, 60.71; H, 6.04; N, 9.89.

Employing the procedure described in Example 58, but substituting the appropriate alkyl or aryl sulfonyl chlorides for the methanesulfonyl chloride used therein, there were obtained the following compounds.

TABLE XVII

R¹⁷—SO₂NH—[structure]—CH₃

| Example | R¹⁷ | Salt | MP (°C.) |
|---|---|---|---|
| 273 | —CH₂CH₃ | — | 64–66 |
| 274 | —(CH₂)₂CH₃ | .0.5H₂O | 67–70 |
| 275 | —C₆H₄CH₃ | .2HCl .H₂O | 193–195 |

EXAMPLE 276

6-Methanesulfonamido-3,4-dihydro-1'-[2-(2-chloropyrid-5-yl)ethyl]-spiro[(2H)-1-benzopyran-2,4'-piperidine]-4-one The title compound was prepared from 3,4-dihydro-6-methanesulfonamidospiro[(2H)-1-benzopyran-2,4'-piperidine]-4-one hydrochloride and 2-chloro-5-chloroethylpyridine hydrochloride by a procedure analogous to that described in Example 92, Step B. [The 2-chloro-5-chloroethylpyridine hydrochloride used in this reaction was obtained by treating 6-chloropyrid-3-yl acetic acid (L. A. Carlson, Acta Pharm. Suecica, 9, 411 (1972)) with borane-tetrahydrofuran complex followed by reaction with thionyl chloride.] mp 213°–215° C. Anal. Calc'd. for $C_{21}H_{24}ClN_3O_4S$: C, 56.05; H, 5.38; N, 9.34. Found: C, 55.93; H, 5.41; N, 9.20.

EXAMPLE 277

6-Methanesulfonamide-3,4-dihydro-1'[2-(2-chloro-1-oxopyrid-5-yl)ethyl]-spiro[(2H)-1-benzopyran-2,4'-piperidine]-4-one The N-oxide of the product of Example 276 was prepared by treating 6-methanesulfonamido-3,4-dihydro-1'-[2-(2-chloro-pyrid-5-yl)ethyl]spiro [(2H)-1-benzopyran-2,4'-piperidine]-4-one (0.170 g, 0.000378 mol) in 120 mL of chloroform with 0.276 g (0.0008 mol) of m-chloroperbenzoic acid at room temperature overnight. Calcium hydroxide (0.12 g, 0.0016 mol) was added, the mixture was stirred one hour at room temperature and was filtered and concentrated in vacuo. Flash chromatography on silica gel using CH₂Cl₂:methanol:concentrated NH₄OH (90:10:2) gave the title compound, mp 170°–171° C.

Anal. Calc'd. for $C_{21}H_{24}ClN_3O_5S$: C, 54.13; H, 5.19; N, 9.02. Found: C, 54.11; H, 5.29; N, 8.94.

EXAMPLE 278

6-Methanesulfonamido-3,4-dihydro-1'-(2-[2-(1H)-pyridon-1-yl]ethyl)spiro[(2H)-1-benzopyran-2,4'-piperidine]-4-one hydrochloride A mixture of 0.752 g of 6-methanesulfonamido-3,4-dihydro-spiro[(2H)-1-benzopyran-2,4'-piperidine]-4-one hydrochloride, 0.912 g sodium bicarbonate (s), 0.463 g of 1-(β-chloroethyl)-2-(1H)-pyridone hydrochloride (E. Wilson and M. Tishler, J. Am. Chem. Soc., 73, 3635 (1951)), a small crystal of potassium iodide and 25 mL of dry acetonitrile was stirred and refluxed overnight. The solvent was removed in vacuo, and the residue was partitioned between ethyl acetate and water. The organic phase was separated and was washed an additional five times with water. The organic phase was dried (MgSO₄), filtered, and evaporated, and the residual oil was converted to a hydrochloride salt. Recrystallization from methanol gave the title compound, mp 258°–260° C.(dec).

Anal. Calc'd. for $C_{21}H_{25}N_3O_5S$.HCl: C, 53.90; H, 5.60; N, 8.98. Found: C, 53.62; H, 5.61; N, 8.91.

The compounds of Table XVIII were prepared by heating a solution of 6-methanesulfonamido-3,4-dihydro-spiro[(2H)-1-benzopyran-2,4'-piperidine]-4-one (Example 70, Method 2, Step D) or 6-methoxy-3,4-dihydrospiro[(2H)-1-benzopyran-2,4'-piperidine]-4-one with an equimolar amount of 2-(tetrazolo[1,5-a]pyrid-6-yl)oxirane (U.S. Pat. No. 4,358,455) in ethanol to reflux for 1.5 hours. The reaction mixture was evaporated and the residue crystallized first from a minimum of ethyl acetate and recrystallized from ethanol to give the desired tetrazolopyridine (essentially as described in U.S. Pat. No. 4,358,455, Example 4, Step D).

TABLE XVIII

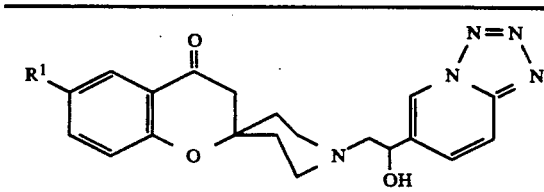

TABLE XVIII-continued

| Example | R$^1$ | Salt | mp (°C.) |
|---|---|---|---|
| 279 | CH$_3$SO$_2$NH— | HCl.0.4H$_2$O.0.3C$_3$H$_8$O* | 164 |
| 280 | CH$_3$O— | — | 173–175 |

*Isopropyl alcohol

The compounds of Table XIX were prepared by heating a solution of 35.4 mmoles of the corresponding compound of Table XVIII and 24 g (106 mmoles) of stannous chloride dihydrate in 60 ml of 12 N HCl to reflux for 2 hours. The reaction was evaporated to dryness, the residue suspended in 150 ml of methanol and basified with concentrated NH$_4$OH. The precipitated salts were removed by filtration and the product in the filtrated chromatographed over 600 g of silica gel, eluting with a mixture of CH$_2$Cl$_2$:CH$_3$OH: concentrated NH$_4$OH (15:5:4), to give, upon evaporation of the eluate, the desired aminopyridine compound (essentially as described in U.S. Pat. No. 4,358,455, Example 4, Step E).

TABLE XIX

| Example | R$^1$ | Salt | mp (°C.) |
|---|---|---|---|
| 281 | CH$_3$SO$_2$NH— | — | 186–188 |
| 282 | CH$_3$O— | — | 207–209 |

The compounds of Table XX were prepared from the corresponding compounds of Table XIX essentially by the method described in the *J. Org. Chem.*, 26, 122 (1961) for the conversion of 2-amino-5-methylpyridine to 2-hydroxy-5-methylpyridine.

TABLE XX

| Example | R$^1$ | Salt | mp (°C.) |
|---|---|---|---|
| 283 | CH$_3$SO$_2$NH— | — | 222–223 |
| 284 | CH$_3$O— | 0.5H$_2$O | 224 (dec) |

EXAMPLE 285

1'-[2-(2-Pyridyl)ethyl]spiro[1-methyl-2-oxo-indoline-3,4'-piperidine dihydrochloride hydrate A mixture of 0.108 g (0.0005 mol) of spiro[1-methyl-2-oxo-indoline-3,4'-piperidine (prepared according to U.S. Pat. No. 4,233,307), 0.21 g (0.002 mol) of 2-vinyl-pyridine, 0.068 g (0.0005 mol) of sodium acetate trihydrate, 2 mL of ethanol, and 3 drops of glacial acetic acid was refluxed for 18 hours. The solvent was evaporated and the residue was dissolved in CH$_2$Cl$_2$. After washing with a solution of sodium bicarbonate, the methylene chloride phase was dried (Na$_2$SO$_4$), filtered and evaporated. The residue was purified by chromatography on silica gel using 4% CH$_3$OH in CH$_2$Cl$_2$. The homogeneous free base was converted to its hydrochloride salt to give the title compound, mp 193°–195° C.

Anal. Calc'd. for C$_{20}$H$_{23}$N$_3$O.HCl.H$_2$O: C, 58.23; H, 6.60; N, 10.19. Found: C, 58.43; H, 6.52; N, 10.12.

EXAMPLE 286

1'-[2-(Benzofurazan-5-yl)ethyl]spiro[1-methyl-2-oxo-indoline-3,4'-piperidine hydrochloride.0.4H$_2$O A mixture of 0.108 g (0.0005 mol) of spiro[1-methyl-2-oxo-indoline-3,4'-piperidine (prepared as described in U.S. Pat. No. 4,233,307) 0.338 g (0.0015 mol) 5-(2-bromoethyl)benzofurazan, 0.083 g (0.0005 mol) of potassium iodide, 0.168 g (0.002 mol) of sodium bicarbonate, and 10 mL of ethanol was refluxed for 24 hours. After cooling, the mixture was concentrated to dryness and the residue was re-dissolved in chloroform. The mixture was filtered and the filtrate was concentrated in vacuo. The residue was purified by chromatography on silica gel using 2% CH$_3$OH in CH$_2$Cl$_2$. The homogeneous free base obtained after chromatography was converted into its hydrochloride salt using ethanolic HCl to give the title compound, mp >275° C.

Anal. Calc'd. for C$_{21}$H$_{22}$N$_4$O$_2$.HCl.0.4H$_2$O: C, 62.11; H, 5.91; N, 13.80. Found: C, 62.15; H, 5.87; N, 13.61.

EXAMPLE 287

1'-[2-(2-Benzofurazan-5-yl)ethyl]spiro[5-methanesulfonamidoisobenzofuran-1(3H),4'-piperidine]hydrochloride 1'-Methyl-spiro[isobenzofuran-1(3H),4'-piperidine]-3-one was prepared by the method of W. E. Parham, et al., *J. Org. Chem.*, 41 (15), 2628 (1976). This compound was nitrated by the procedure of Example 60, Step A, to give the corresponding nitro compound, which was reduced by the method of Example 70, Method 2, Step B. The methanesulfonamide derivative was prepared using the method of Example 70, Method 2, Step C. Using this compound and the procedure described in Example 60, Steps C and D, there was produced spiro[5-methanesulfonamidoisobenzofuran-1(3H),4'-piperidine]hydrochloride. Employing the procedure substantially as described in Example 94, Step B, but substituting for 3,4-dihydro-6-methanesulfonamidospiro[(2H)-1-benzopyran-2,4'-piperidine]-4-one used therein, spiro[5-methanesulfonamidoisobenzofuran-1(3H),4'-piperidine]hydrochloride, there was produced the title compound, mp 272°–274° C.(dec).

Anal. Calc'd. for C$_{21}$H$_{24}$N$_4$O$_4$S.HCl: C, 54.24; H, 5.42; N, 12.05. Found: C, 54.02; H, 5.34; N, 11.96.

EXAMPLE 288

3,4-Dihydro-6-methoxy-1'-(2-[2-benzimidazolon-1-yl]ethyl)spiro[(2H)-1-benzopyran-2,4'-piperidine]-4-one hydrochloride Step 1: 1-Isopropenylbenzimidazolone (J. Davol, *J. Chem. Soc.*, 1960, 308) was alkylated with 1,2-dibromoethane using sodium hydride in DMF. The product was purified by chromatography and crystallization from cyclohexane to give 1-isopropenyl-3-(2-bromoethyl)benzimidazolone.

Anal. Calc'd. for C$_{12}$H$_{13}$BrN$_2$O: C, 51.26; H, 4.66; N, 9.97. Found: C, 51.44; H, 4.67; N, 9.98.

Step 2: Using the procedure described for the preparation of 6-methoxy-3,4-dihydro-1'-(2-(2-methanesulfonamidophenyl)ethyl]spiro-[(2H)-1-benzopyran-2,4'-piperidine]-4-one but substituting 1-isopropenyl-3-(2- bromoethyl)benzimidazolone for the 2-[4-methanesulfonamidophenyl]ethyl methanesulfonate used therein, there is produced an isopropenyl derivative of the title compound. The isopropenyl protecting group was removed by stirring an ethanolic solution of the compound with concentrated hydrochloric acid at room temperature. The title compound crystallized from the reaction mixture and was purified by recrystallization from ethanol, mp 267°–269° C.(dec).

Anal. Calc'd. for $C_{23}H_{25}N_3O_4 \cdot HCl$: C, 62.23; H, 5.90; N, 9.47. Found: C, 62.34; H, 5.82; N, 9.34.

EXAMPLE 289

3,4-Dihydro-6-methoxy-1'-[2-(4-N-cyano-N'-benzyl-S-methylthiourea)ethyl]spiro[(2H)-1-benzopyran-2,4'-piperidine]-4-one hydrochloride Step A: Preparation of 4-(2-hydroxyethyl)benzylamine A solution of 0.74 g (0.005 mol) of p-cyanophenethyl alcohol in 50 ml of ethanol containing 10 ml of concentrated hydrochloric acid was hydrogenated at 30 psi using 0.1 g 5% Pd/C for 72 hours. The catalyst was removed by filtration and the solvent was removed under reduced pressure.

Step B: Preparation of N-cyano-N'-[4-(2-hydroxyethyl)benzyl]-S-methylisothiourea The residue obtained from the hydrogenation reaction (0.88 g, 0.007 mol) was dissolved in 20 ml of acetonitrile and 0.4 g (0.0047 mol) of sodium bicarbonate and 0.687 (0.0047 mole) of dimethylcyanodithioimidocarbonate were added. The mixture was refluxed overnight. After cooling, the white solid was removed by filtration and dried to give 0.93 g of N-cyano-N'-[4-(2-hydroxyethyl)benzyl]-S-methylisothiourea, mp 164°–165° C.

Anal. Calc'd. for $C_{12}H_{15}N_3OS$: C, 57.80; H, 6.06; N, 16.86. Found: C, 57.58; H, 5.88; N, 16.80.

Step C: Preparation of 3,4-dihydro-6-methoxy-1'-[2-(4-N-cyano-N'-benzyl-S-methylthiourea)ethyl]-spiro[(2H)-1-benzopyran-2,4'-piperidine]-4-one hydrochloride N-Cyano-N'-[4-(2-hydroxyethyl)benzyl]-S-methylisothiourea (0.47 g, 0.00189 mol) and triethylamine (0.48 g, 0.0047 mol) were dissolved in dichloromethane. Methanesulfonyl chloride (0.43 g, 0.00378 mol) was added and the mixture was stirred at reflux overnight. The cooled reaction mixture was diluted with methylene chloride and was washed with an aqueous solution of sodium bicarbonate. The organic phase was separated, dried ($Na_2SO_4$), filtered and evaporated. To the residue was added 0.4 g (0.00475 mol) of sodium bicarbonate and 0.426 g (0.0015 g) of 3,4-dihydro-6-methoxy-spiro[(2H)-1-benzopyran-2,4'-piperidine]-4-one hydrochloride and 20 ml of acetonitrile. The mixture was heated at reflux for 60 hours. The cooled mixture was diluted with water and was extracted with methylene chloride. This organic phase was dried over $MgSO_4$, filtered, and the solvent removed under reduced pressure. The residue was purifed by flash column chromatography on silica gel eluting with 5% methanol in chloroform. The purified product was converted to the hydrochloride salt. Recrystallization from methanol gave the title compound, mp 263°–264° C.

Anal. Calc'd. for $C_{26}H_{30}N_4O_3S \cdot HCl$: C, 60.63; H, 6.07; N, 10.88. Found: C, 60.56; H, 5.98; N, 10.84.

EXAMPLE 290

3,4-Dihydro-6-methoxy-1'-[2-(4-N-cyano-N'-methyl-N''-guanidinobenzyl)ethyl]spiro[(2H)-1-benzopyran-2,4'-piperidine]-4-one hydrochloride Step A: Preparation of N-cyano-N'-methyl-N''-[4-(2-hydroxyethyl)benzyl]guanidine A solution of 0.42 g (0.00168 mol) of N-cyano-N'-[4-(2-hydroxyethyl)benzyl]-S-methylisothiourea in 50 ml of methanol and 10 g of methylamine was stirred at room temperature overnight. Evaporation of the solvent gave the title compound.

Step B: Preparation of 3,4-dihydro-6-methoxy-1'-[2-(4-N-cyano-N'-methyl-N''-guanidinobenzyl)ethyl]-spiro[(2H)-1-benzopyran-2,4'-piperidine]-one hydrochloride To a solution of the N-cyano-N'-methyl-N''-[4-(2-hydroxyethyl)benzyl]guanidine in 10 ml of pyridine was added 0.25 g (0.00218 mol) of methanesulfonyl chloride and the mixture was stirred at room temperature for 5 hours. The solvent was removed under reduced pressure and the residue was dissolved in methylene chloride and was washed with a saturated solution of sodium bicarbonate. The organic phase was separated, dried ($MgSO_4$), filtered, and evaporated. To the residue was added 0.426 g (0.0015 mol) of 3,4-dihydro-6-methoxy-spiro[(2H)-1-benzopyran-2,4'-piperidine]-4-one hydrochloride, 0.315 g (0.00375 mol) of sodium bicarbonate, and 25 ml of acetonitrile. The mixture was heated under reflux for 24 hours. After evaporating the solvent, the residue was extracted into methylene chloride. This organic phase was washed with water, dried ($Na_2SO_4$), filtered and evaporated to dryness. The residue was purified by flash column chromatography on silica gel eluting with 5% methanol in methylene chloride. The purified product was converted to the hydrochloride salt. Recrystallization from isopropyl alcohol/methanol gave the title compound, mp about 204° C. (dec).

Anal. Calc'd. for $C_{26}H_{31}N_5O \cdot HCl \cdot 0.5 H_2O$: C, 61.59; H, 6.56; N, 13.81. Found: C, 61.59; H, 6.57; N, 13.62.

EXAMPLE 291

1'-[2-(2-Pyridyl)ethyl]spiro[1-methyl-2-oxo-5-methanesulfonamidoindoline-3,4'-piperidine dihydrochloride Step A: Preparation of 1'-ethoxycarbonyl-spiro[1-methyl-2-oxoindoline-3,4'-piperidine A mixture of 9.09 g (0.03 mol) of 2-bromo-N-(2-bromoethyl)-N-carbethoxyethanamine (S. Huybrechts and G. J. Hoornaert, Syn. Comm., 11 (1), 17-23 (1981)) and 2.94 g (0.02 mol) of 1-methyl-2-oxo-indoline in 10 ml of DMF was warmed at 50° C. in an oil bath. Sodium hydride (2.0 g, 60%, 0.05 mol) was added in small portions, and after the addition was complete, the mixture was heated at 50° C. for 12 hours. The DMF was removed under reduced pressure. The residue was triturated with hexane. The residue crystallized and was filtered off and washed to give 2.7 g 1'-ethoxycarbonyl-spiro[1-methyl-2-oxoindoline-3,4'-piperidine.

Step B: Preparation of spiro[1-methyl-2-oxo-5-methanesulfonamidoindoline-3,4'-piperidine hydrochloride A solution of 0.144 g (0.0005 mol) of the product of Step A in 1.5 ml of methylene chloride and 0.142 ml of acetic anhydride was treated at 0° C. with 0.105 g (0.0015 mol) of 90% fuming nitric acid. When the addition was complete, the solution was allowed to stir at room temperature for 3 hours. The solution was then cooled and saturated sodium bicarbonate solution was added until the mixture was basic. The mixture was extracted with methylene chloride. After drying (Na$_2$SO$_4$), the mixture was filtered, and the solvent was evaporated. The residue was hydrogenated in ethanol over Raney nickel catalyst at 10 psi overnight. The mixture was filtered, and the ethanol was removed under reduced pressure. The residue was dissolved in a mixture of 25 ml of methylene chloride and 0.84 g (0.0083 mol) of triethylamine and then was treated with 0.70 g (0.0069 mol) of methanesulfonyl chloride. The mixture was stirred overnight at room temperature. The reaction mixture was washed with sodium bicarbonate solution, dried (NgSO$_4$), filtered, and evaporated. The crude product was purified by chromatography on silica gel using 3% methanol in methylene chloride. The purified product was refluxed with 6N hydrochloric acid for 3.5 hours. Evaporation of the solvent gave spiro[1-methyl-2-oxo-5-methanesulfonamidoindoline-3,4'-piperidine hydrochloride.

Step C: Preparation of 1'-[2-(2-Pyridyl)ethyl]-spiro[1-methyl-2-oxo-5-methanesulfonamidoindoline-3,4'-piperidine dihydrochloride A mixture of 0.16 g (0.000524 mol) of material from Step B, 0.22 g (0.0021 mol) of vinylpyridine, 0.143 g (0.00105 mol) of sodium acetate trihydrate, and 6 ml of aqueous ethanol (1:1) was refluxed for 12 hours. The solvent was removed under reduced pressure, and the residue was dissolved in methylene chloride and was washed with sodium bicarbonate. The organic phase was dried (Na$_2$SO$_4$), filtered, and evaporated. The residue was purified by chromatography on silica gel using 5% methanol in chloroform. The purified product was converted to its hydrochloride salt using ethanolic hydrogen chloride, and was recrystallized from ethanol, mp 214° C.

Anal. Calcd. for C$_{21}$H$_{26}$N$_4$O$_3$S.2HCl.0.2C$_2$H$_5$OH.0.5H$_2$O: C, 50.83; H, 5.97; N, 11.08. Found: C, 50.84; H, 5.97; N, 11.08.

EXAMPLE 292

1'-[2-(2-Pyridyl)ethyl]spiro[1-methyl-5-methanesulfonamidoindoline-3,4'-piperidine trihydrochloride Step A: Preparation of spiro[1-methyl-5-methanesulfonamidoindoline-3,4'-piperidine]

To a suspension of 0.50 g (0.001616 mol) of spiro[1-methyl-2-oxo-5-methanesulfonamidoindoline-3,4'-piperidine] in 30 ml of dry tetrahydrofuran was added dropwise 4 ml (0.04 mol) of a 1.0M solution of lithium aluminum hydride in THF. The mixture was stirred and refluxed for 5 hours. A saturated solution of ammonium chloride was added dropwise to the cooled reaction mixture until a clear, colorless organic phase was obtained and a semisolid inorganic phase was deposited on the bottom of the flask. The THF phase was decanted and the inorganic phase was washed with chloroform. The combined organic phases were dried (Na$_2$SO$_4$), filtered, and evaporated to afford 0.36 g of spiro[1-methyl-5-methanesulfonamidoindoline-3,4'-piperidine.

Step B: Preparation of 1'-[2-(2-Pyridyl)ethyl]spiro[1-methyl-5-methanesulfonamidoindoline-3,4'-piperidine trihydrochloride A mixture of 0.15 g (0.000537 mol) of spiro[1-methyl-5-methanesulfonamidoindoline-3,4'-piperidine from Step A, 0.22 g (0.00215 mol) of 2-vinylpyridine, 0.073 g (0.000537 mol) of sodium acetate trihydrate, and 6 ml of aqueous acetone (1:1) was stirred and heated at reflux for 12 hours. An additional 0.06 g (0.000537 mol) of 2-vinylpyridine was added and the solution was refluxed for 5 hours. The solvent was removed under reduced pressure and the residue was dissolved in methylene chloride, washed with water, dried (Na$_2$SO$_4$), filtered, and evaporated. The residue was purified by chromatography on silica gel using 5% methanol in chloroform to elute. The purified product was converted to the hydrochloride salt in isopropyl alcohol, mp 183°–189°.

Anal. Calcd. for C$_{21}$H$_{28}$N$_4$O$_2$S.3HCl.H$_2$O: C, 47.77; H, 6.30; N, 10.61. Found: C, 47.99; H, 6.34; N, 10.46.

EXAMPLE 293

3,4-Dihydro-6-methoxy-1'-[1,3-dimethylpyrimidin-2,4-(1H,3H)-dione-6-yl]spiro[(2H)-1-benzopyran-2,4'-piperidine]-4-one A solution of 3,4-dihydro-6-methoxyspiro-[(2H)-1-benzopyran-2,4'-piperidin]-4-one hydrochloride (0.568 g, 2 mmol), 6-chloro-1,3-dimethylpyrimidine-2,4-(1H,3H)-dione (0.349 g, 2 mmol) and sodium bicarbonate (0.42 g, 5 mmol) in acetonitrile was heated at reflux for 42 hours. After cooling, the reaction mixture was concentrated in vacuo to dryness. The residue was partitioned between chloroform and water. The chloroform solution was washed twice with water and once with saturated brine solution and then dried over sodium sulfate and concentrated to dryness in vacuo. The solid residue was recrystallized from methanol/ethanol to give the title compound (0.47 g, 61% yield) mp 202°–203° C.

Anal. Calc'd for C$_{20}$H$_{23}$N$_3$O$_5$: C, 62.33; H, 6.02; N, 10.90. Found: C, 62.46; H, 6.08; N, 10.87.

EXAMPLE 294

3,4-Dihydro-6-methanesulfonamide-1'-[1,3-dimethylpyrimidine0-2,4(1H,3H)-dione-6-yl]spiro[(2H)-1-benzopyran-2,4'-piperidine]-4-one Utilizing the methodology of Example 293, the title compound was prepared, mp 259.5°–262° C.

Anal. Calc'd for C$_{20}$H$_{24}$N$_4$O$_6$S: C, 53.56; H, 5.39; N, 12.49. Found: C, 53.16; H, 5.47; N, 12.24.

EXAMPLE 295

3,4-Dihydro-6-methoxy-1'-[2-(1,3-dimethylpyrimidin-2,4(1H,3H)dione-6-yl)ethylmercapto]spiro[(2H)-1-benzopyran-2,4'-piperidine]-4-one A solution of 6-chloro-1,3-dimethyluracil (0.87 g, 5 mmol), 2-mercaptoethanol (0.39 g, 5 mmol) and sodium bicarbonate (0.63 g, 7.5 mmol) in acetonitrile (15 ml) was heated at reflux for 24 hours. After cooling, the reaction mixture was concentrated in vacuo to dryness. The residue was partitioned between chloroform and water. The combined chloroform solution was dried over magnesium sulfate, filtered and concentrated to dryness. The residue was triturated with ether and filtered off.

A solution of the residue (0.83 g, 3.8 mmol), triethylamine (0.58 g, 5.7 mmol) and methanesulfonyl chloride (0.48 g, 4.2 mmol) in methylene chloride (30 ml) was stirred in an ice bath for 3 hours. The resulting reaction was washed with water and brine, dried over sodium sulfate and concentrated in vacuo to dryness. The residue was triturated with ether, and the solid mesylate was filtered off.

A solution of the mesylate (0.44 g, 1.5 mmol), 3,4-dihydro-6-methoxyspiro[(2H)-1-benzopyran-2,4'-piperidin]-4-one (0.425 g, 1.5 mmol) and sodium bicarbonate (0.315 g, 3.75 mmol) in acetonitrile (15 ml) was heated at reflux for 23 hours. After cooling, the reaction mixture was concentrated in vacuo to dryness. The residue was partitioned between chloroform and water. The chloroform solution was washed with water, brine and dried over sodium sulfate and concentrated in vacuo to dryness. The residue was triturated with hot ethanol/methanol and filtered off to give the title compound, mp 191°–193.5° C. (0.31 g, 46.4%).

Anal. Calc'd for $C_{22}H_{27}N_3O_5S$: C, 59.31; H, 6.11; N, 9.43. Found: C, 59.07; H, 6.08; N, 9.38.

EXAMPLE 296

3,4-Dihydro-6-methanesulfonamido-1'-[2-(1,3-dimethylpyrimidin-2,4(1H,3H)dione-6-yl)ethylmercapto]-spiro[(2H)-1-benzopyran-2,4'-piperidine]-4-one Utilizing the methodology of Example 295, the title compound was prepared, mp 198°–201° C.

Anal. Calc'd for $C_{22}H_{28}N_4O_6S_2$: C, 51.95; H, 5.55; N, 11.02. Found: C, 51.62; H, 5.42; N, 10.99.

EXAMPLE 297

3,4-Dihydro-6-methanesulfonamido-1'-[2-(1,3-dimethylpyrimidine-2,4(1H,3H)-dione-6-yl)ethylamino]-spiro[(2H)-1-benzopyran-2,4'-piperidine]-4-one 1,3-Dimethyl-6-[2-(methylsulfonyloxy)ethylamino]-2,4(1H,3H)-pyrimidinedione (prepared as described in EPO Publication 0,369,627) (0.4 g, 2 mmol) was suspended in pyridine (2 ml) and cooled to 0° C., methanesulfonyl chloride (0.286 g, 2.5 mmol) was added at <5° C. the reaction mixture was stirred in an ice bath for 3 hours and was concentrated in vacuo to dryness. The residue was partitioned between chloroform and saturated sodium bicarbonate. The chloroform layer was dried over sodium sulfate, filtered, and concentrated to give the mesylate.

A solution of the mesylate (0.26 g, 0.94 mmol), 3,4-dihydro-6-sulfamidospirop[(2H)-1-benzopyran-2,4'-piperidin]-4-one (0.347 g, 1 mmol) and sodium bicarbonate (0.25 g, 2.5 mmol) in acetonitrile (30 ml) was heated at reflux for 2 hours. After cooling, the reaction mixture was concentrated in vacuo to dryness. The residue was stirred in chloroform and methanol and filtered off solid. This solid was heated with hot ethanol. After cooling, the title compound was filtered off.

Anal. Calc'd for $C_{22}H_{29}N_5O_6S$: C, 53.76; H, 5.95; N, 14.25. Found: C, 53.50; H, 5.94; N, 14.13.

EXAMPLE 298

3,4-Dihydro-6-methoxy-1'-[2-(1,3-dimethylpyrimidine-2,4(1H,3H)-dione-6-yl)ethylamino]spiro[(2H)-1-benzopyran-2,4'-piperidine]-4-one A suspension of 3,4-dihydro-6-methoxyspiro[(2H)-1-benzopyran-2,4'-piperidin]-4-one (0.284 g, 1 mmol) and sodium bicarbonate (0.42 g, 5 mmol) in acetonitrile was heated at reflux for 1 hour, 2-chloro ethylamine hydrochloride (0.116 g, 1 mmol) was added the solution was heated at reflux for 17 hours, 6-chloro-1,3-dimethyluracil (0.175 g, 1 mmol) and sodium bicarbonate (0.16 g, 2 mmol) were added. Refluxing was continued for 28 hours. After cooling, the reaction mixture was concentrated in vacuo to dryness. The residue was partitioned between chloroform and water. The chloroform solution was washed with water and dried over sodium sulfate. The resulting residue was chromatographed through a pressure column (silica gel) eluting with 5% methanol/chloroform to give the title compound (45 mg, 10.5% yield), mp 235°–238° C. dec.

Anal. Calc'd for $C_{22}H_{27}N_4O_5$: C, 61.67; H, 6.59; N, 13.08. Found: C, 61.40; H, 6.69; N, 12.68.

EXAMPLE 299

1'-[2-(3,4-Diaminophenyl)ethyl]-3,4-dihydro-6-methanesulfonamidospiro[(2H)-(1-benzopyran-2,4'-piperidine]4-one and dihydrochloride Step 1: A suspension of 5.24 g (15.0 mmol) of 1-(8-[2-(4-acetamido-3-nitrophenyl)ethyl]-1,4-dioxa-8-azaspiro[4.5]decane in 30 mL 2N hydrochloric acid was heated at reflux for 1.5 hours. The cooled mixture was basified (pH 9–10) with saturated sodium carbonate solution and 10N sodium hydroxide diluted with 100 ml water, and extracted with methylene chloride (3×150 ml). The extract was washed with 50 ml water and brine, dried over sodium sulfate and filtered. The filtrate was concentrated in vacuo to give 3.95 g (100%) of 1-[2-(4-amino-3-nitrophenyl)ethyl]-4-piperidone as an oil.

$^1$H NMR CDCl$_3$: δ7.98 (d,1H), 7.25 (d of d, 1H), 6.77 (d, 1H), 6.01 (broad s, 2H), 2.82 (t, 4H), 2.76 (m, 2H), 2.70 (m, 2H), 2.48 (t, 4H).

Step 2: A solution of 3.44 g (15.0 mmol) 5-methanesulfonamido-2-hydroxy-acetophenone 0.53 g (7.5 mmol) pyrrolidine, and 3.95 g (15.0 mmol) 1-[2-(4-amino-3-nitrophenyl)ethyl])piperidin-4-one in 30 mL methanol was heated at reflux for 30 hours. The solvent was removed in vacuo and the residue was partitioned between 50 mL ethyl acetate and 25 mL 1N hydrochloric acid. The layers were separated and the ethyl acetate layer was extracted with 1N hydrochloric acid (2×25 mL). The combined aqueous extract was basified with 10N sodium hydroxide to pH 10, then extracted with methylene chloride (3×175 mL). The extract was washed with 50 mL water and brine, dried over sodium sulfate and filtered. The filtrate was concentrated in vacuo to give a residue which was purified by flash chromatography on silica gel eluting with 2.5:97.5 methanol:chloroform saturated with ammonia to give 3.72 g (52%) of 1'-[2-(4-amino-3-nitrophenyl)ethyl]-3,4-dihydro-6-methanesulfonamidospiro](2H)-1-benzopyran-2,4'-piperidine]-4-one as an orange solid, m.p. 69°–78° C.

$^1$H NMR (CDCl$_3$): δ7.96 (d, 1H), 7.64 (d, 1H), 7.52 (d of d, 1H), 7.24 (d of d, 1H), 7.03 (d, 1H), 6.76 (d, 1H), 5.99 (broad s, 2H), 3.01 (s, 1H), 2.73 (s, 2H), 2.72 (m, 4H), 2.62 (m, 2H), 2.50 (t, 2H), 2.08 (d, 2H), 1.78 (m, 2H).

Step 3: To a solution of 3.56 g (7.5 mmol) 1'-[2-(4-amino-3-nitrophenyl)ethyl]-3,4-dihydro-6-methanesulfonamidospiro[(2H)-(1-benzopyran-2,4'-piperidine]-4-one in 30 mL acetic acid was added dropwise over 50 minutes a solution of 22.7 mL (26.3 mmol) titanium trichloride (15%) in 20–30% hydrochloric acid. The solution was stirred 20 minutes, basified (pH 9–10) with saturated sodium carbonate solution and 10N sodium hydroxide, diluted with 200 mL water, and extracted with methylene chloride (3×300 mL). The combined extract was washed with 50 mL water and brine, dried over sodium sulfate and filtered. The filtrate was concentrated in vacuo to give the crude product which was re-crystallized from methylene chloride:ether (1:2) to give 2.16 g (65%) 1'-[2-(3,4-diaminophenyl)ethyl] 3,4-dihydro-6-methanesulfonamidospiro[(2H)-1-benzopyran-2,4'-piperidine]-4-one as a yellow solid mp. 109°–112° C.

Step 4: To a solution of 0.222 g (0.50 mmol) 1'-[2-(3,4-diaminophenyl)ethyl]-3,4-dihydro-6-methanesulfonamidospiro[(2H)-1-benzopyran-2,4'-piperidine] 4-one in 5 ml ethanol was added 0.27 ml (1.6 mmol) 5.9N hydrogen chloride in ethanol. A precipitate formed which was filtered off and dried in vacuo to yield 0.226 g (87%) dihydrochloride salt of 1'-[2-(3,4-diaminophenyl)ethyl]-3,4-dihydro-6-methanesulfonamidospiro[(2H)-1-benzopyran-2,4'-piperidine] 4-one containing 0.65 water as a solvate, as a white solid, mp. 255°–256° C.

Anal Calcd for $C_{22}H_{28}N_4O_4 \cdot HCl \cdot 0.65 H_2O$: C, 49.93; H, 5.96; N, 10.59. Found: C, 49.91; H, 5.86; N, 10.48.

EXAMPLE 300

1'-[2-(3,4-Bis(methanesulfonamido)phenyl)ethyl]-3,4-dihydro-6-methanesulfonamidospiro[(2H)-1-benzopyran-2,4'-piperidine)]-4-one hydrochloride To a solution of 0.222 g (0.50 mmol) 1'-[2-(3,4-diaminophenyl)ethyl]-3,4-dihydro-6-methanesulfonamidospiro[(2H)-1-benzopyran-2,4'-piperidine] 4-one and 0.16 g (2.0 mmol) pyridine in 8 mL methylene chloride was added 0.120 g (1.05 mmol) methanesulfonyl chloride. The resulting mixture was stirred one hour, then diluted with 10 mL methylene chloride. The mixture was washed with 10 mL saturated sodium bicarbonate solution, 3 mL water, and brine, dried over sodium sulfate, and filtered. The filtrate was concentrated in vacuo to give a gum which was purified by flash chromatography on silica gel eluting with 5:95 methanol:chloroform saturated with ammonic to give 0.125 g of the free base.

To a solution of 0.12 g (0.20 mmol) of the free base in 10 mL ethanol was added 0.037 mL (0.22 mmol) 5.9N hydrogen chloride in ethanol to give a white precipitate. The precipitate was filtered off and dried in vacuo to give 0.074 g (24%) hydrochloride as a 0.20 ethanol and 0.75 water solvate as a off-white solid m.p. 178°–181° C.

Anal Calcd for $C_{24}H_{32}N_4O_8S_3 \cdot HCl \cdot 0.20 C_2H_5OH \cdot 0.75 H_2O$: C, 44.41; H, 5.45; N, 8.49. Found: C, 44.41; H, 5.35; N, 8.49.

EXAMPLE 301

1'-[2-(1H-Benzimidazol-5-yl)ethyl]-3,4-dihydro-6-methanesulfonamidospiro[(2H)-1-benzopyran-2,4'-piperidine)]-4-one dihydrochloride A solution of 0.36 g (0.80 mmol) 1'-[2-(3,4-diaminophenyl)ethyl]-3,4-dihydro-6-methanesulfonamidospiro[(2H)-1-benzopyran-2,4'-piperidine] 4-one and 1 mL (6 mmol) triethyl orthoformate in 1 mL ethanol was heated at reflux for 2 hours. The solvent was evaporated in vacuo to give a residue which was purified by flash chromatography on silica gel eluting with 5:95 methanol:chloroform saturated with ammonia to give 0.38 g of the free base as a foam.

To a solution of the free base in 4 mL ethanol was added 0.27 mL (1.6 mmol) 5.9N hydrogen chloride in ethanol to give a gummy precipitate. The mixture was diluted with 10 mL ether, stirred two hours, and the precipitate filtered off and dried in vacuo to give 0.317 g (75%) of the title compound as a 0.35 ethanol and 1.35 water solvate, as a pale yellow solid m.p. 221°–225° C.

Anal Calcd. for $C_{23}H_{26}N_4O_4S \cdot 2HCl \cdot 0.35 C_2H_5OH \cdot 1.35 H_2O$: C, 50.12; H, 5.82; N, 9.87. Found: C, 50.08; H, 6.00; N, 9.96.

EXAMPLE 302

1'-[2-(2,2-Dioxo-1H,3H-2,1,3-benzothiadiazolin-5-yl)ethyl]-3,4-dihydro-6-methanesulfonamidospiro[(2H)-1-benzopyran-2,4'-piperidine]-4-one hydrochloride To 0.7 mL refluxing diglyme was added dropwise over 10 minutes a solution of 0.31 g (0.70 mmol) 1'-[2-(3,4-diaminophenyl)ethyl]-3,4-dihydro-6-methanesulfonamidospiro[(2H)-1-benzopyran-2,4'-piperidine]-4-one and 0.067 g (0.70 mmol) sulfamide in 1.4 mL diglyme. The mixture was heated at reflux for four hours and the diglyme was distilled off under reduced pressure leaving a solid residue. The residue was placed under 5 mL ethanol, the mixture was heated at reflux for 10 minutes, cooled to 40° C., and the solid was filtered off. The solid was extracted with hot methanol (4×25 mL) and filtered. The filtrate was concentrated in vacuo to give 0.042 g impure free base.

To a suspension of the free base in 5 mL ethanol was added 0.015 ml (0.088 mmol) 5.9N hydrogen chloride in ethanol. The solid slowly dissolved. The solution was concentrated in vacuo to 1 ml and diluted with 2 ml ether to give a precipitate. The precipitate was filtered off and recrystallized from ethanol to give 0.012 g (3%) of the title compound as a 0.30 water solvate, as a tan solid, mp 270°–275° C.

Anal. Calcd. for $C_{22}H_{26}N_4O_6S_2 \cdot HCl \cdot 0.30 H_2O$: C, 48.17; H, 5.07; N, 10.20 Found: C, 48.14; H, 5.36; N, 10.02.

EXAMPLE 303

1'-[2-(2,1-3-Benzothiadiazol-5-yl)ethyl]-3,4-dihydro-6-methanesulfonamidospiro[(2H)-1-benzopyran-2,4'-piperidine]-4-one hydrochloride To a mixture of 0.267 g (0.60 mmol) 1'-[2-(3,4-diaminophenyl)ethyl]-3,4-dihydro-6-methanesulfonamidospiro[(2H)-1-benzopyran-2,4'-piperadine] 4-one and 0.30 g (3.0 mmol) triethylamine in 5 mL methylene chloride was added 0.083 g (0.70 mmol) thionyl chloride. The resulting solution was stirred 90 minutes and 0.083 g (0.70 mmol) thionyl chloride was added. The solution was stirred 90 minutes, diluted with 50 mL methylene chloride, and washed with 15 mL saturated sodium bicarbonate. The aqueous layer was extracted with 25 mL methylene chloride. The combined organic layer was washed with 15 mL water and brine, dried over sodium sulfate, and filtered. The filtrate was concentrated in vacuo to give a residue which was purified by flash chromatography on silica gel eluting with 5:95 methanol: chloroform saturated with ammonia. The solid obtained was recrystallized from ethyl acetate to give 0.180 g free base.

To a suspension of the free base in 5 mL ethanol was added 0.064 mL (0.38 mmol) 5.9N hydrogen chloride in ethanol to give a yellow precipitate. The precipitate was filtered off and dried in vacuo to give 0.171 g (56%) of the title compound as a yellow solid mp 259°–260° C.

Anal. Calcd. for $C_{22}H_{24}N_4O_4S_2 \cdot HCl$: C, 51.91; H, 4.95; N, 11.01. Found: C, 51.61; H, 4.86; N, 10.95.

EXAMPLE 304

1'-[2-(2,3-Dihydro-2-oxo-1H-benzimidazol-5-yl)ethyl]3,4-dihydro-6-methanesulfonamidospiro[(2H)-1-benzopyran-2,4'-piperidine]-4-one hydrochloride To a mixture of 0.266 g (0.60 mmol) 1'-[2-(3,4-diaminophenyl)ethyl]-3,4-dihydro-6-methanesulfonamidospiro[(2H)-1-benzopyran-2,4'-piperidine]4-one in 4.5 mL tetrahydrofuran was added a solution of 0.126 g (0.78 mmol) carbonyldiimidazole in 2.5 mL tetrahydrofuran. The resulting solution was stirred for two hours and a precipitate formed which was filtered off to give 0.181 g free base.

To a suspension of 0.176 g (0.38 mmol) free base in 4 mL ethanol was added 0.046 mL (0.38 mmol) 5.9N hydrogen chloride in ethanol. The solid dissolved and a precipitate formed which was filtered off and dried in vacuo to give 0.173 g (58%) of the title compound as a 0.10 ethanol and 0.35 water solvate, as a white solid mp 270°-272° C.

Anal. Calcd. for $C_{23}H_{26}N_4O_5S \cdot HCl \cdot 0.10 C_2H_5OH \cdot 0.35 H_2O$: C, 53.80; H, 5.51; N, 10.82. Found: C, 53.75; H, 5.64; N, 10.84.

EXAMPLE 305

1'-[2-(1-Methyl-1H-benzimidazol-5-yl)ethyl]3,4-dihydro-6-methanesulfonamidospiro-[(2H)-1-benzopyran-2,4'-piperidine]-4-one dihydrochloride and 1'-[2-(1-Methyl-1H-benzamidazol-6-yl)ethyl]-3,4-dihydro-6-methanesulfonamidospiro-[(2H)-1-benzopyran-2,4'-piperidine]-4-one To a mixture of 0.204 g (0.45 mmol) 1'-[2-(3,4-diaminophenyl)ethyl]-3,4-dihydro-6-methanesulfonamidospiro[(2H)-1-benzopyran-2,4'-piperidine]4-one free base and 0.093 g (0.80 mmol) diisopropylethylamine in 1.5 mL methanol was added 0.069 g (0.52 mmol) dimethylsulfate. The mixture was heated at reflux for 2 hours, 0.078 g (0.60 mmol) dimethyl sulfate was added, and the solution was heated at reflux overnight. The solution was concentrated in vacuo and the residue was partitioned between 5 mL saturated sodium bicarbonate solution and 20 mL chloroform. The layers were separated and the aqueous layer was extracted with chloroform (2×10 mL). The combined extract was washed with 5 mL water and brine, dried over sodium sulfate, and filtered. The filtrate was concentrated in vacuo to give a residue which was purified by flash chromatography on silica gel eluted with 5:95 methanol:chloroform saturated with ammonia to give a gum. This was further purified by preparative thin layer chromatography using the above eluent to give 0.018 g free base.

To a solution of the free base in 0.2 ml ethanol was added 0.0136 ml (0.080 mmol) 5.9N hydrogen chloride in ethanol to give a gummy precipitate. The mixture was diluted with 2 ml ether and stirred 2 hours to give a fine yellow solid. The solid was filtered off and dried in vacuo to give 0.014 g (6%) of the title compound as a 0.20 ethanol and 1.00 water solvate as a pale orange solid 220°-232° C.

Anal. Calcd. for $C_{24}H_{28}N_4O_4S \cdot 2HCl \cdot 0.20 C_2H_5OH \cdot 1.00 H_2O$: C, 51.53; H, 5.88; N, 9.85. Found: C, 51.61; H, 5.86; N, 9.84.

EXAMPLE 306

1'[2-(2-methyl-1H-benzimidazol-5-yl)ethyl]-3,4-dihydro-6-methanesulfonamidospiro[(2H)-1-benzopyran-2,4'-piperidine]-4-one dihydrochloride A solution of 0.355 g (0.80 mmol) 1'-[2-(3,4-diaminophenyl)ethyl]-3,4-dihydro-6-methanesulfonamidospiro[(2H)-1-benzopyran-2,4'-piperidine]4-one and 1 mL (6 mmol) triethyl orthoacetate in 1 mL ethanol was heated at reflux for two hours. The solution was concentrated in vacuo to give a residue. The residue was dissolved in 5 mL chloroform, there was added 0.334 g (1.76 mmol) p-toluenesulfonic acid hydrate, and the resulting solution was stirred two hours. The solution was concentrated in vacuo to give a residue which was purified by flash chromatography on silica gel eluting with 5:95 methanol: chloroform saturated with ammonia to give 0.226 g of the free base as a foam.

To a solution of 0.202 g (0.43 mmol) free base in 2 ml ethanol was added 0.152 ml (0.90 mmol) 5.9N hydrogen chloride in ethanol. The resulting solution was stirred 30 minutes, diluted with 5 mL ether, and stirred 3 hours to give a white precipitate. The precipitate was filtered off and dried in vacuo to give 0.181 g (47%) of the title compound as a 0.20 ethanol solvate as a white solid, mp 224°-227° C.

Anal. Calc for $C_{24}H_{28}N_4O_4S \cdot 2HCl \cdot 0.20 C_2H_5OH$: C, 53.21; H, 5.71; N, 10.12. Found: C, 52.85; H, 5.64; N, 10.16.

EXAMPLE 307

3,4-Dihydro-6-methanesulfonomide-1'-[2-(6-quinoxolinyl)ethyl]spiro[(2H)-1-benzopyran-2,4-piperidine]4-one hydrochloride To a mixture of 0.356 g (0.80 mmol) 1'-[2-(3,4-diaminophenyl)ethyl]-3,4-dihydro-6-methanesulfonamidospiro[(2H)-1-benzopyran-2,4'-piperidine]4-one in 1.3 ml water heated to 70° C. was added a hot solution of 0.250 g (0.88 mmol) of glyoxal sodium bisulfite addition compound monohydrate (Aldrich Chemical Co.) in 1 mL water and 0.083 g (0.80 mmol) sodium bisulfite. The mixture was stirred at 70° C. for two hours, cooled to room temperature, diluted with 5 mL water, and extracted with chloroform (3×25 ml). The extract was washed with 5 mL water and brine, dried over sodium sulfate, and filtered. The filtrate was concentrated in vacuo to give a residue which was purified by flash chromatography eluting with 5:95 methanol:chloroform saturated with ammonia to give 0.174 g of the free base.

To a solution of the free base in 2 ml ethanol was added 0.127 ml (0.75 mmol) 5.9N hydrogen chloride in ethanol to give a precipitate. The precipitate was filtered off and dried in vacuo to give 0.133 g (33%) of the title compound as a 0.40 water solvate as a white solid, mp 262°-264° C.

Anal. Calcd. for $C_{24}H_{26}N_4O_4S \cdot HCl \cdot 0.40 H_2O$: C, 56.49; H, 5.49; N, 10.98. Found: C, 56.51; H, 5.53; N, 11.19.

EXAMPLE 308

3,4-Dihydro-1'-[2-(2,3-dihydroxy-6-quinoxolinyl)ethyl]-6-methanesulfanomidospiro[(2H)-1-benzopyran-2,4'-piperidine]-4-one hydrochloride A solution of 0.31 g (0.70 mmol) 1'-[2-(3,4-diaminophenyl)ethyl]-3,4-dihydro-6-methanesulfonamidospiro[(2H)-1-benzopyran-2,4'-piperidine]4-one and 0.083 g (0.74 mmol) oxalic acid dihydrate in 1.5 ml of 4N hydrochloric acid was heated at reflux for one hour to give a precipitate. The mixture was diluted with 1 mL water, heated at reflux for 30 minutes, and cooled to room temperature. The precipitate was filtered off, washed with water, and dried in vacuo to give 0.308 g (82%) of the title compound as a 0.75 water solvate as a white solid, mp 283°–285° C.

Anal. Calcd. for $C_{24}H_{26}N_4O_6S \cdot HCl \cdot 0.75\ H_2O$: C, 52.55; H, 5.24; N, 10.21. Found: C, 52.60; H, 5.28; N, 10.39.

EXAMPLE 309

1'-[2-(2-(5-cyanopyridyl))ethyl]-3,4-dihydro-6-methanesulfonamidospiro[(2H)-1-benzopyran-2,4'-piperidine]-4-one monohydrochloride Step 1: A solution of 4.13 g (35.0 mmol) 5-cyano-2-picoline (Fairfield Chemicals) and 0.28 g (7.0 mmol) sodium hydroxide in 13.2 mL (135 mmol) of 37% aqueous formaldehyde solution was heated at 160° C. in a sealed pressure tube overnight. The cooled mixture was basified with 6 mL saturated sodium carbonate solution and extracted with methylene chloride (3×60 mL). The extract was washed with 10 mL bine, dried over $Na_2SO_4$, and filtered. The filtrate was concentrated in vacuo to give a residue which was partially purified by flash chromatography eluting with 2:98 methanol:chloroform to give 0.21 g of a solid. The solid was recrystallized from ether:hexane (1:2) to give 0.150 g (3%) 5-cyano-2-(2-hydroxyethyl)-pyridine, mp 92°–93° C.

$^1$HNMR $CDCl_3$: δ8.81 (d, 1H), 7.89 (d of d, 1H), 7.33 (d, 1H), 4.06 (t, 2H), 3.22 (broad s, 1H), 3.12 (t, 2H).

Step 2: A mixture of 0.163 g (1.1 mmol) 5-cyano-2-(2-hydroxyethyl)pyridine and 0.029 g (0.15 mmol) p-toluenesulfonic acid hydrate in 10 mL toluene was heated to reflux for five hours in a flask equipped with a Dean-Stark trap. The cooled mixture was neutralized with 5 mL saturated sodium bicarbonate solution and extracted with ether (3×15 mL). The extract was washed with 3 mL brine, dried over sodium sulfate, and filtered. The filtrate was concentrated to give an oil which was purified by flash chromatography on silica gel elating with 1:3 ethyl acetate:hexane to give 0.052 g (36%) 5-cyano-2-vinylpyridine, mp 29°–30° C.

$^1$HNMR $CDCl_3$: δ8.83 (d, 1H), 7.92 (d of d, 1H), 7.42 (d of d, 1H), 6.84 (d of d, 1H), 6.40 (d of d, 1H), 5.70 (d of d, 1H).

Step 3: In a manner similar to that described in Example 70, Method 2, Step E, a solution of 3,4-dihydro-6-methanesulfonamido-spiro[(2H)-1-benzopyran-2,4'-piperidine]-4-one hydrochloride (0.121 g, 0.35 mmol), 5-cyano-2-vinylpyridine (0.046 g, 0.35 mmol), sodium acetate trihydrate (0.095 g, 0.70 mmol) in 1:1 methanol:water was heated at reflux for 13 hours. Purification and crystallization as the hydrochloride salt from ethanol gave 0.067 g (40%) of the title compound as a white solid, mp 203°–204° C.

Analy. Calcd. for $C_{22}H_{24}N_4O_4S \cdot HCl \cdot 0.05\ C_2H_5OH \cdot 0.30\ H_2O$: C, 54.76; H, 5.39; N, 11.56. Found: C, 54.72; H, 5.10; N, 11.51.

EXAMPLE 310

1'-[2-(6-benzothiazolyl)ethyl]-3,4-dihydro-6-methanesulfonamidospiro[(2H)-1-benzopyran-2,4'-piperidine]4-one hydrochloride Step 1: To a solution of t-butyl nitrite (6.60 g, 64.0 mmol) in 60 mL dimethylformamide heated to 65° C. was added a solution of 2-amino-6-benzothiazoleacetic acid (*Indian J. Chem.*, 16B, 605 (1978)) (8.95 g, 43.0 mmol) in 140 mL diemethylformamide. The mixture was stirred at 65° C. for 15 minutes, cooled to room temperature, diluted with 600 mL 6N hydrochloric acid, and extracted with 1:99 methanol:chloroform (3×600 mL). The extract was washed with 30 mL water and brine, dried over sodium sulfate and filtered. The filtrate was concentrated to give crude product which was purified by flash chromatography eluting with 1:2:97 acetic acid:methanol:chloroform to give 1.1 g material. This was stirred under 20 mL ether to give a solid which was filtered off to give 0.42 g (5%) 6-benzothiazoleacetic acid, mp 147°–149° C.

$^1$HNMR DMSO-$d_6$: δ9.35 (s, 1H), 8.04 (m, 2H), 7.44 (d, 1H), 3.75 (s, 2H).

Step 2: To a solution of 6-benzothiazoleacetic acid (0.39 g, 2.0 mmol) in 10 mL dry tetrahydrofuran cooled in an ice-bath was added 4.0 ml (4.0 mmol) 1.0M borane/tetrahydrofuran was added, and the solution was stirred two hours with cooling. The reaction was quenched with 4 mL of 1:1 tetrahydrofuran:water, 2 mL water, and 5 mL saturated sodium potassium tartrate. The mixture was partially concentrated in vacuo and the aqueous residue was extracted with methylene chloride (3×15 mL). The extract was washed with 3 mL saturated sodium bicarbonate solution and brine, dried over sodium sulfate and filtered. The filtrate was concentrated to give a residue which was partially purified by flash chromatography eluting with 1:99 methanol:chloroform to give 0.18 g of a gum. A solution of the gum in 5 mL tetrahydrofuran and 3 mL 6N hydrochloric acid was stirred at 60° for two hours, cooled to room temperature, neutralized with saturated sodium bicarbonate solution, and extracted with methylene chloride (3×20 mL). The extract was concentrated in vacuo to give a residue which was re-chromatographed to give 0.100 g (28%) 6-benzothiazolylethanol as an oil.

$^1$HNMR $CDCl_3$: δ8.85 (s, 1H), 7.96 (d, 1H), 7.74 (s, 1H), 7.30 (dd, 1H), 3.85 (t, 2H), 2.94 (t, 2H), 2.1 (broad s, 1H).

Step 3: To a solution of 6-benzothiazolylethanol (0.099 g, 0.55 mmol) and triethylamine (0.121 g, 1.20 mmol) in 2 mL methylene chloride cooled in an ice bath was added dropwise a solution of methanesulfonyl chloride (0.086 g, 0.75 mmol) in 0.5 mL methylene chloride. The mixture was stirred one hour, diluted with 10 ml methylene chloride and washed with 3 mL saturated sodium bicarbonate solution. The aqueous layer was extracted with 5 mL methylene chloride and the combined extract was washed with 2 mL water and brine, dried over sodium sulfate and filtered. The filtrate was concentrated in vacuo to give crude product which was purified by flash chromatography on silica gel eluting with 1:1 ethyl acetate:hexane to give 0.118 g (83%) 6-benzothiazolylethyl methanesulfonate as an oil.

$^1$HNMR $CDCl_3$: δ8.99 (s, 1H), 8.10 (d, 1H), 7.85 (d, 1H), 7.40 (dd, 1H), 4.49 (t, 2H), 3.22 (t, 2H), 2.89 (s, 3H).

Step 4: In a manner similar to that described in Example 92, Step B a mixture of 3,4-dihydro-6-methanesulfonamido-spiro[(2H)-1-benzopyran-2,4'-piperidine]-4-one hydrochloride (0.146 g, 0.42 mmol), sodium bicarbonate (0.143 g, 1.70 mmol), 6-benzothiazolylethyl methanesulfonate (0.108 g, 0.42 mmol), potassium iodide (0.070 g, 0.42 mmol) and acetonitrile (5 mL) was heated at reflux for 6.5 hours. Purification and crystallization as the hydrochloride salt from ethanol gave 0.102 g (48%) of the title compound as a white solid, mp 214°–215° C.

Analy. Calcd. for $C_{23}H_{25}N_3O_4S_2 \cdot HCl \cdot 0.25 \, H_2O$: C, 53.89; H, 5.21; N, 8.20. Found: C, 53.94; H, 5.06; N, 8.21.

EXAMPLE 311

Preparation of 5'-(substituted methyl)-2'-hydroxyacetophenones

5'-[(Dimethylamino)methyl]-2'-hydroxyacetophenone

Ref: A. Warshawsky, R. Kalir, A. Patchornik, Ger. Offen. 2,733,251 (1978).

2-Hydroxy-5'-(methylthiomethyl)acetophenone

To a solution of 5'-(chloromethyl)-2'-hydroxyacetophenone (prepared by method of *Acta Pharm. Suec.*, 15, 13 (1978))(5.54 g, 30.0 mmol) in 90 mL dimethylformamide was added sodium thiomethoxide (2.31 g, 33.0 mmol). The mixture was stirred one hour and solid iodine was added in portions until a purple color was maintained to oxidize residual methylmercaptan. The mixture was diluted with 100 mL saturated ammonium chloride solution and 2 mL 3N hydrochloric acid and extracted with ether (3×300 mL). The extract was washed with water (2×60 mL) and brine, dried over $Na_2SO_4$, and filtered. The filtrate was concentrated in vacuo to give after drying 5.89 (100%) product as an oil.

$^1$HNMR CDCl$_3$: δ12.20 (s, 1H), 7.66 (d, 1H), 7.43 (dd, 1H), 6.95 (d, 1H), 3.65 (s, 2H), 2.65 (s, 3H), 2.02 (s, 3H).

2'-Hydroxy-5'-(methylsulfinylmethyl)acetophenone

To a solution of 2'-hydroxy-5'-(methylthiomethyl)acetophenone (2.20 g, 11.0 mmol) in 70 mL MeOH cooled in an ice bath was added a solution of sodium metaperiodate (2.49 g, 12.1 mmol) in 115 mL water. The resulting cloudy mixture was stirred two hours with cooling then partially concentrated in vacuo to remove methanol. The remaining aqueous mixture was extracted with chloroform (3×125 mL). The extract was washed with 50 mL water and brine, dried over sodium sulfate, and filtered. The filtrate was concentrated in vacuo to give crude product which was recrystallized from n-butylchloride to give 1.39 g (60%) product, as a pale yellow solid, mp 95°–97° C.

$^1$HNMR CDCl$_3$: δ12.30 (s, 1H), 7.70 (d, 1H), 7.40 (dd, 1H), 7.02 (d, 1H), 3.92 (dd, 2H), 2.66 (s, 3H), 2.50 (s, 3H).

2'-Hydroxy-5'-(methylsulfonylmethyl)acetophenone

To a solution of 2'-hydroxy-5'-(methylthiomethyl)acetophenone (2.20 g, 11.0 mmol) in 88 mL methanol cooled in an ice bath was added a solution of OXONE (commercial potassium peroxymonosulfate mixture, Aldrich Chemical Co.)(20.28 g, 33.0 mmol) in 88 mL water. The mixture was stirred two hours with cooling then partially concentrated in vacuo. The product was isolated in the same manner employed in the previous example to give after recrystallization from n-butylchloride 1.70 g (68%) product, as a white solid, mp 142°–144° C.:

$^1$HNMR CDCl$_3$: δ12.35 (s, 1H), 7.82 (d, 1H), 7.49 (dd, 1H), 7.04 (d, 1H), 4.22 (s, 2H), 2.82 (s, 3H), 2.67 (s, 3H).

2'-Hydroxy-5'-(methanesulfonamidomethyl)acetophenone

To a mixture of sodium hydride (60% dispersion in mineral oil, 1.60 g, 40.0 mmol) in 25 mL DMSO under Argon was added dropwise a solution of methanesulfonamide (3.80 g, 40.0 mmol) in 10 mL DMSO. The resulting mixture was stirred 30 minutes and a solution of 5'-(chloromethyl)-2'-hydroxyacetophenone (3.69 g, 20.0 mmol) in 10 mL DMSO was added. The resulting mixture was stirred three hours, poured into 150 mL ice water, acidified with 14 mL 3N hydrochloric acid, and the mixture extracted with methylene chloride (3×200 mL). The extract was washed with water (50 mL) and brine, dried over sodium sulfate, and filtered. The filtrate was concentrated in vacuo to give an oil which was partially purified by flash chromatography eluting with 3:97 methanol:chloroform to give a gum. The gum was stirred under 25 mL water to remove residual DMSO, the aqueous supernatant was decanted, and the residue was dried in vacuo. The resulting material was crystallized from ethylacetate to remove 0.67 g of a by-product identified as N,N-bis[(3-acetyl-4-hydroxyphenyl)methyl]methanesulfonamide. The mother liquor was concentrated in vacuo to give a residue which was re-chromatography to give a solid. The solid was recrystallized from n-butylchloride to give 0.60 g (12%) product, as a white solid, mp 85°–86.5° C.

$^1$HNMR CDCl$_3$: δ12.38 (s, 1H), 7.73 (d, 1H), 7.47 (dd, 1H), 7.00 (d, 1H), 4.60 (broad t, 1H, NH), 4.29 (d, 2H), 2.92 (s, 3H), 2.66 (s, 3H).

2'-Hydroxy-5'-[(N-methyl-N-acetyl)aminomethyl]acetophenone

To a mixture of sodium hydride (60% dispersion in mineral oil, 1.60 g, 40.0 mmol) in 25 mL DMSO under Argon was added dropwise a solution of N-methylacetamide (2.92 g, 40.0 mmol) in 10 mL DMSO. The resulting mixture was stirred 30 minutes and a solution of 5'-(chloromethyl)-2'-hydroxyacetophenone (3.69, 20.0 mmol) in 10 mL DMSO was added. The resulting mixture was stirred three hours, poured into 150 ml ice water, acidified with 14 mL 3N hydrochloric acid, and the mixture extracted with methylene chloride (3×200 mL). The extract was washed with water (50 mL) and brine, dried over sodium sulfate, and filtered. The filtrate was concentrated in vacuo to give an oil which was partially purified by flash chromatography eluting with 3:97 methanol:chloroform to given an oil. The oil was stirred under 25 mL water to remove residual DMSO, the aqueous supernatant was decanted and the resulting gum was dried in vacuo. The gum was stirred under 50 mL ether and filtered. The filtrate was concentrated in vacuo to give a residue which was re-chromatographed eluting with 3:97 ethyl acetate: hexane to give 0.93 g (21%) product as an oil which crystallized on standing, mp 60°–65° C.

$^1$HNMR CDCl$_3$: major rotamer: δ12.22 (s, 1H), 7.66 (d, 1H), 7.38 (dd, 1H), 6.95 (d, 1H), 4.52 (s, 2H), 2.95 (s, 3H), 2.64 (s, 3H), 2.16 (s, 3H); minor rotamer: δ12.25 (s, 1H), 7.50 (d, 1H), 7.31 (dd, 1H), 7.02 (d, 1H), 4.49 (s, 2H), 2.94 (s, 3H), 2.64 (s, 3H), 2.19 (s, 3H).

1-[(3-Acetyl-4-hydroxyphenyl)methyl]imidazole

To a mixture of 5'-(chloromethyl)-2'-hydroxyacetophenone (1.85 g, 10.0 mmol), sodium dimethylformamide was added imidazole (0.75 g, 11.0 mmol). The mixture was stirred four hours and concentrated in vacuo. The residue was stirred under 50 mL ethanol, filtered, and the filtrate concentrated in vacuo to give a residue. The residue was stirred under 30 mL chloroform, filtered, and the filtrate concentrated in vacuo to give crude product. The crude product was purified by flash chromatography eluting with 5:95 methanol:chloroform to give a solid. The solid was recrystallized from n-butylchloride to give 0.71 g (33%) product as a yellow crystalline solid, mp 106°-107° C.

¹HNMR CDCl₃: δ12.3 (broad s, 1H), 8.03 (s, 1H), 7.62 (d, 1H), 7.34 (dd, 1H), 7.15 (d, 1H), 7.00 (d, 1H), 6.94 (d, 1H), 5.17 (s, 2H), 2.62 (s, 3H).

2'-Hydroxy-5'-(methoxymethyl)acetophenone

Ref: P. Briet, J. J. Berthelon, J. C. Depin, E. Boschetti, Ger. Offen. 2,549,745 (1976).

2'-Hydroxy-5'-(hydroxymethyl)acetophenone

Ref: S. J. Buckman, J. D. Pera, G. D. Mercer, Ger. Offen. 2,051,921 (1971). (Obtained as a by-product in following reaction.)

2'-Hydroxy-5'-([2-(methoxy)ethoxy]methyl)acetophenone

A mixture of 5'-(chloromethyl)-2'-hydroxyacetophenone (1.85 g, 10.0 mmol), potassium carbonate (1.38, 10.0 mmol), 2-methoxyethanol (0.9 g, 12.0 mmol) and 10 mL chloroform was stirred 24 hours, filtered, and the filtrate concentrated in vacuo to give a residue. The residue was purified by flash chromatography eluting with 30:70 ethyl acetate:hexane to give 0.40 g (18%) product as an oil.

¹HNMR CDCl₃: δ12.23 (s, 1H), 7.74 (d, 1H), 7.46 (dd, 1H), 6.96 (d, 1H), 4.52 (s, 2H), 3.63 (m, 2H), 3.58 (m, 2H), 3.40 (s, 3H), 2.64 (s, 3H).

Further elution with 50:50 ethyl acetate: hexanes gave 0.41 g (25%) 2'-hydroxy-5'-(hydroxymethyl)acetophenone as an oil.

1[(3-Acetyl-4-hydroxyphenyl)methyl]-2-pyrrolidinone

To a suspension of sodium hydride (60% dispersion in mineral oil, 0.80 g, 20.0 mmol) in 15 mL dry dimethylformamide under argon, cooled in an ice-bath was added dropwise a solution of 2-pyrrolidinone (1.70 g, 20.0 mmol) in 5 mL dimethylformamide. The ice-bath was removed, the mixture was stirred 30 minutes, and a solution of 5'-(chloromethyl)-2'-hydroxyacetophenone (1.85 g, 10.0 mmol) in 5 mL dimethylformamide was added dropwise. The mixture was stirred four hours, poured into 75 mL ice water, acidified with 7 mL 3N hydrochloric acid, and extracted with methylene chloride (3×75 mL). The extract was washed with water (25 mL) and brine, dried over Na₂SO₄, and filtered. The filtrate was concentrated in vacuo to give crude product which was purified by flash chromatography on silica gel eluting with 2:98 methanol:chloroform to give 1.92 g (82%) product as a viscous oil.

¹HNMR CDCl₃: δ12.22 (s, 1H), 7.64 (d, 1H), 7.37 (dd, 1H), 6.95 (d, 1H), 4.40 (s, 2H), 3.28 (t, 2H), 2.64 (s, 3H), 2.45 (t, 2H), 2.01 (m, 2H).

1-[(3-Acetyl-4-hydroxyphenyl)methyl]-2-imidazolidone

To a suspension of sodium hydride (60% dispersion in mineral oil, 0.80 g, 20.0 mmol) in 15 mL dry dimethylformamide under argon, cooled in an ice-bath was added dropwise a solution of 2-imidazolidone (1.72 g, 20.0 mmol) in 5 mL dimethylformamide. The ice bath was removed, the mixture was stirred 30 minutes and a solution of 5'-chloromethyl-2'-hydroxyacetophenone (1.85 g, 10.0 mmol) in 5 mL dimethylformamide was added dropwise. The mixture was stirred four hours and the product was isolated in the same manner as in the previous example to give a solid. The solid was stirred under 20 mL n-butylchloride, filtered off, and dried in vacuo to give 1.01 g (43%) product as a white solid, mp 131°-133° C.

¹HNMR CDCl₃: δ12.22 (s, 1H), 7.66 (d, 1H), 7.41 (dd, 1H), 6.96 (d, 1H), 4.62 (broad s, 1H, NH), 4.32 (s, 2H), 3.42 (m, 2H), 3.32 (m, 2H), 2.64 (s, 3H).

Employing the procedure substantially as described in Example 339, Step 8, infra, but substituting for the 5-methanesulfonamido-2-hydroxyacetophenone used therein, the appropriately substituted 2'-hydroxyacetophenone from Example 311 there were produced the spiropiperidines described in Table XXI.

TABLE XXI

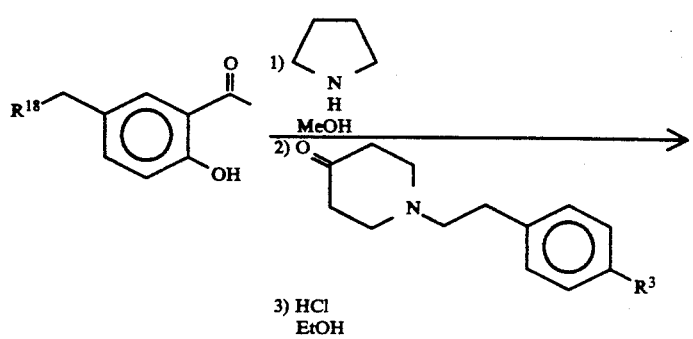

TABLE XXI-continued

| Example | R¹⁸ | R³ | salt | mp (°C.) | yield (%) |
|---------|-----|-----|------|----------|-----------|
| 312 | (CH₃)₂N— | —H | .2HCl .0.25 H₂O | 273-274 | 21 |
| 313 | (CH₃)₂N— | —CN | .2HCl .1.2 H₂O | 278-280 | 52 |
| 314 | CH₃S— | —H | .HCl .1.2 H₂O | 241-242 | 40 |
| 315 | CH₃S— | —CN | .HCl .0.35 C₂H₅OH | 241-242 | 71 |
| 316 | CH₃SO— | —H | .HCl .0.25 C₂H₅OH | 254-255 | 68 |
| 317 | CH₃SO— | —CN | .HCl .0.5 H₂O | 251-252 | 67 |
| 318 | CH₃SO₂— | —H | .HCl | 249-250 | 72 |
| 319 | CH₃SO₂— | —CN | .HCl | 258-260 | 76 |
| 320 | CH₃SO₂NH— | —H | .HCl .0.25 H₂O | 250-251 | 74 |
| 321 | CH₃SO₂NH— | —CN | .HCl | 203-205 | 49 |
| 322 | CH₃CO(CH₃)N— | —H | .HCL | 243-244 | 62 |
| 323 | imidazol-1-yl | —H | .2 HCl 0.05 EtOH 1.45 H₂O | 180-195 | 61 |
| 324 | imidazol-1-yl | —CN | .2 HCl .0.5 EtOH .0.5 H₂O | 185-199 | 75 |
| 325 | CH₃O— | —H | .HCl | 241-243 | 64 |
| 326 | CH₃O— | —CN | .HCl .0.25 EtOH | 234-235 | 68 |
| 327 | CH₃OCH₂CH₂O— | —H | .HCl | 229-230 | 51 |
| 328 | CH₃OCH₂CH₂O— | —CN | .HCl | 190-191 | 54 |
| 329 | HO— | —H | .HCl .0.05 EtOH .0.2 H₂O | 213-214 | 38 |
| 330 | HO— | —CN | .HCl .0.25 H₂O | 168-170 | 46 |
| 331 | 2-oxopyrrolidin-1-yl | —H | .HCl .0.6 H₂O | 236-237 | 29 |
| 332 | 2-oxopyrrolidin-1-yl | —CN | .HCl .0.15 EtOH .0.25 H₂O | 242-244 | 52 |
| 333 | 2-oxoimidazolidin-1-yl | —H | .HCl .0.30 EtOH .0.2 H₂O | 236-237 | 45 |

| 334 | [structure: HN-C(=O)-N in 5-ring] | —CN | .HCl .0.35 EtOH .0.2 H₂O | 162–174 | 68 |

EXAMPLE 335

3,4-Dihydro-6-(methylaminomethyl)-1'-(2-phenylethyl)spiro[2H-(1-benzopyran-2,4'-piperidine)]-4-one dihydrochloride A solution of 3,4-dihydro-6-[N-acetyl(methylaminomethyl]-1'-2(-phenylethyl)spiro[(2H)-1-benzopyran-2,4'-piperidine]-4-one (0.22 g, 0.50 mmol), 6N hydrochloric acid (0.67 ml, 4.0 mmol) and 2.0 mL ethanol was heated at reflux for 18 hours. Additional 6N hydrochloric acid (0.20 ml, 1.2 mmol) was added, the solution was heated at reflux for 4 hours, then concentrated in vacuo. The residue was placed under 5 mL ethanol and concentrated in vacuo to give a solid. The solid was stirred under 2 mL ethanol for one hour, filtered off, and dried in vacuo to give 0.143 g of the title compound product as a 0.50 water solvate as a white solid, mp 247°–248° C.

Anal. Calcd. for $C_{23}H_{28}N_2O_2 \cdot 2HCl \cdot 0.50\ H_2O$: C, 61.88; H, 7.00; N, 6.28. Found: C, 61.86; H, 6.84; N, 6.21.

EXAMPLE 336

3,4-Dihydro-6-[(N-methyl)methanesulfonamidomethyl]-1'-(2-phenylethyl)spiro[2H-1-benzopyran-2,4'-piperidine]-4-one hydrochloride To a mixture of 3,4-dihydro-6-(methylaminomethyl)-1'-(2-phenylethyl)-spiro[(2H)-1-benzopyran-2,4'-piperidine]-4-one hydrochloride (0.162 g, 0.37 mmol), triethylamine (0.076 g, 0.75 mmol) and pyridine (2 mL) was added methanesulfonyl chloride (0.061 g, 0.53 mmol) and the resulting mixture was stirred for 18 hours. The mixture was concentrated in vacuo and the residue was partitioned between 5 mL dilute sodium bicarbonate solution and 15 mL methylene chloride. The layers were separated and the aqueous layer was extracted with methylene chloride (2×15 mL). The combined extract was washed with brine, dried over sodium sulfate, and filtered. The filtrate was concentrated in vacuo to give crude product which was purified by flash chromatography on silica gel eluting with 5:95 methanol:chloroform to give 0.100 g free-base as an oil.

To a solution of the free-base in 1 mL ethanol was added 0.042 mL (0.25 mmol) 5.9N hydrogen chloride in ethanol to give a precipitate. The precipitate was filtered off and dried in vacuo to give 0.078 g (44%) of the title compound as a 0.20 hydrate and 0.10 ethanol solvate as an off-white solid, mp 251°–253° C.

Anal. Calcd. for $C_{24}H_{30}N_2O_4S \cdot HCl \cdot 0.20\ H_2O \cdot 0.10\ C_2H_5OH$: C, 59.95; H, 6.62; N, 5.75. Found: C, 59.65; H, 6.45; N, 5.65.

EXAMPLE 337

N-Methyl [(3,4-dihydro-1'-(2-phenylethyl)-spiro[(2H)-1-benzopyran-2,4'-piperidine]-4-one)-6-yl]methanesulfonamide Hydrochloride Step 1: Sodium (3-acetyl-4-hydroxy)phenylmethylsulfonate A solution of 5'-(chloromethyl)-2'-hydroxyacetophenone (1.85 g, 10.0 mmol) and sodium sulfite (1.32 g, 10.5 mmol) in water (10 mL) was heated at reflux for three hours. The cooled solution was washed with ether (2×10 mL) and concentrated in vacuo to give a solid which was dried in vacuo to give 2.87 g crude product containing sodium chloride and water.

$^1$HNMR (DMSO-d$_6$): δ11.73 (s, 1H), 7.77 (d, 1H), 7.49 (dd, 1H), 6.87 (d, 1H), 3.68 (s, 2H), 2.61 (s, 3H).

Step 2: 1'-Acetyl-3,4-dihydro-spiro[(2H)-1-benzopyran-2,4'-piperidine-4-one]-6-ylmethanesulfonic acid A mixture of sodium (3-acetyl-4-hydroxy) phenylmethanesulfonate (2.57 g, 9 mmol) and pyrrolidine (0.64 g, 9.0 mmol) in methanol (18 mL) was heated at 60° C. for 15 minutes. A solution of N-acetyl-4-piperidone (1.27 g, 9.0 mmol) in methanol (9 ml) was added and the mixture was stirred at 60° C. for four hours. The mixture was concentrated in vacuo to give a residue which was dissolved in water (10 mL), acidified with 3N hydrochloric acid, reconcentrated in vacuo, and the resulting residue was extracted with methylene chloride (3×50 mL). The extract was dried over Na$_2$SO$_4$, filtered, and the filtrate concentrated to give a foam. The foam was dissolved in water (25 mL), basified with 20% sodium hydroxide solution to pH 10, and the solution was washed with ether (2×20 ml) to remove residual pyrolidine. The aqueous solution was acidified with 3N hydrochloric acid and concentrated in vacuo to give a solid. The solid was extracted with hot acetonitrile (4×50 mL) leaving the insoluble solid product (1.21 g, 38%), mp 233°–235° C.

$^1$HNMR (DMSO-d$_6$): δ7.64 (d, 1H), 7.51 (dd, 1H), 6.98 (d, 1H), 4.21 (d, 1H), 3.67 (s, 2H), 3.65 (d, 1H), 3.38 (m, 1H), 2.97 (m, 1H), 2.80 (s, 2H), 2.00 (s, 3H), 1.92 (m, 2H), 1.72 (m, 1H), 1.56 (m, 1H).

Step 3: N-Methyl [(3,4-dihydro-1'-acetylspiro[(2H)-1-benzopyran-2,4'-piperidine]-4-one-6-yl]methanesulfonamide To a mixture of (1'-acetyl-3,4-dihydrospiro[(2H)-1-benzopyran-2,4'-piperidine-4-one]-6-yl)methanesulfonic acid (1.20 g, 2.9 mmol) and dimethylformamide (1 mL) in methylene chloride (20 mL) was added thionyl chloride (0.26 mL, 0.42 g, 3.5 mmol). The mixture was stirred three hours, then concentrated in vacuo to give the sulfonyl chloride. To a solution of the sulfonyl chloride in methylene chloride (20 mL) cooled in an ice bath was added a cold solution of methylamine (0.20 g, 6.4 mmol) in 5 mL methylene chloride. The resulting mixture was stirred three hours with cooling, diluted with methylene chloride (60 mL) washed with 1N hydrochloric acid (10 mL), water (5 mL), and brine, dried over sodium sulfate, and filtered. The filtrate was concentrated in vacuo to give a gum which was purified by flash chromatography on silica gel eluting with 3:97 methanol:chloroform to give 0.36 g (34%) product as a foam.

$^1$HNMR (CDCl$_3$): δ7.83 (d, 1H), 7.59 (dd, 1H), 7.04 (d, 1H), 4.42 (broad s, 1H, —NH), 4.39 (d, 1H), 4.20 (s, 2H), 3.65 (d, 1H), 3.51 (m, 1H), 3.08 (m, 1H), 2.78 (d, 3H), 2.73 (s, 2H), 2.11 (s, 3H), 2.09 (m, 2H), 1.64 (m, 2H).

Step 4: N-Methyl[(3,4-dihydrospiro[(2H)-1-benzopyran-2,4'-piperidine]-4-one)-6-yl]-methanesulfonamide A solution of N-methyl[(3,4-dihydro-1'-acetylspiro[(2H)-1-benzopyran-2,4'-piperidine]-4-one-6-yl]methanesulfonamide (0.348 g, 0.95 mmol), 6N hydrochloric acid (1.25 mL, 7.5 mmol), and 3.75 mL ethanol was heated at reflux for 18 hours. The solution was concentrated in vacuo, the residue was placed under ethanol (10 mL), reconcentrated in vacuo, placed under 1:1 ethanol:toluene (10 mL), reconcentrated in vacuo, placed under carbon tetrachloride (10 mL), reconcentrated, and dried in vacuo to give a hygroscopic foam. The foam was stirred under ether (10 mL) for one hour, filtered off, and dried in vacuo to give the hydrochloride as a white solid, mp 140°-165° C.

$^1$HNMR (DMSO-d$_6$): δ9.1 (broad s, 1H), 8.9 (broad s, 1H), 7.77 (d, 1H), 7.59 (dd, 1H), 7.15 (d, 1H), 6.94 (q, 1H, —NHSO$_2$), 4.35 (s, 2H), 3.25-3.02 (m, 4H), 2.93 (s, 2H), 2.58 (d, 3H), 2.11 (m, 2H), 1.92 (m, 2H).

Step 5: N-Methyl[(3,4-dihydro-1'-(2-phenylethyl)-spiro[(2H)-1-benzopyran-2,4'-piperidine]-4-one)-6-yl]methanesulfonamide hydrochloride A mixture of N-methyl[(3,4-dihydrospiro[(2H)-4-benzopyran-2,4'-piperidine]-4-one)-6-yl]methanesulfonamide hydrochloride (0.144 g, 0.40 mmol), sodium bicarbaonate (0.134 g, 1.50 mmol), (2-bromoethyl)benzene (0,113 mL, 0.148 g, 0.80 mmol), potassium iodide (0.066 g, 0.40 mmol) and acetonitrile (5 mL) was heated at reflux for four hours. The mixture was concentrated in vacuo, the residue was diluted with saturated sodium bicarbonate solution (10 mL) and water (2 mL), and extracted with methylene chloride (3×15 mL). The extract was washed with water (3 mL) and brine, dried over sodium sulfate, and filtered. The filtrate was concentrated in vacuo to give a residue which was purified by flash chromatography to give 0.101 g free-base.

To a suspension of the free base in ethanol (3 mL) was added 5.9N hydrogen chloride in ethanol (0.046 ml, 0.27 mmol) to give a precipitate. The precipitate was filtered off and dried in vacuo to give the title compound as an off-white solid, (0.085 g, 45%), mp 142°-145° C.

Anal. Calcd. for C$_{23}$H$_{28}$N$_2$O$_4$S.HCl.0.65 H$_2$O: C, 57.94; H, 6.41; N, 5.88. Found: C, 58.00; H, 6.68; N, 5.85.

EXAMPLE 338

N-Methyl[(3,4-dihydro-1'-[2-(4-cyanophenyl)ethyl]-spiro[(2H)-1-benzopyran-2,4'-piperidine]-4-one)-6-methanesulfonamide Hydrochloride A mixture of N-methyl[(3,4-dihydrospiro[(2H)-1-benzopyran-2,4'-piperidine]-4-one-6-yl-methanesulfonamide hydrochloride (0.144 g, 0.40 mmol), sodium bicarbonate (0.134 g, 1.60 mmol), 2-(4-cyanophenyl)ethyl methanesulfonate (0.180 g, 0.80 mmol), potassium iodide (0.066 g, 0.40 mmol), and acetonitrile (5 mL) was heated at reflux for four hours. In the same manner as Example 337 [P27], purification and recrystallization from ethanol gave the title compound as an orange solid, (0.065 g, 33%), mp. 146°-158° C.

Anal. Calcd. for C$_{24}$H$_{27}$N$_3$O$_4$.HCl.0.25 C$_2$H$_5$OH: C, 58.67; H, 5.93; N, 8.38. Found: C, 58.96; H, 5.64; N, 8.29.

EXAMPLE 339

N-[(1'-[2-(5-Benzofurazanyl)ethyl]-3,4-dihydrospiro[2H-[1-benzopyran-2,4'-piperidine]-4-one)-6-ul]methanesulfonamide monohydrochloride Step 1: Preparation of 5-amino-2-hydroxyacetophenone hydrochloride 5-Acetamido-2-hydroxyacetophenone (19.03 g, 98.5 mmoles) (prepared as described by C. T. Chang, F. C. Chen, K. K. Hsu, T. Ueng, and M. Hung, *J. Chem. Soc.* 3414 (1961)) dissolved in 300 mL of ethanol and 100 mL of 6N aqueous HCl was heated at reflux for 8 hrs. The solution was concentrated in vacuo, and the residue was flushed with ethanol, and dried in vacuo to give 18.3 g (99%) of 5-amino-2-hydroxyacetophenone hydrochloride as a dark solid.

Step 2: Preparation of 5-methanesulfonamido-2-hydroxyacetophenone

A suspension of 5-amino-2-hydroxyacetophenone hydrochloride, 18.39 g (98 mmole) in 200 mL of methylene chloride cooled to 0° C. was treated with 19.4 mL (240 mmol) of pyridine. Methanesulfonyl chloride, 7.74 mL (100 mmoles) was added dropwise. The mixture was stirred an additional 30 min at 0° C. and then allowed to warm to room temperature over 1 hr. The mixture was diluted with 200 mL of methylene chloride and washed with 50 mL of 1N aqueous HCl. Concentration of the organic layer and trituration with methylene chloride gave a solid which was recrystalized from methylene chloride to give 15.45 g (69%) of 5-methanesulfonamido-2-hydroxyacetophenone as a white solid (mp 121°-122° C.).

Step 3: Preparation of N(2-(4-aminophenyl)ethyl-1,4-dioxa-8-azaspiro[4.5]-decane 1,4-Dioxa-8-azaspiro[4.5]-decane (18.62 g, 130 mmoles) in 50 mL of acetonitrile was stirred under argon and treated with anhydrous potassium carbonate (27.60 g, 200 mmoles). The mixture was cooled to 0° C. and 2-(4-nitrophenyl)ethylbromide (23.01 g, 100 mmoles) was added in one portion. After 10 minutes, the ice bath was removed and the reaction was stirred for 14 hrs at room temperature. The mixture was diluted with 220 mL of ethyl acetate and 200 mL of water. The aqueous phase was separated, the organic phase washed with water (3×100 mL), and brine (2×50 mL). The organic portion was dried (Na2SO4), filtered, and concentrated to give 28.60 g (98%) of N(2-(4-nitrophenyl)ethyl-1,4-dioxa-8-azaspiro[4.5]-decane as a yellow solid.

The crude N(2-(4-nitrophenyl)ethyl-1,4-dioxa-8-azaspiro[4.5]-decane (28.6 g) disolved in 170 mL of tetrahydrofuran and 550 mL of absolute ethanol was treated with 4.0 grams of Raney nickel and shaken under an atmosphere of hydrogen (55 psig) for 48 hrs. Filtration through celite, and concentration in vacuo gave 25.70 g of N(2-(4-aminophenyl)ethyl)-1,4-dioxa-8-azaspiro[4.5]-decane (mp 96.5°-99° C.) as an off white solid (98% from 2-(4-nitrophenyl)ethylbromide).

Step 4: Preparation of N-(2-(4-acetamino-3-nitrophenyl)ethyl-1,4-dioxa-8-azaspiro[4.5]-decaneacetate A mechanically stirred solution of N(2-(4-aminophenyl)ethyl)-1,4-dioxa-8-azaspiro[4.5]-decane in methylene chloride (400 mL) cooled to −5° C. under an argon atmosphere was treated dropwise with acetic anhydride (58.8 mL, 622 mmoles). The reaction was allowed to reach room temperature and was stirred for 18 hr. After the addition of an additional 29.5 mL (312 mmoles) of acetic anhydride, the reaction was cooled to −5° C., and a solution of nitric acid (d=1.49, 22.0 mL, 468 mmoles) in methylene chloride (1:1 by volume) was added dropwise. The reaction mixture was allowed to reach room temperature and was stirred for 4 hours. The mixture was cooled in an ice bath and 100 mL of saturated brine was added. The layers were separated and the aqueous phase was extracted with methylene chloride. The combined organic portion was dried (Na2SO4), concentrated and flushed with toluene (3×200 mL). The crude product crystallized during concentration, was filtered, and triturated with ethyl acetate (550 mL) to yield 56.7 g (89%) of N(2-(4-acetamino-3-nitrophenyl)ethyl)-1,4-dioxa-8-azaspiro[4.5]-decane acetic acid salt. TLC Rf=0.80 (silica gel, 5% methanol in methylene chloride saturated with ammonia).

Step 5: Preparation of 8-[2-(benzofuroxan-5-yl)ethyl]-1,4-dioxa-8-aza spiro[4.5]decane A suspension of 4.09 g (10.0 mmoles) N(2-(4-acetamino-3-nitro-phenyl)ethyl)-1,4-dioxa-8-azaspiro[4.5]-decane acetic acid salt in 60 mL of methanol stirred at 0° C. was treated dropwise with 86% potassium hydroxide (5.22 g, 80 mmol) in 20 mL of methanol over 5 min. The temperature was allowed to warm to 25° C. and the mixture was stirred 2 hr. Solid iodophenyldiacetate (3.86 g, 12 mmol) was added and the mixture was stirred 30 min. An additional portion of iodophenyldiacetate (0.32 g, 1.0 mmol) was added and stirring was continued 20 min. The mixture was concentrated in vacuo and the residue partitioned between 150 mL of ethyl acetate and 75 mL of water. The layers were separated and the aqueous layer was reextracted (2×100 mL) with ethyl acetate. The combined organic portions were washed with water (25 mL), and saturated brine, dried (Na2SO4), and concentrated to a solid orange residue. The solid was triturated with hexane and dried in vacuo to give 2.78 g (91%) of 8-[2-(benzofuroxan-5-yl)ethyl]-1,4-dioxa-8-aza spiro[4.5]decane (mp 117°-119° C.).

Step 6: Preparation of 8-[2-(benzofurazan-5-yl)ethyl]-1,4-dioxa-8-aza spiro[4.5]decane A solution of 8-[2-(benzofuroxan-5-yl)ethyl]-1,4-dioxa-8-aza spiro[4.5]decane (24.0 g, 78.6 mmol) in ethanol (240 mL) was treated with triethylphosphite (27.5 mL, 157 mmol) and heated at reflux for 2.5 hours. The mixture was concentrated and flushed with hexanes (2×200 mL), and then diluted with 400 mL of hexanes and the solids collected by filtration to yield 19.3 g (82%) of 8-[2-(benzofurazan-5-yl)ethyl]-1,4-dioxa-8-aza spiro[4.5] decane. A second crop (2.25 g 13%) was obtained after chromatography of the mother liquors on silica gel (2% methanol in methylene chloride).

1H NMR (300 MHz, CDCl3): δ1.75 (bt, 4H); 2.65 (bt, 4H); 2.70 (t, J=7 Hz, 2H); 2.90 (t, J=7Hz, 2H); 3.95 (s, 4H); 7.30 (d, J=9Hz, 1H); 7.60 (s,1H); 7.75 (d, J=9Hz, 1H).

Step 7: Preparation of 1-[2-(benzofurazan-5-yl)ethyl] piperidin-4-one

A solution of 8-[2-(benzofurazan-5-yl)ethyl]-1,4-dioxa-8-aza spiro[4.5]decane (20.0 g, 69.1 mmol) in 1N aqueous HCl (200 mL, 200 mmol) was heated to reflux for 1.5 hr. The cooled solution was adjusted to pH 8.5 with 40% aqueous sodium hydroxide and extracted with ethyl acetate (250 mL then 100 mL). The combined extracts were washed twice with 1N aqueous HCl (200 mL combined). The acid layers were heated to reflux for 1 hr and then cooled. Basification as above, extraction into ethyl acetate, drying (Na2SO4), concentration, and trituration with hexanes afforded 1-[2-(benzofurazan-5-yl)ethyl]piperidin-4-one as a solid 14.9 g (88%). HPLC: Rt=3.0 min, 90:10 (0.1% H3PO4 in water: acetonitrile) flow=2.0 mL/min, Waters $C^{18}$micro bondapak 25 cmL.

Step 8: Preparation of N-[(1'-[2-(5-Benzofurazanyl)ethyl]-3,4-dihydro-spiro[2H-[1-benzopyran-2,4'-piperidine-4-one)-6-yl]methane sulfonamide A solution of 5-methanesulfonamido-2-hydroxyacetophenone (5.58 g, 24.3 mmol) and pyrrolidine (2.05 mL, 24.3 mmol) in methanol(30 mL) was warmed to 60° C. and treated with 1-[2-(benzofurazan-5-yl)ethyl]piperidin-4-one (6.0 g, 24.3 mmol). The reaction was stirred at 60° C. for 1 hr, cooled to room temperature, and concentrated in vacuo to an oil. The residue was chromatographed on silica gel eluting with ethyl acetate then 3% methanol in ethyl acetate. Concentration of the appropriate fractions and crystalization from isopropyl acetate provided 8.2 g (74%) of methanesulfonamide, N-[1'-[2-(5-benzofurazanyl)ethyl]-3,4-dihydro-4-oxospiro[2H-[1-benzopyran-2,4'-piperidin]-6-yl]. This was converted to its hydrochloride salt, mp=285°-287° C., by disolving the free base in dilute aqueous HCl at 90° C. (2 eq HCl, 10 g in 1.5 L) cooling to precipitate, filtration and drying in vacuo.

EXAMPLE 340

3,4 Dihydro-1'-[2-phenylethyl-6-cyano-spiro[2H-1-benzopyran-2,4'-piperidin]-4-one hydrochloride .¼ H2O.¼ ethanol A solution of 5-cyano-2-hydroxyacetophenone (806 mgs, 5 mmol) (prepared as described by N.G.P. Ellis, D. Shaw, *J. Chem. Soc. Perkin I* 779–783 (1972)) and pyrrolidine (0.42 mL, 5 mmol) in methanol (6 mL) was warmed to 60° C. and treated with 1-[2-phenylethyl]-piperidin-4-one (1.102 g, 5 mmol). The reaction was stirred at 60° C. for 1 hr, cooled to room temperature, and concentrated in vacuo to an oil. The residue was chromatographed on silica gel eluting with ethyl acetate to give 500 mg of which 250 mg free base which was converted to the hydrochloride salt in ethanol at 0° C. yield 270 mgs of a solid after filtration and drying in vacuo mp=253°-255° C.(dec) .HCl.¼ H2O.¼ C2H6O.

EXAMPLE 341

Spiro[2H-1-benzopyran-2,4'-piperidine]-6-aminosulfonyl-1'-[2-phenylethyl]-3,4-dihydro-N-methyl-4-oxo, monohydrochloride Step 1: Preparation of 3-acetyl-4-hydroxy-benzenesulfonyl chloride A mixture of 3-acetyl-4-hydroxy-benzenesulfonic acid (3.0 g) (prepared according to T. Pfliegel et. al., *Acta Chim. Acad. Sci. Hung.*, 98(2) 231–240(1978)) in tetramethylenesulfone (6 mL) and acetonitrile (6 mL) under argon was treated with triethylamine (1.94 mL) and N,N-dimethylacetamide (0.32 mL). This was stirred for 30 min and POCl3 was added dropwise maintaining the temperature below 25° C. The reaction was stirred for 24 hr, cooled to 10° C. and quenched with water (15 mL). This mixture was warmed to 60° C. and stirred for 1 hr, at which point a precipitate formed which was then filtered and dried to give 2.34 g (72%) of 3-acetyl-4-hydroxybenzenesulfonylchloride.

¹H NMR (CDCl₃, 300 MHz): δ2.80 (s, 3H); 7.25 (d, J=12 Hz, 1H); 8.05 (dd, J=3, 12 Hz, 1H); 8.4 (d, J=3 Hz, 1H); 12.75 (s, 1H).

Step 2: Preparation of N-methyl-3-acetyl-4-hydroxy-benzenesulfonic acid amide

A saturated solution of monomethyl amine in acetonitrile cooled to 0° C. was treated with 3-acetyl-4-hydroxy-benzenesulfonyl chloride. The mixture was stirred 5 min, concentrated in vacuo to an oil, disolved in ethyl acetate and treated with 1N aqueous HCl. The organic portion was separated, concentrated, filtered through silica gel (eluted with ethyl acetate) to provide N-methyl-3-acetyl-4-hydroxy-benzenesulfonic acid amide after concentration.

¹H NMR (300 MHz, CDCl₃): δ2.70 (s, 3H); 2.71 (s, 3H); 4.4 (bs, 1H); 7.10 (d, J=12 Hz, 1H); 7.95 (dd, J=3, 12 Hz, 1H); 8.30 (d, J=3 Hz, 1H); 12.75 (s 1H).

Step 3: Preparation of Spiro[2H-1-benzopyran-2,4'-piperidine]-6-aminosulfonyl-1'-[2-phenylethyl]-3,4-dihydro-N-methyl-4-oxo, monohydrochloride Following a procedure similar to that for Step 8 of Example 339 for the preparation of methanesulfonamide, N-[1'-[2-(5-benzofurazanyl)ethyl]-3,4-dihydro-4-oxospiro[2H-[1-benzopyran-2,4'-piperidin]-6-yl]-, monohydrochloride substituting N-methyl-3-acetyl-4-hydroxybenzenesulfonic acid amide for 5-methanesulfonamido-2-hydroxyacetophenone and 1-phenethyl-piperidin-4-one for 1-[2-(benzofurazan-5-yl)ethyl]-piperidin-4-one there was obtained spiro[2H-1-benzopyran-2,4'-piperidine]-6-aminosulfonyl-1'-[2-phenylethyl]-3,4-dihydro-N-methyl-4-oxo, monohydrochloride.0.3 H₂O, mp=232°-233° C. (dec).

EXAMPLE 342

Spiro[2H-1-benzopyran-2,4'-piperidine]-6-aminosulfonyl-1'-[2-phenylethyl]-3,4-dihydro-4-oxo, monohydrochloride Step 1: Preparation of 3-acetyl-4-hydroxy-benzenesulfonic acid amide The title compound was prepared in a similar manner as for the preparation of N-methyl-3-acetyl-4-hydroxy-benzenesulfonic acid amide, but substituting ammonia for mono methyl amine.

Step 2: Preparation of Spiro[2H-1-benzopyran-2,4'-piperidine]-6-aminosulfonyl-1'-[2-phenylethyl]3,4-dihydro-4-oxo, monohydrochloride This was prepared in a manner similar to the preparation of spiro[2H-1-benzopyran-2,4'-piperidine]-6-aminosulfonyl-1'-[2-phenylethyl]-3,4-dihydro-N-methyl-4-oxo, monohydrochloride but using 3-acetyl-4-hydroxy-benzenesulfonic acid amide in place of 5-methanesulfonamido-2-hydroxyacetophenone to give spiro[2H-1-benzopyran-2,4'-piperidine]-6-aminosulfonyl-1'-[2-phenyl-ethyl]-3,4-dihydro-4-oxo, monohydrochloride mp=265°-266° C.

Employing the procedure described in Examples 340, 341 and 342, but substituting the appropriate 2-hydroxy-5-substituted acetophenone and the appropriate 1-substituted 4-piperidinone there were obtained the compounds of Table XXII.

TABLE XXII

| EXAMPLE | R¹ | RM | SALT | MP (°C.) |
|---|---|---|---|---|
| 343 | NC—ᵃ | —CH₂CH₂Ph | •HCl <br> •¼ H₂O <br> •¼ CH₃CH₂OH | 253–55 (dec) |
| 344 | CH₃C(O)—ᵇ | —CH₂CH₂Ph | •HCl | 228–230 (dec) |
| 345 | CH₃SO₂—ᶜ | —CH₂CH₂Ph | •HCl | 253–255 (dec) |
| 346 | CH₃C(O)— | —(tetrahydronaphthyl)-CN(±) | •HCl | 214–220 (dec) |
| 347 | CH₃SO₂— | —CH₂CH₂—(phenyl)—CN | •HCl <br> •¼ H₂O | 156–158 |
| 348 | CH₃SO₂— | —(tetrahydronaphthyl)-CN(±) | •HCl <br> •0.5 H₂O | 194–196 (dec) |
| 349 | CH₃SO₂—ᶜ | —(tetrahydronaphthyl)-CN(+) | •HCl <br> •0.5 H₂O | 218–222 |

TABLE XXII-continued

Structure: R¹-substituted benzene fused to pyran ring with ketone linker to spiro piperidine N—R—M

| EXAMPLE | R¹ | RM | SALT | MP (°C.) |
|---|---|---|---|---|
| 350 | CH₃SO₂—[c] | 6-cyano-tetrahydronaphthalen-2-yl, CN(−) | •HCl | 225–228 |
| 351 | CH₃O— | tetrahydronaphthalen-2-yl (±) | •HCl<br>•0.15 (CH₃CH₂O₂C₂CH₃) | 251–253 |
| 352 | F— | —CH₂CH₂—C₆H₄—NHSO₂CH₃ | •HCl<br>•0.6 CH₃CH₂OH | 142 (d) |
| 353 | F— | —CH₂CH₂—benzofurazan-N-oxide | •0.15 H₂O<br>•HCl | 254–256 (dec) |
| 354 | H₂NSO₂— | —CH₂CH₂—C₆H₄—CN | •HCl<br>•0.15 H₂O | 272–274 |
| 355 | H₂NSO₂— | 6-cyano-tetrahydronaphthalen-2-yl | =HCl<br>•0.3 H₂O | 264–265 |
| 356 | CH₃SO₂NH | 1-(2-methoxyethoxy)-tetrahydronaphthalen-2-yl | •HCl | 231–232 |
| 357 | CH₃SO₂NH— | 6-(NHSO₂CH₃-methyl)-tetrahydronaphthalen-2-yl | •HCl | 243–245 |
| 358 | MeSO₂HN | —CH₂CH₂—C(=O)—C₆H₄—CN | HCl<br>•0.33 H₂O | 208–211 (Dec.) |
| 359 | MeSO₂HN | —CH₂CH₂—CH(OH)—C₆H₄—CN | HCl<br>•0.5 H₂O | 245–248 (Dec.) |
| 360 | MeO | —(CH₂)₂—thiophen-2-yl | HCl | 271–273 (Dec.) |

TABLE XXII-continued

Structure: substituted chromanone with spiro-piperidine, R¹ on aromatic ring, N—R—M on piperidine nitrogen, 4-oxo group.

| EXAMPLE | R¹ | RM | SALT | MP (°C.) |
|---|---|---|---|---|
| 361 | MeO | —(CH₂)₂-(2-thienyl) | HCl | 244–246 (Dec.) |
| 362 | F | —(CH₂)₂-(2-thienyl) | HCl | 268–270 (Dec.) |
| 363 | F | —(CH₂)₂-(3-thienyl) | HCl | 270–272 (Dec.) |
| 364 | MeSO₂ | —(CH₂)₅CH₃ | HCl | 247–249 (Dec.) |
| 365 | MeSO₂ | —(CH₂)₆CH₃ | HCl | 238–240 (Dec.) |
| 366 | HO | —(CH₂)₂-(4-CN-phenyl) | HCl | 276–279 (Dec.) |
| 367 | HO | —(CH₂)₆CH₃ | HCl | 243–245 |
| 368 | HO | —(CH₂)₃CH₃ | HCl | 251–253 |

*hydroxyacetophenone prep. according to G. P. Ellis, D. Shaw, J. Chem. Soc. Perkin I 779–783 (1972)
*hydroxyacetophenone prep. according to N. K. Sangwan, B. S. Verma, K. S. Dhindsa Ind. J. Chem. 25B 672–674 (1986)
*hydroxyacetophenone prep. according to K. Burdeska, Synthesis (11) 940–942 (1982)

EXAMPLE 369

Spiro[2H-1-benzopyran-2,4'-piperidine]-6-aminocarbonyl-1'-[2-phenylethyl]-3,4-dihydro-4-oxo, monohydrochloride A solution of 3,4-dihydro-1'-[2-phenylethylcyanospiro[2H-1-benzopyran-2,4'-piperidin]-4-one (0.30 g, 0.87 mmol) in tetrahydrofuran (10 mL) and methanol (3 mL) was stirred at 0° C. Aqueous KOH in water (1N, 6 mL) and hydrogen peroxide (0.6 mL) was added dropwise and the reaction was stirred for 2.5 hrs. The reaction was quenched with 10% aqueous sodium bisulfite and the product was extracted with ethyl acetate. The organic portion was washed with 10% aqueous sodium carbonate, water, and brine, dried (Na₂SO₄), concentrated and chromatographed (silica gel, 5% methanol in methlyene chloride) to give spiro[2H-1-benzopyran-2,4'-piperidine]-6-aminocarbonyl-1'-[2-phenylethyl]-3,4-dihydro-4-oxo, monohydrochloride (140 mg) after conversion to the salt in ethanol; mp 261°–263.5° C. (dec).

EXAMPLE 370

Spiro[2H-1-benzopyran-2,4'-piperidine]-6-carboxy-1'-[2-phenylethyl]-3,4-dihydro-4-oxo, monohydrochloride A mixture of 3,4-dihydro-1'-[2-phenylethyl-6-cyanospiro[2H-1-benzopyran-2,4'-piperidin]-4-one (500 mg) in 30 mL of 4N aqueous HCl was refluxed for 18 hrs. The mixture was diluted with isopropyl alcohol and concentrated. This was rediluted with isopropyl alcohol, cooled to 0° C. and the resulting solid isolated by filtration and drying in vacuo. yield 0.51 g (98%) of spiro[2H-1-benzopyran-2,4'-piperidine]-6-carboxy-1'-[2-phenylethyl]-3,4-dihydro-4-oxo, monohydrochloride.0.3 H₂O, mp=264°–265° C. (dec).

EXAMPLE 371

Spiro[2H-1-benzopyran-2,4'-piperidine]-6-[2-[4,5-dihydro-1H-imidazoyl]]-1'-[2-phenylethyl]-3,4-dihydro-4-oxo, dihydrochloride A solution of 3,4-dihydro-1'-[2-phenylethyl-6-cyanospiro[2H-1-benzopyran-2,4'-piperidin]-4-one (0.30 g, 0.87 mmol) in methanol (30 mL) was cooled to 0° C. and treated with HCl gas until the solution was saturated. This was allowed to warm to room temperature and stirred 18 hrs. The mixture was concentrated in vacuo to an oil, redissolved in methanol (30 mL) and treated with 1,2-diamino-ethane(0.26 mL) and stirred at room temperature. The mixture was concentrated in vacuo and chromatographed (silica gel, methylene chloride/methanol/ammonium hydroxide (90:10:2)) to give after concentration of appropriate fractions and conversion to the hydrochloride salt with HCl in ethyl acetate 120 mg of spiro[2H-1-benzopyran-2,4'-piperidine]-6-[2-[4,5-dihydro-1H-imidazoyl]]-1'-[2-phenylethyl]-3,4-dihydro-4-oxo, dihydrochloride dihydrochloride.0.5 H₂O, mp=269°–271° C.

EXAMPLE 372

Spiro[2H-1-benzopyran-2,4'-piperidine]-6-[2-[1H-imidazoyl]]-1'-[2-phenylethyl]-3,4-dihydro-4-oxo, dihydrochloride A solution of spiro[2H-1-benzopyran-2,4'-piperidine]-6-[2-[4,5-dihydro-1H-imidazoyl]]-1'-[2-phenylethyl]-3,4-dihydro-4-oxo, dihydrochloride (0.218 g) in methylene chloride (50 mL) under an argon atmosphere was treated with BaMnO$_4$ (2.20 g) and the mixture stirred and refluxed for 48 hr. The mixture was filtered to remove solids and the cake washed with methanol (100 mL). The filtrate was concentrated and flash chromatographed (silica gel, methylene chloride/methanol-/amonium hydroxide (90:10:2)) to give after concentration of appropriate fractions and conversion to the hydrochloride salt with HCl, 65 mg of spiro[2H-1-benzopyran-2,4'-piperidine]-6-[2-[4,5-dihydro-1H-imidazoyl]]-1'-[2-phenylethyl]-3,4-dihydro-4-oxo, dihydrochloride.0.2 H$_2$O, mp=262°-264° C. (dec).

EXAMPLE 373

Spiro[2H-1-benzopyran-2,4'-piperidine]-6-aminocarbonyl-1'-[2-phenylethyl]-3,4-dihydro-N-methyl-4-oxo, monohydrochloride A suspension of spiro[2H-1-benzopyran-2,4'-piperidine]-6-carboxy-1'-[2-phenylethyl]-3,4-dihydro-4-oxo, monohydrochloride (100 mg) in methylene chloride (10 mL) was treated with anhydrous dimethylformamide (0.005 mL) and oxalyl chloride (0.033 mL). This was stirred for 18 hrs at room temperature and then concentrated to an oil. The oil was dissolved in methylene chloride and added to a cold (0° C.) stirring solution of mono methyl amine (76 mg) in methylene chloride. After 5 minutes the mixture was concentrated and disolved in methylene chloride, washed with water, dried (Na$_2$SO$_4$), and concentrated to an oil. The hydrochloride was formed and crystalized from ethanol to give 102 mgs of spiro[2H-1-benzopyran-2,4'-piperidine]-6-aminocarbonyl-1'-[2-phenylethyl]-3,4-dihydro-N-methyl-4-oxo, monohydrochloride.0.3 H$_2$O, mp=246°-248° C.

EXAMPLE 374

Spiro[2H-1-benzopyran-2,4'-piperidine]-6-aminocarbonyl-1'-[2-phenylethyl]-3,4-dihydro-N,N-dimethyl-4-oxo, monohydrochloride In a manner similar for the preparation of spiro[2H-1-benzopyran-2,4'-piperidine]-6-aminocarbonyl-1'-[2-phenylethyl]-3,4-dihydro-N-methyl-4-oxo, monohydrochloride, but substituting dimethyl amine for monomethylamine was prepared spiro[2H-1-benzopyran-2,4'-piperidine]-6-aminocarbonyl-1'-[2-phenylethyl]-3,4-dihydro-N,N-dimethyl-4-oxo, monohydrochloride, mp=259°-261° C.

EXAMPLE 375

Trans-(+ −)-N-[(1'-(6-Cyano-1,2,3,4-tetrahydro-1-hydroxy-2-naphthalenyl)-3,4-dihydro-spiro[(2H)-1-benzopyran-2,4'-piperidine]-4-one-6-yl-methanesulfonamide, monohydrochloride Step 1: Preparation of 1,4-dioxa-8-(6'-cyano-1'-oxa1',2',3',4'-tetrahydronaphth-2'-yl)-8-azaspiro[4.5]decane A solution of 6-cyano-tetralin-1-one (1.712 g 10 mmol) (prepared as described by N. L. Allinger and E. S. Jones, J. Org. Chem., 27 70–76(1962)) in 25 mL of anhydrous tetrahydrofuran (THF) cooled to −10° C. and under an argon atmosphere was treated dropwise with a solution of phenyltrimethylammonium tribromide (3.76 g, 10 mmol) in THF (25 mL) over one hour. The reaction was quenched with an aqueous solution of 10% sodium thio- sulfate and saturated aqueous sodium bicarbonate. The mixture was extracted with ethyl acetate (3×75 mL), the organic portion washed with water (3×50 mL) and brine, dried (Na$_2$SO$_4$) and concentrated to give 2.50 g of an orange solid (100%). The crude product was disolved in 25 mL of anhydrous dimethylfomamide (DMF) and added to a solution of 5.73 g (40 mmol) 1,4-dioxa-8-azaspiro [4.5]-decane in 25 mL of DMF cooled to −15° C. over 15 min. The reaction was stirred an additional 2 hrs while the temperature was allowed to warm to -5° C. The mixture was diluted with ethyl acetate (200 mL) washed with water (3×150 mL) and then 1N aqueous HCl (2×40 mL). The acid washes were combined and washed with ethyl acetate (50 mL). Neutralization with saturated aqueous NaHCO$_3$, extraction into ethyl acetate (300 mL) drying (Na2SO4), and concentration afforded 2.2 g (67%) of 1,4-dioxa-8-(6'-cyano-1'-oxa-1',2',3',4'-tetrahydronaphth-2'-yl)-8-azaspiro[4.5]decane.

Step 2: Preparation of Trans-1,4-Dioxa-8-(6'-cyano-1'-hydroxy-1',2',3',4'-tetrahydronaphth-2'-yl)-8-azaspiro[4.5]decane A solution of lithium aluminum hydride (19.2 mL, 0.5M in diglyme) was cooled to −20° C. under argon and treated dropwise with 2.0 grams of 1,4-dioxa-8-(6'-cyano-1'-oxa-1',2',3',4'-tetrahydronaphth-2'-yl)8-azaspiro[4.5]decane (6.40 mmol) in 50 mL of diglyme over 25 min. The reaction was quenched with a saturated aqueous solution of sodium potassium tartrate (25 mL) and extracted with ethyl acetate. The organic portion was washed with water, and the product extracted into 1N HCl. The acid extract was washed with ether (10×100 mL) and basified with saturated sodium bicarbonate. The product was extracted into ethyl acetate which was washed with water and brine, dried (Na$_2$SO$_4$), and concentrated in vacuo to give crude product yield 1.51 g. This was subjected to flash chromatography (silica gel, 75% ethyl acetate in hexane) which provided 600 mg of trans-1,4-dioxa-8-(6'-cyano-1'-hydroxy-1',2',3',4'-tetrahydronaphth-2'-yl)-8-azaspiro[4.5]decane 99.6% pure (HPLC), 300 mg 98% pure and 100 mg 90% pure. (The minor component was the cis stereoisomer.)

$^1$H NMR (300 MHz,CDCl$_3$): δ1.55-1.90 (m, 5H); 2.04–2.15 (m, 1H); 2.55 (m, 2H); 2.66 (m, 1H); 2.80–3.03 (m, 4H); 3.97 (s, 4H); 4.58 (d, J=10 Hz, 1H); 7.36 (s, 1H); 8.49 (d, J=8 Hz, 1H); 7.70 (d, J=8 Hz, 1H).

Step 3: Preparation of Trans-(±)-N-[(1'-(6-Cyano-1,2,3,4-tetrahydro-1-hydroxy-2-naphthalenyl)-3,4-dihydro-spiro[(2H)-1-benzopyran-2,4'-piperidine]-4-one)-6-yl -methanesulfonamide, monohydrochloride A solution of 600 mg (1.91 mmol) of trans-1,4-dioxa-8-(6'-cyano-1'-hydroxy-1',2',3',4'-tetrahydronaphth-2'-yl)-8-azaspiro[4.5]decane in 25 mL of 1N HCl was heated to 100° C. for 1.5 hr and cooled to room temperature. The mixture was neutralized with saturated Na$_2$CO$_3$, extracted with methylene chloride (3×30 mL), and the organic portion dried (Na$_2$SO$_4$). Concentration in vacuo provided 520 mg (100%) of trans-N-(6'-cyano-1'-hydroxy-1',2',3',4'-tetrahydronaphth-2'-yl)-4-piperidinone. This material was suspended in 10 mL of methanol warmed to 60° C., and stirred under argon. In a separate flask, a solution of 5-sulfonamido-2-hydroxyacetophenone (0.876 g, 3.82 mmol) and pyrrolidine (0.319 mL, 3.82 mmol) in methanol (2.0 mL) was warmed to 60° C. for 10 min. This solution was transfered to the trans-N-(6'-cyano-1'-hydroxy-1',2',3',4'-tetrahydronaphth-2'-yl)-4-piperidinone and the final mixture stirred for 1.5 hrs at 60° C. Concentration in vacuo and chromatography (silica gel, 1% methanol in methylene chloride to 2.5% methanol in methylene chloride) provided after concentration of appropriate fractions, and recrystallization from ethanol, the free base (450 mgs) of trans-(+−)-methanesulfonamide, N-[1'-(6-cyano-1,2,3,4-tetrahydro-1-hydroxy-2-naphthalenyl)-3,4-dihydro-4-oxospiro[2H-1-benzopyran-2,4'-piperidin]-6-yl-, as a pale yellow solid. This was suspended in ethanol containing 10% methanol and treated with 1.3 N HCl in isopropanol to furnish the hydrochloride salt after concentration and trituration with ethanol. This was dried in vacuo to give 470 mgs trans-(+−)-methanesulfonamide, N-[1'-(6-cyano-1,2,3,4-tetrahydro-1-hydroxy-2-naphthalenyl)-3,4-dihydro-4-oxospiro[2H-1-benzopyran-2,4'-piperidin]-6-yl-, monohydrochloride (MP=193°-196° C.) which contained 0.3 mole equivalents of ethanol by NMR and 0.35 mole equivalents of water by microanalysis.

Essentially employing the procedure described in Example 375 there were obtained the compounds of Table XXIII.

TABLE XXIII

CH₃SO₂HN—[structure]—N—RM

| EXAMPLE | RM | SALT | M.P. (°C.) |
|---|---|---|---|
| 376 | OH [naphthalenyl structure] (±) | 1.0 HCl 0.3 CH₃CH₂OH 0.6 H₂O | 199-203 (dec) |
| 377 | OH [naphthalenyl structure] (±) | 1.0 HCl 0.6 H₂O | 195-197 |
| 378 | CH₃ OH [naphthalenyl structure] (±) | 1.0 HCl | 223.5-225 (dec) |

EXAMPLE 379

Trans(±)-Methanesulfonamide, N-[3,4-dihydro-4-oxo-1'-(1,2,3,4-tetrahydro-3-hydroxy-2-naphthalenyl)spiro-[2H-1-benzppyran-2,4'-piperidine]-6-yl-, monohydrochloride Step 1: Preparation of trans-1,4-dioxa-8-(2'-hydroxy-1',2',3',4'-tetrahydronaphth-3'-yl)-8-azaspiro[4.5]decane A stirred solution of 1,4-dihydronaphthalene (1.0 g, 7.7 mmol) in 20 mL of methylene chloride was treated with saturated aqueous sodium bicarbonate (8 mL) and meta-chloroperoxybenzoic acid (1.72 g of 80% pure, 8 mmol). After 20 hours at room temperature the mixture was diluted with methylene chloride (200 mL) and washed with saturated aqueous sodium bicarbonate, water, and brine. The organic portion was dried (Na₂SO₄), concentrated to an oil and disolved in ethanol (15 mL). 1,4-Dioxa-8-aza spiro[4.5]decane (0.99 mL, 7.7 mmol) was added and the mixture refluxed for 20 hrs. The solvent was removed in vacuo and the residue partitioned between ether and water. This was extracted with 1N HCl and the aqueous layer washed with ether (3×50 mL). The aqueous layer was basified with 40% NaOH and then extracted with ether (4×50 mL). The organic portion was dried (Na₂SO₄) and concentrate to a gummy solid which was crystrallized from ether to give 0.95 g (43%) trans-1,4-dioxa-8-(2'-hydroxy-1',2',3',4'-tetrahydronaphth-3'-yl)-8-azaspiro[4.5]decane as a white solid.

¹H NMR (CDCl₃, 300 MHz): δ1.81 (m, 4H); 2.61 (m 2H); 2.75-2.90 (m, 6H); 3.31 (dd, 1H); 3.85 (m, 1H); 3.98 (s, 4H); 4.37 (s, 1H); 7.10 (m, 4H).

Step 2 and Step 3 are carried out in the manner of Step 7 and Step 8 for the preparaton of methanesulfonamide,N-[1'-[2-(5-benzofurazanyl)ethyl]-3,4-dihydro-4-oxospiro[2H-[1-benzopyran-2,4'-piperidin]-6-yl]-, monohydrochloride substituting trans-1,4-dioxa-8-(2'-hydroxy-1',2',3',4'-tetrahydronaphth-3'-yl)-8-azaspiro[4.5]decane to give trans(+−)-methanesulfonamide, N-[3,4-dihydro-4-oxo-1'-(1,2,3,4-tetrahydro-3-hydroxy-2-naphthalenyl)spiro[2H-1-benzopyran-2,4'-piperidine]-6-yl-,monohydrochloride in 40% yield, mp=276°-277° C.(dec).

EXAMPLE 380

Trans(±)-Methanesulfonamide, N-[3,4-dihydro-4-oxo-1'-[1,2,3,4-tetrahydro-3-(2-methoxyethoxy)-2-naphthalenyl]spiro[2H-1-benzopyran-2,4'-piperidine]-6-yl-, monohydrochloride Step 1: Preparation of trans-1,4-dioxa-8-(2'-(2"-methoxyethoxy)-1',2',3',4'-tetrahydronaphth-3'-yl)-8-azaspiro[4.5]decane A solution of trans-1,4-dioxa-8-(2'-hydroxy-1',2',3',4'-tetrahydronaphth-3'-yl)-8-azaspiro[4.5]-decane (289.4 mgs,1.0 mmol) in dimethyl formamide (2.0 mL) was treated with sodium hydride (50% by weight in oil, 225 mgs, 4.7 mmol) and stirred for 30 min. This was treated with 2-bromoethyl methyl ether (0.48 g, 3.42 mmol) and stirred at room temperature 20 hrs. This was quenched with water and extracted with ether (3×50 mL). The product was extracted into aqueous 1N HCl and then after basification of the aqueous layer into ether. The organic portion was dried (Na₂SO₄) and concentrated to give trans-1,4-dioxa-8-(2'-(2"-methoxy-ethoxy)-1',2',3',4'-tetrahydronaphth-3'-yl)-8-azaspiro[4.5]decane as an oil (260 mg, 90%).

¹H NMR (300 MHz, CDCl₃): δ1.74 (t, 4H); 2.74 (t, 4H); 2.80-3.20 (m, 5H); 3.40 (s, 3H); 3.58 (m, 1H); 3.65-3.90 (m, 3H); 3.97 (s, 4H); 7.10 (m, 4H).

Step 2 and Step 3 were carried out in the manner of Step 7 and Step 8 for the preparaton of methanesulfonamide,N-[1'-[2-(5-benzofurazanyl)ethyl]-3,4-dihydro-4-oxospiro[2H-[1-benzopyran-2,4'-piperidin]-6-yl]-,monohydrochloride, but substituting trans-1,4-dioxa-8-(2'-(2"-methoxyethoxy)-1',2',3',4'-tetrahydronaphth-3'-yl)-8-azaspiro[4.5]decane to give trans(±−)-methanesulfonamide, N-[3,4-dihydro-4-oxo-1'-[1,2,3,4-tetrahydro-3-(2-methoxyethoxy)-2-naphthalenyl]-spiro[2H-1-benzppyran-2,4'-piperidine]-6-yl-, monohydrochloride, mp=254°-256° C. (dec).

EXAMPLE 381

Methanesulfonamide,
N-[1'-(6-cyano-1,2,3,4-tetrahydro-2-naphthalenyl)-3,4-dihydro-4-oxospiro[2H-1-benzopyran-2,4'-piperidin]-6-yl]-, monohydrochloride and separation into its enantiomers Step 1: Preparation of 6-cyano-2-tetralone A flame dried 1 liter round bottom flask with argon inlet, digital thermometer, and magnetic stir bar, was charged with a 68% NaCN/alumina mixture (21.22 g, 433 mmol)(NaCN and alumina were ground together in a morter and pestle according to the procedure of Dalton et al. *J. Org. Chem.*, 44, (24) 4443(1979)), and tetrakis (triphenylphospine) palladium(0) (10.0 g, 8.65 mmol). The flask was purged three times via vacuum with argon and a solution of 6-bromo-2-tetralone (19.46 g, 86.5 mmol) in degassed toluene (400 mL) was added. The mixture was heated to 80° C. and stirred for 64 hrs at that temperature. Analysis by HPLC indicated 89% conversion (HPLC conditions, column: Waters C18 Bondapak, eluent: 80:20 (0.1% $H_3PO_4$ in $H_2O$: $CH_3CN$), flow: 2 mL/min, wavelength: 220 nm, Rt: bromotetralone =9.65 min, cyanotetralone=3.46 min). The reaction was cooled and the mixture filtered through silica gel (elution with 60% ethyl acetate in hexane.) Concentration of the appropriate fractions gave 9.4 g (68%) of 6-cyano-2-tetralone (98.7% by HPLC).

$^1$H NMR (300 MHz, $CDCl_3$): δ2.56 (t, J=7Hz, 2H); 3.12 (t, J=7Hz, 2H); 3.65 (s, 2H), 7.24 (d, J=9Hz, 1H); 7.52 (d, J=9Hz, 1H); 7.57 (s, 1H).

Step 2: Preparation of 1,4-dioxa-8-(6'-cyano-1', 2', 3', 4'-tetrahydronaphth-2'-yl)-8-azaspiro[4.5]decane hydrochloride A 500 mL round bottom flask fitted with an argon inlet, and Dean-Stark apparatus was charged with a solution of 6-cyano-2-tetralone (8.4 g, 49.0 mmol) in toluene (150 mL). Para-toluenesulfonic acid (0.40 g, 2 mmol) and 1,4-dioxa-8-azaspiro[4.5]-decane (7.90 g, 54.0 mmol) were added and the stirred mixture heated to reflux and the water removed (4.5 hrs). The mixture was cooled, and concentrated to an oil in vacuo. The oil was disolved in anhydrous tetrahydrofuran (400 mL) and cooled to 0° C. under argon. Dry HCl gas was introduced (<10° C.) and a solid precipitate formed. The mixture was concentrated on a rotary evaporator to approximately 50 mL. Anhydrous tetrahydrofuran (250 mL) was added and the mixture stirred and cooled to 0° C. Sodium cyanoborohydride (4.2 g, 63 mmol) was added in two portions. The reaction was allowed to warm gradually to room temperature and stirred 16 hrs. This was quenched with 1N aqueous sodium hydroxide (160 mL) and stirred for 0.5 hr (pH=13.5). The layers were separated and the aqueous layer was washed with diethyl ether (2×200 mL). The combined organic layers were combined and concentrated on a rotary evaporator to an oil which was disolved into methylene chloride (200 mL). This was washed with saturated aqueous NaCl and then stirred with 1N HCl (100 mL) for 15 minutes. The layers were separated and the aqueous was extracted with methylene chloride (2×100 mL). The combine methylene chloride extract was concentrated on a rotary evaporator and ethyl acetate (200 mL) was added during the distillation to effect crystallization. The resultant slurry was cooled to 0° C. for 3 hrs and the 1,4-dioxa-8-(6'-cyano-1', 2', 3', 4'-tetrahydronaphth-2'-yl)-8-azaspiro[4.5]decane hydrochloride was collected by filtration (8.70 g, 53%). A second crop was obtained upon concentration of the mother liqours and dilution with diethyl ether (3.6 g, 22%). The combined solids were 98% pure by HPLC.

Step 3: Resolution of 1,4-dioxa-8-(6'-cyano-1', 2', 3', 4'-tetrahydronaphth-2'-yl)-8-azaspiro[4.5]decane To a solution of 5.00 g (0.0168 mol) of racemic 1-4-dioxa-8-(6'-cyano-1', 2', 3', 4'-tetrahydronaphth-2'-yl)-8-azaspiro[4.5]decane in 500 mL of boiling absolute ethanol was added 6.47 g (0.01676 mol) of di-p-toluoyl-D-tartaric acid. The solution was concentrated by boiling to 450 mL and allowed to stand overnight at room temperature. The product that crystallized was removed by filtration and was washed with ethanol to give 4.45 of a salt, A. The filtrate and washings were combined and evaporated to give B.

The solid A was recrystallized three times from absolute thanol to yield 2.82 g of salt having $[\alpha]_{589}= +106.1°$ (c=1.151;pyridine). This salt was converted to the free base using sodium bicarbonate solution and extracting into ethyl acetate. The ethyl acetate phase was dried over magnesium sulfate, filtered, and concentrated in vacuo to give 1.15 g of the (+)-enantiomer of the title compound: mp=124°-126° C.; $[\alpha]_{589}= +55.4°$ (c=1.605; $CHCl_3$).

The solid B was converted to the free base as described above to give 2.84 g of material. This solid (0.00938 mol) was dissolved in 275 mL of boiling ethanol and was treated with 3.794 g (0.00938 mol) of di-p-toluoyl-L-tartaric acid monohydrate. The salt that crystallized on cooling was collected by filtration and was washed with ethanol to give 4.47 g of material having $[\alpha]_{589}= -102.6°$ (c=1.131; pyridine). Recrystallization of this material from ethanol gave 3.71 g of salt, $[\alpha]_{589}= -106.1°$ (c=0.985, pyridine), and further recrystallization from ethanol gave 3.24 g of salt having essentially no change in rotation, $[\alpha]_{589}= -105.9°$ (c=1.472, pyridine). This salt was converted to the free base as described above to give 1.34 g of the (−)-enantiomer of the title compound: mp=124°-126° C.; $[\alpha]_{589}= -54.5°$ (c=1.954; $CHCl_3$).

Step 4: Preparation of N-(6'-cyano-1', 2', 3', 4'-tetrahydronaphth-2'-yl)piperidin-4-one A solution of 1,4-dioxa-8-(6'-cyano-1', 2', 3', 4'-tetrahydronaphth-2'-yl)-8-azaspiro[4.5]decane hydrochloride (10.0 g, 30.0 mmol) or the resolved free base was disolved on 1N HCl (100 mL). This was stirred and heated to 100° C. under an argon atmosphere for 1.5 hrs. The solution was cooled in an ice bath to 25° C. and methylene chloride added (200 mL). The mixture was stirred and basified to pH 9.0 with saturated aqueous sodium carbonate. The organic layer was separated and the aqueous extracted with methylene chloride (2×50 mL). The combined organic extract was dried ($Na_2SO_4$), and concentrated to a foam to give 7.5 g (99%) of N-(6'-cyano-1', 2', 3', 4'-tetrahydronaphth-2'-yl)piperidin-4-one (98% by HPLC, HPLC conditions, column: Waters C18 Bondapak, eluent: 85:15 (0.1% $H_3PO_4$ in $H_2O$: $CH_3CN$), flow: 2 mL/min, wavelength: 220 nm, Rt: ketal=6.20 min, ketone=2.1 min).

Step 5: Preparation of Methanesulfonamide, N-[1'-(6-cyano-1,2,3,4-tetrahydro-2-naphthalenyl)-3,4-dihydro-4-oxospiro[2H-1-benzopyran-2,4'-piperidin]-6-yl]-, monohydrochloride A solution of 2-hydroxy-5-methanesulfonamido acetophenone (5.58 g, 24.3 mmol), and pyrolidine (2.05 mL, 24.3 mmol) in methanol (30 mL) was stirred at 60° C.

for 10 min. N-(6'-cyano-1', 2', 3', 4'-tetrahydronaphth-2'-yl)piperidin-4-one (3.09 g, 12.2 mmol) was added in one portion and the mixture stirred for 1.5 hrs at 60° C. The reaction was concentrated to an oil in vacuo and flash chromatographed (silica gel, ethyl acetate) to afford the product in appropriate fractions which were combined and concentrated to 350 mL and treated with 1.3N HCl in isopropyl alcohol. The precipitate was stirred 2hrs, filtered, and dried in vacuo (60° C., 0.1 torr) to give 3.91 g (64%) of Methanesulfonamide, N-[1'-(6-cyano-1,2,3,4-tetrahydro-2-naphthalenyl)-3,4-dihydro-4-oxospiro[2H-1-benzopyran-2,4'-piperidin]-6-yl]-, monohydrochloride, mp=250°-252° C.

Starting from the (+)1,4-dioxa-8-(6'-cyano-1', 2', 3', 4'-tetrahydronaphth-2'-yl)-8-azaspiro[4.5]decane the (+) enantiomer of methanesulfonamide, N-[1'-(6-cyano-1,2,3,4-tetrahydro-2-naphthalenyl)-3,4-dihydro-4-oxospiro[2H-1-benzopyran-2,4'-piperidin]-6-yl]-, monohydrochloride was obtained. $[\alpha]_D = +40.7°$ (c=0.17 MeOH); mp=262°-264° C. (dec). Starting from the (−) 1,4-dioxa-8-(6'-cyano-1', 2', 3', 4'-tetrahydronaphth-2'-yl)-8-azaspiro[4.5]decane the (−) enantiomer of methanesulfonamide, N-[1'-(6-cyano-1,2,3,4-tetrahydro-2-naphthalenyl)-3,4-dihydro-4-oxospiro[2H-1-benzopyran-2,4'-piperidin]-6yl]-, monohydrochloride was obtained. $[\alpha]_D = -41.36°$ (c=0.191 MeOH); mp=263°-265° C. (dec).

EXAMPLE 382

(+)-Methanesulfonamide, N-[1'-(6-cyano-1,2,3,4-tetrahydro-2-napthalenyl)-3,4-dihydro-4-oxospiro[2H-1-benzopyran-2,4'-piperidin]-6-yl]-, monohydrochloride [Alternate Method]

Step 1: Preparation of 6-Bromo-2-tetralone

A single neck 3 liter round bottom flask under an Ar atmosphere was charged with 4-bromo-phenyl acetic acid (250.0 g, 1.15 m), methylene chloride (1.5 L), and dimethylformamide (0.5 mL). This magnetically stirred solution was cooled to 0° C. and treated dropwise with oxalyl chloride (156 mL, 1.74 m). The reaction was allowed to reach room temperature and stirred 16 hrs. The reaction was concentrated on a rotary evaporator to approximately 1 L of volume. A separate dry 5 liter 3 neck round bottom flask under Ar, fitted with gas inlet tube, overhead stirrer, and digital thermometer was charged with methylene chloride (1.5 L) and AlCl₃ (312.0 g, 2.34 m). This suspension was cooled to 0° C. and stirred while the above solution of acid chloride was added to it slowly via cannula. When the addition was complete, ethylene gas was introduced for 1–2 hrs to the vigorously stirred suspension while maintaining the internal temperature at 15° C. Upon completion by HPLC, the reaction was warmed to room temperature and stirred for 0.5 hrs. The mixture was recooled to 0° C. and cautiously quenched slowly with water (1.5L). The layers were separated, and the aqueous one washed with 500 mL of methylene chloride. The organic portion was washed with 2N aqueous HCl (2×800 mL), brine (400 mL), and saturated aqueous NaHCO₃ (2×800 mL). Each aqueous extract was washed with the same 500 mL methylene chloride extract from above. The methylene chloride extracts were combined, dried (Na₂SO₄), filtered, and concentrated to approximately 500 mL of volume. This was then added to 5.0L of hexane warmed to 50° C. The methylene chloride was distilled off and the hot solution decanted from an insoluble brown tar. The solution was allowed to cool to 25° C. and placed in the freezer overnight. The precipitate was collected and washed with hexane (200 mL), and dried in vacuo to give 229.0 g of the compound as a pale yellow solid (88%).

Step 2: Preparation of (±)-1,4-dioxa-8-(6'-bromo-1',2',3',4'-tetrahydronaphth-2'-yl)-8-azaspiro[4.5]decane A 3L round bottom flask fitted with an argon inlet, and Deak-Stark apparatus was charged with a solution of 6-bromo-2-tetralone (100.0 g, 445 mmol) in toluene (2.0L). Para-toluenesulfonic acid (0.50 g) and 1,4-dioxa-8-azaspiro[4,5]-decane (81.5 g, 489 mmol) were added and the stirred mixture heated to reflux and the water removed (4.5 hrs). The mixture was cooled, and concentrated to an oil in vacuo. The oil was dissolved in anhydrous tetrahydrofuran (1.5L) and cooled to 0° C. under argon. Dry HCl gas was introduced (at below 5° C.) and a solid precipitate formed. Sodium cyanoborohydride (36.3 g, 578 mmol) was added in four portions. The reaction was allowed to warm gradually to room temperature and stirred 16 hrs. This was quenched with 1N aqueous sodium hydroxide (500 mL) and stirred for 0.5 hr (pH=13.5). The mixture was concentrated on a rotary evaporator to remove THF, and diluted with 1N NaOH (1.1L) and diethyl ether (1.5L). This mixture was stirred 15 min and the layers were separated and the aqueous layer was washed with diethyl ether (2×200 mL). The organic layers were combined, washed with water (2×500 mL) and saturated aqueous NaCl (2×250 mL) and then with 1N HCl (1×1.0L, 2×500 mL). The acid extracts were combined, stirred with methylene chloride (1.0L), and basified with 40% aq. NaOH (pH=10). The layers were separated, and the aqueous extracted with methylene chloride (500 mL). The methylene chloride extracts were combined, dried (Na₂SO₄), and concentrated to an oil. The oil was flushed with toluene (2×400 mL) and dried in vacuo to give the title compound as a solid on standing (128.8 g, 87%) which was greater than 98% pure by HPLC and used in the next step without purification. Note: The amount of excess HCl gas present (pH=3–4, THF suspension on wet pH paper) critically determines the yield free amine. Additional HCl may be added during the introduction of the cyano borohydride. In runs in which the pH was not adjusted properly the yield was reduced to 50%; the balance being a borane complex which was isolated from the ether layers. This borane complex could be quantitatively converted to the free amino by heating in 40% aq NaOH/ethylene glycol (1:1) at 100° C.

Step 3(a): Preparation of Phenyl cyanate

The title compound was prepared by a modification of the procedure described in *Organic Syntheses*, 61, 35 (1983). A 3-necked, 2L R. B. flask, equipped with a 500 ml pressure equalized dropping funnel, a mechanical stirrer and a thermometer, was charged with water and cooled in an ice-salt bath. Cyanogen bromide (189.1 g, 1.78 mol) was added and the mixture was stirred for 5 min. Phenol (160.0 g., 1.7 mol) in carbon tetrachloride (535 ml) was added in one portion. The mixture was stirred vigorously while triethylamine (236.9 ml, 172.0 g., 1.7 mol) was added dropwise at a rate such that the reaction temperature did not exceed 5° C. (total addition time=45 min.). The mixture was stirred for a further 15 min. then transferred to a 2L separatory funnel. The organic layer was separated and the aqueous layer was extracted with carbon tetrachloride (2×90 ml). The combined organic layers were washed with water (3×90 ml) then dried by stirring with phosphorus pentoxide (10 g) for 15 min. The mixture was filtered and the solvent was evaporated under reduced pressure (water aspirator) at 20° C. to give a yellow oil. Polyphosphate ester (Y. Kanaoka, et al., *Chem. Pharm. Bull.*, 13, 1065-1072 (1965)) (0.2 ml) was added and the mixture was distilled under reduced pressure through a 15 cm vigreux column to give phenyl cyanate (165.8 g, 82%) as a colorless oil, b.p. 79°-82° C. (16 mmHg)[1]. The product was stored under nitrogen at −10° C. (freezes).

$^1$H NMR (300 MHz, CDCl$_3$) δ: 7.49-7.30 (5H, m).

Step 3 (b): Preparation of (±)-1,4-Dioxa-8-(6'-cyano-1',2',3',4'-tetrahydronapath-2yl)-8-azaspiro[4.5]decane (±)-1,4-Dioxa-8-(6'-bromo-1',2',3',4-tetrahydronaphth-2-yl)-8-azaspiro[4.5]decane (70.4 g, 0.2 mol) under nitrogen in a 1L R. B. flask was dissolved in anhydrous THF (600 ml, distilled from Na/benzophenone) and cooled to −75° C. Phenyl cyanate (26.06 ml, 28.5 g, 0.24 mol) dissolved in anhydrous THF (400 ml) under nitrogen in a 2L R. B. flask equipped with a digital thermometer was cooled to −75° C. n-Butyl lithium (1.6M in hexane, 137.5 mL, 0.22 mmol) was added over 5 min. to the bromide solution. Further n-butyl lithium (12.5 mL, 0.02 mmol) was added to the phenyl cyanate solution. After 5 min., the lithiated bromide solution was added over 5 min., via cannual, to the phenyl cyanate solution (reaction temperature rises to −35° C.). The mixture was stirred and cooled to −75° C. for 30 min. then the cooling bath was removed and HCl-H$_2$O (1M, 200 mL) was added with vigorous stirring. The mixture was warmed to room temperature, diluted with HCl-H$_2$O (1M, 1800 mL) and washed with ether (2×1000 mL.). Methylene chloride (1000 mL) was added and the mixture was stirred and cooled in ice during the addition of aqueous sodium hydroxide 10M, 180 mL). The layers were separated, and the aqueous layer was extracted with methylene chloride (500 mL). The combined organic layers were dried (Na$_2$SO$_4$), and the solvent was evaporated under reduced pressure to give crude (±) 1,4-dioxa-8-(6'-cyano-1',2',3',4'-tetrahydronaphth-2'-yl)-8-azaspiro[4.5]decane as a tan solid (56.2 g). Crude (±)1,4-dioxa-8-(6'-cyano-1',2',3',4'-tetrahydronaphth-2'yl)-8-azaspiro-[4.5]-decane in three batches (56.4 g, 56.2 g, 27.7 g; total 140.3 g) were separately dissolved in refluxing methyl-cyclohexane (1000 mL each) and combined by decanting into a 5L, 4-necked flask equipped with a mechanical stirrer, thermometer, reflux condenser and a stopper. The mixture was heated to reflux (clear solution formed), then allowed to cool with stirring to room temperature, then to 5° C. The mixture was stored at −15° C. for 15 hr. The solid was collected by filtration, washed with cold methylcyclohexane (2×150 ml) and dried in vacuo at room temperature to give the spirodecane as a pale yellow solid (121.3 g), .m.p. 136°-138° C. Purity=99.3%

Step 4: Resolution of 1,4-dioxa-8-(6'-cyano-1'2',3'4'-tetrahydronaphth-2'-yl)-8-azaspiro[4.5]decane A 12L round bottom flask fitted with a reflux condenser, digital thermometer, and overhead stirrer was charged with absolute ethanol (10.6L) and 1,4-dioxa-8-(6'-cyano-1',2',3',4'-tetrahydronaphth-2'yl)-8-azaspiro[4.5]decane 120.0 g, 402 mmol). The mixture was warmed to 65° C. to give a clear solution, and 97% di-p-toluoyl-L-tartaric acid monohydrate (167.7 g, 402 mmol) was added. The resulting clear solution was seeded with this salt and allowed to cool to room temperature with stirring overnight. The precipitate was collected by filtration and washed with absolute ethanol (600 mL). The solid was dried in vacuo to a solid and converted to free base in a stirred mixture of ethyl acetate (2.0L) and saturated aqueous NaHCO$_3$(3.0L). The layers were separated, and the aqueous one washed with ethyl acetate (2×500 mL). The organic layers were combined, washed with brine (2×200 mL), dried (Na$_2$SO$_4$), and concentrated to 69.4 g of a solid (59% yield). The solid free base (69.4 g, 233 mmol) was dissolved in absolute ethanol (4.25L) at 60° C. and 97% di-p-toluoyl-D-tartaric acid (92.64 g, 233 mmol) was added. The resulting clear solution was seeded with a sample of this salt and allowed to cool to room temperature overnight. The precipitate which formed was collected, washed with absolute ethanol (800 mL), and dried in vacuo at 40° C. to give 122.5 g (44.5%). This +D salt was completely dissolved in absolute ethanol (8.0 L) at reflux and concentrated to approximately 7.0 L of volume by distillation at 1 atmosphere. The solution was seeded and cooled to room temperature overnight. The solid was collected, washed with absolute ethanol (800 mL) dried in vacuo to give 100.9 g [α]$_D$= +104.7° (c=1.0 pyridine)) (36.7%). This salt was dissolved in hot absolute ethanol (8.3 L), concentrated at 1 atmosphere to 3.1 L of total volume, seeded and cooled to room temperature overnight. This solid was collected, washed with absolute ethanol (900 mL) and dried in vacuo to give 89.7 g [α]$_D$= 105.4° (c=1.0 pyridine)) (32.6%). A further crystallization from 7.0 L hot ethanol concentrated to 2.9 L volume gave 74.3 g ([α]$_D$= +105.4° (c=1.0 pyridine)) (32.6%). A further recrystallization from 7.0 L hot ethanol concentrated to 2.9 L volume gave 74.3 g [α]$_D$=104.9° (c=1.0 pyridine)) (27% yield). The free base was obtained by treating a stirred mixture of saturated aq. NaHCO$_3$ (250 mL) and methylene chloride (250 mL) with 1,4-dioxa-8-(6'-cyano 1',2',3',4'-tetrahydronaphth-2'yl)-8-azaspiro]4.5]-decane di-p-toluoyl-D-tartaric acid salt (10.0 g, 33.5 mmol). After 15 min the layers were separated, the aqueous washed with methylene chloride (100 mL), and the combined organics washed with saturated aq. NaHCO$_3$ (100 mL), dried Na$_2$SO$_4$) and concentrated to give 4.30 g (99%) of a solid. A sample of free base was analyzed by chiral shift reagent proton NMR to be 99.8% pure (+) enantiomer.

Step 5: Preparation of N-(6'-Cyano-1',2', 3',4'-tetrahydronaphth-2'-yl)piperidin-4-one A solution of (+)-1,4-dioxa-8-(6'-cyano-1',2',3',4'-tetrahydronaphth-2'yl)-8-azaspiro[4.5]-decane (10.0 g, 33.5 mmol) was dissolved in 1N HCl (100 mL). This was stirred and heated to 100° C. under an argon atmosphere for 1.5 hrs. The solution was cooled in an ice bath to 25° C. and methylene chloride added (200 mL). The mixture was stirred and basified to pH=9.0 with saturated aqueous sodium carbonate. The organic layer was separated and the aqueous extracted with methylene chloride (2×50 mL). The combined organic extract was dried (Na$_2$SO$_4$), and concentrated to a foam to give 7.5 g (99%) of N-(6'-cyano-1',2',3',4'-tetrahydronaphth-2'-yl)-piperdin-4-one (98% by HPLC).

Step 6: Methanesulfonamide, N-[1'-(6-cyano-1, 2,3,4-tetrahydro-2-naphthalenyl)-3,4-dihydro-4-oxospiro[2H-1-benzopyran-2,4'-piperidin]-6-yl]-, monohydrochloride A solution of 2-hydroxy-5-methanesulfonamidoacetophenone (26.98 g, 117.7 mmol), and pyrrolidine (9.8 mL, 117.7 mmol) in methanol (480 mL) was stirred at 25° C. for 10 min. (+)-N-(6'-Cyano-1', 2',3',4'-tetrahydronaphth-2'-yl)-piperidin-4-one (20.0 g, 78.4 mmol) was added in one portion and the mixture stirred for 24 hrs at 25° C. The reaction was concentrated to an oil in vacuo and flash chromatographed (silica gel, ethyl acetate) to afford the product in appropriate fractions which were combined and concentrated to a foam. This was crystallized from isopropyl alcohol (525 mL) to give a solid which was collected by filtration, washed with IPA (50 mL) and dried in vacuo (30.8 g). This was dissolved in ethyl acetate (1.5 L) and treated with 1.3N HCl in IPA (55 mL). The precipitate was stirred 20 hrs, filtered and dried in vacuo (60° C., 0.1 torr) to give 32.3 g (84%) of (+) Methanesulfonamide, N-[1'-(6-cyano-1,2,3,4-tetrahydro-2-naphthalenyl)-3,4-dihydro-4-oxospiro[2H-1-benzopyran-2,4'-piperidin]-6-yl]-, $[\alpha]_D = +40.7$ (c=0.17, MeOH).

EXAMPLE 383

Resolution of 6-Methanesulfonamido-3,4-dihydro-1'-(1,2,3,4-tetrahydronaphth-2-yl)spiro[(2H)-1-benzopyran-2,4'-piperidine]-4-one To a warm solution of 2.112 g (0.00479 mole) of racemic 6-Methanesulfonamido-3,4-dihydro-1'-(1,2,3,4-tetrahydronaphth-2-yl)spiro[2H)-1-benzopyran-2,4'-piperidine]-4one in 50 mL of acetone was added a solution of 1.852 g di-p-toluoyl-D-tartaric acid (0.00479 mol) in 20 mL of acetone. After standing at room temperature for 48 hours, a hard solid, A, had precipitated out. The solvent was decanted, and the solid was washed four times with acetone. The original decanted solvent and washings were combined and evaporated to afford B.

The solid A was recrystallized from absolute methanol four times to afford 0.636 g of salt having mp=203°-204° (dec.) and $[\alpha]_{589}^{25°} = +85.8°$ (c=0.975; pyridine). This salt was converted to the free base form using sodium bicarbonate solution, and the hydrochloride salt of the amine was prepared and crystallized from isopropyl alcohol to give 0.303 g of the (+)-enantiomer of the title compound; mp 283°-285° C. (dec.); $[\alpha]_{589} = +36.9°$ (c=0.449; DMF).

Anal. Calc'd. for $C_{24}H_{28}N_2O_4S \cdot HCl$: C, 60.43; H, 6.13; N, 5.87. Found: C, 60.03; H. 6.25; N, 5.61.

The solid B was treated with saturated sodium bicarbonate solution and extracted into ethyl acetate. The ethyl acetate phase was dried over magnesium sulfate, filtered, and concentrated in vacuo to give 1.112 g of material. This solid (0.00252 mol) was dissolved in 10 mL of warm acetone and was treated with a solution of 1.019 g (0.00252 mol) of di-p-toluoyl-L-tartaric acid in 15 mL of acetone. After standing overnight, the precipitate that formed was removed by filtration and was washed with acetone. Two recrystallizations from methanol gave 0.803 g of salt having mp=203°-204° (dec.) and $[\alpha]_{589} = -85.4°$ (c=0.830; pyridine.) This salt was converted to the free base form using sodium bicarbonate solution, and the hydrochloride salt of the amine was prepared and crystallized from isopropyl alcohol to give 0.146 g of the (−)-enantiomer of the title compound; mp 284°-286° C. (dec.); $[\alpha]_{589} = -37.7°$ (c=0.779; DMF).

Anal. Calc'd. for $C_{24}H_{28}N_2O_4S_8 \cdot HCl$: C, 60.43; H, 6.13; N, 5.87. Found: C, 60.28; H, 6.17; N. 5.78.

Essentially employing the procedures described in Example 381, steps 2, 4 and 5, but substituting 6-cyano-2-tetralone with an appropriate ketone, the compounds of Table XXIV were prepared.

TABLE XXIV

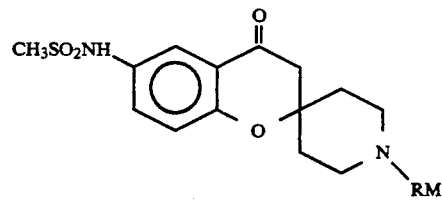

| EXAMPLE | RM | ISOMER | SALT | M.P. (°C.) |
|---|---|---|---|---|
| 384 | tetrahydronaphthalen-2-yl | (±) | •HCl | 275 (d) |
| 385 | tetrahydronaphthalen-2-yl | (±) | •HCl | 283–285 (dec) |
| 386 | tetrahydronaphthalen-2-yl | (−) | •HCl | 284–286 (dec) |
| 387 | 6-methoxy-tetrahydronaphthalen-2-yl (OCH₃) | (±) | •HCl | 252–255 (dec) |

TABLE XXIV-continued

[Structure: CH3SO2NH-phenyl-C(=O)-CH2-CH2-spiro[benzopyran-piperidine]-N-RM]

| EXAMPLE | RM | ISOMER | SALT | M.P. (°C.) |
|---|---|---|---|---|
| 388 | 6-bromo-1,2,3,4-tetrahydronaphthalen-2-yl | (±) | •HCl | 272–274 (dec) |
| 388a[1] | 1,2,3,4-tetrahydronaphthalene-6-carboxylic acid-2-yl | (+) | •HCl | 305–306 (dec) |
| 389 | chroman-3-yl | (±) | •HCl •¼ H2O | 263–265 (dec) |
| 390 | indan-1-yl | | •HCl •0.9 CH3CH2OH •0.5 H2O | 279–280 (dec) |
| 391 | 5-(methanesulfonamido)indan-2-yl | (±) | •HCl •1.4 H2O | 204–208 (dec) |
| 392 | 1-phenylethyl (CH3) | (±) | •HCl | 275–277 (dec) |
| 393 | 2,3,4,5,6,7-hexahydro-1H-benzocyclohepten-yl | | •HCl •0.75 CH3CH2OH •0.7 H2O | 198° (dec) |

[1] Prepared from the corresponding nitrile by hydrolysis in refluxing aqueous HCl for 3 days and recrystallization of the resulting solid from ethanol-water.

EXAMPLE 394

1,4-Dihydro-1'-[2-(4-methanesulfonamidopheny)-ethyl]-7-methanesulfonamido-spiro-[(3H)-2-benzopyran-3,3'-piperidine] hydrochloride.0.7 H2O.0.35 isopropanol Step A: Preparation of 1,4-Dihydro-1'-ethylspiro[2-benzopyran-3,3'-piperidone]

A solution of N-methyltoluamide (12.0 g) in tetrahydrofuran cooled to 0° C. was treated with n-butyllithium (103 mL of 1.6M in hexane) and the solution stirred for 1 hr. The mixture was cooled to −78° C. and a solution of N-ethyl-3-piperidinone (15.34 g in 50 mL of THF) was added. After 0.5 hr the mixture was warmed to 0° C. and quenched into ice (200 g). The organic phase was separated and the aqueous extracted with chloroform (200 mL). The combined organic extract was concentrated to a foam (25.0 g) which was disolved in 50% aqueous acetic acid (50 mL) and treated with concentrated sulfuric acid (15 mL). The mixture was stirred at 110° C. for 6 hrs, quenched into ice, and basified to pH 8.5 with 40% aqueous NaOH. Extraction with chloroform (3×250 mL), drying (Na2SO4), and concentration gave an oil which was chromatographed (silica gel, 5% methanol in methylene chloride). Concentration of appropriate fractions gave 1,4-dihydro-1'-ethyl-spiro-[2-benzopyran-3,3'-piperidone] as an oil (17.2 g).

$^1$H NMR (300 MHz, CDCl3): δ0.95 (t, 3H); 1.57 (m, 4H); 2.35 (m, 4H); 2.65 (t, 2H); 3.2 (dd, 2H); 7.25 (d, 1H); 7.38 (t, 1H); 7.54 (dt, 1H), 8.1 (d, 1H).

Step B, C, D, E, and F are carried out in a manner analogous to Steps A, B, C, D, and E in Example 60 for the preparation of 1,4-dihydro-1'-[2-(4-methanesulfonamidopheny)ethyl]-7-methanesulfonamidospiro-[(3H)-2-benzopyran-3,4'-piperidine]hydrochloride substituting 1,4-dihydro-1'-ethyl-spiro[2-benzopyran-3,3'-piperidone] for 1,4-dihydro-1'-methyl-spiro[2-benzopyran-3,4'-piperidone] in Step A. This gave 1,4-dihydro-1'-[2-(4-methanesulfonamidophenyl)ethyl]-7-methanesulfonamido-spiro-[(3H)-2-benzopyran-3,3'-piperidine]hydrochloride.0.7 H2O.0.35 isopropanol, mp =169°-171° C. (dec).

Essentially employing the procedures described in Example 394, but substituting for 2-[4-(methanesulfonamido)phenyl]ethylmethanesulfonate used therein, the appropriate electrophiles there were produced spiropiperidines described in Table XXV.

TABLE XXV

CH3SO2NH—[aryl]—O—[spiro piperidine]—N—R—M

| Example | RM | salt | mp (°C.) |
|---|---|---|---|
| 395 | —CH2CH2—[isoxazoline/pyridine N-oxide ring] | •HCl •0.35 H2O •0.15 IPA* | 150–155 |
| 396 | —CH2CH2—[phenyl]—NHSO2CH3 | •HCl •0.5 H2O | 184–187 (dec) |
| 397 | —CH2—[phenyl]—NHSO2CH3 | •HCl •11/2 H2O •0.25 IPA | 171–173 (dec) |
| 398 | —CH2CH2—[phenyl]—NHSO2CH3 | •HCl •1.25 H2O •0.2 IPA | 150–150 |
| 399 | —CH2CH2—[pyridyl] | •2 HCl | 158–160 |
| 400 | —CH2CH2—[pyridyl-CH3] | •2 H2SO4 •0.85 IPA | 120–(dec) |

(*IPA is isopropyl alcohol).

EXAMPLE 401

1,4-Dihydro-1,1-dimethyl-1'-methyl-7-methanesulfonamido)-spiro(3H-2-benzopyran-3,4'-piperidine)

A solution of 1,4-dihydro-1'-methyl-7-methanesulfonamido-spiro[(3H)-2-benzopyran-3,4'-piperidine-1-one (from Example 60, Step B) in THF (3.3 mmol in 10 mL) was cooled to −78° C. and treated dropwise with methyl magnesium bromide in THF (10 mmol). The reaction was warmed to 25° C. and quenched with water (1 mL). The mixture was concentrated on a rotary evaporator, redissolved in 85% H3PO4 (10 mL) and heated at 100° C. for 1.5 hours. The mixture was poured into ice and the pH adjusted to 8.5 with 40% aqeuous NaOH. Extraction with CH2Cl2, drying (Na2SO4), and evaporation of solvents gave the crude product which was purified by chromatography on silica gel (50% EtOAc in hexane). The title compound was obtained in 85% yield and converted to the hydrochloride salt, mp 203°-205° C.

By treating 1,4-dihydro-1,1-dimethyl-1'-methyl-7-methanesulfonamido)-spiro-(3H)-2-benzopyran-3,4'-piperidine as for 1,4-dihydro-1'-methyl-7-methanesulfonamido-spiro[(3H)-2-benzopyran-3,4'-piperidine in Example 60, Step D, there was obtained an intermediate which when treated as in Example 60, Step E, substituting for the 2-[4-(methanesulfonamido)phenyl]ethyl methane sulfonate used therein, the appropriate electrophiles there were produced the spiropiperidines described in Table XXVI.

TABLE XXVI

CH3SO2NH—[aryl with gem-dimethyl]—O—[spiro piperidine]—N—RM

| Example | RM | salt | mp |
|---|---|---|---|
| 402 | —CH2CH2—[phenyl]—CN | .HCl .0.55 H2O 0.2 ethylacetate | >255° C. |
| 403 | —CH2CH2—[phenyl] | .HCl | 243–45° C. |

EXAMPLE 404

6-Methanesulfonamide-1'-hexyl-4-hydroxy-3,4-dihydrospiro[(2H)-1-benzopyran-2,4'-piperidine]

A stirred solution of 6-methanesulfonamido-1'-hexyl-3,4-dihydrospiro[(2H)-1-benzopyran-2,4'-piperidine]-4-one(0.915 g, 2.32 mmol) in 50 ml of absolute ethanol was chilled to 0° C., blanketed in N2, and was treated with NaBH4 (0.878 g, 23.2 mmol). The resulting solution was allowed to warm 25° C. over 18 h. The clear solution was concentrated in vacuo, and the residue was dissolved in a total of 125 ml of ethyl acetate and was washed with 50 ml of water, followed by washing with 25 ml of saturated aq. NaCl. The organic phase was dried (MgSO4), filtered, and concentrated in vacuo to clear oil to give 0.710 g (88.3%) of the desired product. The hydrochloride salt was generated in ethanol using 1 equivalent of 3.22M ethanolic HCl to give a dense crystalline solid, mp=249°-250° C. (dec.).

Anal. Calcd. For $C_{20}H_{33}ClN_2O_4S$: C, 55.48; H, 7.68; N, 6.47. Found: C, 55.69; H, 7.80; N, 6.41.

EXAMPLE 405

6,7-Dimethoxy-1'-[2-(4-nitrophenyl)ethyl]-2-(4-nitrobenzyl)-spiro[1,2,3,4-tetrahydroisoquinoline-1,4'-piperidine]-4-one A mixture of 6,7-dimethoxy-1'-[2-(4nitrophenyl)ethyl]-spiro[1,2,3,4-tetrahydro-isoquinoline-1,4'-piperidin]-4-one hydrochloride (0.33 g) sodium bicarbonate (0.1 g) and p-nitrobenzylbromide (0.25 g) in ethanol were refluxed for 18 hours. The reaction was concentrated and chromotographed on silica (methylene chloride/methanol, 90:10) to give 60 mg upon concentration and crystallization of the dihydrochloride salt from isopropanol. mp 174°–177° C.

EXAMPLE 406

6,7-Dimethoxy-spiro[1,2,3,4-tetrahydroisoquinoline-1,4'-piperidine]-4-one Dihydrochloride To a solution of 6,7-dimethoxy-1'-methyl-spiro[1,2,3,4-tetrahydroisoquinoline-1,4'-piperidin]-4-one (Helv. Chem. Acta., 58, Fasc. 1, Nr. 8 (1975)) (1.0 g) and N,N,N',N'-tetramethyl-1,8-napthalenediamine (1.9 g) in dichloroethane at 0° C. under nitrogen was added 1-chloroethyl chloroformate (9.5 ml) and the mixture stirred at reflux for 1 hr. The reaction was cooled, passed thru silica and the product eluted with 10% ethyl acetate in methylene chloride. After evaporation, methanol was added and the mixture refluxed for 1 hr. Upon evaporation the foam was crystallized from ethanol/ether to give 0.6 g of the title compound as dihydrochloride salt.

$^1$N NMR (300 mHz, DMSO) δ:11.2 (Broad s,2H), 9.2 (Broad s,2H), 7.4(s,1H), 4.5(s,2H), 3.9(s,3H), 3.8(S,3H) 3.6(m,2H), 3.3(m,2H), 2.3(m,4H).

EXAMPLE 407

6,7-Dimethoxy-1'-[2-(4-methanesulfonamidophenyl)ethyl]-2-(4-nitrobenzyl)-spiro[1,2,3,4-tetrahydroisoquinoline-1,4'-piperidine]-4-one Dihydrochloride A mixture of 6,7-dimethoxy-1'-(4-nitrophenethyl)-spiro[1,2,3,4-tetrahydroquinoline-1,4'-piperidin]-4-one (0.2 g), 2-(4-methanesulfonamidophenyl)ethyl methane sulfonate (0.185 g), and sodium bicarbonate (0.2 g) was refluxed for 24 hrs. The reaction was concentrated to an oil and chromatographed on silica using methylene chloride/methanol as eluent. Concentration and crystallization from isopropyl alcohol by addition of isopropyl alcohol saturated with anhydrous HCl gave 6,7-dimethoxy-1'-[2-(4-methanesulfonamidophenyl)ethyl]-2-(4-nitrobenzyl)-spiro[1,2,3,4-tetrahydroisoquinoline-1,4'-piperidine]-4-one dihydrochloride (0.130 g); mp 240°–242° C.

Employing the procedure substantially as described in Example 407 using the appropriate mesylate, there was produced the isoquinolines described in Table XXVII.

TABLE XXVII

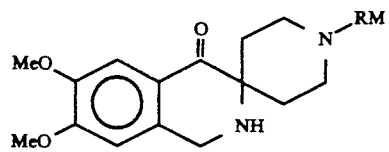

| Example | RM | salt | |
|---|---|---|---|
| 408 | —CH$_2$CH$_2$-(2-pyridyl) | .3 HCl .H$_2$O | Calcd: C, 51.92; H, 6.34; N, 8.26. Found: C, 51.84; H, 6.60; N, 8.11. |
| 409 | —CH$_2$CH$_2$-(4-nitrophenyl) | .EtOH | m.p. = 153–154° C. |

EXAMPLE 410

6-7-Dimethoxy-1'-[2-(4-nitrophenyl)ethyl]-2-(4-nitrobenzyl)-spiro[1,2,3,4-tetrahydroisoquinoline-1,4'-piperidine]-4-one Dihydrochloride To a solution of 6,7-dimethoxy-1'-[2-(4-nitrophenyl)ethyl]-spiro[1,2,3,4-tetrahydroquaoline-1,4'-piperidin]-4-one was added NaBH$_4$ (0.284 g) in two portions. The mixture was stirred for 15 min 10° C., and quenched into an ice/water mixture. The reaction was concentrated to remove methanol and extracted with methylene chloride (2×50 ml). The methylene chloride extracts were dried over sodium sulfate and concentrated to an oil. The oil was dissolved in isopropyl alcohol and a solution of HCl/isopropyl alcohol added. The resulting slurry was filtered, washed with isopropyl alcohol and dried to yield 0.80 g of the title compound. MP 194°–196° C. (Dec)

Calc'd: C, 55.20: H, 6.24; N, 8.40. Found: C, 54.59; H, 6.35; N, 8.20.

EXAMPLE 411

6-7-Dimethoxy-1'-[2-(4-nitrophenyl)ethyl]-spiro[3,4-dihydroisoquinoline-3,4'-piperidine] Dihydrochloride A mixture of 6,7-dimethoxy-1'-[2-(4-nitrophenyl)ethyl]-spiro[1,2,3,4-tetrahydroisoquioline-3,4'-piperidin]-4-ol dihydrochloride (0.4 g) in polyphosphoric acid (20 g) was maintained at 100° C. for 6 hrs. The reaction mixture was cooled to 40° C. and quenched into an ice/water mixture. The pH was adjusted to 10 with 40% NaOH and extracted with CH$_2$Cl$_2$ (2×50 ml). The methylene chloride extracts were dried over Na$_2$SO$_4$ and concentrated into an oil. The oil was chromatagraphed on silica using methylene chloride/methanol (98:2), and the product concentrated to an oil and the dihydrochloride salt was crystallized from isopropanol by addition of isopropanol/HCL. The slurry was diluted with diethyl ether, filtered and dried to give 0.170 g of the title compound. MP 237°–230° C. (Dec).

EXAMPLE 412

6,7-Dimethoxy-1'-[2-(4-nitrophenyl)ethyl]-spiro[1,2,3,4-tetrahydroisoquinoline-3,4'-piperidine]Dihydrochloride To a solution of 6,7-dimethoxy-1'-[2-(4-nitrophenyl)ethyl]-spiro[3,4-dihydroisoquinoline-3,4'-piperidine]-dihydrochloride (100 mg) in methanol (6 ml) at 0° C. was added NaBH$_4$ (23.8 mg). The reaction was stirred for 15 min. The aqueous solution was extracted with methylene chloride (2×50 ml). The methylene chloride layers were dried over Na$_2$SO$_4$, concentrated to an oil and redissolved in ethanol. Addition of HCL/diethyl ether gave a solid which was filtered, and dried to yield 0.082 g of the title compound. MP 247°-250° C. (Dec).

EXAMPLE 413

N-Benzyl-2-methyl-spiro-3,4-dihydroquinol-1-one[3,4]-piperidine

To sulfuric acid (50 ml) at 0° C. was slowly added a solution of 1-benzyl-4-hydroxy-4-[2-(methylcarbamoyl)benzyl]piperidine (*J. Med. Chem.*, 24, 194–198 (1981); *J. Am. Chem. Soc.*, 107, 2323 (1985)) (11.5 g) in dichloroethane. The reaction was stirred at 45° C. for 5 hours, cooled and quenched into ice water. Diethyl ether (200 ml) was added and the pH was adjusted to 10 with 40% NaOH. The aqueous phase was extracted with diethyl ether (200 ml) and the extracts were concentrated to an oil. The oil was chromatographed on silica using ethyl acetate as an eluent to give after concentration 4.5 g of the title compound.

$^1$H NMR (300 MHz, CDCl$_3$) 8.05 (d, 1H), 7.3 (m, 7H), 7.1 (d, 1H) 3.58 (S, 2H), 3.17 (S, 3H), 2.9 (S, 2H) 2.7 (m, 2H), 2.45 (d of t, 2H), 1.8 (M, 4H).

N-Benzyl-2-methylspiro-3,4-dihydroquinolin-1-one-[3,4']piperidine was treated in a manner similar to the conditions in Step D and Step E of Example 60 to provide the compounds described in Table XXVIII below.

TABLE XXVIII

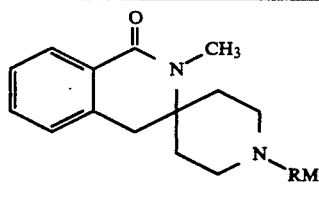

| Example | RM | salt | mp (°C.) |
|---|---|---|---|
| 414 | —(CH$_2$)$_2$—C$_6$H$_4$—NHSO$_2$CH$_3$ | .HCl .2.8 H$_2$O .0.15 IPA | 177–179 |
| 415 | —(CH$_2$)$_2$-pyridyl | .HCl | 187–188 |

EXAMPLE 416

3,4-Dihydro-1'-(1-hexyl)-6-methanesulfonamido-spiro[(2H)-1-benzopyran-2,4'-piperidine]-4-N-acetamide Hydrochloride To a solution of (3,4-dihydro-1'-(1-hexyl)-6-methanesulfonamido-spiro[(2H)-1-benzopyran-2,4'-piperidine]-4-ol (0.8 g) in acetonitrile (16 ml) at −15° C. and under argon was added sulfuric acid (0.6 ml). The reaction was aged at −15° C. for ¼ hour and allowed to warm to 25° C. over 1 hour. The solution was quenched into ice/water (50 ml), concentrated to remove acetonitrile and 1N NaOH was added to adjust pH to 9.0. The product was extracted into methylene chloride, dried over sodium sulfate, concentrated and crystallized from ethanol as the hydrochloride salt to yield 0.65 g of the title compound. mp >300° C. (dec).

EXAMPLE 417

3,4-Dihydro-1'-(1-hexyl)-6-methanesulfonamido-spiro[(2H)-1-benzopyran-2,4'-piperidine]-4-N-ethylamine Dihydrochloride To a solution of 3,4-dihydro-1'-(1-hexyl)-6-methanesulfonamido-spiro[(2H)-1-benzopyran-2,4'-piperidine]-4-N-acetamide (0.20 g) in tetrahydrofuran at 0° C. under argon was added a 1.0M solution of lithium aluminum hydride in THF (1.0 ml). The reaction was warmed to 50° C. for 3 hours and then quenched by addition of ice/water (20 ml). The reaction was diluted with methylene chloride (50 ml), filtered and the organic layer removed. The organic layer was washed with brine (20 ml), dried over sodium sulfate and concentrated to an oil. The oil was chromotographed on silica (methylene chloride/methanol/ammonium hydroxide 90/10/2) to give 130 mg foam upon concentration. The foam was crystallized from ethanol as its dihydrochloride salt to give the title compound. mp 220°-222° C.

EXAMPLE 418

3,4-Dihydro-1'-[(6-cyano-1,2,3,4-tetrahydronaphthalene)-2-yl]-6-methanesulfonamido-spiro[(2H)-1-benzopyran-2,4'-piperidine]-4-N-acetamide Hydrochloride The title compound was prepared in a manner similar to that for the preparation of 3,4-dihydro-1'-hexyl)-6-methanesulfonamido-spiro-[(2H)-1-benzopyran-2,4'-piperidine]-4-N-acetamide hydrochloride by substituting the appropriate alcohol prepared in Example 479 for the starting alcohol in the preparation of Example 416 to give the title compound as the hydrochloride, mp 317° C. (dec.).

EXAMPLE 419

3,4-Dihydro-1'-(benzofurazan-5-methyl)-6-methanesulfonamido-spiro[(2H)-1-benzopyran-2,4'-piperidine]-4-one hydrochloride 3,4-Dihydro-6-methanesulfonamido-spiro[(2H)-1-benzo-pyran-2,4'-piperidine]-4-one hydrochloride was alkylated with 5-(methanesulfonyloxymethyl)benzofurazan according to the method described in Example 86, Step B to give the hydrochloride as a white solid, m.p. >285° C.

Anal. Calc'd. for C$_{21}$H$_{23}$ClN$_4$O$_5$S.0.33H$_2$O: C, 52.01; H, 4.92; N, 11.55. Found: C, 52.09; H, 4.94; N, 11.35.

EXAMPLE 420

Preparation of Alcohols (±)-1-Acetyl-2,3-dihydro-α-methyl-1H-indole-5-methanol 1-Acetyl-2,3-dihydro-1H-indole (16.1 g, 0.1 mol) in 1,2-dichloroethane (60 ml) was added dropwise to refluxing mixture of acetyl chloride (21.33 ml, 23.55 g, 0.3 mol) and aluminum chloride (40.0 g, 0.3 mol) in 1,2-dichloroethane (40 ml). The mixture was heated under reflux for 2 hours, cooled and poured onto crushed ice (1 Kg). The mixture was extracted with dichloromethane (3×500 ml) and the combined organic fractions were dried ($Na_2SO_4$) and evaporated under reduced pressure. Ethanol (400 ml) was added and the mixture was cooled in a water bath. Sodium borohydride (7.57 g, 0.2 mol) was added and the mixture was stirred for 1 hour. Water (100 ml) was added and the ethanol was evaporated under reduced pressure. Water (500 ml) was added and the mixture was extracted with dichloromethane (3×500 ml) and the combined organic fractions were dried ($Na_2SO_4$) and evaporated under reduced pressure. The residue was recrystallized from ethyl acetate to give the alcohol as an off-white solid (18.43 g, 90%).

$^1$H NMR ($CDCl_3$): δ8.14 (1H, d, J=8.2 Hz), 7.23 (1H, s), 7.16 (1H, d, J=8.2 Hz), 4.86 (1H, br q, J=6.4 Hz), 4.06 (2H, t, J 8.4 Hz), 3.19 (2H, t, J=8.4 Hz), 2.22 (3H, s), 1.9 (1H, br s), 1.48 (3H, d, J=6.4 Hz).

1-Acetyl-2,3-dihydro-5-ethenyl-1H-indole

1-Acetyl-2,3-dihydro-α-methyl-1H-indole-5-methanol (10.25 g, 50 mmol) and p-toluenesulfonic acid (monohydrate, 190 mg, 1 mmol) in toluene (250 ml) were heated under reflux with azeotropic removal of water for 20 min. The mixture was cooled, diluted with ethyl acetate (1000 ml), washed with aqueous sodium hydrogen carbonate (saturated, 500 ml) and brine (400 ml), dried ($Na_2SO_4$) and evaporated under reduced pressure. The residue was purified by flash column chromatography on silica gel, eluting with ethyl acetate, to give the indole as a white solid (6.55 g, 70%).

$^1$H NMR ($CDCl_3$): δ8.14 (1H, d, J=8.3 Hz), 7.24 (2H, m), 6.66 (1H, dd, J=17.6, 11.0 Hz), 5.65 (1H, d, J 17.6 Hz), 5.15 (1H, d, J=11.0 Hz), 4.66 (2H, t, J=8.4 Hz), 3.19 (2H, t, J=8.4 Hz), 2.22 (3H, s).

1-Acetyl-2,3-dihydro-1H-indole-5-ethanol

Borane-tetrahydrofuran complex (1.0M in THF, 20 ml, 20 mmol) was added dropwise to an ice cooled solution of 1-acetyl-2,3-dihydro-5-ethenyl-1H-indole (5.61 g, 30 mmol) in THF (150 ml). The mixture was stirred at 0° C. for 30 minute then at room temperature for 1 hr. Trimethylamine N-oxide dihydrate (8.88 g, 80 mmol) was added and the mixture was heated under reflux for 3 hr, cooled and poured into water (400 ml) and aqueous HCl (6N, 10 ml). The mixture was extracted with dichloromethane (3×400 ml) and the combined organic fractions were dried ($Na_2SO_4$) and evaporated under reduced pressure. The residue was purified by flash column chromatography on silica gel, eluting with ethyl acetate, to give the alcohol as a white solid (3.41 g, 55%).

$^1$H NMR ($CDCl_3$): δ8.13 (1H, d, J=8.7 Hz), 7.06 (2H, m), 4.04 (2H, t, J=8.4 Hz), 3.83 (2H, t, J=6.5 Hz), 3.18 (2H, t, J=8.4 Hz), 2.82 (2H, t, J=6.5 Hz), 2.21 (3H, s), 1.61 (1H, br s).

EXAMPLE 421

Preparation of Methanesulfonates

The following methanesulfonates were synthesized from the corresponding alcohols by the method described in Example 89, Step C:

[2-(Methanesulfonyloxy)ethyl]cyclohexane; $^1$H NMR ($CDCl_3$): δ4.27 (2H, t, J=6.8 Hz), 3.01 (3H, s), and 1.8–0.8 (13H, m).

2-[2-(Methanesulfonyloxy)ethyl]thiophene; $^1$H NMR ($CDCl_3$): δ7.20 (1H, d, J=5.1 Hz), 6.97 (1H, dd, J=5.1, 3.4 Hz), 6.92 (1H, d, J=3.4 Hz), 4.42 (2H, t, J=6.7 Hz), 3.28 (2H, t, J=6.7 Hz), 2.93 (3H, s).

3-[2-(Methanesulfonyloxy)ethyl]thiophene; $^1$H NMR ($CDCl_3$): δ7.31 (1H, dd, J=4.9, 3.0 Hz), 7.10 (1H, br s), 6.99 (1H, dd, J=4.9, 1.2 Hz), 4.42 (2H, t, J=6.7 Hz), 3.10 (2H, t, J=6.7 Hz), 2.89 (3H, s).

1-[2-(Methanesulfonyloxy)ethyl]-2-imidazolidinone; $^1$H NMR ($CDCl_3$): δ4.8 (1H, br s), 4.36 (2H, t, J=5.1 Hz), 3.59–3.45 (6H, m), 3.05 (3H, s).

2-[2-(Methanesulfonyloxy)ethyl]furan; $^1$H NMR ($CDCl_3$): δ7.35 (1H, d, J=1.8 Hz), 6.32 (1H, dd, J=3.0, 1.8 Hz), 6.16 (1H, d, J=3.0 Hz), 4.46 (2H, t, J=6.6 Hz), 3.10 (2H, t, J=6.6 Hz), 2.92 (3H, s).

3-[2-(Methanesulfonyloxy)ethyl]furan; $^1$H NMR ($CDCl_3$): δ7.39 (1H, s), 7.33 (1H, s), 6.33 (1H, s), 4.32 (2H, t, J=6.7 Hz), 2.96 (3H, s), 2.90 (2H, t, J=6.7 Hz).

2,3-Dihydro-5-[2-(methanesulfonyloxy)ethyl]benzonfuran; $^1$H NMR ($CDCl_3$): δ7.06 (1H, s), 6.95 (1H, d, J=8.1 Hz), 6.72 (1H, d, J 8.1 Hz), 4.56 (2H, t, J=8.7 Hz), 4.36 (2H, t, J=7.0 Hz), 3.19 (2H, t, J=8.7 Hz), 2.98 (2H, t, J=7.0 Hz), 2.88 (3H, s).

1-Acetyl-2,3-dihydro-5-[2-(methanesulfonyloxy)ethyl]indole; $^1$H NMR ($CDCl_3$): δ8.14 (1H, d, J=8.8 Hz), 7.06 (2H, m), 4.38 (2H, t, J 6.8 Hz), 4.06 (2H, t, J=8.5 Hz), 3.19 (2H, t, J=8.5 Hz), 3.00 (2H, t, J=6.8 Hz), 2.88 (3H, s), 2.22 (3H, s).

4-[2-(Methanesulfonyloxy)ethyl]benzonitrile; $^1$H NMR ($CDCl_3$): δ7.64 (2H, d, J=8.3 Hz), 7.37 (2H, d, J=8.3 Hz), 4.45 (2H, t, J=6.6 Hz), 3.13 (2H, t, J=6.6 Hz), 2.92 (3H, s).

EXAMPLE 422

Preparation of Alcohols

1-Methanesulfonyloxy-6-methylheptan-6-ol

Methylmagnesium chloride (2.8M in THF, 21 ml, 60 mmol) was added dropwise to an ice-cooled solution of 2-oxepanone (2.22 ml, 2.28 g, 20 mmol) in THF (20 ml). The mixture was stirred for 1 hour, then water (100 ml) was added dropwise. The pH was adjusted to 7 with aqueous HCl (3N) and the mixture was extracted with ethyl acetate (3×100 ml). The combined organic fractions were dried ($Na_2SO_4$) and evaporated under reduced pressure. Dichloromethane (20 ml) and pyridine (3.24 ml, 3.16 g, 40 mmol) were added and the mixture was cooled in ice. Methanesulfonyl chloride (1.55 ml, 2.29 g, 20 mmol) was added dropwise and the mixture was stirred at room temperature for 3 hours. Dichloromethane (50 ml) was added and the mixture was washed with aqueous HCl (2M, 50 ml) and aqueous sodium hydrogen carbonate (saturated, 50 ml), dried ($Na_2SO_4$) and evaporated under reduced pressure to give the alcohol as a pale yellow oil (4.38 g, 98%).

$^1$H NMR ($CDCl_3$): δ4.24 (2H, t, J 6.6 Hz), 3.01 (3H, s), 1.85–1.40 (9H, m), 1.22 (6H, s).

(+/−)-1-Methanesulfonyloxyheptan-6-ol (±)-Heptan-1,6-diol (1.06 g, 8 mmol) and pyridine (1.36 ml, 1.33 g, 16.8 mmol) were dissolved in dichloromethane (20 ml) and the mixture was cooled in ice. Methanesulfonyl chloride (0.65 ml, 0.96 g, 8.4 mmol) was added dropwise and the mixture was stirred at room temperature for 18 hours. Dichloromethane (50 ml) was added and the mixture was washed with aqueous HCl (1M, 50 ml) and brine (30 ml), dried (Na$_2$SO$_4$) and evaporated under reduced pressure. The residue was purified by flash column chromatography on silica gel, eluting with EtOAc/20% hexane, to give the alcohol as an oil (1.01 g, 60%).

$^1$H NMR (CDCl$_3$): δ4.24 (2H, t, J 6.6 Hz), 3.80 (1H, m), 3.01 (3H, s), 1.77–1.22 (9H, m), 1.20 (3H, d, J=1.1 Hz).

EXAMPLE 423

Preparation of 1-Substituted-4-Piperidinones

The following compounds were synthesized by alkylation of 1,4-dioxa-8-azaspiro[4.5]decane with the appropriate methanesulfonate or bromide according to the method described for the synthesis of 8-[2-(nitrophenyl)ethyl]-1,4-dioxa-8-azaspiro [4.5] decane (Example 339 [C1], Step 3), followed by ketal hydrolysis according to the method described for the synthesis of 1-[2-(benzofurazan-5-yl)ethyl]-4-piperidinone (Example 339 [C1], Step 7).

1-[2-(Thiophen-2-yl)ethyl]-4-piperidinone; $^1$H NMR (CDCl$_3$): δ7.15 (1H, d, J=5.1 Hz), 6.94 (1H, dd, J=5.1, 3.4 Hz), 6.85 (1H, d, J=3.4 Hz), 3.06 (2H, t, J=7.5 Hz), 2.83 (6H, m), 2.49 (4H, t, J=6.1 Hz).

1-[2-(Thiophen-3-yl)ethyl]-4-piperidinone; $^1$H NMR (CDCl$_3$): δ7.27 (1H, m), 7.02 (1H, br s), 6.98 (1H, d, J=4.9 Hz), 2.91–2.72 (8H, m), 2.48 (4H, t, J 6.1 Hz).

1-[2-(4-Cyanophenyl)ethyl]-4-piperidinone; $^1$H NMR (CDCl$_3$): δ7.60 (2H, d, J=8.2 Hz), 7.34 (2H, d, J=8.2 Hz), 2.92–2.71 (8H, m), 2.47 (4H, t, J=6.2 Hz).

1-n-Hexyl-4-piperidinone; $^1$H NMR (CDCl$_3$): δ2.74 (4H, t, J=6.0 Hz), 2.46 (6H, m), 1.70–1.31 (8H, m), 0.90 (3H, t, J=6.6 Hz).

1-n-Heptyl-4-piperidinone; $^1$H NMR (CDCl$_3$): δ2.75 (4H, t, J=6.1 Hz), 2.47 (6H, m), 1.55–1.26 (10H, m), 0.89 (3H, t, J=6.7 Hz).

8-[2-Oxo-2-(4-cyanophenyl)ethyl]-1,4-dioxa-8-azaspiro [4.5]decane

Sulfuryl chloride (3.53 ml, 5.94 g, 44 mmol) was added dropwise to a solution of 4-acetylbenzonitrile (5.81 g, 40 mmol) in chloroform (40 ml). The mixture was stirred for 24 hours, diluted with chloroform (40 ml), washed with water (40 ml) and aqueous sodium hydrogen carbonate (saturated, 40 ml), dried (Na$_2$SO$_4$) and evaporated under reduced pressure. The residue was dissolved in acetonitrile (40 ml), potassium carbonate (11.06 g, 80 mmol) and 1,4 dioxa-8-azaspiro[4.5]decane (5.13 ml, 5.73 g, 40 mmol) were added. The mixture was stirred for 2.5 hours then aqueous HCl (2N, 120 ml) was added. The mixture was washed with ethyl acetate (2×50 ml), aqueous sodium hydroxide (20%, 80 ml) was added and the mixture was extracted with ethyl acetate (3×100 ml). The combined organic extracts were dried (Na$_2$SO$_4$) and evaporated under reduced pressure. The residue was purified by flash column chromatography on silica gel, eluting with CH$_2$Cl$_2$/MeOH/NH$_3$(Aq.); 98:2:0.2 to give the spirodecane as a yellow solid (3.24 g, 28%).

$^1$H NMR (CDCl$_3$): δ8.14 (2H, d, J=8.3 Hz), 7.76 (2H, d, J=8.3 Hz), 3.96 (4H, s), 3.80 (2H, s), 2.67 (4H, t, J=5.6 Hz), 1.79 (4H, t, J=5.6 Hz).

1-[2-Oxo-2-(4-cyanophenyl)ethyl]-4-piperidinone

8-[2-Oxo-2-(4-cyanophenyl)ethyl]-1,4-dioxa8-azaspiro[4.5]decane (300 mg, 1.05 mmol) was dissolved in aqueous HCl (1N, 10 ml) and the mixture was heated under reflux for 30 minutes. The mixture was cooled, aqueous sodium hydroxide (20%, 5 ml) was added and the mixture was extracted with ethyl acetate (3×10 ml). The combined organic fractions were dried (Na$_2$SO$_4$) and evaporated under reduced pressure to give the piperidinone as a yellow solid (157 mg, 62%).

$^1$H NMR (CDCl$_3$): δ8.12 (2H, d, J=8.3 Hz), 7.80 (2H, d, J=8.3 Hz), 3.96 (2H, s), 2.93 (4H, t, J=6.1 Hz), 2.53 (4H, t, J=6.1 Hz).

(±)-1-[2-Hydroxy-2-(4-cyanophenyl)ethyl]-4-piperidinone

Sodium borohydride (76 mg, 2 mmol) was added to an ice cooled solution of 8-[2-oxo-2-(4-cyanophenyl)ethyl]-1,4-dioxa-8-azaspiro[4.5]decane (300 mg, 1.05 mmol) in ethanol (5 ml). The mixture was stirred at room temperature for 16 hours and the solvent was evaporated under reduced pressure. Water (5 ml) and aqueous sodium hydrogen carbonate (saturated, 10 ml) were added and the mixture was extracted with dichloromethane (3×10 ml). The combined organic fractions were dried (Na$_2$SO$_4$) and evaporated under reduced pressure. Aqueous HCl (1N, 10 ml) was added and the mixture was heated under reflux for 30 minutes. The mixture was cooled, aqueous sodium hydroxide (20%, 5 ml) was added and the mixture was extracted with ethyl acetate (3×10 ml). The combined organic fractions were dried (Na$_2$SO$_4$) and evaporated under reduced pressure to give the piperidinone as a yellow gum (153 mg, 60%).

$^1$H NMR (CDCl$_3$): δ7.66 (2H, d, J=8.3 Hz), 7.52 (2H, d, J=8.3 Hz), 4.83 (1H, dd, J=10.5, 3.5 Hz), 3.97 (1H, br s), 3.06 (2H, m), 2.81 (2H, m), 2.70 (1H, dd J=12.6, 3.5 Hz), 2.54 (5H, t, J=6.1 Hz).

EXAMPLE 424

3,4-Dihydro-1′-[2-(2,3-dihydro-1H-indol-5-yl)ethyl]6-methanesulfonamido-spiro[(2H)-benzopyran-2,4′-piperidine]-4-one dihydrochloride 1′-[2-(1-Acetyl-2,3-dihydro-1H-indol-5-yl)ethyl]-3,4-dihydro-6-methanesulfonamido-spiro[(2H)-benzopyran-2,4′-piperidine]-4-one (1.96 g, 3.9 mmol) was dissolved in ethanol (40 ml) and aqueous HCl (6N, 40 ml). The mixture was heated under reflux for 2 hours, cooled and the ethanol was evaporated under reduced pressure. Water (100 ml) was added and the pH was adjusted to 8 with aqueous sodium hydroxide (20%). The mixture was extracted with dichloromethane and the combined organic fractions were dried (Na$_2$SO$_4$) and evaporated under reduced pressure to give the crude pyranone as a tan solid (1.85 g). A sample (200 mg) was purified by flash column chromatography on silica gel, eluting with CH$_2$Cl$_2$/MeOH/NH$_3$(Aq.) (96:4:0.4) to give a pale yellow foam which was dissolved in ethanol (5 ml) and treated with ethanolic HCl (6N, 0.5 ml). The mixture was stirred for 1 hour, cooled and the precipitate was collected and dried in vacuo to give the dihydrochloride as a white solid (157 mg, 70%), m.p. 250°-252° C.

Anal. Calc'd for $C_{24}H_{31}Cl_2N_3O_4S.0.33H_2O$: C, 53.93; H, 5.97; N, 7.86. Found: C, 53.93; H, 5.77; N, 7.92.

EXAMPLE 425

3,4-Dihydro-1'-[2-(2,3-dihydro-1-methanesulfonamido-1H-indol-5-yl)ethyl]-6-methanesulfonamido-spiro[(2H-)benzopyran-2,4'-piperidine]-4-one hydrochloride Methanesulfonyl chloride (55 mg, 0.48 mmol) was added to a suspension of 3,4-dihydro-1'-[2-(2,3-dihydro-1H-indol-5-yl)ethyl]-6-methanesulfonamidospiro[(2H)-benzopyran-2,4'-piperidine]-4-one (crude, 84% pure, 217 mg, 0.4 mmol) in pyridine (5 ml). The mixture was stirred for 22 hours, then the solvent was evaporated under reduced pressure. Aqueous sodium hydrogen carbonate (saturated, 20 ml) and water (5 ml) were added and the mixture was extracted with dichloromethane (3×25 ml). The combined organic fractions were dried ($Na_2SO_4$) and evaporated under reduced pressure. The residue was purified by flash column chromatography on silica gel, eluting with $CH_2Cl_2$/MeOH/$NH_3$(Aq.) (96:4:0.4) to give a yellow glass which was suspended in ethanol (5 ml) and treated with ethanolic HCl (6N, 0.5 ml). The mixture was stirred for 1 hr, cooled and the precipitate was collected and dried in vacuo to give the hydrochloride as a white solid (91 mg, 40%), m.p. >285° C.

Anal. Calc'd. for $C_{25}H_{32}ClN_3O_6S_2$: C, 52.67; H, 5.66; N, 7.37. Found: C, 53.00; H, 5.71; N, 7.30.

EXAMPLE 426

3,4-Dihydro-1'-[2-(1H-indol-5-yl)ethyl]-6-methanesulfanomido-spiro[(2H)-benzopyran-2,4'-piperidine]4-one hydrochloride DMSO (0.32 g, 0.36 g, 4.6 mmol) in dichloromethane (5 ml) was added dropwise to a cooled (−60° C.) solution of oxalyl chloride (0.20 ml, 0.29 g, 2.3 mmol) in dichloromethane (5 ml). The mixture was stirred at −60° C. for 3 minutes, then 3,4-dihydro-1'-[2-(2,3-dihydro-1H-indol-5-yl)ethyl]-6-methanesulfonamido-spiro[(2H)-benzopyran-2,4'-piperidine]-4-one (crude, 84% pure, 1.03 g, 1.9 mmol) in DMSO (5 ml) was added. The mixture was stirred at −60° C. for 10 minutes, then triethylamine (5 ml) was added and the mixture was allowed to warm to room temperture. The mixture was poured into aqueous sodium hydrogen carbonate (saturated, 100 ml) and the mixture was extracted with dichloromethane (3×100 ml). The combined organic fractions were dried ($Na_2SO_4$) and evaporated under reduced pressure. The residue was purified by repeated flash column chromatography on silica gel, eluting with $CH_2Cl_2$/MeOH/$NH_3$(Aq.) (96:4:0.4) to give a blue foam which was dissolved in ethanol (0.5 ml). The mixture was stirred for 1 hour, cooled and the precipitate was collected, washed with hot ethanol and dried in vacuo to give the hydrochloride as a white solid (232 mg, 25%), m.p. 260°-262° C. (dec.).

Anal. Calc'd. for $C_{24}H_{28}ClN_3O_4S.0.75H_2O$: C, 57.25; H, 5.90; N, 8.34. Found: C, 57.34; H, 5.68; N, 8.30.

EXAMPLE 427

3,4-Dihydro-1'-[2-(benzofurazan-5-yl)ethyl]-6-methanesulfonamido-4-(methoxyimino)-spiro[(2H)-1-benzopyran2,4'-piperidine] hydrochloride 3,4-Dihydro-1'-[2-(benzofurazan-5-yl)ethyl]6-methanesulfonamido-spiro[(2H)-1-benzopyran-2,4'-piperidine]-4-one [prepared as described in Example 94, Step B] 0.137 g, 0.3 mmol) was dissolved in DMF (2 ml) and pyridine (1 ml) and methoxylamine hydrochloride (28 mg, 0.33 mmol) were added. The mixture was stirred for 17 hours, then further methoxylamine hydrochloride (112 mg) was added and the mixture was stirred at 50° C. for 3 hours. Further methoxylamine hydrochloride (100 mg) was added and the mixture was stirred at 50° C. for 3 hours. The mixture was cooled, the solvent was evaporated under reduced pressure, aqueous sodium hydrogen carbonate (Saturated, 20 ml) was added and the mixture was extracted with dichloromethane (3×20 ml). The combined organic fractions were dried ($Na_2SO_4$) and evaporated under reduced pressure. The residue was purified by flash column chromatography on silica gel, eluting with $CH_2Cl_2$/MeOH/$NH_3$(Aq.) (98:2:0.2 then 94:6:0.6) to give the isomeric oximes as colorless gums; higher running fraction: 100 mg, 68%; lower running fraction: 46 mg, 32%. The higher running fraction was dissolved in ethyl acetate and ethanolic HCl was added. The precipitate was collected and dried in vacuo to give the hydrochloride as a white solid (83 mg), m.p. 248°-250° C.

Anal. Calc'd. for $C_{23}H_{28}ClN_5O_5S.0.4\ H_2O$: C, 52.20; H, 5.49; N, 13.23. Found: C, 52.13; H, 5.42; N, 12.99.

EXAMPLE 428

3,4-Dihydro-6-methanesulfonamido-4-(hydroxyimino)-1'-(2-phenylethyl)-spiro[(2H)-1benzopyran-2,4'-piperidine]

In the manner of Example 427, 3,4-dihydro-6-methane-sulfonamido-1'-(2-phenylethyl)-spiro [(2H)-benzopyran-2,4'-piperidine]-4-one was treated with hydroxylamine hydrochloride to give, after chromatography, the piperidine as a solid, m.p. 95°-99° C.

Anal. Calc'd for $C_{22}H_{27}N_3O_4S.0.6CHCl_3$: C, 54.16; H, 5.55; N, 8.39. Found: C, 54.37; H, 5.49; N, 8.48.

EXAMPLE 429

(±)-3,4-Dihydro-1'-[2-(benzofurazan-5-yl)ethyl]-6-methanesulfonamido-spiro[(2H)-1-benzopyran-2,4'-piperidine]-4-ol hydrochloride Sodium borohydride (7.5 mg, 0.2 mmol) was added to a stirred suspension of 3,4-dihydro-1'-[2-(benzofurazan-5-yl)ethyl]-6-methanesulfonamidospiro[(2H)-1-benzopyran-2,4'-piperidine]-4-one [prepared as described in Example 94, Step B](45.6 mg, 0.1 mmol) in ethanol (2 ml). The mixture was stirred for 16 hours, then poured into aqueous sodium hydrogen carbonate (saturated, 10 ml) and extracted with dichloromethane (3×10 ml). The combined organic fractions were dried ($Na_2SO_4$) and evaporated under reduced pressure to give a pale yellow oil. The residue was dissolved in ethyl acetate (2 ml) and ethanolic HCl (6N, 0.5 ml) was added. The mixture was cooled and the precipitate collected and dried in vacuo to give the hydrochloride as a white solid (32 mg, 65%), m.p. =242°-244° C.

Anal. Calc'd. for $C_{22}H_{27}ClN_4O_5S$: C, 53.38; H, 5.50; N, 11.32. Found: C, 53.05; H, 5.51; N, 11.09.

EXAMPLE 430

1'-[2-(Benzofurazan-5-yl)ethyl]-6-methanesulfonamidospiro[(2H)-1-benzopyran-2,4'-piperidine]hydrochloride Sodium borohydride (23 mg, 0.6 mmol) was added to a stirred suspension of 3,4-dihydro-1'-[2-(benzofurazan- 5-yl)ethyl]-6-methanesulfonamidospiro[(2H)-1-benzo-pyran-2,4'-piperidine]-4-one [prepared as described by Example 94, Step B](137 mg, 0.3 mmol) in ethanol (3 ml). The mixture was stirred for 20 hours, then poured into aqueous sodium hydrogen carbonate (saturated, 20 ml) and extracted with dichloromethane (3×20 ml). The combined organic fractions were dried (Na$_2$SO$_4$) and evaporated under reduced pressure. p-Toluenesulfonic acid (monohydrate, 86 mg, 0.45 mmol) and toluene were added and the mixture was heated under reflux for 30 minutes, cooled and poured into aqueous sodium hydrogen carbonate (saturated, 20 ml). The mixture was extracted with dichloromethane (3×20 ml) and the combined organic fractions were dried (Na$_2$SO$_4$) and evaporated under reduced pressure to give a foam (123 mg, 93%). The residue was dissolved in ethanol (5 ml) and ethanolic HCl (6N, 0.5 ml) was added. The mixture was stirred for 1 hour, cooled and the precipitate collected and dried in vacuo to give the hydrochloride as a white solid (108 mg, 75%), m.p. 271°–273° C. (dec.).

Anal. Calc'd. for C$_{22}$H$_{25}$ClN$_4$O$_4$S.0.25H$_2$O: C, 54.88; H, 5.34; N, 11.64. Found: C, 54.98; H, 5.26; N, 11.73.

EXAMPLE 431

6-Amino-3,4-dihydro-1'-[2-(benzofurazan-5-yl)ethyl]-spiro[(2H)-1-benzopyran-2,4'-piperidine]-4-one 1-[2-(Benzofurazan-5-yl)ethyl]-4-piperidinone (0.98 g, 4 mmol), N-(3-acetyl-4-hydroxyphenyl)-acetamide (0.77 g, 4 mmol) and pyrrolidine (0.33 ml, 0.28 g, 4 mmol) in methanol (20 ml) were heated under reflux for 3 hours, cooled and the solvent was evaporated under reduced pressure. Water (50 ml) and aqueous sodium hydroxide (20%, 10 ml) were added and the mixture was extracted with ethyl acetate (3×50 ml). The combined organic fractions were dried (Na$_2$SO$_4$) and evaporated under reduced pressure to give a yellow solid. Ethanol (40 ml) and aqueous HCl (6N, 40 ml) were added and the mixture was heated under reflux for 2 hours. The mixture was cooled and the ethanol was evaporated under reduced pressure. Water (40 ml) was added and the mixture was washed with ethyl acetate (50 ml). Aqueous sodium hydroxide (20%, 60 ml) was added slowly, with stirring and cooling, and the mixture was extracted with dichloromethane (3×100 ml). The combined organic fractions were dried (Na$_2$SO$_4$) and evaporated under reduced pressure. The residue was triturated with ethyl acetate-hexane (1:1, 20 ml) and the solid was collected and dried in vacuo to give a yellow solid (1.17 g, 77%). A sample was recrystallized from chloroform-hexane to give the pyranone as a yellow solid, m.p. 191°–193° C.

Anal. Calc'd. for C$_{21}$H$_{22}$N$_4$O$_3$.0.75H$_2$O: C, 64.35; H, 6.04; N, 14.29. Found: C, 64.35; H, 5.75; N, 14.29.

EXAMPLE 432

Ethyl [(3,4-dihydro-1'-[2-(benzofurazan-5-yl)-ethyl]-4-oxo-spiro[(2H)-1-benzopyran-2,4'-piperidine]-6-yl)amino]-sulfonyl acetate hydrochloride Ethyl chlorosulfonylacetate (140 mg, 0.75 mmol) in DMF (1 ml) was added dropwise to a stirred solution of 6-amino-3,4-dihydro-1'-[2-(benzofurazan-5-yl)-ethyl]-spiro[(2H)-1-benzopyran-2,4'-piperidine]-4-one (189 mg, 0.5 mmol) and pyridine (40 mg, 3 mmol) in DMF (5 ml). The mixture was stirred for 4 hours, then additional ethyl chlorosulfonylacetate (46 mg, 0.25 mmol) was added. The mixture was stirred for 1 hour, poured into aqueous sodium hydrogen carbonate (saturated, 25 ml) and extracted with dichloromethane (3×25 ml). The combined organic fractions were dried (Na$_2$SO$_4$) and evaporated under reduced pressure. The residue was purified by flash column chromatography on silica gel, eluting with CH$_2$Cl$_2$/MeOH/NH$_3$(Aq.) (97:3:0.3) to give a yellow foam which was dissolved in ethyl acetate (2 ml) and treated with ethanolic HCl (6N, 0.5 ml). The mixture was stirred for 1 hour, cooled and the solid was collected and dried in vacuo to give the hydrochloride as a white solid (171 mg, 61%), m.p. 250°–251° C.

Anal. Calc'd. for C$_{25}$H$_{29}$ClN$_4$O$_7$S: C, 53.14; H, 5.17; N, 9.92. Found: C, 53.00; H, 5.39; N, 9.86.

EXAMPLE 433

[{3,4-Dihydro-1'-[2-(benzofurazan-5-yl)ethyl]-4-oxospiro[(2H)-1-benzopyran-2,4'-piperidine]-6-yl}amino] sulfonyl acetic acid Aqueous lithium hydroxide (1M, 0.55 ml) was added to a stirred suspension of ethyl[{3,4-dihydro-1'-[2-(benzofurazan-5-yl)ethyl]-4-oxo-spiro [(2H)-1-benzopyran-2,4'-piperidine]-6-yl}amino] sulfonyl acetate (264 mg, 0.5 mmol) in methanol-water (1:1, 20 ml) and the mixture was stirred for 2 hours. Further aqueous lithium hydroxide (1M, 1.45 ml) was added and the mixture was stirred for 24 hours. The solvent was evaporated under reduced pressure, water (10 ml) was added and the pH was adjusted to 1.5 with aqueous HCl (3M). The mixture was cooled and the solid was collected and dried in vacuo to give the acid as a white solid (198 mg, 79%), m.p. =187°–189° C.

Anal. Calc'd. for C$_{23}$H$_{24}$N$_4$O$_7$S.0.6 H$_2$O: C, 54.03; H, 4.97; N, 10.96. Found: C, 53.97; H, 4.92; N, 10.83.

EXAMPLE 434

1'-Benzoyl-3,4-dihydro-6-methoxy-spiro[(2H)-1-benzopyran-2,4'-piperidine]-4-one

Pyrrolidine (8.35 ml, 7.11 g, 0.1 mol) was added to a suspension of 2'-hydroxy-5'-methoxyacetophenone (16.62 g, 0.1 mol) in methanol (100 ml). The mixture was stirred for 10 minutes, then 1-benzoyl-4-piperidone (20.32 g, 0.1 mol) was added and the mixture was heated under reflux for 7 hr. The mixture was cooled and the solvent was evaporated under reduced pressure. Water (400 ml) was added and the mixture was extracted with ethyl acetate (3×400 ml). The combined organic fractions were evaporated under reduced pressure and the residue was recrystallized from methanol to give the ketone as a pale yellow solid (29.54 g, 84%).

$^1$H NMR (CDCl$_3$): δ7.41 (5H, s), 7.30 (1H, d, J=3.1 Hz), 7.12 (1H, dd, J=9.0, 3.1 Hz), 6.94 (1H, d, J=9.0 Hz), 4.5 (1H, br s), 3.8 (3H, s), 3.7–3.2 (3H, m), 2.73 (2H, s), 2.3–1.5 (4H, m).

EXAMPLE 435

1'-Benzoyl-3,4-dihydro6-methanesulfonamido-spiro [(2H)-1-benzopyran-2,4'-piperidine]

Sodium borohydride (1.13 g, 30 mmol) was added in portions over 5 minutes to a stirred, ice cooled suspension of 1'-benzoyl-3,4-dihydro-6-methanesulfonamidos-piro[(2H)-1-benzopyran-2,4'-piperidine]-4-one (prepared as described in Example 70, Method 2, Step C) (6.21 g, 15 mmol) in ethanol (150 ml). The mixture was stirred at room temperature for 22 hours, poured into water (150 ml) and the ethanol was evaporated under reduced pressure. The mixture was extracted with dichloromethane (4×150 ml) and the combined organic fractions were dried (Na₂SO₄) and evaporated under reduced pressure to give a white foam (6.61 g). A sample (6.41 g) and p-toluenesulfonic acid (Monohydrate, 100 mg) in toluene (150 ml) were heated under reflux for 1 hr, cooled and diluted with methylene chloride (600 ml). The mixture was washed with aqueous sodium hydrogen carbonate (saturated, 150 ml), dried (Na₂SO₄) and evaporated under reduced pressure. The residue was suspended in ethanol-methanol (1:1, 200 ml), palladium on carbon (5%, 1 g) was added and the mixture was stirred under hydrogen (1 Atm.) for 24 hours. The mixture was filtered through celite, washing with methanol, and the filtrate was evaporated under reduced pressure. The residue was redissolved in dichloromethane, filtered through celite and evaporated under reduced pressure to give the piperidine as a foam (5.44 g, 93%).

$^1$H NMR (CDCl₃): δ7.4 (5H, s), 6.98 (2H, m), 6.83 (1H, d, J 8.4 Hz), 4.5 (1H, br m), 3.6–3.2 (3H, m), 2.96 (3H, s), 2.8 (2H, m), and 2.0–1.5 (7H, m).

EXAMPLE 436

1′-Benzoyl-3,4-dihydro-6-methoxy-spiro[(2H)-1-benzopyran-2,4′-piperidine]

Following the procedures as described in Example 435, 1′-benzoyl-3,4-dihydro-6-methoxy-spiro[(2H)-1-benzopyran-2,4′-piperidine]-4-one was reduced with sodium borohydride, dehydrated with p-toluenesulfonic acid and hydrogenated with palladium on carbon (5%) under hydrogen (50 psi) to give the piperidine as a foam (54%).

$^1$H NMR (CDCl₃): δ7.41 (5H, s), 6.77 (1H, d), 6.69 (1H, dd), 6.61 (1H, d), 4.4 (1H, br s), 3.75 (3H, s), 3.6 (1H, br s), 3.40 (2H, m), 2.78 (2H, m), 1.82 (4H, m), 1.60 (2H, m).

EXAMPLE 437

3,4-Dihydro-6-methanesulfonamido-spiro[(2H)-1-benzopyran-2,4′-piperidine] hydrochloride 1′-Benzoyl-3,4-dihydro-6-methanesulfonamido-spiro[(2H)-1-benzopyran-2,4′-piperidine] (5.44 g, 13.6 mmol) was dissolved in methanol (70 ml) and aqueous HCl (6N, 105 ml) was added. The mixture was heated under reflux for 24 hr, then the volume was reduced to 50 ml by distillation. Ethanol (200 ml) was added and the volume was reduced to 50 ml. Further ethanol (200 ml) was added, the volume was reduced to 100 ml and the mixture was cooled. The precipitate was collected and dried in vacuo to give the hydrochloride as a white solid (3.77 g, 83%). A sample was recrystallized from ethanol to give the hydrochloride as a white solid, m.p.=282°–285° C. (dec.).

$^1$H NMR (DMSO): δ9.35 (1H, s), 9.1 (2H, br s), 6.95 (2H, m), 6.79 (1H, d, J 9.5 Hz), 3.17–2.90 (4H, m), 2.88 (3H, s), 2.72 (2H, m), and 1.84 (6H, m).

Anal. Calc'd. for C₁₄H₂₁ClN₂O₃S: C, 50.52; H, 6.36; N, 8.42. Found: C, 50.69; H, 6.24; N, 8.40.

EXAMPLE 438

3,4-Dihydro-6-methoxy-spiro[(2H)-1-benzopyran-2,4′-piperidine] hydrochloride

1′-Benzoyl-3,4-dihydro-6-methoxy-spiro[(2H)-1-benzopyran-2,4′-piperidine] (5.23 g, 15.5 mmol) was dissolved in methanol (80 ml) and aqueous HCl (6N, 120 ml) was added. The mixture was heated under reflux for 24 hours, then the volume was reduced to 50 ml by distillation. Ethanol (200 ml) was added and the volume was reduced to 50 ml. Further ethanol (200 ml) was added, the volume was reduced to 100 ml and the mixture was cooled. The mixture was filtered and evaporated under reduced pressure and the residue was crystallized from ethanol-ether to give, in two crops, the hydrochloride as a white solid (1.29 g, 31%), m.p.=240°–242° C.

Anal. Calc'd. for C₁₄H₂₀ClNO₂·0.3H₂O: C, 61.10; H, 7.55; N, 5.09. Found: C 61.04; H 7.22; N 4.91.

The compounds of Table XXIX were prepared from 3,4-dihydro-6-methanesulfonamido-spiro[(2H)-1-benzopyran-2,4′-piperidine] hydrochloride by the method described in Example 92, Step B, using the appropriate mesylate or bromide as indicated.

TABLE XXIX

| Example | Ar²–(R³)ₛ | LG | salt | mp (°C.) |
|---|---|---|---|---|
| 439 | phenyl | Br | .HCl | 269–271 (dec) .0.5 EtOH |
| 440 | 4-NO₂-phenyl | Br | .HCl | 264–266 (dec) |
| 441 | 4-CN-phenyl | MeSO₃ | .HCl .0.5 EtOH | 269–271 (dec) |
| 442 | 3,4-difluorophenyl | MeSO₃ | .HCl | 242–244 |
| 443 | 2,3-dihydrobenzofuran-5-yl | MeSO₃ | .HCl | 273–275 (dec) |
| 444 | benzoxadiazolyl | Br | .HCl | 267–269 (dec) |

TABLE XXIX-continued

[Structure: CH₃SO₂NH-aryl-chroman-spiro-piperidine NH·HCl + LG-CH₂CH₂-Ar²-(R³)ₛ → product]

| Example | Ar²—(R³)ₛ | LG | salt | mp (°C.) |
|---|---|---|---|---|
| 445 | 2-thienyl | MeSO₃ | .HCl | 272–274 (dec) |
| 446 | 3-thienyl | MeSO₃ | .HCl | 281–283 (dec) |
| 447 | —(CH₂)₃CH₃ | Br | .HCl | 230–232 |
| 447a | —(CH₂)₅OH | Br | .HCl | 247–249 |
| 447b | —(CH₂)₄OH | Br | .HCl | 187–189 |
| 447c | —CH₂S(CH₂)₂CH₃ | Cl | .HCl | 212–214 |
| 447d[1] | —CH₂SO(CH₂)₂CH₃ | | .HCl .0.9 H₂O | 144–150 |
| 447e[2] | —CH₂SO₂(CH₂)₂CH₃ | | .HCl .0.5 H₂O | 238–239 |

[1]This compound was produced by oxidation of the corresponding sulfide using sodium metaperiodate (1.1 moles per mole of sulfide) in aqueous methanol at room temperature.

[2]This compound was produced by oxidation of the corresponding sulfide using Oxone ® (2 moles per mole of sulfide) in aqueous methanol at room temperature.

The compounds of Table XXX were prepared from 3,4-dihydro-6-methoxy-spiro[(2H)-1-benzopyran-2,4'-piperidine] hydrochloride by the method described in Example 92, Step B, using the appropriate mesylate or bromide as indicated.

TABLE XXX

[Structure: MeO-chroman-spiro-piperidine NH·HCl + LG-CH₂CH₂-Ar²-(R³)ₛ → product]

| Example | Ar²—(R³)ₛ | LG | salt | mp (°C.) |
|---|---|---|---|---|
| 448 | benzofurazan | Br | .HCl | 245–247 |
| 449 | phenyl | Br | .HCl .0.25 H₂O | 262–263 |
| 450 | 4-NO₂-phenyl | Br | .HCl | 229–230 |
| 451 | 4-CN-phenyl | MeSO₃ | .HCl .0.35 H₂O | 243–245 |
| 452 | 2,3-dihydrobenzofuran | MeSO₃ | .HCl .0.1 EtOH .0.85 H₂O | 256–258 |
| 453 | 2-thienyl | MeSO₃ | .HCl .0.2 H₂O | 255–257 |
| 454 | 3-thienyl | MeSO₃ | .HCl .0.05 EtOH .0.2 H₂O | 253–255 |
| 455 | 2,4-difluorophenyl | MeSO₃ | .HCl .0.5 H₂O | 255–257 |

EXAMPLE 456

N-(4-Acetyl-5-hydroxy-2-nitrophenyl)acetamide and

N-(4-Acetyl-3-hydroxy-2-nitrophenyl)acetamide

A mixture of N-(4-acetyl-3-hydroxyphenyl)acetamide (9.66 g, 50 mmol) and acetic anhydride (14.2 ml, 15.3 g, 150 mmol) in dichloromethane (150 ml) was cooled to 5° C. and nitric acid (90%, d 1.49, 4.70 ml, 7.00 g, 100 mmol) was added dropwise. The mixture was stirred at room temperature for 1 hour, poured into water (150 ml) and extracted with dichloromethane (3×150 ml). The combined organic fractions were dried (Na$_2$SO$_4$) and evaporated under reduced pressure and the residue was purified by repeated flash column chromatography on silica gel, eluting with hexane/30% ethyl acetate then hexane/50% ethyl acetate. The first isomer to elute was N-(4-acetyl-5-hydroxy-2-nitrophenyl)acetamide as a yellow solid (3.87 g, 33%).

$^1$H NMR (CDCl$_3$): δ12.83 (1H, s), 10.78 (1H, br s), 8.78 (1H, s), 8.43 (1H, s), 2.68 (3H, s), 2.32 (3H, s).

The second isomer to elute was N-(4-acetyl-3-hydroxy-2-nitrophenyl)acetamide as a yellow solid (0.41 g, 3%).

$^1$H NMR (CDCl$_3$): δ13.74 (1H, s), 8.94 (1H, br s), 8.09 (1H, d, J 9.1 Hz), 7.88 (1H, d, J 9.1 Hz), 2.66 (3H, s), 2.26 (3H, s).

EXAMPLE 457

7-Amino-3,4-dihydro-6-nitro-1'-[2-(4-cyanophenyl)ethyl]spiro[(2H)-1-benzopyran-2,4'-piperidine]-4-one hydrochloride Pyrrolidine (108 μl, 92 mg, 1.3 mmol) was added to N-(4-acetyl-5-hydroxy-2-nitrophenyl)acetamide (309 mg, 1.3 mmol) in methanol (2 ml). The mixture was stirred for 10 minutes, then 1-[2-(4-cyanophenyl)ethyl]-4-piperidionone (296 mg, 1.3 mmol) in methanol (2 ml) was added and the mixture was heated under reflux for 8 hours, cooled and poured into aqueous sodium hydrogen carbonate (saturated, 25 ml). The mixture was extracted with dichloromethane (3×25 ml) and the combined organic fractions were dried (Na$_2$SO$_4$) and evaporated under reduced pressure. The residue was purified by flash column chromatography on silica gel, eluting with CH$_2$Cl$_2$/MeOH/NH$_3$(Aq.) (97:3:0.3) to give the pyranone as a yellow solid (300 mg, 57%). A sample (30 mg) was suspended in ethanol (1 ml) and treated with ethanolic HCl (6N, 0.2 ml). Ether (5 ml) was added dropwise and the precipitate was collected and dried in vacuo to give the hydrochloride as a yellow solid (17 mg), m.p. 174°-177° C. (dec.).

Anal. Calc'd. for C$_{23}$H$_{23}$ClN$_4$O$_4$·0.33H$_2$O: C, 58.86; H, 5.31; N, 12.48. Found: C, 58.87; H, 5.24; N, 12.34.

EXAMPLE 458

7-Amino-3,4-dihydro-8-nitro-1'-[2-(4-cyanophenyl)ethyl]spiro[(2H)-1-benzopyran-2,4'-piperidine]-4-one In the manner of Example 457, N-(4-acetyl-3-hydroxy-2-nitrophenyl)acetamide (405 mg, 1.7 mmol), pyrrolidine (142 ml, 121 mg, 1.7 mmol) and 1-[2-(4-cyanophenyl)ethyl]-4-piperidinone (388 mg, 1.7 mmol) in methanol (2 ml) gave, after chromatography, the title compound as an orange foam, (302 mg, 44%) $^1$H NMR (CDCl$_3$): δ 7.80 (1H, d, J=8.8 Hz), 7.58 (2H, d, J=8.2 Hz), 7.31 (2H, d, J=8.2 Hz), 6.38 (1H, d, J=8.8 Hz), 5.82 (2H, br s), 2.90–2.60 (10H, m), 2.13 (2H, m), 1.76 (2H, m).

EXAMPLE 459

(±)-7-Amino-3,4-dihydro-6-nitro-1'-[(5,6,7,8-tetrahydro-2-napthalenecarbonitrile)-6-yl]-spiro[(2H)-1-benzopyran-2,4'-piperidine]-4-one In the manner of Example 457, N-(4-acetyl-5-hydroxy-2-nitrophenyl)acetamide (643 mg, 2.7 mmol) and (±)-1-[(5,6,7,8tetrahydro-2-napthalenecarbonitrile)-6-yl]-4-piperidinone (687 mg, 2.7 mmol) in methanol (16 ml) gave, after chromatography, the title compound as an orange foam, (730 mg, 62%)

$^1$H NMR (CDCl$_3$): δ8.80 (1H, s), 7.38 (2H, m), 7.18 (1H, d, J 9 Hz), 6.42 (2H, br s), 6.30 (1H, s), 3.42 (1H, m), 3.02–2.78 (6H, m), 2.72 (2H, m), 2.70 (2H, s), 2.08 (2H, m), and 1.85–1.60 (4H, m).

EXAMPLE 460

7-Amino-3,4-dihydro-1'-hexyl-6-nitrospiro[(2H)-1-benzopyran-2,4'-piperidin]-4-one In the manner of Example 457, N-(4-acetyl-5-hydroxy-2-nitrophenyl)acetamide (1.07 g, 4.5 mmol), pyrrolidine (380 μl, 320 mg, 4.5 mmol) and 1-hexyl-4-piperidone (820 mg, 4.5 mmol) in methanol (15 ml) gave, after chromatography, the title compound as an orange gum (1.07 g, 66%)

$^1$H NMR (CDCl$_3$): δ8.78 (1H, s), 6.4 (2H, br s), 6.28 (1H, s), 2.68 (2H, s), 2.63 (2H, m), 2.35 (4H, m), 2.00 (2H, m), 1.77 (2H, m), 1.50 (2H, m), 1.29 (6H, m), 0.88 (3H, t).

EXAMPLE 461

7-Amino-3,4-dihydro-1'-heptyl-6-nitrospiro[(2H)-1-benzopyran-2,4'-piperidin]-4-one In the manner of Example 457, N-(4-acetyl-5-hydroxy-2-nitrophenyl)acetamide (1.07 g, 4.5 mmol), pyrrolidine (380 μl, 320 mg, 4.5 mmol) and 1-heptyl-4-piperidone (890 mg, 4.5 mmol) in methanol (15 ml) gave, after chromatography, the title compound as an orange gum (980 mg, 58%).

$^1$H NMR (CDCl$_3$): δ 8.79 (1H, s), 6.4 (2H, br s), 6.28 (1H, s), 2.68 (2H, s), 2.65 (2H, s), 2.35 (4H, m), 2.01 (2H, m), 1.77 (2H, m), 1.50 (2H, m), 1.28 (8H, m), 0.88 (3H, t).

EXAMPLE 462

6,7-Diamino-3,4-dihydro-1'-[2-(4-cyanophenyl)ethyl]-spiro[(2H)-1-benzopyran-2,4'-piperidine]-4-one dihydrochloride Titanium trichloride (15 wt% solution in 20-30% aqueous HCl, 5 ml) was added dropwise to a solution of 7-amino-3,4-dihydro-6-nitro-1'-[2-4-cyanophenyl)ethyl]spiro[(2H)-1-benzopyran-2,4'-piperidine]-4-one (238 mg, 0.59 mmol) in acetic acid (20 ml). The mixture was stirred for 2 hours, then further titanium chloride (15 wt%, 2.5 ml) was added. The mixture was stirred for 2 hours, poured into aqueous sodium hydroxide (20%, 80 ml) and aqueous sodium hydrogen carbonate (saturated, 200 ml) was added. The mixture was extracted with ethyl acetate (3×100 ml) and the combined organic fractions were dried (Na$_2$SO$_4$) and evaporated under reduced pressure. The residue was purified by flash column chromatography on silica gel, eluting with CH$_2$Cl$_2$/MeOH/NH$_3$(Aq.) (96:4:0.4) to give the pyranone as an orange foam (152 mg, 69%). A sample (30 mg) was suspended in ethanol (1 ml) and treated with ethanolic HCl (6M, 0.2 ml). The mixture was stirred for 1 hour, cooled and the precipitate was collected and dried in vacuo to give the dihydrochloride as a pale yellow solid (29 mg), m.p. >250° C.

Anal. Calc'd for $C_{22}H_{26}Cl_2N_4O_2$: C, 58.80; H, 5.83; N, 12.47. Found: C, 58.63; H, 5.84; N, 12.31.

EXAMPLE 463

7,8-Diamino-3,4-dihydro-1'-[2-(4-cyanophenyl)ethyl]-spiro[(2H)-1-benzopyran-2,4'-piperidine]-4-one In the manner of Example 462, 7-amino-3,4-dihydro-8-nitro-1'-[2-(4-cyanophenyl)ethyl]spiro[(2H)-1-benzopyran-2,4'-piperidine]-4-one (291 mg, 0.72 mmol) was reduced to give after chromatography, the title compound as a pale yellow foam (239 mg, 89%). 0 Hz), 7.36 (1H, d, J=8.5 Hz), 7.31 (2H, d, J=8.1 Hz), 6.37 (1H, d, J=8.5 Hz), 4.0 (2H, br s ), 3.31 (2H, br s), 2.89-2.42 (10H, m), 2.10 (2H, m), 1.76 (2H, m).

EXAMPLE 464

(±)-6,7-Diamino-3,4-dihydro-1'-[(5,6,7,8-tetrahydro-2-napthalenecarbonitrile)-6-yl]-spiro[(2H)-1-benzopyran-2,4'-piperidine]-4-one In the manner of Example 462, (±)-7-amino-3,4-dihydro-6-nitro-1'-[(5,6,7,8-tetrahydro-2napthalenecarbonitrile)-6-yl]-spiro[(2H)-1-benzopyran-2,4'-piperidine]-4-one (690 mg, 1.6 mmol) was reduced to give, after chromotography, the pyranone as an orange solid (314 mg, 49%), m.p.=184°-185° C.

$^1$H NMR (CDCl$_3$): δ 7.37 (2H, m), 7.22 (1H, s), 7.16 (1H, d, J 9 Hz), 6.23 (1H, s), 4.18 (2H, s), 3.10-2.75 (7H, m), 2.71 (4H, m), 2.61 (2H, m), 2.61 (2H, s), 2.10 (2H, m), 1.23 (4H, m).

EXAMPLE 465

6,7-Diamino-3,4-dihydro-1'-hexylspiro[(2H)-1-benzopyran-2,4'-piperidin]-4-one

In the manner of Example 462, 7-amino-3,4-dihydro-1'-hexyl-6-nitrospiro[(2H)-1-benzopyran-2,4'-piperidin]-4-one (1.05 g, 2.9 mmol) was reduced to give, after chromatography, the title compound as an orange foam (640 mg, 67%).

$^1$H NMR (CDCl$_3$): δ 7.21 (1H, s), 6.21 (1H, s), 4.15 (2H, br s), 3.04 (2H, br s), 2.62 (2H, m), 2.59 (2H, s), 2.37 (4H, m), 2.03 (2H, m), 1.70 (2H, m), 1.49 (2H, m), 1.29 (6H, m), 0.88 (3H, t).

EXAMPLE 466

6,7-Diamino-3,4-dihydro-1'-heptylspiro[(2H)-1-benzopyran-2,4'-piperidin]-4-one

In the manner of Example 462, 7-amino-3,4-dihydro-1'-heptyl-6-nitrospiro[(2H)-1benzopyran-2,4'-piperidin]-4-one (975 mg, 2.6 mmol) was reduced to give, after chromatography, the title compound as an orange foam (560 mg, 62%).

$^1$H NMR (CDCl$_3$): δ 7.21 (1H, s), 6.21 (1H, s), 4.15 (2H, br s), 3.05 (2H, br s), 2.62 (2H, m), 2.59 (2H, s), 2.35 (4H, m), 2.03 (2H, m), 1.71 (2H, m), 1.49 (2H, m), 1.28 (6H, m), 0.88 (3H, t).

EXAMPLE 467

1-[2-(4-Cyanophenyl)ethyl]-7',8'-dihydro-8'-oxo-spiro[piperidine-4,6'(1'H)-pyrano[2,3-f]benzimidazole]dihydrochloride Triethyl orthoformate (75 ml, 67 mg, 0.45 mmol) was added to a stirred suspension of 6,7-diamino-3,4-dihydro-1'-[2-(4-cyanophenyl)ethyl]spiro[(2H)-1-benzopyran-2,4'-piperidine]-4-one (56 mg, 0.15 mmol) and p-toluensulfonic acid (monohydrate, 10 mg) in ethyl acetate (5 ml). The mixture was heated under reflux for 1 hour, further triethyl orthoformate (75 ml) was added and the mixture was heated under reflux for 1.5 hour. The mixture was cooled and aqueous HCl (1N, 5 ml) was added. The mixture was stirred for 15 minutes, poured into aqueous sodium hydrogen carbonate (saturated, 25 ml) and extracted with dichloromethane (3×25 ml). The combined organic fractions were dried (Na$_2$SO$_4$) and evaporated under reduced pressure. The residue was purified by column chromatography on silica gel, eluting with CH$_2$Cl$_2$/MeOH/NH$_3$(Aq.) (95:5:0.5) to give a yellow solid which was suspended in ethanol (1 ml) and treated with ethanolic HCl (6M, 0.2 ml). The mixture was stirred for 1 hour, cooled and the precipitate was collected and dried in vacuo to give the title compound as a tan solid (40 mg, 55%), m.p >250° C.

Anal. Calc'd. for $C_{23}H_{24}Cl_2N_4O_2._{0.5}$ EtOH: C, 59.76; H, 5.64; N, 11.61. Found: C, 59.62; H, 5.63; N, 11.88.

EXAMPLE 468

1-[2-(4-Cyanophenyl)ethyl]-6',7'-dihydro-6'-oxo-spiro[piperidine-4,8'(1'H)-pyrano[2,3-e]benzimidazole] dihydrochloride In the manner of Example 467, 7,8-diamino-3,4-dihydro-1'-[2-(4-cyanophenyl)ethyl]spiro[(2H)-1-benzopyran-2,4'-piperidine]-4-one (113 mg, 0.3 mmol) gave, after chromatography and salt formation, the title compound as a white solid (63 mg, 46%), m.p.=226°-229° C.

Anal. Calc'd. for $C_{23}H_{24}Cl_2N_4O_2$: C, 60.14; H, 5.27; N, 12.20. Found: C, 60.24; H, 5.46; N, 12.20.

EXAMPLE 469

(±)- and (+)-1-[(5,6,7,8-Tetrahydro-2-napthalenecarbonitrile)-6-yl]-7',8'-dihydro-8'-oxo-spiro[piperidine-4,6'(1'H)-pyrano[2,3-f]benzimidazole] dihydrochloride In the manner of Example 467, (±)-6,7-diamino-3,4-dihydro-1'-[(5,6,7,8-tetrahydro-2-napthalenecarbonitrile)-6-yl]-spiro[(2H)-1-benzopyran-2,4'-piperidine]-4-one (161, mg, 0.4 mmol) gave, after chromatography and salt formation, the title compound as a light tan solid (92 mg, 47%), m.p. 228°-230° C.

Anal. Calc'd. for $C_{25}H_{26}Cl_2N_4O_2.0.5$ EtOH: C, 61.41; H, 5.75; N, 11.02. Found: C, 61.32; H, 5.99; N, 10.94.

In the same way, (+)-6,7-diamino-3,4-dihydro-1'-[(5,6,7,8-tetrahydro-2-napthalenecarbonitrile)-6-yl]-spiro[(2H)-1-benzopyran-2,4'-piperidine]-4-one gave, after chromatography and salt formation, the (+)-dihydrochloride (solvated with 0.75 equivalents of water), m.p. 274°-276° C., [α]$_d$+50.2° (c 0.118, MeOH).

EXAMPLE 470

7',8'-Dihydro-1-hexyl-8'-oxospiro[piperidine-4,6'-(1H)-pyrano[2,3-f]benzimidazole]dihydrochloride In the manner of Example 467, 6,7-diamino-3,4-dihydro-1'-hexylspiro[(2H)-1-benzopyran-2,4'-piperidin]-4-one (298 mg, 0.90 mmol) gave, after chromatography and salt formation, the title compound as an off-white solid (172 mg, 46%) mp 234°-237°.

Anal. Calc'd for $C_{20}H_{27}N_3O_2.2HCl$: C, 57.97; H, 7.05; N, 10.14. Found: C, 58.31; H, 7.21; N, 10.19.

EXAMPLE 471

7',8'-Dihydro-1-heptyl-8'-oxospiro[piperidine-4,6'-(1H)-pyrano[2,3-f]benzimidazole]dihydrochloride In the manner of Example 467, 6,7-diamino-3,4-dihydro-1'-heptylspiro[(2H)-1-benzopyran-2,4'-piperidin]-4-one (275 mg, 0.80 mmol) gave, after chromatography and salt formation, the title compound as an off-white solid (151 mg, 44%) mp 248°-252°.

Anal. Calc'd for $C_{21}H_{29}N_3O_2.2HCl.0.75H_2O$: C, 57.07; H, 7.41; N, 9.51. Found: C, 56.96; H, 7.14; N, 9.43.

EXAMPLE 472

1-[2-(4-Cyanophenyl)ethyl]-2',3',7',8'-tetrahydro-2',8'dioxo-spiro[piperidine-4,6'(1'H)-pyrano[2,3-f]benzimidazole] hydrochloride Carbonyl diimidazole (122 mg, 0.75 mmol) was added to a solution of 6,7-diamino-3,4-dihydro-1'-[2-(4-cyanophenyl)ethyl]-spiro[(2H)-1-benzopyran-2,4'-piperidine]-4-one (188 mg, 0.5 mmol) in THF (5 ml) and the mixture was stirred for 3 hours. The mixture was cooled and the solid was collected and triturated with hot ethanol. The solid was suspended in ethanol (2 ml) and treated with ethanolic HCl (6N, 0.5 ml). The mixture was stirred for 1 hour, cooled and the precipitate was collected and dried in vacuo to give the title compound as a white solid (119 mg, 52%), m.p. >285° C.

Anal. Calc'd. for $C_{23}H_{23}ClN_4O_3.H_2O$: C, 60.46; H, 5.51; N, 12.26. Found: C, 60.43; H, 5.12; N, 12.08.

EXAMPLE 473

1-[2-(4-Cyanophenyl)ethyl]-2',3',6',7'-tetrahydro-2',6'-dioxo-spiro[piperidine-4,8'(1'H)-pyrano[2,3-e]-benzimidazole] hydrochloride In the manner of Example 472, 7,8-diamino-3,4-dihydro-1'-[2-(4-cyanophenyl)ethyl]spiro[(2H)-1-benzopyran-2,4'-piperidine]-4-one (113 mg, 0.3 mmol) gave, after column chromatography on silicia gel, eluting with $CH_2Cl_2/MeOH/NH_2$ (Aq.) (93:7:0.7 then 90:10:1), and salt formation, the title compound as a white solid (78 mg, 58%), m.p.=262°-265° C. (dec.).

Anal. Calc'd. for $C_{23}H_{23}ClN_4O_3.0.75H_2O$: C, 61.06; H, 5.46; N, 12.38. Found: C, 60.99; H, 5.60; N, 12.07.

EXAMPLE 474A (±)- and (±)-
1-[(5,6,7,8-Tetrahydro-2-napthalenecarbonitrile)6-yl]-2',3',7',8'-tetrahydro-2',8'-dioxospiro[piperidine-4,6'(1'H)-pyrano[2,3-f]benzimidazole] hydrochloride In the manner of Example 472, (±)-6,7-diamino-3,4-dihydro-1'-[(5,6,7,8-tetrahydro-2-naptha-lenecarbonitrile)-6-yl]-spiro[(2H)-1-benzopyran-2,4'-piperidine]-4-one (141 mg, 0.35 mmol) gave, after flash column chromatography on silica gel, eluting with $CH_2Cl_2/MeOH$; 95:5, and salt formation, the title compound as an off-white solid (98 mg, 60%), m.p.=248°-250° C.

Anal. Calc'd. for $C_{25}H_{25}ClN_4O_3.0.25EtOH.0.75H_2O$: C, 62.50; H, 5.76; N, 11.43. Found: C, 62.47; H, 5.67; N, 11.43.

In the same way, (+)-6,7-diamino-3,4-dihydro-1'-[(5,6,7,8-tetrahydro-2-napthalenecarbonitrile)-6-yl]-spiro[(2H)-1-benzopyran-2,4'-piperidine]-4-one gave, after chromatography and salt formation, the (+)-hydrochloride (solvated with 0.5 equivalents of water), m.p. >285° C., $[\alpha]_d + 47.0°$ (c 0.115, MeOH).

EXAMPLE 474B

1-Hexyl-2',3',7',8'-tetrahydro-2',8'-dioxospiro[piperidine-4,6'(1'H)-pyrano[2,3-f]benzimidazole]hydrochloride In the manner of Example 457, 6,7-diamino-3,4-dihydro-1'-hexylspiro[(2H)-1-benzopyran-2,4'-piperidin]-4-one (298 mg, 0.90 mmol) gave, after chromatography and salt formation, the title compound as an pale yellow solid (156 mg, 45%) mp 293°-298°.

Anal. Calc'd for $C_{20}H_{27}N_3O_3.HCl.0.3 H_2O$: C, 60.15; H, 7.22; N, 10.52. Found: C, 60.17; H, 6.98; N, 10.50.

EXAMPLE 474C

1-Heptyl-2',3',7',8'-tetrahydro-2',8'-dioxospiro[piperidine-4,6'(1'H)-pyrano[2,3-f]benzimidazole]hydrochloride In the manner of Example 457, 6,7-diamino-3,4-dihydro-1'-heptylspiro[(2H)-1-benzopyran-2,4'-piperidin]-4-one (275 mg, 0.80 mmol) gave, after chromatography and salt formation, the title compound as a white solid (137 mg, 42%) mp 299°-301°.

Anal. Calc'd for $C_{21}H_{29}N_3O_3.HCl.0.3 H_2O$: C, 61.02; H, 7.46; N, 10.17. Found: C, 61.04; H, 7.59; N, 10.16.

EXAMPLE 475

1'-(2-Phenylethyl)-7,8-dihydro-8-oxospiro[6H-1,3-dioxolo[4,5-g][1]benzopyran-6,4'-piperidine] hydrochloride Pyrrolidine (83 ml, 71 mg, 1 mmol) was added to a mixture of 1-(6-hydroxy-1,3-benzodioxol-5-yl)ethanone [prepared as described by K. Fukui and M. Nakayama, Bull. Chem. Soc. Jap., 1963, 37, 300.](180 mg, 1 mmol) in methanol (1 ml). The mixture was stirred for 10 minutes, then 1-(2-phenylethyl)-4-piperidinone (203 mg, 1 mmol) in methanol (1 ml) was added and the mixture was heated under reflux for 1.5 hours. The mixture was cooled, the solvent was evaporated under reduced pressure and aqueous sodium hydrogen carbonate (saturated, 20 ml) was added. The mixture was extracted with dichloromethane (3×20 ml) and the combined organic fractions were dried ($Na_2SO_4$) and evaporated under reduced pressure. The residue was purified by column chromatography on silica gel, eluting with $CH_2Cl_2/MeOH/NH_3$(Aq.) (98:2:0.2) to give a yellow glass which was suspended in ethanol (5 ml) and treated with ethanolic HCl (6N, 0.5 ml). The mixture was stirred for 1 hour, cooled and the precipitate was collected and dried in vacuo to give the title compound as a white solid (153 mg, 38%), m.p. >285° C.

Anal. Calc'd. for $C_{22}H_{24}ClNO_4$: C, 65.75; H, 6.02; N, 3.48. Found: C, 65.61; H, 6.22; N, 3.42.

EXAMPLE 476

1'-[2-(4-Cyanophenyl)ethyl]-7,8-dihydro-8-oxos-piro[6H-1,3-dioxolo[4,5-g][1]benzopyran-6,4'-piperidine]hydrochloride As described in Example 475, 1-(6-hydroxy-1,3-benzo-dioxol-5-yl)ethanone (180 mg, 1 mmol) was condensed with 1-[2-(4-cyanophenyl)ethyl]-4-piperidinone (228 mg, 1 mmol) to give, after chromatography and salt formation, the title compound as a white solid (173 mg, 41%), m.p. 268°-270° C. (dec.).

Anal. Calc'd. for $C_{23}H_{23}ClN_2O_4$: C, 64.71; H, 5.43; N, 6.56. Found: C, 64.61; H, 5.61; N, 6.46.

EXAMPLE 477

1-(Benzofuroxan-5-carbonyl)spiro[piperidine-4,6'-(6H)-thieno(2,3-b)thiopyran-4'(5'H)-one]

To a suspension of benzofuroxan-5-carboxylic acid (673 mg, 3.7 mmol) in methylene chloride (13 ml) was added DMF (2 drops) and oxalyl chloride (0.36 ml, 0.52 g, 4.1 mmol). The mixture was stirred for 3 h, the solvent was evaporated under reduced pressure and flushed with methylene chloride (13 ml). The residue was dissolved in methylene chloride (13 ml) and a portion (3 ml) was added to an ice cooled solution of spiro[piperidine-4,6'-(6H)-thieno(2,3-b)thiopyran-4'-(5'H)-one](276 mg, 1.0 mmol) and diisopropylethylamine (0.52 ml, 3.0 mmol) in methylene chloride (1.7 ml). The mixture was stirred for 30 min., the solvent was evaporated under reduced pressure and the residue was purified by flash column chromatography on silica gel, eluting with hexanes/40% EtOAc. The product was triturated with hexanes/EtOAc and the solid was collected and dried in vacuo to give the pyranone as a white solid (307 mg, 90%), m.p. 195°-196° C.

Anal. Calc'd. for $C_{18}H_{15}N_3O_4S_2$: C 53.84; H 3.77; N 10.47. Found: C 53.75; H 3.59; N 10.47.

EXAMPLE 478

1-(Benzofurazan-5-carbonyl)spiro[piperidine-4,6'-(6H)thieno(2,3-b)thiopyran-4'(5'H)-one]

1-(Benzofuroxan-5-carbonyl)spiro[piperidine-4,6'-(6H)-thieno(2,3-b)thiopyran-4'(5'H)-one](100 mg, 0.25 mmol) and triethyl phosphite (0.10 g, 0.62 mmol) in THF (3.8 ml) were heated under reflux for 4 h., the solvent was evaporated under reduced pressure and the residue was purified by flash column chromatography on silica gel, eluting with hexanes/40% EtOAc. The product was triturated with hexanes/EtOAc and the solid was collected and dried in vacuo to give the pyranone as a white solid (59 mg, 61%), m.p. 199°-201° C.

Anal. Calcd. for $C_{18}H_{15}N_3O_3S_2.0.25H_2O$: C 55.43; H 4.02; N 10.78. Found: C 55.09; H 3.88; N 10.66.

EXAMPLE 479

(±)-, (+)-and
(−)-N-[1'-(6-Cyano-1,2,3,4-tetrahydro-2-napthalenyl)-3,4-dihyro-4-hydroxyspiro[2H-1-benzopyran-2,4'-piperidin]yl]methanesulfonamide hydrochloride In the manner of Example 429, (±)-3,4-dihydro-1'-[6-cyano-1,2,3,4-tetrahydronapthalene)-2-yl]-6-methanesulfonamido-spiro[(2H)-1-benzopyran-2,4'-piperidine]-4-one (651 mg, 1.4 mmol) was reduced to give, after chromatography, the alcohol as a foam (618 mg, 95%). A sample (200 mg) was treated with etha- nolic HCl to give the (±)-hydrochloride as a white solid (164 mg), m.p. 216°-218° C.

Anal. Calcd. for $C_{25}H_{30}ClN_3O_4S.0.33H_2O$: C 58.87; H 6.06; N 8.23. Found: C 58.96; H 5.95; N 8.18.

In the same way, (+)-3,4-dihydro-1'-[(6-cyano-1,2,3,4-tetrahydronapthalene)-2-yl]-6-methanesulfonamido-spiro[(2H)-1-benzopyran-2,4'-piperidine]-4-one gave, after chromatography and salt formation, the (+)-hydrochloride, m.p. 182°-184° C., $[\alpha]_d+43.0°$ (c 0.128, MeOH).

In the same way, (−)-3,4-dihydro-1'-[(6-cyano-1,2,3,4-tetrahydronapthalene)-2-yl]-6-methanesulfonamido-spiro[(2H)-1-benzopyran-2,4'-piperidine]-4-one gave, after chromatography and salt formation, the (−)-hydrochloride, m.p. 207°-210° C., $[\alpha]_d-47.3°$ (c 0.165, MeOH).

EXAMPLE 480

(±)-, (+)- and
(−)-1'-[(6-Cyano-1,2,3,4-tetrahydronapthalene)-2-yl]-6-methanesulfonamido-spiro[(2H)-1-benzopyran-2,4'-piperidine] hydrochloride (±)-3,4-Dihydro-1'-[(6-cyano-1,2,3,4-tetrahydronapthalene)-2-yl]-6-methanesulfonamido-spiro[(2H)-1-benzopyran-2,4'-piperidine]-4-ol (350) mg, 0.75 mmol) and p-toluenesulfonic acid (monohydrate, 214 mg, 1.125 mmol) in toluene (15 ml) was heated under reflux with azeotropic removal of water for 30 min., cooled and aqueous sodium hydrogen carbonate (saturated, 40 ml) and water (10 ml) were added. The mixture was extracted with dichloromethane (3×40 ml) and the combined organic fractions were dried ($Na_2SO_4$) and evaporated under reduced pressure to give a tan foam which was purified by flash column chromatography on silica gel, eluting with $CH_2Cl_2$/MeOH/$NH_3$(Aq.) (97:3:0.3) to give a foam (289 mg, 86%). A sample (115 mg) was treated with ethanolic HCl to give the (±)-hydrochloride as a white solid (104 mg), m.p. 272°-274° C. In the same way, (+)-3,4-dihydro-1'-[6-cyano-1,2,3,4-tetrahydronapthalene)2-yl]-6-methanesulfonamido-spiro[(2H)-1-benzopyran-2,4'-piperidine]-4-ol gave, after chromatography and salt formation, the (+)-hydrochloride, m.p. 276°-278° C., $[\alpha]_d+48.2°$ (c 0.112,MeOH).

In the same way, (−)-3,4-dihydro-1'-[(6-cyano-1,2,3,4-tetrahydronapthalene)-2-yl]-6-methanesulfonamido-spiro[(2H)-1-benzopyran-2,4'-piperidine]-4-ol gave, after chromatography and salt formation, the (−)-hydrochloride, m.p. 275°-277° C., $[\alpha]_d-49.4°$ (c 0.124, MeOH).

EXAMPLE 481

(+)-and
(−)-3,4-Dihydro-1'-[(6-cyano-1,2,3,4-tetrahydronapthalene)-2-yl]-6-methanesulfonamidospiro[(2H)-1-benzopyran-2,4'-piperidine]-hydrochloride (+)-1'-[(6-Cyano-1,2,3,4-tetrahydronapthalene)-2-yl]-6-methanesulfonamido-spiro[(2H)-1-benzopyran-2,4'-piperidine] (359 mg, 0.8 mmol) was suspended in methanol (17 ml). 5% Palladium on carbon (25 mg) was added and the mixture was stirred under hydrogen (1 Atm.). Further 5% palladium on carbon (20 mg portions) was added after 7, 24 and 31 h. After 48 h, the mixture was filtered through celite, washing with methanol, and evaporated under reduced pressure to give a foam which was purified by flash column chromatography on silica gel, eluting with $CH_2Cl_2$/MeOH/$NH_3$(Aq.) (96:4:0.4) to give a foam (312 mg, 86%). A sample (300 mg) was treated with ethanolic HCl to give the (+)-hydrochloride as a white solid (261 mg), m.p. 284°-286° C., $[\alpha]_d +55.6°$ (c 0.126, MeOH).

In the same way, (−)-1'-[(6-cyano-1,2,3,4-tetrahydronapthalene)-2-yl]-6-methanesulfonamidospiro[(2H)-1-benzopyran-2,4'-piperidine] gave, after chromatography and salt formation, the (−)-hydrochloride, m.p. 285°-287° C., $[\alpha]_d −48.4°$ (c 0.144, MeOH).

EXAMPLE 482

7-Amino-3,4-dihydro-6-nitro-1'-(2-phenylethyl)-spiro[(2H)-1-benzopyran-2,4'-piperidine]-4-one In the manner of Example 457, N-(4-acetyl-5-hydroxy-2-nitrophenyl)acetamide (1.07 g, 4.5 mmol) and 1-(2-phenylethyl)-4-piperidinone (910 mg, 4.5 mmol) in methanol (15 ml) gave, after chromatography, the pyranone as an orange foam, (1.23 g, 72%).

$^1$HNMR (CDCl$_3$) δ:8.80 (1H, s), 7.28 (2H, m), 7.21 (3H, m), 6.4 (2H, br s), 6.28 (1H, s), 2.75-2.60 (6H, m), 2.70 (2H, s), 2.49 (2H, m), 2.02 (2H, m), and 1.79 (2H, m).

EXAMPLE 483

7-Amino-3,4-dihydro-6-nitro-1'-[(2,3-dihydro-1H-indene)-2-yl]-spiro[(2H)-1-benzopyran-2,4'-piperidine]-4-one dihydrochloride In the manner of Example 457, N-(4-acetyl-5-hydroxy-2-nitrophenyl)acetamide (1.07 g, 4.5 mmol) and 1-[(2,3-dihydro-1H-indene)-2-yl]-4-piperidinone (970 mg, 4.5 mmol) in methanol (15 ml) gave, after hydrolysis in refluxing ethanol (3 ml) and HCl-H$_2$O (6M, 1 ml), the dihydrochloride as a yellow solid, (0.87 g, 41%).

$^1$HNMR (DMSO) δ:11.5-11.1 (1H, s), 8.47 (1H, s), 8.00 (2H, br s), 7.24 (4H, m), 6.53 (1H, s), 4.15 (1H, m), 3.47 (2H, m), 3.32 (6H, m), 2.84 (2H, s), and 2.28-2.04 (4H, m).

EXAMPLE 484

(±)-7-Amino-3,4-dihydro-6-nitro-1'-[(1,2,3,4-tetrahydronapthalene)-2-yl]-spiro[(2H)-1-benzopyran-2,4'-piperidine]-4-one In the manner of Example 457, N-(4-acetyl-5-hydroxy-2-nitrophenyl)acetamide (1.07 g, 4.5 mmol) and (±)-1-[(1,2,3,4-tetrahydronapthalene)-2-yl]-4-piperidinone (1.03 g, 4.5 mmol) in methanol (9 ml) gave, after acid hydrolysis in refluxing ethanol (20 ml) and HCl-H$_2$O (6M, 10 ml) and chromatography, the pyranone as an orange foam, (418 mg, 23%).

$^1$HNMR (CDCl$_3$) δ: 8.80 (1H, s), 7.11 (4H, m), 6.4 (2H, br s), 6.30 (1H, s), 2.91-2.71 (11H, m), and 2.52-1.60 (6H, m).

EXAMPLE 485

7-Amino-3,4-dihydro-6-nitro-1'-[(6,7,8,9-tetrahydro-5H-benzocycloheptene)-7-yl]-spiro[(2H)-1-benzopyran-2,4'-piperidine]-4-one In the manner of Example 457, N-(4-acetyl-5-hydroxy-2-nitrophenyl)acetamide (785 mg, 3.3 mmol) and 1-[(6,7,8,9-tetrahydro-5H-benzocycloheptene)-7-yl]-4-piperidinone (802 mg, 3.3 mmol) in methanol (7 ml) gave, after acid hydrolysis in refluxing ethanol (20 ml) and HCl-H$_2$O (6M, 10 ml) and chromatography, the pyranone as an orange solid, (217 mg, 16%).

$^1$HNMR (CDCl$_3$) δ: 8.78 (1H, s), 7.12 (4H, s), 6.4 (2H, br s), 6.26 (1H, s), 2.9-2.5 (11H, m), and 2.2-1.35 (8H, m).

EXAMPLE 486

6,7-Diamino-3,4-dihydro-1'-(2-phenylethyl)-spiro[(2H)-1-benzopyran-2,4'-piperidine]-4-one In the manner of Example 462, 7-amino-3,4-dihydro-6-nitro-1'-(2-phenylethyl)-spiro[(2H)-1-benzopyran-2,4'-piperidine]-4-one (1.22 g, 3.2 mmol) was reduced to give, after chromatography, the pyranone as a yellow foam (790 mg, 70%).

$^1$HNMR (CDCl$_3$) δ: 7.32-7.10 (6H, m), 6.22 (1H, s), 4.16 (2H, br s), 3.05 (2H, br s), 2.80 (2H, m), 2.75-2.53 (4H, m), 2.61 (2H, s), 2.48 (2H, m), 2.07 (2H, m), and 1.73 (2H, m).

EXAMPLE 487

6,7-Diamino-3,4-dihydro-1'-[(2,3-dihydro-1H-indene)-2-yl]-spiro[(2H)-1-benzopyran-2,4'-piperidine]-4-one In the manner of Example 462, 7-amino-3,4-dihydro-6-nitro-1'-[(2,3-dihydro-1H-indene)-2-yl]spiro[(2H)-1-benzopyran-2,4'-piperidine]-4-one dihydrochloride (863 mg, 1.85 mmol) was reduced to give the pyranone as an orange solid (301 mg, 45%).

$^1$HNMR (CDCl$_3$) δ: 7.16 (5H, m), 6.23 (1H, s), 4.16 (2H, br s), 3.22 (1H, m), 3.09 (4H, m), 2.90 (2H, m), 2.72 (2H, m), 2.61 (2H, s), 2.47 (2H, m), 2.08 (2H, m) and 1.75 (2H, m).

EXAMPLE 488

(±)-6,7-Diamino-3,4-dihydro-1'-[(1,2,3,4-tetrahydronapthalene)-2-yl]-spiro[(2H)-1-benzopyran-2,4'-piperidine]-4-one In the manner of Example 462, (±)-7-amino-3,4-dihydro-6-nitro-1'-[(1,2,3,4-tetrahydronapthalene)-2-yl]-spiro[(2H)-1-benzopyran-2,4'-piperidine]-4-one (407 mg, 1.00 mmol) was reduced to give, after chromatography, the pyranone as an orange foam (331 mg, 88%).

$^1$HNMR (CDCl$_3$) δ: 7.26 (1H, s), 7.10 (4H, m), 6.25 (1H, s), 4.17 (2H, br s), 3.05 (2H, br s), 3.00-2.78 (7H, m), 2.72 (4H, m), 2.62 (2H, s), 2.10 (2H, m), and 1.72 (2H, m).

EXAMPLE 489

6,7-Diamino-3,4-dihydro-1'-[(6,7,8,9-tetrahydro-5H-benzocycloheptene)-7-yl]-spiro[(2H)-1-benzopyran-2,4'-piperidine]-4-one In the manner of Example 462, 7-amino-3,4-dihydro-6-nitro-1'-[(6,7,8,9-tetrahydro-5H-benzocyclo-heptene)-7-yl]-spiro[(2H)-1-benzopyran-2,4'-piperidine]-4-one (215 mg, 0.51 mmol) was reduced to give, after chromatography, the pyranone as an orange foam (146 mg, 73%).

$^1$HNMR (CDCl$_3$) δ: 7.20 (1H, s), 7.12 (4H, s), 6.20 (1H, s), 4.14 (2H, br s), 3.03 (2H, br s), 2.82 (2H, m), 2.71 (5H, m), 2.58 (2H, s), 2.53 (2H, m), 2.12 (2H, m), 2.02 (2H, m), and 1.42 (2H, m).

EXAMPLE 490

1-(2-Phenylethyl)-7',8'-dihydro-8'-oxo-spiro[piperidine-4,6'(1'H)-pyrano[2,3-f]benzimidazole] Dihydrochloride In the manner of Example 467, 6,7-diamino-3,4-dihydro-1'-(2-phenylethyl)-spiro[(2H)-1-benzopyran-2,4'-piperidine]-4-one (316, mg, 0.90 mmol) gave, after chromatography and salt formation, the dihydrochloride as a light tan solid (107 mg, 27%), m.p. 247°–249° C.

Anal Calcd. for C22H25Cl2N3O2.0.05EtOH.0.30H2O: C 60.04; H 5.91; N 9.51. Found: C 60.08; H 5.70; N 9.45.

EXAMPLE 491

1-[(2,3-Dihydro-1H-indene)-2-yl]-7',8'-dihydro-8'-oxo-spiro[piperidine-4,6'(1'H)-pyrano[2,3-f]benzimidazole] Dihydrochloride In the manner of Example 467, 6,7-diamino-3,4-dihydro-1'-[(2,3-dihydro-1H-indene)-2-yl]-spiro[(2H)-1-benzopyran-2,4'-piperidine]-4-one (73, mg, 49 mmol) gave, after chromatography and salt formation, the dihydrochloride as a light tan solid (73 mg, 49%), m.p. 233°–236° C.

Anal. Calcd. for C23H25Cl2N3O2.0.30H2O: C 61.14; H 5.71; N 9.30. Found: C 61.14; H 5.58; N 9.22.

EXAMPLE 492

(±)-1-[(1,2,3,4-Tetrahydronapthalene)-2-yl]-7',8'-dihydro-8'-oxo-spiro[piperidine-4,6'(1'H)-pyrano[2,3-f]benzimidazole] dihydrochloride In the manner of Example 467, (±)-6,7-diamino-3,4-dihydro-1'-[(1,2,3,4-tetrahydronapthalene)-2-yl]-spiro[(2H)-1-benzopyran-2,4'-piperidine]-4-one (132 mg, 0.35 mmol) gave, after chromatography and salt formation, the dihydrochloride as a tan solid (90 mg, 55%), m.p. 233°–236° C.

Anal. Calc'd. for C24H27Cl2N3O2.0.55EtOH: C 62.06; H 6.29; N 8.65. Found: C 62.08; H 6.66; N 8.75.

EXAMPLE 493

1-[(6,7,8,9-Tetrahydro-5H-benzocycloheptene)-7-yl]-7',8'-dihydro-8'-oxo-spiro[piperidine-4,6'(1'H)-pyrano[2,3-f]benzimidazole] dihydrochloride In the manner of Example 467, 6,7-diamino-3,4-dihydro-1'-[(6,7,8,9-tetrahydro-5H-benzocyclo-heptene)-7-yl]-spiro[(2H)-1-benzopyran-2,4'-piperidine]-4-one (29, mg, 0.075 mmol) gave, after chromatography and salt formation, the dihydrochloride as a tan solid (17 mg, 47%), m.p. 232°–235° C.

Anal. Calc'd. for C25H29Cl2N3O2: C 63.29; H 6.16; N 8.86. Found: C 62.91; H 6.44; N 8.55.

EXAMPLE 494

1-(2-Phenylethyl)-2',3',7',8'-tetrahydro-2',8'-dioxo-spiro[piperidine-4,6'(1'H)-pyrano[2,3-f]benzimidazole] hydrochloride In the manner of Example 472, (6,7-diamino-3,4-dihydro-1'-(2-phenylethyl)-spiro[(2H)-1-benzopyran-2,4'-piperidine]-4-one (316 mg, 0.90 mmol) gave, after chromatography and salt formation, the hydrochloride as a pale yellow solid (137 mg, 36%), m.p. 298°–300° C.

Anal. Calc'd. for C22H24ClN3O3.0.50H2O: C 62.48; H 5.96; N 9.84. Found: C 62.49; H 5.69; N 9.89.

EXAMPLE 495

1-[(2,3-Dihydro-1H-indene)-2-yl]-2',3',7',8'-tetrahydro-2',8'-dioxo-spiro[piperidine-4,6'(1'H)-pyrano[2,3-f]benzimidazole] Hydrochloride In the manner of Example 472, 6,7-diamino-3,4-dihydro-1'-[(2,3-dihydro-1H-indene)-2-yl]-spiro[(2H)-1-benzopyran-2,4'-piperidine]-4-one (180 mg, 0.5 mmol) gave, after chromatography and salt formation, the hydrochloride as a pale orange solid (126 mg, 58%), m.p. 257°–260° C.

Anal. Calc'd. for C23H24ClN3O3.0.65EtOH.0.75H2O: C, 62.18; H, 6.31; N, 8.95. Found: C, 62.18; H, 6.10; N, 8.81.

EXAMPLE 496

(±)-1-[(1,2,3,4-Tetrahydronapthalene)-2-yl]-2',3',7', 8'-tetrahydro-2',8'-dioxo-spiro[piperidine-4,6'(1'H)-pyrano[2,3-f]benzimidazole] Hydrochloride In the manner of Example 472, (±)-6,7-diamino-3,4-dihydro-1'-[(1,2,3,4-tetrahydronapthalene)-2-yl]spiro[(2H)-1-benzopyran-2,4'-piperidene]-4-one (170 mg, 0.45 mmol) gave, after chromatography and salt formation, the hydrochloride as a yellow solid (89 mg, 45%), m.p. 254°–257° C.

Calcd. for C24H26ClN3O3.0.05EtOH.1.20H2O: C 62.40; H 6.24; N 9.06. Found: C 62.42; H 5.97; N 8.94.

EXAMPLE 497

1-[(6,7,8,9-Tetrahydro-5H-benzocycloheptene)-7-yl]2',3',7',8'-tetrahydro-2',8'-dioxo-spiro[piperidine-4,6'(1'H)-pyrano[2,3-f]benzimidazole] Hydrochloride In the manner of Example 472, 6,7-diamino-3,4-dihydro-1'-[(6,7,8,9-tetrahydro-5H-benzocycloheptene-7-yl]-spiro[(2H)-1-benzopyran-2,4'-piperidine]-4-one (98 mg, 0.25 mmol) gave, after chromatography and salt formation, the hydrochloride as a yellow solid (47 mg, 41%), m.p. 260°–263° C.

Calc'd. for C25H28ClN3O3.1.50H2O: C 62.42; H 6.50; N 8.74. Found: C 62.32; H 6.35; N 8.59.

In the manner of Example 339, step 8, 1-(3-hydroxypyridinyl)ethanone was condensed with suitably 4-substituted piperidinones using pyrrolidine in methanol to give the following 1'-substituted 2,4-dihydro(2H-pyrano[3,2-b]pyridine-2,4'-piperidine)-4-ones of Table XXXI.

TABLE XXXI

| EXAMPLE | RM | SALT | M.P. (°C.) |
|---|---|---|---|
| 704, 211 | —(CH2)2—⟨phenyl⟩ | .2 HCl .0.5 H2O | 159–161 |
| 704, 238 | —(CH2)2—⟨phenyl⟩—CN | .2 HCl .0.15 H2O | 185–186.5 |

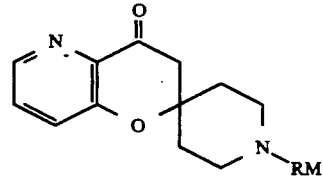

In the manner of Example 339, step 8, 1-(3-hydroxypyridinyl)ethanone can be condensed with suitably 4-substituted piperidinones using pyrrolidine in methanol to give the following 1'-substituted 2,4-dihydro(2H-pyrano[3,2-b]pyridine-2,4'-piperidine)-4-ones of Table XXXII.

TABLE XXXII

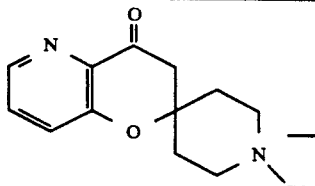

wherein RM is —(CH$_2$)$_5$CH$_3$,
—(CH$_2$)$_6$OH, —(CH$_2$)$_7$OH,
—(CH$_2$)$_6$CH$_3$,

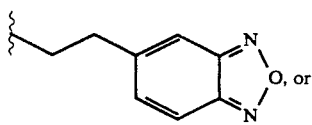, or

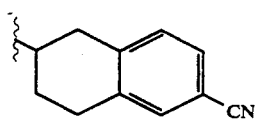

In the manner of Example 429, the appropriate pyran-4-ones were reduced with sodium borohydride in ethanol to give the following 1'-substituted 3,4-dihydro-6-methanesulfonyl-spiro[(2H)-benzopyran-2,4'-piperidine]-4-ols of Table XXXIII.

TABLE XXXIII

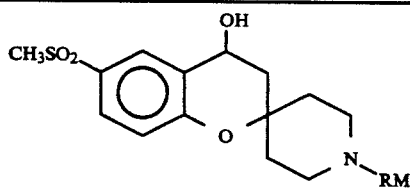

| EXAMPLE | RM | ISOMER | SALT | M.P. (°C.) |
|---|---|---|---|---|
| 500 | tetrahydronaphthalene-CN | (−) | .HCl .0.25 H$_2$O | 271–276 |
| 501 | tetrahydronaphthalene-CN | (+) | .HCl .0.5 H$_2$O | 193–200 |

In the manner of Example 429, the appropriate pyran-4-one was reduced with sodium borohydride in ethanol to give the following 1-substituted 7',8'-dihydro-8'-hydroxy-spiro[piperidine-4,6'(1'H)-pyrano[2,3-f]benzimidazole]of Table XXXIV.

TABLE XXXIV

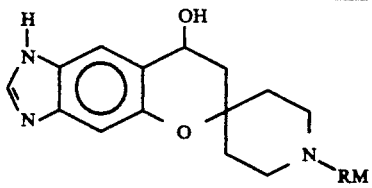

| EXAMPLE | RM | ISOMER | SALT | M.P. (°C.) |
|---|---|---|---|---|
| 502 | tetrahydronaphthalene-CN | (+) | .2HCl .0.35 EtOH .0.6 H$_2$O | 248–250(dec) |

In the manner of Example 429, the appropriate pyran-4-ones can be reduced with sodium borohydride in ethanol to give the following 1'-substituted 3,4-dihydro-6-methanesulfonyl-spiro[(2H)-benzopyran-2,4'-piperidine]-4-ols, 1-substituted 7',8'-dihydro-8'-hydroxy-spiro[piperidine-4,6'(1'H)-pyrano[2,3-f] benzimidazole]'s and 1-substituted 2',3',7',8'-tetrahydro-8'-hydroxy-2'-oxo-spiro[piperidine-4,6'(1'H)pyrano[2,3-f]benzimidazole]'s of Table XXXV.

TABLE XXXV

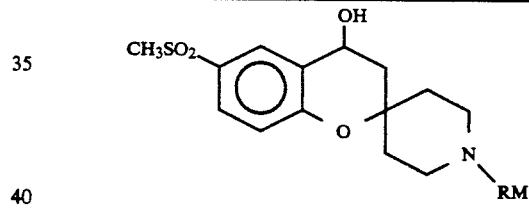

TABLE XXXV-continued

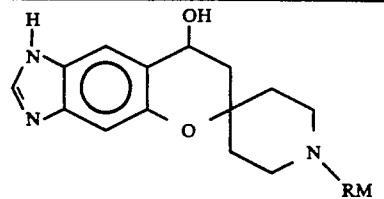

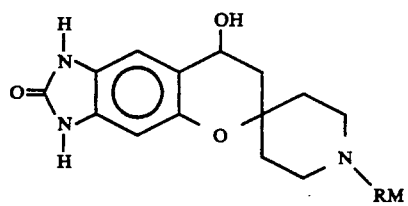

wherein —RM is —(CH₂)₅CH₃, —(CH₂)₆OH, —(CH₂)₆CH₃, —(CH₂)₇OH,

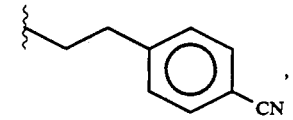

or

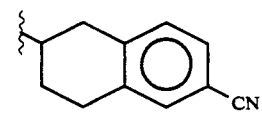

In the manner of Example 480, the appropriate pyran-4-ols were dehydrated with p-toluenesulfonic acid in toluene to give the following 1'-substituted 6-methanesulfonyl-spiro[(2H)-benzopyran-2,4'-piperidines]'s Table XXXVI.

TABLE XXXVI

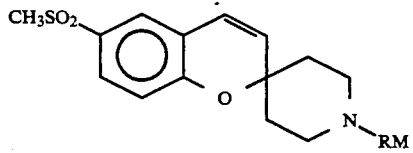

| EXAMPLE | RM | ISOMER | SALT | M.P. (°C.) |
|---|---|---|---|---|
| 503 | 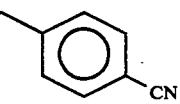 | (+) | .HCl | 281–285 |
| 504 | 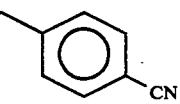 | (−) | .HCl | 283–285 |

In the manner of Example 480, the appropriate pyran-4-ols can be dehydrated with p-toluenesulfonic acid in toluene to give the following 1'-substituted 6-methanesulfonyl-spiro[(2H)-benzopyran-2,4'-piperidines]'s, 1-substituted spiro[piperidine-4,6'(1'H)-pyrano[2,3-f]-benzimidazole]'s and 1-substituted 2',3'-dihydro-2'-oxo-spiro-[piperidine-4,6'(1'H)-pyrano[2,3-f]benzimidazole]'s of Table XXXVII.

TABLE XXXVII

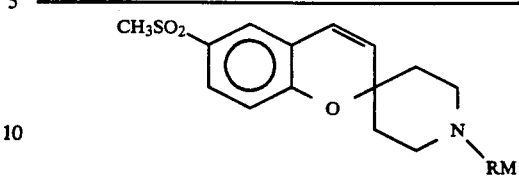

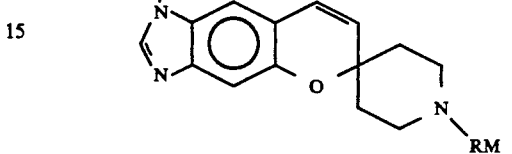

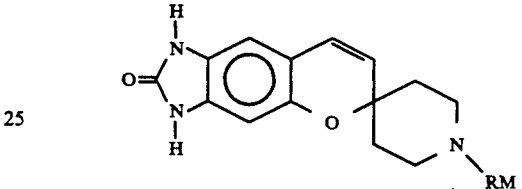

wherein —RM is —(CH₂)₅CH₃, —(CH₂)₆OH, —(CH₂)₆CH₃, —(CH₂)₇OH, or

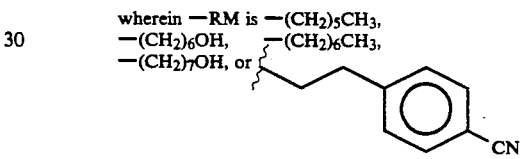

In the manner of Example 481, the appropriate pyrans were hydrogenated over 5% palladium on carbon to give the following 1'-substituted 3,4-dihydro-6-methanesulfonyl-spiro[(2H)-benzopyran-2,4'-piperidine]'s, of Table XXXVIII.

TABLE XXXVIII

[Structure: CH₃SO₂-substituted benzopyran spiro-piperidine with N-RM]

| EXAMPLE | RM | ISOMER | SALT | M.P. (°C.) |
|---|---|---|---|---|
| 505 | [tetrahydronaphthalene-CN] | (−) | .HCl | 299–301 |
| 506 | [tetrahydronaphthalene-CN] | (+) | .HCl .0.25 H₂O | 297–300 |

In the manner of Example 481, the appropriate pyrans were hydrogenated over 5% palladium on carbon to give the following 1-substituted 2′,3′,7′,8′-tetrahydro-2′-oxo-spiro [piperidine-4,6′(1′H)-pyrano-[2,3-f]benzimidazole]'s of Table XXXIX.

TABLE XXXIX

[Structure: oxo-benzimidazole fused pyran spiro-piperidine with N-RM]

| EXAMPLE | RM | ISOMER | SALT | M.P. (°C.) |
|---|---|---|---|---|
| 507 | [propyl-phenyl-CN] | | .HCl .0.3 H₂O | 291–293 |
| 508 | [tetrahydronaphthalene-CN] | (+) | .HCl .0.4 H₂O | >285 |

In the manner of Example 481, the appropriate pyrans can be hydrogenated over 5% palladium on carbon to give the following 1-substituted 7′,8′-dihydrospiro[-piperidine-4,6′(1′H)-pyrano[2,3-f]benzimidazole]'s and 1-substituted 2′,3′,7′,8′-tetrahydro-2′-oxo-spiro[piperidine-4,6′(1′H)-pyrano[2,3-f]benzimidazole]'s of Table XL.

TABLE XL

[Structure: benzimidazole fused pyran spiro-piperidine with N-RM]

TABLE XL-continued

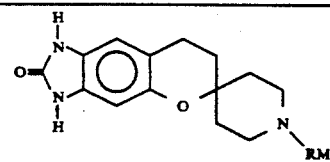

wherein —RM is —(CH₂)₅CH₃, —(CH₂)₆OH, —(CH₂)₆CH₃, —(CH₂)₇OH,

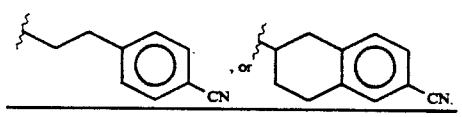

EXAMPLE 509

3-Methyl-6-methylsulfonyl-3,4-dihydro-spiro[(2H)-1-benzopyran-2,4′-piperidin]-4-one hydrochloride Step A:

A mixture of 4-(methylsulfonyl)phenol (23.0 g, 0.134 mol), 17.37 g (0.134 mol) of propionic anhydride and 0.50 g of dimethylaminopyridine in 460 mL of methylene chloride was stirred at room temperature for two hours. The reaction mixture was washed with water, a saturated solution of sodium bicarbonate, and dried over magnesium sulfate. Filtration and evaporation of the solvent gave 30.72 g of a white solid. A mixture of 2.28 g (0.01 mol) of this solid and 2.33 g (0.015 mol) of aluminium chloride was heated at 180° C. for 5 hours. After cooling, ice, 8.5 mL of concentrated hydrochloric acid and 20 mL of methylene dichloride were added, and the mixture was stirred overnight. The organic phase was separated, washed with water, dried over Na₂SO₄, filtered, and concentrated to dryness. The residue was purified by chromatography on silica gel using a Still column, and the mixture eluted with 0.5% methanol-methylene chloride to yield 1.15 g of 2-hydroxy-5-methylsulfonyl-propiophenone.

Step B:

A solution of 1.15 g (0.005 mol) of 2-hydroxy-5-methylsulfonylpropiophenone, 0.706 g (0.005 mol) of 1-acetyl-4-piperidone, and 0.356 g (0.005 mol) of pyrrolidine in CH₃OH (25 mL) was heated at reflux for 96 hours. The reaction was concentrated to dryness. The residue was chromatographed on silica gel using a Still column and the mixture eluted with 2% CH₃OH in CH₂Cl₂. Evaporation of the solvent and recrystallization of the residue from isopropyl alcohol-methanol gave 0.57 g of 1'-acetamido-3,4-dihydro-3-methyl-6-methylsulfonyl-spiro [(2H)-1-benzopyran-2,4'-piperidin]-4-one.

Step C:

The product of Step B (0.5 g) in CH₃OH (15 mL) and 6N HCl (15 mL) was heated at reflux for 10 hours. The reaction was concentrated to dryness and the residue flushed with ethanol (4 times) and then toluene to yield 0.5 g of the title compound.

Employing the procedure substantially as described in Example 83, but substituting 3-methyl-6-methanesulfonyl-3,4-dihydro-spiro[(2H)-1-benzopyran-2,4'-piperidine]-4-one hydrochloride for the 3,4-dihydro-6-methanesulfonamido-spiro [(2H)-1-benzopyran-2,3'-piperidine]-4-one hydrochloride used therein, and substituting an appropriate electriphile for the 5-(2-bromoethyl) benzofurazan, the following compounds of Table XLI were prepared:

TABLE XLI

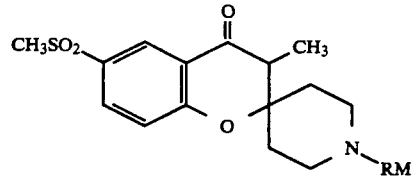

| Example | RM | Salt | MP (°C.) |
|---|---|---|---|
| 510 | —(CH₂)₃S(CH₂)₂CH₃ | .HCl | 271–273 |
| 511ᵃ | —(CH₂)₃SO(CH₂)₂CH₃ | .HCl.0.75 H₂O | 227–229 |
| 512 | —(CH₂)₂—⬡—CN | .HCl.0.25 H₂O | 277–279 |

TABLE XLI-continued

| Example | RM | Salt | MP (°C.) |
|---|---|---|---|
| 513 | 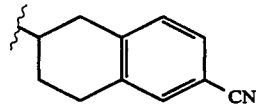 | .HCl | 234–236 |

ᵃThis compound was produced by oxidation of the corresponding sulfide using sodium metaperiodate (1.1 moles per mole of sulfide) in an aqueous methanol mixture at room temperature.

In a manner similar to that of Example 339, step 8, 5-methylsulfonyl-2-hydroxypropiophenone can be condensed with suitably 4-substituted piperidinones using pyrrolidine in methanol to give the following 3,4-dihydro-3-methyl-6-methanesulfonyl-1'-substituted-spiro[(2H)-1-benzopyran-2,4'-piperidine]-4-ones of Table XLII.

TABLE XLII

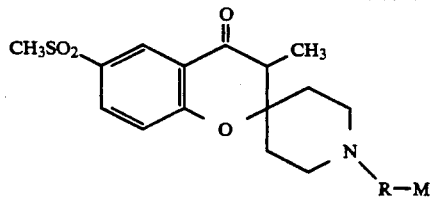

wherein RM is —(CH₂)₅CH₃,
—(CH₂)₆OH, —(CH₂)₆CH₃,
—(CH₂)₇OH, or

[tetrahydronaphthalene-CN structure]

EXAMPLE 514

Ethyl 1-methyl-3-(2'-fluorobenzyl-nipecotate

To a solution of ethyl 1-methylnipecotate (10.0 g, 58.4 mmol) in dry tetrahydrofuran (350 ml) was added at −78° C. lithium bis(trimethylsilyl)amide (80.0 ml, 80.0 mmol) as a 1.0M solution in tetrahydrofuran and the resulting solution was allowed to stir at −78° C. for 3 hours. To this was added 2-fluorobenzylchloride (7.0 ml, 8.5 g, 59 mmol) and the resulting solution was allowed to warm to room temperature over 5 hours. Thin-layer chromatography showed reaction was not complete. More 2-fluorobenzylchloride (20 ml, 2.4 g, 17 mmol) was added to the reaction mixture and the resulting solution was allowed to stir overnight, ca. 18 hours. The tetrahydrofuran was removed by evaporation in vacuo and the orange residue was dissolved in ethyl acetate. The organic solution was extracted with 0.5N HCl (4×100 ml) and the aqueous acid extracts were combined and made basic with 10N NaOH. The aqueous was then extracted with ethyl acetate (5×100 ml)

and the combined extracts were dried over MgSO4 and concentrated to yield 12.1 g (74.4%) of ethyl 1-methyl-3-(2'-fluoro)-benzyl-nipecotate as an orange oil.

1H-NMR (CDCl3) δ: 7.22–7.15 (m, 1H), 7.10–6.95 (m, 3H), 4.14–4.05 (m, 2H), 3.01 (bd, 1H, J=10.3 Hz), 2.87 (s, 2H), 2.58 (bd, 1H, J=10.3 Hz), 2.24 (s, 3H), 2.04-1.95 (m, 3H), 1.69–1.60 (m, 2H), 1.30–1.22 (m, 1H), 1.16 (t, 3H, J=7.1 Hz).

EXAMPLE 515

1-Methyl-3-hydroxymethyl-3-(2'-fluorobenzyl)-piperidine

To a mixture of lithium aluminum hydride (2.00 g, 50.0 mmol) in diethyl ether (100 ml) at 0° C. was added over 0.5 hour, ethyl 1-methyl-3-(2'-fluoro)-benzyl-nipecotate (121 g, 43.5 mmol) in diethyl ether (10 ml) and tetrahydrofuran (50 ml) and the resulting solution was stirred for 0.5 hour at 0° C. and then warmed to room temperature for 4 hours. To the mixture was added saturated sodium potassium tartrate (50 ml) followed by crushed ice. The layers were separated and the aqueous was extracted with ethyl acetate. The combined extracts were dried over MgSO4 and concentrated. The product was crystallized from a small amount of hexane to yield 8.77 g (85%) of 1-methyl-3-hydroxymethyl-3-(2'-fluoro)benzyl-piperidine as a pale yellow solid: mp 58°–60° C.

1H-NMR (CDCl3) δ: 7.21–6.98 (m, 4H), 5.20–4.20 (bs, 1H), 3.66 (d, 1H, J=10.5 Hz), 3.57 (d, 1H, J=10.5 Hz), 2.65–2.55 (m, 2H), 2.54 (s, 2H), 2.04 (s, 3H), 2.01–1.95 (m, 3H), 1.64–1.54 (m, 2H), 1.33–1.28 (m, 1H).

EXAMPLE 516

N-Methyldihydrospirobenzopyran-3,3'-piperidine

A solution of 1-methyl-3-hydroxymethyl-3-(2'-fluorobenzyl)piperidine (400 mg, 1.68 mmol) in DMF (3 mL) was treated with NaH (200 mg of 60% dispersion, 5 mmol) and heated to 120° C. for 3 hours. The reaction mixture was then cooled to RT and diluted with ethyl acetate (20 mL) and poured into 20 mL saturated sodium bicarbonate. The layers were separated and the aqueous phase was extracted with 20 mL ethyl acetate. The organics were combined, dried over MgSO4, filtered and concentrated in vacuo. The residue was chromatographed on silica gel eluting with 3% MeOH/chloroform to give 266 mg (76%) of the title compound. The hydrochloride salt was generated in EtOH with excess ethanolic HCl. The solid was collected and dried in vacuo to give 150 mg, mp=227.

1H-NMR (CDCl3) δ: 7.2–7.0 (m, 2H), 3.95 (br s, 2H), 2.8 (d, J=Hz, 1H), 2.58 (d, J=Hz, 1H), 2.39 (m, 2H), 2.20 (m, 2H), 2.20 (s, 3H), 1.65 (m, 2H), 1.5-12 (m, 2H).

Employing the reaction sequence substantially as described in Examples 498, 499 and 500, there are produced the following compounds of Table XLIII (starting with an appropriate N-substituted ethyl nipecotate).

TABLE XLIII

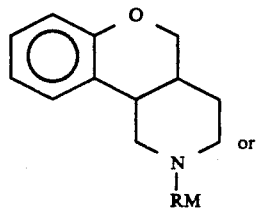

or

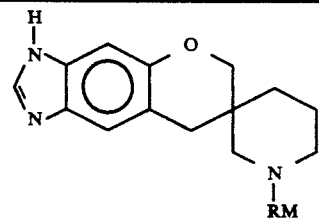

wherein RM is

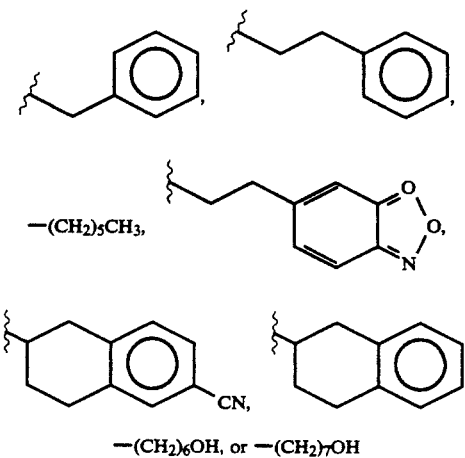

Employing the reaction sequence of Examples 498, 499, and 500, except starting with the appropriate N-substituted ethyl isonipecotate and 2-fluorobenzyl halide, there are produced the compounds of Table XLIV.

TABLE XLIV

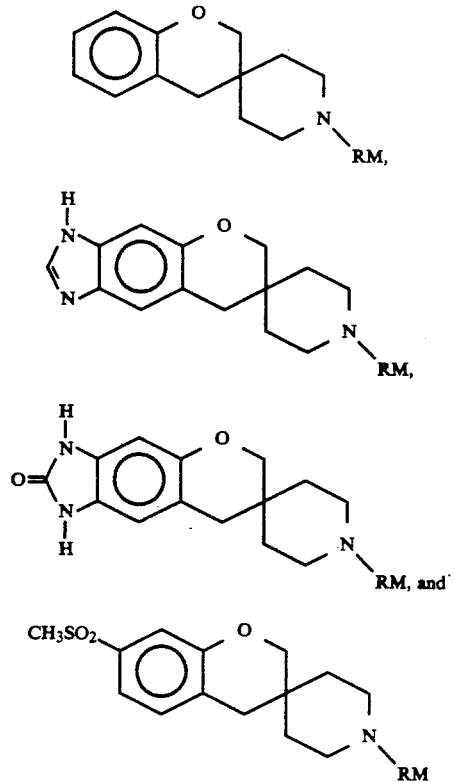

TABLE XLIV-continued wherein —RM is

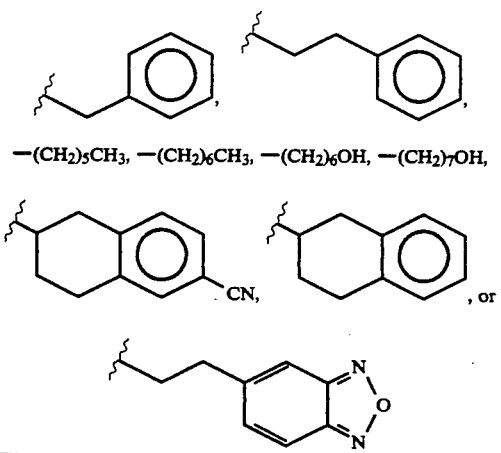

—(CH$_2$)$_5$CH$_3$, —(CH$_2$)$_6$CH$_3$, —(CH$_2$)$_6$OH, —(CH$_2$)$_7$OH,

Employing the procedures of Example 416 and substituting the appropriate alcohol and the appropriate nitrile for acetonitrile, there were produced the compounds of XLV.

TABLE XLV

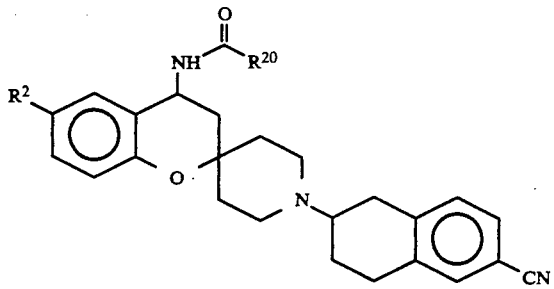

| EXAMPLE | R$^2$ | R$^{20}$ | SALT | M.P. (°C.) |
|---|---|---|---|---|
| 517 | CH$_3$SO$_2$NH— | CH$_3$ | .HCl .0.35 H$_2$O | 317(dec) |
| 518 | CH$_3$SO$_2$NH— | —CH$_2$CH$_2$CO$_2$CH$_3$ | .HCl .0.25 H$_2$O | 232–234(dec) |
| 519 | CH$_3$SO$_2$NH— | —CH$_2$CH$_2$OCH$_3$ | .HCl | 258–260(dec) |
| 520 | CH$_3$SO$_2$NH— | —(CH$_2$)$_2$OH | .HCl | 178–180(dec) |
| 521 | CH$_3$SO$_2$— | CH$_3$ | .HCl .0.45 H$_2$O | 296–298 |

Employing the procedures of Example 416 and substituting the appropriate alcohol and the appropriate nitrile, there are produced the compounds of Table XLVI.

TABLE XLVI

[Structure with R$^1$, R$^2$ substituents on benzopyran-piperidine-tetrahydronaphthalene-CN core with NHC(O)R$^{20}$ group]

| R$^1$ | R$^2$ | R$^{20}$ |
|---|---|---|
| H | CH$_3$SO$_2$— | —CH$_2$CH$_2$OH |
| H | CH$_3$SO$_2$— | —CH$_2$CH$_2$OCH$_3$ |
| H | CH$_3$SO$_2$— | —CH$_2$CH$_2$COOCH$_3$ |
| —NHCONH— | | —CH$_2$CH$_2$OH |
| —NHCONH— | | —CH$_3$ |
| —NHCONH— | | —CH$_2$CH$_2$COOCH$_3$ |
| —NHCONH— | | —CH$_2$CH$_2$OCH$_3$ |
| —N=CH—NH— | | —CH$_3$CH$_2$OH |
| —N=CH—NH— | | —CH$_3$ |
| —N=CH—NH— | | —CH$_3$CH$_2$OCH$_3$ |
| —N=CH—NH— | | —CH$_2$CH$_2$COOCH$_3$ |

Employing the procedure substantially as described in Example 83 but substituting 6-methanesulfonamido-3,4-dihydro-3-methyl-spiro[(2H)-1-benzopyran-2,4'-piperidin]-4-one hydrochloride for the 3,4-dihydro-6-methanesulfonamido-spiro[(2H)-1-benzopyran-2,3'-piperidine]-4-one hydrochloride used therein, and substituting an appropriate electrophile for the 5-(2-bromoethyl)benzofurazan, the following compounds of Table XLVII were prepared.

TABLE XLVII

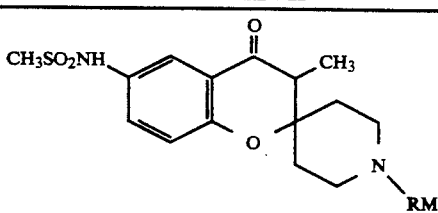

| EXAMPLE | RM | SALT | M. P. (°C.) |
|---|---|---|---|
| 522 | —(CH$_2$)$_5$CH$_3$ | .HCl | 261–264 |
| 523 | —(CH$_2$)$_7$OH | .HCl | 234–236 |
| 524 | —(CH$_2$)$_3$SCH$_2$CH$_2$CH$_3$ | .HCl | 241–243 |
| 525$^a$ | —(CH$_2$)$_3$SOCH$_2$CH$_2$CH$_3$ | .HCl | (Foam) |

$^a$This compound was produced by oxidation of the corresponding sulfide using sodium meta-periodate (1.1 moles per mole of sulfide) in an aqueous methanol mixture at room temperature.

The compounds of Table XLVIII are prepared by methods previously described:

TABLE XLVIII

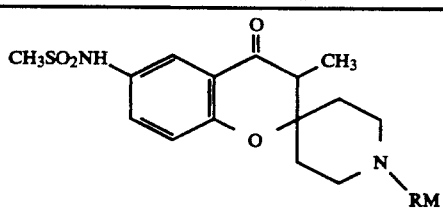

wherein RM is

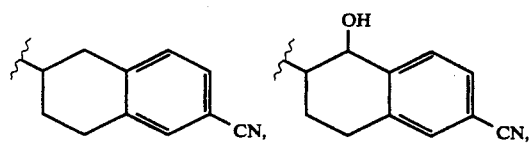

TABLE XLVIII-continued

—(CH$_2$)$_6$—OH, —(CH$_2$)$_6$CH$_3$, or —CH$_2$CH$_2$—⟨C$_6$H$_4$⟩—CN

The compounds of Table XLIX are prepared by methods previously described:

TABLE XLIX

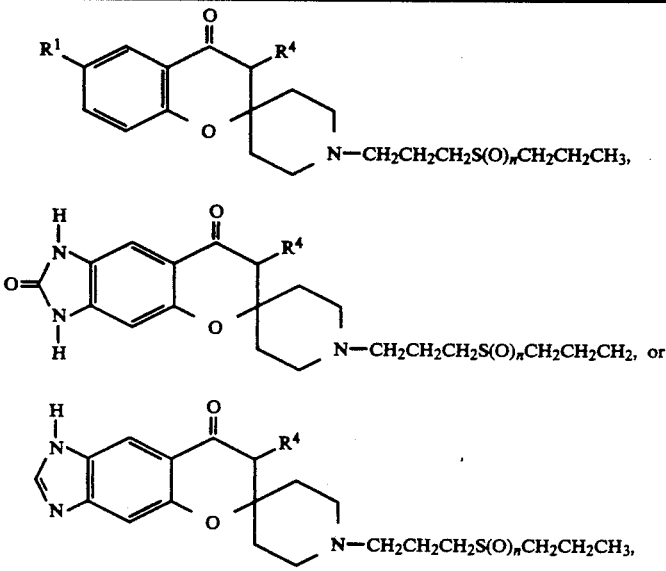

wherein R$^1$ is CH$_3$SO$_2$NH or CH$_3$SO$_2$,
n is 0, 1 or 2 and R$^4$ is H or C$_{1-6}$ alkyl.

The compounds of Table L are prepared by methods previously described:

TABLE L

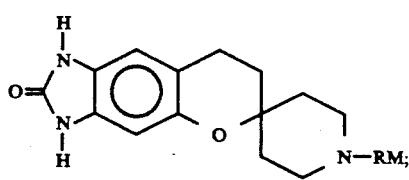

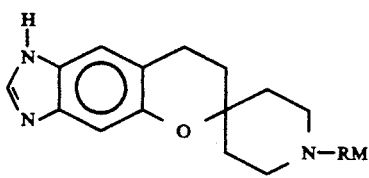

wherein —RM is

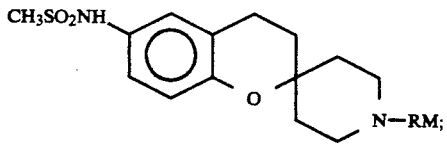

TABLE L-continued

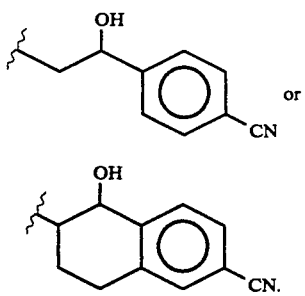

Utilizing the procedures essentially as described in Example 31 (Steps A, B, C and D), substituting N-benzoyl-ethyl nipecotate and p-methoxybenzyl bromide for the ethyl-1-benzoyl-4-piperidine carboxylate and benzyl bromide use therein and an appropriate electrophile for Step E, there were produced the compounds of Table LI:

TABLE LI

| EXAMPLE | MP (°C.) |
|---|---|
| 526 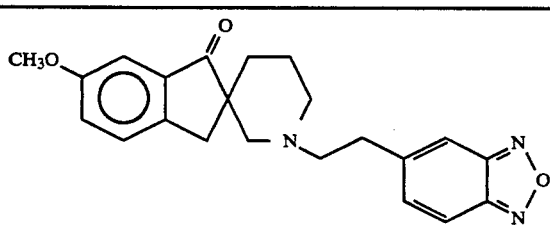 | 235–237 |
| 527 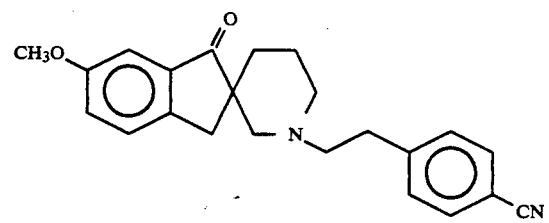 | 212–215 |

Employing the procedures previously described, there were produced the compounds of Table LII.

TABLE LII

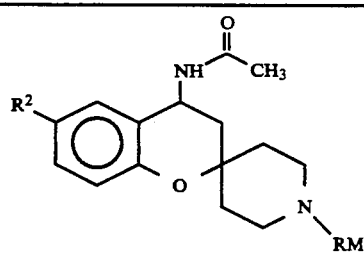

| EXAMPLE | $R^2$ | RM | SALT | M. P. (°C.) |
|---|---|---|---|---|
| 528a | $CH_3SO_2NH$ | $-(CH_2)_5CH_3$ | .HCl .0.2 $H_2O$ | >300 (dec.) |
| 528b | NC— | $-(CH_2)_2C_6H_5$ | .HCl .0.45 $H_2O$ | 298–300 |
| 528c | H | $-CH_2C_6H_5$ | .HCl .$H_2O$ | 282–285 (dec.) |

Employing the procedures previously described, there are produced the compounds of Table LIII.

TABLE LIII

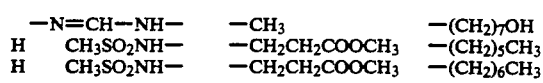

| $R^1$ | $R^2$ | $R^{20}$ | RM |
|---|---|---|---|
| H | $CH_3SO_2NH-$ | $-CH_3$ | $-(CH_2)_6CH_3$ |
| H | $CH_3SO_2NH-$ | $-CH_3$ | $-(CH_2)_6OH$ |
| H | $CH_3SO_2NH-$ | $-CH_3$ | $-(CH_2)_7OH$ |
| H | $CH_3SO_2-$ | $-CH_3$ | $-(CH_2)_5CH_3$ |
| H | $CH_3SO_2-$ | $-CH_3$ | $-(CH_2)_6CH_3$ |
| H | $CH_3SO_2-$ | $-CH_3$ | $-(CH_2)_6OH$ |
| H | $CH_3SO_2-$ | $-CH_3$ | $-(CH_2)_7OH$ |
| —NHCONH— | | $-CH_3$ | $-(CH_2)_5CH_3$ |
| —NHCONH— | | $-CH_3$ | $-(CH_2)_6CH_3$ |
| —NHCONH— | | $-CH_3$ | $-(CH_2)_6OH$ |
| —NHCONH— | | $-CH_3$ | $-(CH_2)_7OH$ |
| —N=CH—NH— | | $-CH_3$ | $-(CH_2)_5CH_3$ |
| —N=CH—NH— | | $-CH_3$ | $-(CH_2)_6CH_3$ |
| —N=CH—NH— | | $-CH_3$ | $-(CH_2)_6OH$ |
| —N=CH—NH— | | $-CH_3$ | $-(CH_2)_7OH$ |
| H | $CH_3SO_2NH-$ | $-CH_2CH_2COOCH_3$ | $-(CH_2)_5CH_3$ |
| H | $CH_3SO_2NH-$ | $-CH_2CH_2COOCH_3$ | $-(CH_2)_6CH_3$ |

TABLE LIII-continued

Structure: R²/R¹-substituted benzopyran with NH-C(=O)-R²⁰ at 4-position, spiro piperidine with N-RM.

| R¹ | R² | R²⁰ | RM |
|---|---|---|---|
| H | CH₃SO₂NH— | —CH₂CH₂COOCH₃ | —(CH₂)₆OH |
| H | CH₃SO₂NH— | —CH₂CH₂COOCH₃ | —(CH₂)₇OH |
| H | CH₃SO₂— | —CH₂CH₂COOCH₃ | —(CH₂)₅CH₃ |
| H | CH₃SO₂— | —CH₂CH₂COOCH₃ | —(CH₂)₆CH₃ |
| H | CH₃SO₂— | —CH₂CH₂COOCH₃ | —(CH₂)₆OH |
| H | CH₃SO₂— | —CH₂CH₂COOCH₃ | —(CH₂)₇OH |
| —NHCONH— | | —CH₂CH₂COOCH₃ | —(CH₂)₅CH₃ |
| —NHCONH— | | —CH₂CH₂COOCH₃ | —(CH₂)₆CH₃ |
| —NHCONH— | | —CH₂CH₂COOCH₃ | —(CH₂)₆OH |
| —NHCONH— | | —CH₂CH₂COOCH₃ | —(CH₂)₇OH |
| —N=CH—NH— | | —CH₂CH₂COOCH₃ | —(CH₂)₅CH₃ |
| —N=CH—NH— | | —CH₂CH₂COOCH₃ | —(CH₂)₆CH₃ |
| —N=CH—NH— | | —CH₂CH₂COOCH₃ | —(CH₂)₆OH |
| —N=CH—NH— | | —CH₂CH₂COOCH₃ | —(CH₂)₇OH |
| H | CH₃SO₂NH— | —CH₂CH₂OH | —(CH₂)₅CH₃ |
| H | CH₃SO₂NH— | —CH₂CH₂OH | —(CH₂)₆CH₃ |
| H | CH₃SO₂NH— | —CH₂CH₂OH | —(CH₂)₆OH |
| H | CH₃SO₂NH— | —CH₂CH₂OH | —(CH₂)₇OH |
| H | CH₃SO₂— | —CH₂CH₂OH | —(CH₂)₅CH₃ |
| H | CH₃SO₂— | —CH₂CH₂OH | —(CH₂)₆CH₃ |
| H | CH₃SO₂— | —CH₂CH₂OH | —(CH₂)₆OH |
| H | CH₃SO₂— | —CH₂CH₂OH | —(CH₂)₇OH |
| —NHCONH— | | —CH₂CH₂OH | —(CH₂)₅CH₃ |
| —NHCONH— | | —CH₂CH₂OH | —(CH₂)₆CH₃ |
| —NHCONH— | | —CH₂CH₂OH | —(CH₂)₆OH |
| —NHCONH— | | —CH₂CH₂OH | —(CH₂)₇OH |
| —N=CH—NH— | | —CH₂CH₂OH | —(CH₂)₅CH₃ |
| —N=CH—NH— | | —CH₂CH₂OH | —(CH₂)₆CH₃ |
| —N=CH—NH— | | —CH₂CH₂OH | —(CH₂)₆OH |
| —N=CH—NH— | | —CH₂CH₂OH | —(CH₂)₇OH |
| H | CH₃SO₂NH— | —CH₂CH₂OCH₃ | —(CH₂)₅CH₃ |
| H | CH₃SO₂NH— | —CH₂CH₂OCH₃ | —(CH₂)₆CH₃ |
| H | CH₃SO₂NH— | —CH₂CH₂OCH₃ | —(CH₂)₆OH |
| H | CH₃SO₂NH— | —CH₂CH₂OCH₃ | —(CH₂)₇OH |
| H | CH₃SO₂— | —CH₂CH₂OCH₃ | —(CH₂)₅CH₃ |
| H | CH₃SO₂— | —CH₂CH₂OCH₃ | —(CH₂)₆CH₃ |
| H | CH₃SO₂— | —CH₂CH₂OCH₃ | —(CH₂)₆OH |
| H | CH₃SO₂— | —CH₂CH₂OCH₃ | —(CH₂)₇OH |
| —NHCONH— | | —CH₂CH₂OCH₃ | —(CH₂)₅CH₃ |
| —NHCONH— | | —CH₂CH₂OCH₃ | —(CH₂)₆CH₃ |
| —NHCONH— | | —CH₂CH₂OCH₃ | —(CH₂)₆OH |
| —NHCONH— | | —CH₂CH₂OCH₃ | —(CH₂)₇OH |
| —N=CH—NH— | | —CH₂CH₂OCH₃ | —(CH₂)₅CH₃ |
| —N=CH—NH— | | —CH₂CH₂OCH₃ | —(CH₂)₆CH₃ |
| —N=CH—NH— | | —CH₂CH₂OCH₃ | —(CH₂)₆OH |
| —N=CH—NH— | | —CH₂CH₂OCH₃ | —(CH₂)₇OH |
| H | CH₃SO₂NH— | —CH₂CH₃ | —(CH₂)₅CH₃ |
| H | CH₃SO₂NH— | —CH₂CH₃ | —(CH₂)₆CH₃ |
| H | CH₃SO₂NH— | —CH₂CH₃ | —(CH₂)₆OH |
| H | CH₃SO₂NH— | —CH₂CH₃ | —(CH₂)₇OH |
| H | CH₃SO₂— | —CH₂CH₃ | —(CH₂)₅CH₃ |
| H | CH₃SO₂— | —CH₂CH₃ | —(CH₂)₆CH₃ |
| H | CH₃SO₂— | —CH₂CH₃ | —(CH₂)₆OH |
| H | CH₃SO₂— | —CH₂CH₃ | —(CH₂)₇OH |
| —NHCONH— | | —CH₂CH₃ | —(CH₂)₅CH₃ |
| —NHCONH— | | —CH₂CH₃ | —(CH₂)₆CH₃ |
| —NHCONH— | | —CH₂CH₃ | —(CH₂)₆OH |
| —NHCONH— | | —CH₂CH₃ | —(CH₂)₇OH |
| —N=CH—NH— | | —CH₂CH₃ | —(CH₂)₅CH₃ |
| —N=CH—NH— | | —CH₂CH₃ | —(CH₂)₆CH₃ |
| —N=CH—NH— | | —CH₂CH₃ | —(CH₂)₆OH |
| —N=CH—NH— | | —CH₂CH₃ | —(CH₂)₇OH |

EXAMPLE 529

3,4-Dihydro-5-methoxy-6-methanesulfonamido-spiro[2H-1-benzopyran-2,4′-piperidine]-4-one hydrochloride Step A: Preparation of 1′-Acetyl-3,4-dihydro-5-hydroxy-spiro[2H-1-benzopyran-2,4′-piperidine]-4-one 2′,5′-Dihydroxyacetophenone and 1-acetyl-4-piperidone were condensed according to the method of Example 434 to give the ketone as a yellow solid, m.p. 114°–116° C. (from EtOAc/hexane).

Step B: Preparation of 1′-Acetyl-3,4-dihydro-5-hydroxy-6-nitro-spiro[2H-1-benzopyran-2,4′-piperidine]-4-one 1′-Acetyl-3,4-dihydro-5-hydroxy-spiro[2H-1-benzopyran-2,4′-piperidine]-4-one was nitrated according to the method of Example 456 to give a mixture of regioisomeric nitration products. This was recrystallized from ethyl acetate to give a single isomer which was identified by long range $^1$H-$^{13}$C coupling NMR experiments as 1′-acetyl-3,4-dihydro-5-hydroxy-6-nitro-spiro[2H-1-benzopyran-2,4′-piperidine]-4-one, yellow solid, m.p. 201°–202° C.

Step C: Preparation of 1′-acetyl-3,4-dihydro-5-methoxy-6-nitro-spiro[2H-1-benzopyran-2,4′-piperidine]-4-one A mixture of 1′-acetyl-3,4-dihydro-5-hydroxy-6-nitro-spiro[2H-1-benzopyran-2,4′-piperidine]-4-one (3.84 g, 12 mmol), potassium carbonate (1.66 g, 12 mmol) and methyl iodide (3.74 ml, 8.51 g, 60 mmol) in DMF (30 ml) was stirred in a sealed vessel at room temperature for 3 days, adding further portions of methyl iodide (1 ml) after 24 and 48 h. The solvent was evaporated under reduced pressure, water (60 ml) was added, the pH was adjusted to 6.5 with HCl-H₂O (2M) and the mixture was extracted with methylene chloride (3×60 ml). The combined organic fractions were dried (Na₂SO₄) and evaporated under reduced pressure. The crude product was re-subjected to the above procedure, the solvent was evaporated under reduced pressure, water (60 ml) was added and the mixture was extracted with methylene chloride (3×60 ml). The combined organic fractions were dried (Na₂SO₄) and evaporated under reduced pressure to give the ketone (4.08 g) as a yellow solid, m.p. 160°–165° C.

Step D: Preparation of 1′-Acetyl-3,4-dihydro-5-methoxy-6-methanesulfonamido-spiro[2H-1-benzopyran-2,4′-piperidine]-4-one 1′-Acetyl-3,4-dihydro-5-methoxy-6-nitrospiro-[2H-1-benzopyran-2,4′-piperidine]-4-one (3.91 g, 11.5 mmol) was dissolved in acetic acid (46 ml) and titanium trichloride (15% solution in 20–30% HCl-H₂O, 44.7 ml) was added dropwise over 75 min. The mixture was stirred at room temperature for 1 h., the pH was adjusted to 10 with aqueous sodium carbonate (saturated), water (500 ml) was added and the mixture was extracted with ethyl acetate (3×500 ml). The combined organic fractions were washed with water (100 ml) and brine (100 ml), dried (Na₂SO₄) and evaporated under reduced pressure to give an orange foam (3.85 g). Methylene chloride (50 ml), pyridine (1.82 ml, 1.79 g, 22.6 mmol) and methanesulfonyl chloride (1.08 ml, 1.60 g, 14 mmol) were added and the mixture was stirred overnight at room temperature. Ethyl acetate (150 ml) and aqueous sodium hydrogen carbonate (saturated, 75 ml) were added and the layers were separated. The aqueous layer was extracted with ethyl acetate (150 ml) and the combined organic fractions were washed with water (50 ml) and brine (50 ml), dried (Na₂SO₄) and evaporated under reduced pressure. The residue was purified by flash column chromatography on silica gel, eluting with CHCl₃/MeOH (97:3) to give the ketone (3.78 g, 88%) as a pale yellow foam.

¹H(CDCl₃) δ7.73 (1H, d, J 9.0 Hz), 6.83 (1H, d, J 9.0 Hz), 6.78 (1H, s), 4.4 (1H, br m), 3.90 (3H, s), 3.6, 3.5, 3.1 (Each 1H, br m), 3.00 (3H, s), 2.72 (2H, s), 2.12 (3H, s), 2.1 and 1.7 (Each 2H, m).

Step E: Preparation of 3,4-Dihydro-5-methoxy-6-methane-sulfonamido-spiro[2H-1-benzopyran-2,4'-piperidine]-4-one hydrochloride 1'-Acetyl-3,4-dihydro-5-methoxy-6-methanesulfonamido-spiro[2H-1-benzopyran-2,4'-piperidine]-4-one was hydrolyzed according to the method of Example 437 to give the hydrochloride as a white solid, m.p. 263°–267° C.

The compounds of Table LIV were prepared from 3,4-dihydro-5-methoxy-6-methanesulfonamido-spiro[2H-1-benzopyran-2,4'-piperidine]-4-one hydrochloride by the method described in Example 92, step B.

hydride (4.6 g, 122 mmol) was added in portions and the mixture was stirred at room temperature for 1.5 h. The mixture was poured into water (600 ml), the ethanol was evaporated under reduced pressure and the mixture was extracted with methylene chloride (4×400 ml). The combined organic fractions were dried (Na₂SO₄) and evaporated under reduced pressure to give the pyran as a yellow foam (22.93 g, 65%), m.p. 215°–220° C.

Step B: Preparation of (±)-3,4-dihydro-6-methanesulfonamido-4-(1-pyrrolidinyl)-spiro[2H-1-benzopyran-2,4'-piperidine]dihydrochloride (±)-1'-Benzoyl-3,4-dihydro-6-methanesulfonamido-4-(1-pyrrolidinyl)-spiro[2H-1-benzopyran-2,4'-piperidine] was hydrolyzed according to the method of Example 437 to give the dihydrochloride as a white solid, m.p. 215°–233° C. (softens at 150°–160° C.).

The compounds of Table LV were prepared from (±)-3,4-dihydro-6-methanesulfonamido-4-(1-pyrrolidinyl)-spiro[2H-1-benzopyran-2,4'-piperidine] dihydrochloride by the method described in Example 92, step B.

TABLE LIV

| EXAMPLE | RM | SALT | M.P. (°C.) |
|---|---|---|---|
| 530 | (3-(4-cyanophenyl)propyl) | .HCl | 224–225 |
| 531 | (3-(benzofurazan-5-yl)propyl) | .HCl | 225–226 |
| 532 | —(CH₂)₅CH₃ | .HCl .0.1C₂H₅OH | 213–214 |
| 533 | —(CH₂)₆CH₃ | .HCl .0.75H₂O .0.05C₂H₅OH | 209–210 |
| 534 | —(CH₂)₇OH | .HCl | 195–196 |
| 535 | —(CH₂)₆OH | .HCl | 206–207 |

EXAMPLE 536

(±)-3,4-Dihydro-6-methanesulfonamido-4-(1-pyrrolidinyl)-spiro[2H-1-benzopyran-2,4'-piperidine]dihydrochloride Step A: Preparation of (±)-1'-benzoyl-3,4-dihydro-6-methanesulfonamido-4-(1-pyrrolidinyl)-spiro[2H-1-benzopyran-2,4'-piperidine]

A solution of 2'-hydroxy-5'-methanesulfonamidoacetophenone (16.1 g, 75 mmol) and pyrrolidine (6.3 ml, 75 mmol) in methanol (185 ml) was added to a solution of 1-benzoyl-4-piperidone (15.2 g, 75 mmol) in methanol (110 ml). The mixture was stirred at room temperature overnight and the resulting solid was collected and dried in vacuo. Ethanol (600 ml) was added and the mixture was cooled in ice. Sodium borohydride

TABLE LV

| Example | RM | Salt | M.P. (°C.) |
|---|---|---|---|
| 537 | —(CH₂)₅CH₃ | .2HCl .0.5H₂O | 243–245 |
| 538 | —(CH₂)₆CH₃ | .2HCl | 180–185 |

TABLE LV-continued

Structure: CH₃SO₂NH-phenyl fused to benzopyran with pyrrolidine-N substituent at position adjacent, spiro-linked to piperidine (N—RM)

| Example | RM | Salt | M.P. (°C.) |
|---|---|---|---|
| 539 | ~~~-(CH₂)₂-benzofurazan | .2HCl .1.25H₂O | 205–215 |
| 540 | ~~~-(CH₂)₂-C₆H₄-CN (para) | .2HCl .H₂O | 246–253 |

EXAMPLE 541

3,4-Dihydro-6-methanesulfonyl-spiro[2H-1-benzopyran-2,4'-piperidine] hydrochloride Step A: Preparation of 1'-benzoyl-3,4-dihydro-6-methanesulfonyl-spiro[2H-1-benzopyran-2,4'-piperidine]-4-one 2'-Hydroxy-5'-methanesulfonylacetophenone and 1-benzoyl-4-piperidone were condensed according to the method of Example 434 to give the ketone as a white solid, m.p. 155°–157° C.

Step B: Preparation of 3,4-dihydro-6-methanesulfonyl-spiro[2H-1-benzopyran-2,4'-piperidine] hydrochloride 1'-Benzoyl-3,4-dihydro-6-methanesulfonyl-spiro[2H-1-benzopyran-2,4'-piperidine]-4-one was reduced, dehydrated, hydrogenated and hydrolyzed according to the methods of Examples 435 and 437 to give the hydrochloride as a white solid, m.p. >320° C.

The compounds of Table LVI were prepared from 3,4-dihydro-6-methanesulfonyl-spiro[2H-1-benzopyran-2,4'-piperidine]hydrochloride by the method described in Example 92, step B.

TABLE LVI

Structure: CH₃SO₂-phenyl fused to benzopyran spiro-linked to piperidine (N—RM)

| Example | RM | Salt | M.P. (°C.) |
|---|---|---|---|
| 542 | ~~~-(CH₂)₂-benzofurazan | .HCl .0.25H₂O | 205–215 |
| 543 | ~~~-(CH₂)₂-C₆H₄-CN (para) | .HCl .0.5H₂O | 246–253 |
| 544 | —(CH₂)₅CH₃ | .HCl | 240–245 |
| 545 | —(CH₂)₆CH₃ | .HCl | 230–234 |
| 546 | —(CH₂)₃S(CH₂)₂CH₃ | .HCl .0.25H₂O | 238–240 |
| 547[a] | —(CH₂)₃SO(CH₂)₂CH₃ | .HCl | 218–220 |
| 548[b] | —(CH₂)₃SO₂(CH₂)₂CH₃ | .HCl | 254–256 |
| 549 | —(CH₂)₆OH | .HCl | 179–186 |
| 550 | —(CH₂)₇OH | .HCl .0.5H₂O | 178–185 |

[a]This compound was produced by oxidation of the corresponding sulfide using sodium metaperiodate (1.1 moles per mole of sulfide) in aqueous methanol at room temperature.

[b]This compound was produced by oxidation of the corresponding sulfide using Oxone ® (2 moles per mole of sulfide) in aqueous methanol at room temperature.

EXAMPLE 551

3,4-Dihydro-6-methanesulfonyl-spiro[2H-1-benzopyran-2,4'-piperidine]-4-one hydrochloride Step A: Preparation of 1'-Acetyl-3,4-dihydro-6-methanesulfonyl-spiro[2H-1-benzopyran-2,4'-piperidine]-4-one 2'-Hydroxy-5'-methanesulfonylacetophenone and 1-acetyl-4-piperidone were condensed according to the method of Example 434 to give the ketone as a white solid, m.p. 105°–110° C.

Step B: Preparation of 3,4-Dihydro-6-methanesulfonylspiro[2H-1-benzopyran-2,4'-piperidine]-4-one hydrochloride 1'-Acetyl-3,4-dihydro-6-methanesulfonylspiro[2H-1-benzopyran-2,4'-piperidine]-4-one was hydrolyzed according to the method of Example 437 to give the hydrochloride as a white solid, m.p. 260°–264° C. (darkens at 241° C.). The compounds of Table LVII were prepared from 3,4-dihydro-6-methanesulfonyl-spiro[2H-1-benzopyran-2,4'-piperidine]-4-one hydrochloride by the method described in Example 92, step B.

TABLE LVII

Structure: CH₃SO₂-phenyl fused to benzopyran-4-one spiro-linked to piperidine (N—RM)

| Example | RM | Salt | M.P. (°C.) |
|---|---|---|---|
| 552 | —(CH₂)₃S(CH₂)₂CH₃ | .HCl | 248–249 |
| 553[a] | —(CH₂)₃SO(CH₂)₂CH₃ | .HCl | 232–234 |
| 554 | —(CH₂)₇OH | .HCl | 189–191 |
| 555 | —(CH₂)₆OH | .HCl .0.75H₂O | 197–199 |

EXAMPLE 556

(+)-N-[1'-(6-Cyano-1,2,3,4-tetrahydro-2-napthalenyl)-3,4-dihydro-4-hydroxyspiro[2H-1-benzopyran-2,4'-piperidin]yl]methanesulfonamide hydrochloride (+)-N-[1'-(6-Cyano-1,2,3,4-tetrahydro-2-napthalenyl)-3,4-dihydro-4-oxospiro[2H-1-benzopyran-2,4'-peridin]yl]methanesulfonamide (581 mg, 1.25 mmol) was dissolved with warming in methylene chloride (20 ml) and cooled to −20° C. A solution of (S)-tetrahydro-1-methyl-3,3-diphenyl-1H,3H-pyrrolo[1,2,c][1,3,2]oxazaborole-borane complex (400 mg, 1.38 mmol) in methylene chloride (4 ml) was added dropwise [Reaction temperature <−15° C.] and the mixture was stirred under argon at −20° to −15° C. for 1 h, then at ambient temperature for 30 min. Methanol (20 ml) was added, followed after 10 min. by HCl—H$_2$O (1M, 10 ml). The mixture was stirred for 1 h., diluted with aqueous sodium hydrogen carbonate (Saturated, 20 ml) and extracted with methylene chloride (3×20 ml). The combined organic fractions were dried (Na$_2$SO$_4$) and evaporated under reduced pressure to give a white foam (981 mg). This was dissolved in methylene chloride (25 ml) and cooled in ice. Four portions of acetic anhydride (132 ml, 142 mg, 1.4 mmol) were added at hourly intervals. After 4 h. at 0° C., the mixture was stirred at ambient temperature for a further 20 h. Methanol (10 ml) and aqueous sodium hydrogen carbonate (Saturated, 10 ml) were added and the mixture was stirred vigorously for 1 h. Aqueous sodium hydrogen carbonate (Saturated, 20 ml) was added and the mixture was extracted with methylene chloride (3×20 ml). The combined organic fractions were dried (Na$_2$SO$_4$) and evaporated under reduced pressure to give a white foam (1.05 g). The residue was purified by flash column chromatography on silica gel, eluting with CH$_2$Cl$_2$/MeOH/NH$_3$—H$_2$O (94:6:0.6 increasing to 90:10:1), re-chromatographing impure fractions. Pure fractions were evaporated under reduced pressure, re-dissolved in CH$_2$Cl$_2$ (20 ml), filtered through anhydrous Na$_2$SO$_4$ and evaporated under reduced pressure to give a white foam (369 mg, 63%). The residue was dissolved in ethanol (4 ml) and HCl—EtOH (6M, 0.5 ml) was added dropwise with stirring. The mixture was stirred at ambient temperature for 1 h., then refrigerated over night. The solid was collected by filtration under argon, then dried in vacuo at ambient temperature for 48 h. and at 35° C. for 24 h to give the hydrochloride as a white solid (321 mg), m.p. 211°–213° C., [α]$_d$+30.5° (c=0.102, MeOH).

HPLC analysis [Ultron ES OVM column; 0.3% n-propanol/ammonium foramate-water (12 g/l)] showed this to be the faster eluting diastereoisomer.

Elementary analysis: Calc'd for C$_{25}$H$_{30}$ClN$_3$O$_4$S: C 59.57; H 6.00; N 8.34%. Found: C 59.45; H 5.76; N 8.40%.

The compounds of Table LVIII were prepared according to the method described in Example 556 by reducing the appropriate ketone with (R)- or (S)-tetrahydro-1-methyl-3,3-diphenyl-1H,3H-pyrrolo-[1,2,c][1,3,2]oxazaborole-borane complex as indicated.

TABLE LVIII

| EXAMPLE | RM | (R)-/(S)-Boron [α]$_d$ Complex | SALT | M.P. (°C.) |
| --- | --- | --- | --- | --- |
| 557 | tetrahydronaphthalene-CN | R +57.5° | .HCl .0.4H$_2$O .0.55EtOH | 179–181 |
| 558 | benzoxadiazole-ethyl | S −12.2° | .HCl | 233–235 |
| 559 | benzoxadiazole-ethyl (isomer) | R +14.9° | .HCl | 225–227 |

EXAMPLE 560

(±)-1-[(5,6,7,8-Tetrahydro-2-napthalenecarbonitrile)-6-yl]-2',3'-dihydro-2'-oxo-spiro[piperidine-4,6'(1'H)-pyrano[2,3-f]benzimidazole] hydrochloride Sodium borohydride (42 mg, 1.1 mmol) was added to a suspension of (±)-1-[(5,6,7,8-tetrahydro-2-napthalenecarbonitrile)-6-yl]-2',3',7',8'-tetrahydro-2',8'-dioxo-spiro[piperidine-4,6'(1'H)-pyrano[2,3-f]benzimidazole] (235 mg, 0.55 mmol) in ethanol (5.5 ml). The mixture was stirred at room temperature for 19 h., further sodium borohydride (42 mg, 1.1 mmol) was edded and the mixture was stirred for a further 48 h. Aqueous sdium hydrogen carbonate (saturated, 25 ml) and water (10 ml) were added and the mixture was extracted with ethyl acetate (6×25 ml). The combined organic fractions were dried (Na₂SO₄) and evaporated under reduced pressure. The residue was purified by flash column chromatography on silica gel, eluting with CH₂Cl₂/MeOH/NH₃-H₂O (92:8:0.8 increasing to 86:14:1.4). Pure fractions were evaporated under reduced pressure, redissolved in CH₂Cl₂, filtered through anhydrous Na₂SO₄ and evaporated under reduced pressure to give a white solid (172 mg). A sample (25 mg) was suspended in ethanol (1 ml) and HCl-EtOH (6M, 0.5 ml) was added dropwise with stirring. The mixture was stirred at ambient temperature over night and the solvent was evaporated under reduced pressure. The residue was triturated with ehtanol (2 ml) and the solid was collected and dried in vacuo to give the hydrochloride as a white solid (19 mg, 73%), m.p. >285° C., [α]$_d$+60.2° (c=0.120, MeOH).

Elementary analysis for C₂₅H₂₅ClN₄O₂.0.5H₂O: Calculated: C 65.57; H 5.72; N 12.23%. Found: C 65.55; H 5.37; N 12.28%.

EXAMPLE 561

(±)-4-Ethylamino-3,4-dihydro-1'-(1-hexyl)-6-methanesulfonamido-spiro[(2H)-1-benzopyran-2,4'-piperidine] dihydrochloride To a solution of (±)-3,4-dihydro-1'-(1-hexyl)-6-methanesulfonamido-spiro[(2H)-1-benzopyran-2,4'-piperidine]-4-N-acetamide (340 mg, 0.778 mmol) in anhydrous THF (5 ml) was added a solution of lithium aluminum hydride in ethylene glycol dimethyl ether (1.71 ml, 0.855 mmol). The reaction was stirred at 50° C. for 2 h., quenched with water, the pH was adjusted to 11.0 with 40% NaOH-H₂O and the mixture was extracted with methylene chloride (3×25 ml). The combined organic fractions were evaporated under reduced pressure and the residue was purified by chromatography on silica (CH₂Cl₂/MeOH/NH₄OH, 90/10/2) to give 144 mg product which was crystallized from EtOAc by addition of a 1.3M anhydrous HCl-isopropanol solution to give the dihydrochloride (solvated with 0.25 equivalents of water), m.p. 220°-222° C.

EXAMPLE 562

(±)-4-Amino-3,4-dihydro-1'-(1-hexyl)-6-methanesulfonamido-spiro[(2H)-1-benzopyran-2,4'-piperidine] dihydrochloride A mixture of (±)-3,4-dihydro-1'-(1-hexyl)-6-methanesulfonamido-spiro[(2H)-1-benzopyran-2,4'-piperidine]-4-N-acetamide (1.0 g), ethanol (10 ml) and HCl-H₂O (12N, 10 ml) was refluxed for 24 h., cooled and the ethanol was evaporated under reduced pressure. Water was added, the mixture was basified with 40% NaOH-H₂O and extracted with methylene chloride. The combined organic fractions were evaporated under reduced pressure and the residue was purified by chromatography on silica gel (CH₂Cl₂/MeOH/NH₄OH, 90/10/2) to give, after salt formation, the dihydrochloride (solvated with 0.25 equivalents of water), m.p. 281°-283° C.

The compound of Table LIX was prepared from the corresponding acetamide by the method described in Example 562.

TABLE LIX

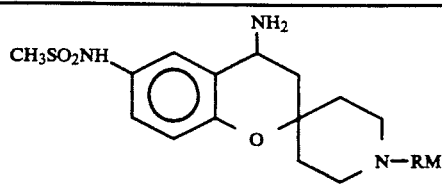

| Example | RM | Salt | M.P. (°C.) |
|---|---|---|---|
| 563 | ![naphthalene-CN] | .2HCl .H₂O .0.25EtOAc | 223–226 |

EXAMPLE 564

(±)-4-[1-(2-Oxopyrrolidinyl)]-3,4-dihydro-1'-(1-hexyl)-6-methanesulfonamido-spiro[(2H)-1-benzopyran-2,4'-piperidine]hydrochloride A mixture of (±)-4-amino-3,4-dihydro-1'-(1-hexyl)-6-methanesulfonamido-spiro[(2H)-1-benzopyran-2,4'-piperidine] (100 mg, 0.25 mmol) sodium bicarbonate (32 mg, 0.375 mmol) and ethyl-4-bromobutyrate (0.075 ml, 0.5 mmol) in acetonitrile (5 ml) was heated at 80° C. for 16–20 h. The solvent was evaporated under reduced pressure and the residue was purified by chromatography on silica (CH₂Cl₂/MeOH/NH₄OH, 90/10/2). The product was heated at 100° C. (sealed tube) with 1-hydroxybenzotriazole (12 mg) in toluene (0.5 ml) and dimethoxyethane (0.5 ml) for 8 h. The solvent was evaporated under reduced pressure and the residue was purified by chromatography on silica (CH₂Cl₂/MeOH, 97/3) to give, after salt formation, the hydrochloride (solvated with 0.5 equivalents of water, 21 mg, 16%), m.p. 263°-265° C.

The compound of Table LX was prepared from the corresponding amine by the method described in Example 564.

TABLE LX

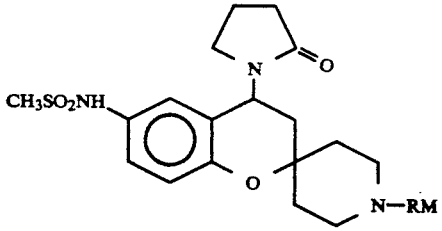

| Example | RM | M.P. (°C.) |
|---|---|---|
| 565 | ![naphthalene-CN] | >260 |

EXAMPLE 566

4-Acetamido-3,4-dihydro-1'-[(6-cyano-1,2,3,4-tetrahydronaphthalene)-2-yl]-6-methanesulfonamido-spiro-[(2H)-1-benzopyran-2,4'-piperidine]

A solution of the alcohol of Example 556 (0.198 g, 0.423 mmole) in methylene chloride (5 ml) was prepared, sieve dried 4A°, and filtered. The solution was cooled under argon to −50° C. and a solution of methanesulfonic anhydride (0.177 g, 1.02 mmole) slowly added. Diisoprolyethylamine (0.15 ml, 0.869 mmole) was then added at −50° C. and th reaction allowed to warm to −25° C. After 15 minutes at −25° C. the reaction was judged complete by TLC (90:10, $CH_2Cl_2$:MeOH) and a solution of tetrabutylammonium azide (0.423 g, 1.48 mmole) in methylene chloride (2 ml) added. The reaction was stirred at room temperature for ¼ hour (complete by TLC) and then passed thru a bed of silica gel (30 ml). The silica gel was washed with methylene chloride (25 ml) and the product then eluted with ethyl acetate (150 ml). Concentration of the ethyl acetate gave a foam (0.240 g) which was dissolved in methanol and treated with 10 ml of 1N NaOH. The solution was stirred for 4 hours, concentrated to remove the methanol and dissolved in water (50 ml) and methylene chloride (50 ml). The pH was adjusted to 8.5 with conc. HCl and the organic layer removed. The aqueous layer was washed with methylene chloride (25 ml). The organic layer were combined, dried over sodium sulfate, filtered and concentrated to a foam (0.180 g) the foam was dissolved in ethanol (30 ml) and hydrogenated over 10% Pd/C (36 mg, 20 wt%) at 1 atm for 18 hours. The mixture was filtered, cake washed with ethanol and filtrate concentrated to a foam (0.170 g). The foam was dissolved in methylene chloride (5 ml) cooled to 0° C. and triethylamine (0.051 ml, 0.366 mmole) and acetate anhydride (0.038 ml, 0.403 mmole) added. The solution was stirred at room temperature for 30 minutes diluted with an aqueous solution of sodium bicarbonate (10 ml) and organic layer removed. The aqueous layer was washed with methylene chloride (20 ml). The organic layers were combined concentrated to an oil and chromatographed on silica using methylene chloride/methanol (93:7) to give (0.160 g) of this Free Base). The solid 0.160 g was crystallized from isopropanol (5 ml) to give 0.132 g, m.p.=145°-147° C. The hydrochloride salt was prepared by addition of an isopropanol/HCl solution (1.1 eq) to a solution of the free base in isopropanol. Yield 0.124 g,-m.p. >300° C. Dec

EXAMPLE 567

According to the method of Example 566, the alcohol of Example 557 was converted to the corresponding acetamide, m.p. =180°-181° C., disastereomeric to the acetamide of Example 566.

EXAMPLE 568

In Vitro Test for Class III Antiarrhythmic Activity

Purpose

This in vitro assay is designed to assess possible potassium channel blocking activity of a compound based on its ability to prolong effective refractory period (ERP) in isolated papillary muscle.

Tissue Preparation

Ferrets (700 to 1200 grams) are anesthetized with 0.7 ml of a mixture of xylazine and ketamine HCL in 1:7 ratio. Papillary muscles from the right ventricle are quickly excised from the isolated heart and mounted in 50 ml organ baths containing Krebs-Henseleit solution (pH=7.2-7.4) at 37° C. The composition of the solution in millimoles per liter are as follows: NaCl, 118; KCl, 4.7; $NaHCO_3$, 23; $CaCl_2 2H_2O$ 2.0; $MgSO_4 7H_2O$, 1.2; $KH_2PO_4$, 1.2; Dextrose, 11.1. Timolol ($10^{-7}$M) is added to the solution to block the effects of catecholamines released during stimulation of the muscles. This solution is aerated with 95% $O_2$ and 5% $CO_2$. The tissue is stimulated at 1 Hz at one msec pulse duration by a square wave stimulator at a voltage 30% above threshold through platinum electrodes that touch the tissue just above the bottom attachment point. The tendenous end of the tissue is connected by thread to an isometric force transducer leading to a polygraph.

Effective Refractory Period (ERP) Measurement

The ERP is determined by a standard 2 pulse protocol. Both pulses are stimulated at 1.3× voltage threshold. While pacing the tissue at a basal frequency of 1 Hz, a single extrastimulus is delivered after a variable time delay. The shortest delay resulting in a propagated response is defined as the ERP.

Protocol

1. Tissues are mounted with a resting tension of 0.5 gms, stimulated at 1 Hz, and allowed to equilibrate for 2 hours with washings at 15-20 minute intervals.
2. Voltage is adjusted to 30% above threshold and resting tension is adjusted for maximum developed tension, and the tissue is allowed 5 min. reequilibration time.
3. Effective refractory period is measured at 1 Hz. Changes in resting tension and developed force are noted.
4. After equilibration, ERP's and developed force are measured at 30 minutes following the addition of increasing cumulative concentrations for test agent to the organ bath. Four to five concentrations of test agents were used to generate a concentration-response curve.
5. Four tissues per compound are tested.

Results

Employing the above protocol, it has been found that the effective concentration of most of the compounds of this invention required to increase the refractory period by an increment of 25% above base-line is less than or equal to 10 micromolar, i.e. $EC_{25} \leq 10\mu M$, whereas sotalol in the same protocol has an $EC_{25} \sim 20$ micromolar.

EXAMPLE 569

Preparation of intravenous solutions

A solution containing 0.5 mg of active ingredient per ml of injectable solution is prepared in the following manner.

A mixture of 0.5 mg of active ingredient is dissolved in 1 ml of acetate buffer. The pH is adjusted using hydrochloric acid or aqueous sodium hydroxide to about pH 5.5.

If it is desired that the intravenous solution be used for multi-dose purposes, 1.0 mg of methyl-p-hydroxy benzoate (methyl paraben) and 0.10 mg of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.001, 0.01, and 0.1 mg, respectively, of active ingredient per ml of solution are similarly prepared substituting the indicated amount for the above-illustrated 10 mg quantity. Bulk injectable solutions of convenient volume for subsequent delivery in unit dosage form are readily prepared following the above procedure.

EXAMPLE 570

Tablet Preparation

Tablets containing 1.0, 2.0, 25.0, 26.0, 50.0 and 100.0 mg, respectively, of active ingredient are prepared as illustrated below.

| TABLE FOR DOSES CONTAINING FROM 1-25 MG OF THE ACTIVE COMPOUND | | | |
|---|---|---|---|
| | Amount - mg | | |
| Active ingredient | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount - mg | | |
| Active ingredient | 26.0 | 50.0 | 100.0 |
| Microcrystalline cellulose | 25.0 | 100.0 | 200.0 |
| Modified food corn starch | 2.21 | 4.25 | 8.5 |
| Magnesium stearate | .39 | 0.75 | 1.5 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg, and 100.0 mg of active ingredient per tablet.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of structural formula:

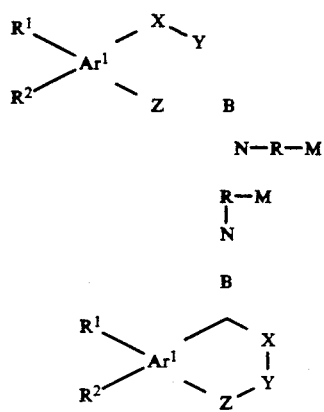

or a pharmaceutically acceptable salt thereof, wherein $Ar^1$ is benzo;

the ring system comprising X, Y and Z is a 5-, 6- or 7-membered ring system wherein X is CHOH or CO; Y is CH, a bond or $(CR_4R_5)_m$; and Z is —O—; wherein:
$R^4$ and $R^5$ are independently
  a) hydrogen, or
  b) $C_{1-6}$alkyl;
M is
  1) —H,
  2) —OH,
  3) —O($C_{1-6}$alkyl),
  4) —CN,
  5) —NHSO$_2$C$_{1-6}$alkyl,
  6) —COOH,
  7) —COOC$_{1-6}$alkyl,
  8) —CONR$^{12}$R$^{13}$, wherein R$^{12}$ and R$^{13}$ are independently
    a) hydrogen,
    b) C$_{1-6}$alkyl, or
    c) R$^{12}$ and R$^{13}$ taken together with the nitrogen atom to which they are attached represent a 5 or 6 membered saturated heterocyclic ring which may contain an additional heteroatom selected from N, S(O)$_n$ or O, wherein n is 0-2, selected from the group consisting of pyrrolidine, morpholine, piperidine, piperazine or N-methylpiperazine,
  9) —NR$^{12}$R$^{13}$,
  10) halo,
  11) C$_{5-8}$cycloalkane,
  12) C$_{5-8}$cycloalkene, or
  13)

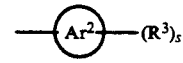

wherein s is 1-3 and the R$^3$ groups may be the same or different;

R is —(CR$^4$R$^5$)$_m$—Q—(CR$^4$R$^5$)$_q$—, wherein R$^4$ and R$^5$ are as defined above, m and q are O, Q is a bond;

R$^1$, R$^2$, and R$^3$ are independently selected from:
  1) hydrogen,
  2) C$_{1-6}$ alkyl, either unsubstituted or substituted with
    a) —NR$^4$R$^5$, wherein R$^4$ and R$^5$ are as defined above,
    b) —N(R$^5$)COC$_{1-6}$alkyl,
    c) —NHSO$_2$(C$_{1-6}$alkyl),
    d) —CONR$^{12}$R$^{13}$, wherein R$^{12}$ and R$^{13}$ are as defined above,
    e) —CO(C$_{1-6}$alkyl),
    f) —OH,
    g) —O(C$_{1-6}$alkyl),
    h) —O(C$_{1-6}$alkyl)—O—(C$_{1-3}$alkyl),
    i) —S(O)$_n$(C$_{1-6}$alkyl),
    j) imidazole,
    k) 2-imidazolidinone,
    l) 2-pyrrolidinone,
    m) —NH—C(NHR$^5$)=N—CN, or
    n) —NH—C(SR$^5$)=N—CN,
  3) —OH,
  4) C$_{1-3}$ alkoxy, either unsubstituted or substituted with C$_{1-3}$ alkoxy,
  5) —N(R$^5$)SO$_2$(C$_{1-6}$alkyl),
  6) —N(R$^5$)SO$_2$(CH$_2$)$_g$CO$_2$H,
  7) —N(R$^5$)SO$_2$(CH$_2$)$_g$CO$_2$C$_{1-6}$alkyl,
  8) —NO$_2$, 9) —N($R^5$)CO$C_{1-6}$alkyl,
10) —N($R^5$)SO$_2$—$C_6H_4$—$R^4$,
11) —N($R^5$)CO—$C_6H_4$—$R^4$,
12) —N$R^4R^5$,
13) halo,
14) —CO—$C_{1-6}$alkyl,
15) —CON$R^{12}R^{13}$,
16) —CN,
17) —CO$_2R^5$,
18) —C($R^5$)=N—O$R^9$,
19) benzoyl, either unsubstituted or substituted with $C_{1-6}$alkyl, $C_{1-6}$alkoxy, halo, or hydroxy,
20) —N($R^5$)COO($C_{1-6}$alkyl),
21) —N($R^5$)COO—phenyl either unsubstituted or substituted with $C_{1-6}$alkyl, $C_{1-6}$alkoxy, hydroxy or halo,
22) —N($R^5$)CON$R^4R^5$,
23) —S(O)$_n C_{1-6}$alkyl,
24) —S(O)$_n$—$C_6H_4$—$R^4$,
25) —CF$_3$,
26) phenyl, either unsubstituted or substituted with $C_{1-6}$alkyl, $C_{1-6}$alkoxy, halo or hydroxy,
27) imidazolyl,
28) —SO$_2$N$R^{12}R^{13}$,
29) —N[S(O)$_2C_{1-6}$alkyl][(CH$_2$)$_p$CN], wherein p is 2-5,
30) —N($R^5$)—C(N$R^4R^5$)=N—CN, or
31) —N($R^5$)—C(S$R^5$)=N—CN;

B is piperidine; and
Ar$^2$ is benzene or naphthalene;
with the proviso that if Ar$^1$ is benzo, and $R^1$ and $R^2$ are hydrogen, hydroxyalkyl or alkoxy, then M is other than unsubstituted phenyl or hydrogen.

2. The compound of claim 1 wherein
M is:
a) —OH,
b) —CN, or
c) —(Ar$^2$)—($R^3$)$_s$,
wherein Ar$^2$ is: benzene, and wherein s is 1 or 2, and $R^3$ is:
i) hydrogen,
ii) $C_{1-6}$ alkyl, either unsubstituted or substituted with
  A) —OH, or
  B) —N$R^4R^5$, wherein $R^4$ and $R^5$ are hydrogen or $C_{1-6}$ alkyl,
iii) —OH,
iv) $C_{1-3}$ alkoxy, either unsubstituted or substituted with $C_{1-3}$ alkoxy,
v) —N($R^5$)SO$_2$($C_{1-6}$alkyl),
vi) —NO$_2$,
vii) —N($R^5$)CO$C_{1-6}$alkyl,
viii) —N($R^5$)COO($C_{1-6}$alkyl),
ix) halo,
x) —CO—$C_{1-6}$alkyl,
xi) —CN, or
xii) —S(O)$_n C_{1-6}$alkyl, wherein n is 0-2.

3. A pharmaceutical formulation comprising a carrier and a therapeutically effective amount of the compound of claim 1.

4. A method of threating arrhythmia or impaired cardiac pump function in a patient in need of such treatment which comprises administering to such patient a therapeutically effective amount of the compound of claim 1.

* * * * *